(12) United States Patent
Kehne et al.

(10) Patent No.: US 8,216,973 B2
(45) Date of Patent: Jul. 10, 2012

(54) 2-[(1H-PYRAZOLE-4-YLMETHYL)-SULFONYL]-OXAZOLE-DERIVATIVE, 2-[(1H-PYRAZOLE-4-YLMETHYL)-SULFANYL]-OXAZOLE-DERIVATIVES, AND CHIRAL 2-[(1H-PYRAZOLE-4-YMETHYL)SULFINYL]OXAZOLE DERIVATIVES, METHODS FOR THE PRODUCTION THEREOF, AND USE THEREOF AS HERBICIDES AND PLANT GROWTH REGULATORS

(75) Inventors: Heinz Kehne, Hofheim (DE); Hansjorg Dietrich, Liederbach am Taunus (DE); Dieter Feucht, Eschborn (DE); Dirk Schmutzler, Hattersheim (DE); Isolde Hauser-Hahn, Leverkusen (DE); Christian Paulitz, Liederbach (DE); Jan Dittgen, Frankfurt (DE); Arianna Marteletti, Sulzbach (DE); Christopher Hugh Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 38 days.

(21) Appl. No.: 12/988,965

(22) PCT Filed: Apr. 15, 2009

(86) PCT No.: PCT/EP2009/002742
§ 371 (c)(1),
(2), (4) Date: Oct. 21, 2010

(87) PCT Pub. No.: WO2009/129954
PCT Pub. Date: Oct. 29, 2009

(65) Prior Publication Data
US 2011/0039696 A1 Feb. 17, 2011

(30) Foreign Application Priority Data
Apr. 22, 2008 (EP) .................................. 08007742

(51) Int. Cl.
*A01N 25/32* (2006.01)
*C07D 413/12* (2006.01)
*C07D 413/14* (2006.01)
*A01P 13/00* (2006.01)

(52) U.S. Cl. ........ 504/103; 504/139; 504/270; 548/229; 548/230

(58) Field of Classification Search ........................ None
See application file for complete search history.

(56) References Cited

FOREIGN PATENT DOCUMENTS
WO WO 2006/123088 11/2006
WO WO 2007/071900 6/2007

*Primary Examiner* — Kamal Saeed
(74) *Attorney, Agent, or Firm* — Frommer Lawrence & Haug LLP

(57) ABSTRACT

The invention relates to 2-[(1H-pyrazol-4-ylmethyl)-sulfonyl]-oxazole derivatives, chiral 2-[(1H-pyrazol-4-ylmethyl)-sulfinyl]-oxazole derivatives, and 2-[(1H-pyrazol-4-ylmethyl)-sulfanyl]-oxazole derivatives of general formula (I) and the salts thereof, methods for the production thereof, and the use thereof as herbicides and plant growth regulators, in particular as herbicides for selectively controlling weeds in plant crops.

16 Claims, No Drawings

2-[(1H-PYRAZOLE-4-YLMETHYL)-SULFONYL]-OXAZOLE-DERIVATIVE, 2-[(1H-PYRAZOLE-4-YLMETHYL)-SULFANYL]-OXAZOLE-DERIVATIVES, AND CHIRAL 2-[(1H-PYRAZOLE-4-YMETHYL)SULFINYL] OXAZOLE DERIVATIVES, METHODS FOR THE PRODUCTION THEREOF, AND USE THEREOF AS HERBICIDES AND PLANT GROWTH REGULATORS

The present invention relates to 2-[(1H-pyrazol-4-ylmethyl)sulfonyl]oxazole derivatives, chiral 2-[(1H-pyrazol-4-ylmethyl)sulfinyl]oxazole derivatives, and 2-[(1H-pyrazol-4-ylmethyl)sulfanyl]oxazole derivatives, and to specific processes for their preparation. The present invention furthermore provides their use as herbicide, in particular as herbicide for the selective control of harmful plants in crops of useful plants, as plant growth regulators on their own or in combination with safeners and/or as a mixture with other herbicides.

It is already known from various publications that certain oxazole derivatives have herbicidal and pesticidal properties.

Thus, WO 2004/013112 A describes herbicidally active oxazole derivatives which have a fluoroalkene-containing thioether group at the 2-position of the oxazole ring.

U.S. Pat. No. 4,022,607 describes 2-(alkylsulfinyl)oxazole derivatives, their preparation and their use as herbicide.

DE 10 254 876 A describes 2-(fluoroalkenylthio)oxazoles and their use as herbicides.

EP 0 435 794 A describes 1-heterocyclylsulfonyl-2-phenyl-2-propenes and their use as herbicides.

Pesticidal properties of 2-trifluorobutenethiooxazole derivatives are described, for example, in WO 2001/066529 A, WO 99/52874 A and WO 95/024403 A.

1-Alkyl-5-nitroimidazolyl 2-alkylheteroaryl sulfides in which the heteroaryl is a substituted oxazole are described in DE 23 59 922 A.

2-[(1H-Pyrazol-4-ylmethyl)sulfinyl] and 2-[(1H-pyrazol-4-ylmethyl)sulfonyl] derivatives having herbicidal properties have also been described. Thus, WO 2007/071900 A, WO 02/62770 A and WO 2006/123088 describe a number of 2-[(1H-pyrazol-4-ylmethyl)sulfinyl] and 2-[(1H-pyrazol-4-ylmethyl)sulfonyl] derivatives which carry a suitable substituted (1H-pyrazol-4-ylmethyl) group as substituent at the 2-sulfonyl or 2-sulfinyl group. The publications mentioned above also describe a process for their preparation.

2-(Arylmethylsulfonyl)-substituted derivatives having herbicidal properties have also been described. Thus, JP 2003/096059 A, WO 2001/112613 A and U.S. Pat. No. 3,960,542 describe a number of 2-(arylmethylsulfonyl) derivatives having a suitable substituted phenylmethyl group as substituent at the 2-sulfonyl group. The publications mentioned above also describe a process for their preparation.

However, the active compounds already known from the publications mentioned above, when used as herbicides, have disadvantages, be it (a) that they have insufficient, if any, herbicidal activity against harmful plants, (b) that the spectrum of harmful plants which can be controlled by one active compound is not wide enough, or (c) that their selectivity in crops of useful plants is too low.

For these reasons, it is desirable to provide alternative chemical active compounds which can be employed as herbicides or plant growth regulators, if appropriate with advantages.

The present invention now provides 2-[(1H-pyrazol-4-ylmethyl)sulfonyl]oxazole derivatives, chiral 2-[(1H-pyrazol-4-ylmethyl)sulfinyl]oxazole derivatives and 2-[(1H-pyrazol-4-ylmethyl)sulfanyl]oxazole derivatives which have advantages compared to the compounds described in the prior art.

Accordingly, the present invention provides compounds of the formula (I) according to the invention and agrochemically acceptable salts thereof

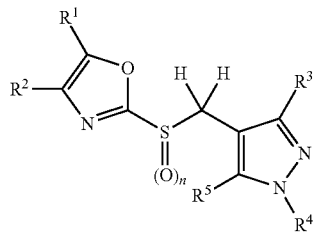

(I)

in which the radicals and indices have the following meaning:

n is 0, 1 or 2;

the substituents $R^1$ and $R^2$ are each independently of one another selected from the group consisting of hydrogen, halogen, nitro, cyano, formyl, C(O)OH, hydroxyl, amino, ($C_1$-$C_6$)-alkyl, ($C_1$-$C_6$)-alkylcarbonyl, ($C_1$-$C_6$)-alkylcarbonyl-($C_1$-$C_4$)-alkyl, ($C_1$-$C_6$)-alkylcarbonyloxy, ($C_1$-$C_6$)-alkoxy, ($C_1$-$C_6$)-alkoxycarbonyl, ($C_1$-$C_6$)-alkoxycarbonyl-($C_1$-$C_6$)-alkyl, ($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy, ($C_2$-$C_6$)-alkenyl, ($C_2$-$C_6$)-alkenyloxy, ($C_2$-$C_6$)-alkynyl, ($C_2$-$C_6$)-alkynyloxy, ($C_1$-$C_6$)-alkylthio, ($C_1$-$C_6$)-alkylsulfinyl, ($C_1$-$C_6$)-alkylsulfonyl, ($C_1$-$C_6$)-alkylsulfonyloxy, ($C_1$-$C_6$)-alkylsulfonyl-($C_1$-$C_6$)-alkyl, ($C_1$-$C_6$)-alkyl-sulfinyl-($C_1$-$C_6$)-alkyl, ($C_1$-$C_6$)-alkylthio-($C_1$-$C_6$)-alkyl, ($C_1$-$C_6$)-alkylthio-($C_1$-$C_6$)-alkoxy, mono-(($C_1$-$C_6$)-alkyl)amino, di-(($C_1$-$C_6$)-alkyl)amino, N—(($C_1$-$C_6$)-alkanoyl)amino, aminocarbonyl-($C_1$-$C_6$)-alkyl, mono-(($C_1$-$C_6$)-alkyl)aminocarbonyl, di-(($C_1$-$C_6$)-alkyl)aminocarbonyl, mono-(($C_1$-$C_6$)-alkyl)aminosulfonyl, di-(($C_1$-$C_6$)-alkyl)aminosulfonyl, ($C_3$-$C_8$)-cycloalkyl, ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-alkoxy, ($C_3$-$C_8$)-cycloalkylcarbonyl, ($C_3$-$C_8$)-cycloalkoxycarbonyl, ($C_3$-$C_8$)-cycloalkenyl, ($C_3$-$C_8$)-cycloalkenyloxy, ($C_3$-$C_6$)-cycloalkylthio, ($C_3$-$C_8$)-cycloalkylsulfinyl, ($C_3$-$C_8$)-cycloalkylsulfonyl, ($C_3$-$C_8$)-cyclo-alkylsulfonyloxy, cyano-($C_1$-$C_6$)-alkoxy, cyano-($C_1$-$C_6$)-alkyl, —CONN—$SO_2$—($C_1$-$C_6$)-alkyl, —NHCHO, —NHCO—($C_1$-$C_6$)-alkyl, —$NHCO_2$—($C_1$-$C_6$)-alkyl, —NHCONH—($C_1$-$C_6$)-alkyl, —$NHSO_2$—($C_1$-$C_6$)-alkyl, —OCONH—($C_1$-$C_6$)-alkyl, ($C_1$-$C_6$)-alkylaminosulfonyl-($C_1$-$C_2$)-alkyl, di-($C_1$-$C_6$)-alkylaminosulfonyl-($C_1$-$C_2$)-alkyl,

—C(O)$NHR^9$, —C(O)$NR^9R^{10}$, where $R^9$ and $R^{10}$ are independently of one another hydrogen, ($C_1$-$C_6$)-alkyl, ($C_3$-$C_6$)-cycloalkyl, ($C_1$-$C_6$)-haloalkyl, or where $R^9$ and $R^{10}$ together form a $(C_1\text{-}C_6)$-alkylene group which may contain an oxygen or a sulfur atom or one or two amino or $(C_1\text{-}C_6)$-alkylamino groups, where the abovementioned radicals $R^1$ and $R^2$ may be mono- or polysubstituted independently of one another;

the substituents $R^3$ to $R^5$ are each independently of one another selected from the group consisting of hydrogen, halogen, hydroxyl, cyano, nitro, amino, C(O)OH, formyl, $(C_1\text{-}C_6)$-alkyl, $(C_1\text{-}C_6)$-haloalkyl, $(C_1\text{-}C_6)$-alkylcarbonyl, $(C_1\text{-}C_6)$-haloalkylcarbonyl, $(C_1\text{-}C_6)$-alkylcarbonyloxy, $(C_1\text{-}C_6)$-haloalkyl-carbonyloxy, $(C_1\text{-}C_6)$-alkylcarbonyl-$(C_1\text{-}C_4)$-alkyl, $(C_1\text{-}C_6)$-haloalkyl-carbonyl-$(C_1\text{-}C_4)$-alkyl, $(C_1\text{-}C_6)$-alkylcarbonyl-$(C_1\text{-}C_4)$-haloalkyl, $(C_1\text{-}C_6)$-haloalkylcarbonyl-$(C_1\text{-}C_4)$-haloalkyl, $(C_1\text{-}C_6)$-alkoxy, $(C_1\text{-}C_6)$-haloalkoxy, $(C_1\text{-}C_6)$-alkoxycarbonyl, $(C_1\text{-}C_6)$-haloalkoxycarbonyl, $(C_1\text{-}C_6)$-alkoxycarbonyl-$(C_1\text{-}C_6)$-alkyl, $(C_1\text{-}C_6)$-haloalkoxycarbonyl-$(C_1\text{-}C_6)$-alkyl, $(C_1\text{-}C_6)$-alkoxycarbonyl-$(C_1\text{-}C_6)$-haloalkyl, $(C_1\text{-}C_6)$-haloalkoxycarbonyl-$(C_1\text{-}C_6)$-haloalkyl, $(C_2\text{-}C_6)$-alkenyl, $(C_2\text{-}C_6)$-haloalkenyl, $(C_2\text{-}C_6)$-alkenylcarbonyl, $(C_2\text{-}C_6)$-haloalkenylcarbonyl, $(C_2\text{-}C_6)$-alkenyloxy, $(C_2\text{-}C_6)$-halo-alkenyloxy, $(C_2\text{-}C_6)$-alkenyloxycarbonyl, $(C_2\text{-}C_6)$-haloalkenyloxycarbonyl, $(C_2\text{-}C_6)$-alkynyl, $(C_2\text{-}C_6)$-haloalkynyl, $(C_2\text{-}C_6)$-alkynylcarbonyl, $(C_2\text{-}C_6)$-haloalkynylcarbonyl, $(C_2\text{-}C_6)$-alkynyloxy, $(C_2\text{-}C_6)$-halo-alkynyloxy, $(C_2\text{-}C_6)$-alkynyloxycarbonyl, $(C_2\text{-}C_6)$-haloalkynyloxy-carbonyl, $(C_1\text{-}C_6)$-alkylthiocarbonyl, $(C_1\text{-}C_6)$-haloalkylthiocarbonyl, alkylthiocarbonyloxy, $(C_1\text{-}C_6)$-haloalkylthiocarbonyloxy, $(C_1\text{-}C_6)$-alkylthio-$(C_1\text{-}C_6)$-alkoxy, $(C_1\text{-}C_6)$-alkylthio-$(C_1\text{-}C_6)$-alkyl-carbonyl, $(C_1\text{-}C_6)$-alkylthio-$(C_1\text{-}C_6)$-alkylcarbonyloxy, $(C_6\text{-}C_{14})$-aryl, $(C_6\text{-}C_{14})$-aryloxy, $(C_6\text{-}C_{14})$-arylcarbonyl, $(C_6\text{-}C_{14})$-aryloxycarbonyl, $(C_6\text{-}C_{14})$-aryl-$(C_1\text{-}C_6)$-alkyl, $(C_6\text{-}C_{14})$-aryl-$(C_1\text{-}C_6)$-alkoxy, $(C_6\text{-}C_{14})$-aryloxy-$(C_1\text{-}C_6)$-alkyl, $(C_6\text{-}C_{14})$-aryl-$(C_1\text{-}C_6)$-alkylcarbonyl, $(C_6\text{-}C_{14})$-aryl-$(C_1\text{-}C_6)$-alkylcarbonyloxy, $(C_6\text{-}C_{14})$-aryl-$(C_1\text{-}C_6)$-alkoxy-carbonyl, $(C_6\text{-}C_{14})$-aryl-$(C_1\text{-}C_6)$-alkoxycarbonyloxy, $(C_1\text{-}C_6)$-alkylsulfonyl, $(C_1\text{-}C_6)$-alkylthio, $(C_1\text{-}C_6)$-alkylsulfinyl, $(C_1\text{-}C_6)$-haloalkylsulfonyl, $(C_1\text{-}C_6)$-haloalkylthio, $(C_1\text{-}C_6)$-haloalkyl-sulfinyl, $(C_1\text{-}C_6)$-alkylsulfonyl-$(C_1\text{-}C_6)$-alkyl, $(C_1\text{-}C_6)$-alkylthio-$(C_1\text{-}C_6)$-alkyl, $(C_1\text{-}C_6)$-alkylsulfinyl-$(C_1\text{-}C_6)$-alkyl, $(C_1\text{-}C_6)$-haloalkyl-sulfonyl-$(C_1\text{-}C_6)$-alkyl, $(C_1\text{-}C_6)$-haloalkylthio-$(C_1\text{-}C_6)$-alkyl, haloalkyl-sulfinyl-$(C_1\text{-}C_6)$-alkyl, $(C_1\text{-}C_6)$-alkylsulfonyl-$(C_1\text{-}C_6)$-haloalkyl, $(C_1\text{-}C_6)$-alkylthio-$(C_1\text{-}C_6)$-haloalkyl, $(C_1\text{-}C_6)$-alkylsulfinyl-$(C_1\text{-}C_6)$-haloalkyl, $(C_1\text{-}C_6)$-haloalkylsulfonyl-$(C_1\text{-}C_6)$-haloalkyl, $(C_1\text{-}C_6)$-haloalkylthio-$(C_1\text{-}C_6)$-haloalkyl, $(C_1\text{-}C_6)$-haloalkylsulfinyl-$(C_1\text{-}C_6)$-haloalkyl, $(C_1\text{-}C_6)$-alkylsulfonyloxy, $(C_1\text{-}C_6)$-haloalkyl-sulfonyloxy, $(C_4\text{-}C_{14})$-arylsulfonyl, $(C_6\text{-}C_{14})$-arylthio, $(C_6\text{-}C_{14})$-arylsulfinyl, mono-$((C_1\text{-}C_6)$-alkyl)amino, mono-$((C_1\text{-}C_6)$-haloalkyl)amino, di-$((C_1\text{-}C_6)$-alkyl)amino, di-$((C_1\text{-}C_6)$-haloalkyl)amino, $((C_1\text{-}C_6)$-alkyl-$(C_1\text{-}C_6)$-haloalkyl)amino, N—$((C_1\text{-}C_6)$-alkanoyl)amino, N—$((C_1\text{-}C_6)$-haloalkanoyl)amino, aminocarbonyl-$(C_1\text{-}C_6)$-alkyl, mono-$(C_1\text{-}C_6)$-alkylaminocarbonyl-$(C_1\text{-}C_6)$-alkyl, di-$(C_1\text{-}C_6)$-alkylaminocarbonyl-$(C_1\text{-}C_6)$-alkyl, mono-$((C_1\text{-}C_6)$-alkyl)aminocarbonyl, $(C_1\text{-}C_6)$-alkoxy-$(C_1\text{-}C_6)$-alkyl, $(C_1\text{-}C_6)$-alkoxy-$(C_1\text{-}C_6)$-alkoxy, $(C_1\text{-}C_6)$-alkoxycarbonyl-$(C_1\text{-}C_6)$-alkoxy, $(C_3\text{-}C_8)$-cycloalkyl, $(C_3\text{-}C_8)$-cycloalkoxy, $(C_3\text{-}C_8)$-cycloalkyl-$(C_1\text{-}C_6)$-alkyl, $(C_3\text{-}C_8)$-cycloalkyl-$(C_1\text{-}C_6)$-haloalkyl, $(C_3\text{-}C_8)$-cycloalkyl-$(C_1\text{-}C_6)$-alkoxy, $(C_3\text{-}C_8)$-cycloalkyl-$(C_1\text{-}C_6)$-haloalkoxy, $(C_3\text{-}C_8)$-cycloalkylcarbonyl, $(C_3\text{-}C_8)$-cycloalkoxycarbonyl, $(C_3\text{-}C_8)$-cycloalkyl-$(C_1\text{-}C_6)$-alkylcarbonyl, $(C_3\text{-}C_8)$-cycloalkyl-$(C_1\text{-}C_6)$-haloalkylcarbonyl, $(C_3\text{-}C_8)$-cycloalkyl-$(C_1\text{-}C_6)$-alkoxycarbonyl, $(C_3\text{-}C_8)$-cycloalkyl-$(C_1\text{-}C_6)$-haloalkoxycarbonyl, $(C_3\text{-}C_8)$-cycloalkylcarbonyloxy, $(C_3\text{-}C_8)$-cycloalkoxycarbonyloxy, $(C_3\text{-}C_8)$-cycloalkyl-$(C_1\text{-}C_6)$-alkylcarbonyloxy, $(C_3\text{-}C_8)$-cycloalkyl-$(C_1\text{-}C_6)$-haloalkylcarbonyloxy, $(C_3\text{-}C_8)$-cycloalkyl-$(C_1\text{-}C_6)$-alkoxycarbonyloxy, $(C_3\text{-}C_8)$-cycloalkyl-$(C_1\text{-}C_6)$-haloalkoxycarbonyloxy, $(C_3\text{-}C_8)$-cycloalkenyl, $(C_3\text{-}C_8)$-cycloalkenyloxy, $(C_3\text{-}C_8)$-cyclo-alkenyl-$(C_1\text{-}C_6)$-alkyl, $(C_3\text{-}C_8)$-cycloalkenyl-$(C_1\text{-}C_6)$-haloalkyl, $(C_3\text{-}C_8)$-cycloalkenyl-$(C_1\text{-}C_6)$-alkoxy, $(C_3\text{-}C_8)$-cycloalkenyl-$(C_1\text{-}C_6)$-haloalkoxy, $(C_3\text{-}C_8)$-cycloalkenylcarbonyl, $(C_3\text{-}C_8)$-cycloalkenyloxy-carbonyl, $(C_3\text{-}C_8)$-cycloalkenyl-$(C_1\text{-}C_6)$-alkylcarbonyl, $(C_3\text{-}C_8)$-cycloalkenyl-$(C_1\text{-}C_6)$-haloalkylcarbonyl, $(C_3\text{-}C_8)$-cycloalkenyl-$(C_1\text{-}C_6)$-alkoxycarbonyl, $(C_3\text{-}C_8)$-cycloalkenyl-$(C_1\text{-}C_6)$-haloalkoxy-carbonyl, $(C_3\text{-}C_8)$-cycloalkenylcarbonyloxy, $(C_3\text{-}C_8)$-cycloalkenyl-oxycarbonyloxy, $(C_3\text{-}C_8)$-cycloalkenyl-$(C_1\text{-}C_6)$-alkylcarbonyloxy, $(C_3\text{-}C_8)$-cycloalkenyl-$(C_1\text{-}C_6)$-haloalkylcarbonyloxy, $(C_3\text{-}C_8)$-cycloalkenyl-$(C_1\text{-}C_6)$-alkoxycarbonyloxy, $(C_3\text{-}C_8)$-cycloalkenyl-$(C_1\text{-}C_6)$-haloalkoxycarbonyloxy, $(C_3\text{-}C_8)$-cycloalkylthio, $(C_3\text{-}C_8)$-alkenylthio, $(C_3\text{-}C_8)$-cycloalkenyl-thio, $(C_3\text{-}C_6)$-alkynylthio, hydroxy-$(C_1\text{-}C_6)$-alkyl, hydroxy-$(C_1\text{-}C_6)$-alkoxy, cyano-$(C_1\text{-}C_6)$-alkoxy, cyano-$(C_1\text{-}C_6)$-alkyl, 3-oxetanyloxy-,

—C(O)NR$^9$R$^{10}$, where $R^9$ and $R^{10}$ are independently of one another hydrogen, $(C_1\text{-}C_6)$-alkyl, $(C_3\text{-}C_6)$-cycloalkyl or $(C_1\text{-}C_6)$-haloalkyl, or where $R^9$ and $R^{10}$ together form a $(C_1\text{-}C_6)$-alkylene group which may contain an oxygen or a sulfur atom or one or two amino or $(C_1\text{-}C_6)$-alkylamino groups, where the abovementioned radicals $R^3$ to $R^5$ may be mono- or polysubstituted independently of one another, and/or adjacent radicals $R^4$ and $R^5$ may be cyclically attached to one another and/or form a $(C_1\text{-}C_6)$-alkylene group which may contain one or more oxygen and/or sulfur atoms, where the $(C_1\text{-}C_6)$-alkylene group may be mono- or polysubstituted by halogen and the respective halogen substituents may be identical or different.

If the radicals, in particular radicals comprising an aryl group, a cycloalkyl group, an alkyl group, an alkenyl group, an alkynyl group and a cycloalkenyl group, comprise one or more substituents, such as, for example, cycloalkyl or aryl, the substituents are preferably selected from the group consisting of $(C_1-C_6)$-alkyl, $(C_1-C_6)$-haloalkyl, $(C_1-C_6)$-alkoxy, nitro, cyano, $(C_1-C_3)$-cycloalkyl, $(C_1-C_6)$-haloalkoxy, $(C_1-C_6)$-alkylthio, $(C_1-C_6)$-alkylcarbonyl, $(C_1-C_6)$-alkoxycarbonyl or halogen, where the radicals mentioned may optionally be cyclically attached to one another, with the proviso that they are ortho to one another.

A first embodiment of the present invention comprises compounds of the formula (I) in which $R^1$ is preferably selected from the group consisting of H, halogen, nitro, cyano, carboxyl, $(C_1-C_6)$-alkyl, $(C_3-C_6)$-cycloalkyl, $(C_3-C_6)$-cycloalkoxy, $(C_1-C_6)$-alkoxy, $(C_1-C_6)$-alkylcarbonyl, $(C_3-C_6)$-cycloalkylcarbonyl, $(C_1-C_6)$-alkoxycarbonyl, $(C_3-C_6)$-cycloalkoxycarbonyl, mono-$((C_1-C_4)$-alkyl)aminocarbonyl, di-$((C_1-C_4)$-alkyl)aminocarbonyl, mono-$((C_1-C_4)$-alkyl)aminosulfonyl, di-$((C_1-C_4)$-alkyl)aminosulfonyl, $(C_1-C_4)$-alkylthio, $(C_3-C_6)$-cycloalkylthio, $(C_1-C_4)$-alkylsulfinyl, $(C_3-C_6)$-cycloalkylsulfinyl, $(C_1-C_4)$-alkylsulfonyl, $(C_3-C_6)$-cycloalkylsulfonyl, $(C_1-C_4)$-alkylsulfonyloxy, $(C_3-C_6)$-cyclo-alkylsulfonyloxy, $(C_2-C_3)$-alkenyl, $(C_2-C_3)$-alkynyl, $(C_2-C_3)$-alkenyloxy, $(C_2-C_3)$-alkynyloxy, —NHCO—$(C_1-C_3)$-alkyl, —NHCO$_2$—$(C_1-C_3)$-alkyl, —NHCONH—$(C_1-C_3)$-alkyl, —NHSO$_2$—$(C_1-C_3)$-alkyl, —OCONH—$(C_1-C_3)$-alkyl, —CONHR$^9$, —CONR$^9$R$^{10}$, where R$^9$ and R$^{10}$ are independently of one another selected from the group consisting of hydrogen, $(C_1-C_6)$-alkyl, $(C_3-C_6)$-cycloalkyl and $(C_1-C_6)$-haloalkyl; and where the abovementioned radical $R^1$ may be mono- or polysubstituted independently of one another by radicals selected from the group consisting of halogen and $(C_1-C_6)$-alkyl, $R^1$ is particularly preferably selected from the group consisting of H, F, Cl, Br, I, Me, Et, NO$_2$, CHF$_2$ and CF$_3$; and $R^1$ is very particularly preferably selected from the group consisting of H, F, Cl, Br, I and Me.

A second embodiment of the present invention comprises compounds of the formula (I) in which $R^2$ is preferably selected from the group consisting of H, halogen, nitro, cyano, carboxyl, $(C_1-C_6)$-alkyl, $(C_3-C_6)$-cycloalkyl, $(C_3-C_6)$-cycloalkoxy, $(C_1-C_6)$-alkoxy, $(C_1-C_6)$-alkylcarbonyl, $(C_3-C_6)$-cycloalkylcarbonyl, $(C_1-C_6)$-alkoxycarbonyl, $(C_3-C_6)$-cycloalkoxycarbonyl, mono-$((C_1-C_4)$-alkyl)aminocarbonyl, di-$((C_1-C_4)$-alkyl)aminocarbonyl, mono-$((C_1-C_4)$-alkyl)aminosulfonyl, di-$((C_1-C_4)$-alkyl)aminosulfonyl, $(C_3-C_6)$-cycloalkylthio, $(C_1-C_4)$-alkylsulfinyl, $(C_3-C_6)$-cycloalkylsulfinyl, $(C_1-C_4)$-alkylsulfonyl, $(C_3-C_6)$-cycloalkylsulfonyl, $(C_1-C_4)$-alkylsulfonyloxy, $(C_3-C_6)$-cyclo-alkylsulfonyloxy, $(C_2-C_3)$-alkenyl, $(C_2-C_3)$-alkynyl, $(C_2-C_3)$-alkenyloxy, $(C_2-C_3)$-alkynyloxy, —NHCO—$(C_1-C_3)$-alkyl, —NHCO$_2$—$(C_1-C_3)$-alkyl, —NHCONH—$(C_1-C_3)$-alkyl, —NHSO$_2$—$(C_1-C_3)$-alkyl, —OCONH—$(C_1-C_3)$-alkyl, —CONHR$^9$, —CONR$^9$R$^{10}$, where R$^9$ and R$^{10}$ are independently of one another hydrogen, $(C_1-C_6)$-alkyl, $(C_3-C_6)$-cycloalkyl, $(C_1-C_6)$-haloalkyl, where the abovementioned radical $R^2$ may be mono- or polysubstituted independently of one another by radicals selected from the group consisting of halogen and $(C_1-C_6)$-alkyl;

$R^2$ is particularly preferably selected from the group consisting of H, F, Cl, Br, I, Me, Et, NO$_2$, CHF$_2$ and CF$_3$; and $R^2$ is very particularly preferably selected from the group consisting of H, F, Cl and Br.

A third embodiment of the present invention comprises compounds of the formula (I) in which $R^3$ is preferably selected from the group consisting of hydrogen, halogen, hydroxyl, cyano, nitro, amino, $(C_1-C_4)$-alkyl, $(C_3-C_6)$-cycloalkyl, $(C_1-C_4)$-haloalkyl, $(C_1-C_4)$-alkoxy, $(C_1-C_4)$-alkoxy-$(C_1-C_2)$-alkyl, $(C_3-C_6)$-cycloalkoxy, $(C_1-C_4)$-haloalkoxy, $(C_1-C_4)$-alkylthio, $(C_1-C_4)$-alkylthio-$(C_1-C_2)$-alkyl, $(C_1-C_4)$-alkylsulfinyl, $(C_1-C_4)$-alkylsulfinyl-$(C_1-C_2)$-alkyl, $(C_1-C_4)$-alkylsulfonyl, $(C_1-C_4)$-alkylsulfonyl-$(C_1-C_2)$-alkyl), di-$(C_1-C_4)$-alkylamino, $(C_2-C_4)$-alkenyl, $(C_2-C_4)$-alkynyl, $(C_3-C_4)$-alkenyloxy, $(C_3-C_4)$-alkynyloxy, $(C_3-C_6)$-cycloalkyl-$(C_1-C_2)$-alkoxy, hydroxy-$(C_1-C_2)$-alkyl, hydroxy-$(C_1-C_2)$-alkoxy, cyano-$(C_1-C_2)$-alkoxy, cyano-$(C_1-C_2)$-alkyl; phenyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; phenyl-$(C_1-C_2)$-alkyl which is optionally substituted by one or more identical or different radicals from the group consisting of halogen, nitro, cyano, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; phenyl-$(C_1-C_2)$-alkoxy, phenoxy which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy or $(C_1-C_6)$-alkylthio; $(C_1-C_4)$-alkylcarbonyloxy, $(C_3-C_6)$-cycloalkyl-$(C_1-C_2)$-alkyl, $(C_1-C_4)$-alkylcarbonyl-$(C_1-C_2)$-alkyl, $(C_1-C_4)$-alkoxycarbonyl-$(C_1-C_2)$-alkyl, aminocarbonyl-$(C_1-C_2)$-alkyl and 3-oxetanyloxy, —C(O)NR$^9$R$^{10}$, where R$^9$ and R$^{10}$ are independently of one another selected from the group consisting of hydrogen, $(C_1-C_6)$-alkyl, $(C_3-C_6)$-cycloalkyl, $(C_1-C_6)$-haloalkyl, or where R$^9$ and R$^{10}$ together form a $(C_1-C_6)$-alkylene group which may contain an oxygen or sulfur atom or one or two amino or $(C_1-C_6)$-alkylamino groups;

and $R^3$ is particularly preferably selected from the group consisting of H, F, Cl, Br, I, CN, Me, Et, Pr, iPr, tBu, CHF$_2$, CF$_3$, OMe, OEt, OCHF$_2$ and OCH$_2$CF$_3$; and $R^3$ is very particularly preferably selected from the group consisting of F, Cl, Br, CHF$_2$, CF$_3$, OCHF$_2$, OCF$_3$, OCH$_2$CF$_3$, Me, OMe, Pr, iPr and Et.

A fourth embodiment of the present invention comprises compounds of the formula (I) in which $R^4$ is preferably selected from the group consisting of hydrogen; $(C_1-C_4)$-alkyl; $(C_1-C_4)$-haloalkyl; phenyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; phenyl-$(C_1-C_2)$-alkyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; $(C_3-C_6)$-cycloalkyl; $(C_3-C_6)$-cycloalkyl-$(C_1-C_2)$-alkyl where the cycloalkyl radical is optionally substituted by $(C_1-C_4)$-alkyl; $(C_2-C_4)$-alkenyl, $(C_2-C_4)$-alkynyl, $(C_1-C_4)$-alkoxy-$(C_1-C_2)$-alkyl, $(C_1-C_4)$-alkylsulfinyl-$(C_1-C_2)$-alkyl, cyano-$(C_1-C_2)$-alkyl, $(C_1-C_4)$-alkylsulfonyl-$(C_1-C_2)$-alkyl, $(C_1-C_4)$-alkoxycarbonyl-$(C_1-C_2)$-alkyl, aminocarbonyl-$(C_1-C_2)$-alkyl, mono-$(C_1-C_4)$-alkylaminocarbonyl-$(C_1-C_2)$-alkyl, di-$(C_1-C_4)$-alkylaminocarbonyl-$(C_1-C_2)$-alkyl, hydroxy-$(C_1-C_4)$-alkyl, $(C_1-C_4)$-alkylcarbonyl-$(C_1-C_4)$-alkyl, $(C_1-C_4)$-alkoxycarbonyl-$(C_1-C_2)$-alkyl, $(C_1-C_4)$-alkylsulfonyl; phenylsulfonyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; $(C_1-C_4)$-alkylcarbonyl; phenylcarbonyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; and $(C_1-C_4)$-alkoxycarbonyl;

$R^4$ is particularly
preferably selected from the group consisting of H, Me, Et, Pr, cPr, iPr, Bu, iBu, sBu, tBu, cPen, cHex, $CHF_2$, $CH_2CF_3$, Ph, Ph(4-Cl), $CH_2cPr$, $CH_2cPr(2-Me)$, CHMecPr, $CH_2cBu$, $CH_2cPen$, $CH_2cHex$, $CH_2Ph$, $CH_2CH=CH_2$, $CH_2C\equiv CH$, CHMeC$\equiv$CH, $CH_2C\equiv CMe$, $CH_2OMe$, $CH_2OEt$, $CH_2CH_2OH$, $CH_2CH_2OMe$, $CH_2CH_2OEt$, $CH_2CH_2C(O)Me$, $CH_2SMe$, $CH_2SO_2Me$, $CH_2CN$, $CH_2C(O)OMe$, $CH_2C(O)OEt$, $CH_2C(O)NH_2$, $CH_2C(O)NMe_2$, $CH_2C(O)Me$, $SO_2Me$, $SO_2Ph$, $C(O)Me$, $C(O)Ph$ and $C(O)OMe$; and $R^4$ is very particularly
preferably selected from the group consisting of Me, Et and $CHF_2$.

A fifth embodiment of the present invention comprises compounds of the formula (I) in which $R^5$ is preferably selected from the group consisting of hydrogen, halogen, hydroxyl, cyano, nitro, amino, $(C_1-C_4)$-alkyl, $(C_1-C_4)$-haloalkyl, $(C_3-C_6)$-cycloalkyl, $(C_1-C_4)$-alkoxy, $(C_1-C_4)$-alkoxy-$(C_1-C_4)$-alkoxy, $(C_1-C_4)$-alkoxy-$(C_1-C_2)$-alkyl, $(C_3-C_6)$-cycloalkoxy, $(C_1-C_4)$-haloalkoxy, $(C_1-C_4)$-alkylthio, $(C_1-C_4)$-alkylthio-$(C_1-C_2)$-alkyl, $(C_{1-4})$-alkylsulfinyl, $(C_1-C_4)$-alkylsulfinyl-$(C_1-C_2)$-alkyl, $(C_1-C_4)$-alkylsulfonyl, $(C_1-C_4)$-alkylsulfonyl-$(C_1-C_2)$-alkyl, di-$(C_1-C_4)$-alkylamino, $(C_2-C_4)$-alkenyl, $(C_2-C_4)$-haloalkenyl, cyano-$(C_1-C_4)$-alkyl, $(C_2-C_4)$-alkynyl, $(C_3-C_4)$-alkenyloxy, $(C_3-C_4)$-alkynyloxy, $(C_3-C_6)$-cycloalkyl-$(C_1-C_2)$-alkoxy, hydroxy-$(C_1-C_2)$-alkyl, hydroxy-$(C_1-C_2)$-alkoxy, cyano-$(C_1-C_2)$-alkoxy, cyano-$(C_1-C_2)$-alkyl; phenyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; phenyl-$(C_1-C_2)$-alkyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; phenyl-$(C_1-C_2)$-alkoxy; phenoxy which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; $(C_1-C_4)$-alkylcarbonyl, $(C_3-C_6)$-cycloalkyl-$(C_1-C_2)$-alkyl, $(C_1-C_4)$-alkylcarbonyl-$(C_1-C_2)$-alkyl, $(C_1-C_4)$-alkoxycarbonyl-$(C_1-C_2)$-alkyl, aminocarbonyl-$(C_1-C_2)$-alkyl and 3-oxetanyloxy, $-C(O)NR^9R^{10}$, where $R^9$ and $R^{10}$ are independently of one another selected from the group consisting of hydrogen, $(C_1-C_6)$-alkyl, $(C_3-C_6)$-cycloalkyl, $(C_1-C_6)$-haloalkyl, or where $R^9$ and $R^{10}$ together form a $(C_1-C_6)$-alkylene group which may contain an oxygen or sulfur atom or one or two amino or $(C_1-C_6)$-alkylamino groups; and $R^5$ is particularly
preferably selected from the group consisting of H, F, Cl, Br, I, CN, Me, Et, $CHF_2$, $CF_3$, $OCHF_2$, $OCH_2CF_3$, OMe, OEt, OPr, OiPr, OtBu, $SO_2Me$, $SO_2iPr$, 3-oxetanyloxy, OPh, $OCH_2CH=CH_2$, $OCH_2C\equiv CH$, $OCH_2CHF_2$, SEt, $OCH_2CH_2OCH_3$, SMe, $OCH_2CH_2CH_2F$, $OCH(CH_2F)_2$, $OCH_2CF=CH_2$, $OCH(CH_3)CF_3$, $OCH_2CN$, $OCH(CH_3)CH_2F$, $OCH_2CF_2CHF_2$ and $OCH(CH_3)_2$; and $R^5$ is very particularly
preferably selected from the group consisting of H, F, Cl, Br, $CHF_2$, $CF_3$, $OCHF_2$ and $OCH_2CF_3$.

In the context of the present invention, it is possible to combine the individual preferred, particularly preferred and very particularly preferred meanings of the substituents $R^1$ to $R^5$ as defined in the five embodiments above with one another as desired. This means that the present invention embraces compounds of the formula (I) in which, for example, the substituent $R^3$ has a preferred meaning and the substituents $R^1$, $R^2$, $R^4$ and $R^5$ have the general meaning or else the substituent $R^4$ has a preferred meaning, the substituent $R^5$ has a particularly preferred meaning and the substituents $R^1$ to $R^3$ have a very particularly preferred meaning.

In the context of the present invention, the compounds of the formula (I) also comprise compounds quaternized at a nitrogen atom by a) protonation, b) alkylation or c) oxidation.

If appropriate, the compounds of the formula (I) are able to form salts by forming an adduct with a suitable inorganic or organic acid, such as, for example, HCl, HBr, $H_2SO_4$ or $HNO_3$, or else oxalic acid or sulfonic acids, to a basic group, such as, for example, amino or alkylamino. Suitable substituents present in deprotonated form, such as, for example, sulfonic acids or carboxylic acids, are capable of forming inner salts with groups, such as amino groups, which can be protonated for their part. Salts can also be formed by replacing the hydrogen of suitable substituents, such as, for example, sulfonic acids or carboxylic acids, with a cation suitable in the agrochemical sector. These salts are, for example, metal salts, in particular alkali metal salts or alkaline earth metal salts, especially sodium salts and potassium salts, or else ammonium salts, salts with organic amines or quaternary ammonium salts having cations of the formula [NRR'R''R''']⁺ in which R to R''' in each case independently are an organic radical, in particular alkyl, aryl, arylalkyl or alkylaryl. In the formula (I) and in all the other formulae of the present invention, the radicals alkyl, alkoxy, haloalkyl, haloalkoxy, alkylamino, alkylthio, haloalkylthio, alkylsulfinyl, alkylsulfonyl, haloalkylsulfinyl and haloalkylsulfonyl and the corresponding unsaturated and/or substituted radicals can in each case be straight-chain or branched in the carbon skeleton. Unless indicated specifically, preference is given for these radicals to the lower carbon skeletons, for example those having 1 to 6 carbon atoms, especially 1 to 4 carbon atoms, or in the case of unsaturated groups having 2 to 6 carbon atoms, especially 2 to 4 carbon atoms. Alkyl radicals, also in composite definitions such as alkoxy, haloalkyl, etc., are for example methyl, ethyl, n-propyl or isopropyl, n-, iso-, t- or 2-butyl, pentyls, hexyls, such as n-hexyl, isohexyl and 1,3-dimethylbutyl, heptyls, such as n-heptyl, 1-methylhexyl or 1,4-dimethyl-pentyl; alkenyl and alkynyl radicals have the meaning of the possible unsaturated radicals corresponding to the alkyl radicals; where at least one double bond or triple bond is present, preferably one double bond or triple bond, respectively. Alkenyl is, for example, vinyl, allyl; 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, ethynyl, propargyl, but-2-yn-1-yl, but-3-yn-1-yl and 1-methylbut-3-yn-1-yl.

Halogen is fluorine, chlorine, bromine or iodine; haloalkyl, haloalkenyl and haloalkynyl are alkyl, alkenyl and alkynyl, respectively, which are fully or partially substituted by halogen, preferably by fluorine, chlorine or bromine, in particular by fluorine and/or chlorine, examples being monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$, and $OCH_2CH_2Cl$; this correspondingly applies to haloalkenyl and other halogen-substituted radicals.

Optionally substituted aryl is preferably phenyl which is unsubstituted or mono- or polysubstituted, preferably up to trisubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy, $(C_3-C_6)$-cycloalkyl, $(C_1-C_6)$-alkylthio, cyano and nitro, for example o-, m- and p-tolyl, dimethylphenyls, 2-, 3- and 4-chlorophenyl, 2-, 3- and 4-trifluoromethyl- and 2-, 3- and 4-trichloromethylphenyl, 2,4-, 3,5-, 2,5- and 2,3-dichlorophenyl, o-, m- and p-methoxyphenyl.

The definition "substituted by one or more radicals" refers, unless otherwise defined, to one or more identical or different radicals.

The substituents given by way of example ("first substituent level") can, if they include hydrocarbon-containing fractions, be further substituted therein if desired ("second substituent level"), for example by one of the substituents as defined for the first substituent level. Corresponding further substituent levels are possible. The term "substituted radical" preferably embraces just one or two substituent levels.

In the case of radicals having carbon atoms, preference is given to those having 1 to 6 carbon atoms, preferably 1 to 4 carbon atoms, in particular 1 or 2 carbon atoms. Preference is generally given to substituents from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano.

The invention also provides all stereoisomers embraced by formula (I), and mixtures thereof. Such compounds of the formula (I) contain one or more asymmetric carbon atoms (=asymmetrically substituted carbon atoms), or/and asymmetric sulfur atoms in the form of sulfoxides (n=1), which can exist in two enantiomeric forms, or else double bonds, which are not expressly shown in the formula (I). Formula (I) embraces all possible stereoisomers, such as enantiomers, diastereomers and Z and E isomers, defined by their specific spatial form, and these stereoisomers can be obtained by customary methods from mixtures of the stereoisomers or else be prepared by stereoselective reactions in combination with the use of stereochemically pure starting materials.

The abovementioned general or preferred radical definitions apply both to the end products of the formula (I) and, correspondingly, to the starting materials or the intermediates required in each case for the preparation. These radical definitions can be exchanged for one another as desired, i.e. including combinations between the given preferred ranges.

For the possible combinations of the various substituents of the formula (I) the general principles of the construction of chemical compounds have to be observed, i.e. the formula (I) does not comprise any compounds known to the person skilled in the art as being chemically impossible.

The present invention also provides processes for preparing the compounds of the formula (I) and/or salts thereof.

The compounds of the formula (I) according to the invention can be prepared alternatively by various processes.

In some of the processes below, solvents are used. In this context, "inert solvents" in each case refers to solvents which are inert under the reaction conditions in question, but which do not have to be inert under all reaction conditions.

a.) To prepare optically active sulfoxides of the formula (III) (n=1) or sulfones of the formula (IV) (n=2) in which $R^1$, $R^2$, $R^3$, $R^4$, $R^5$ have the meanings given above for formula (I),

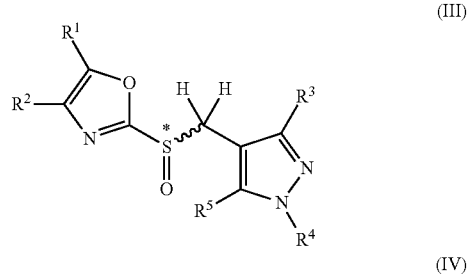

(III)

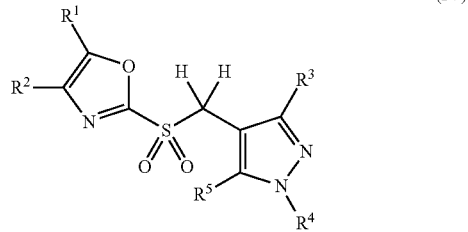

(IV)

for example, a thioether of the formula (II)

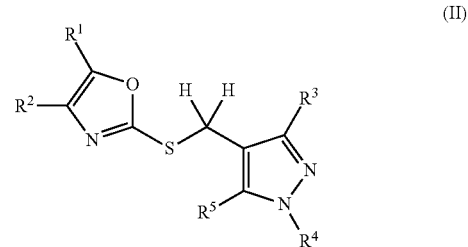

(II)

in which $R^1$, $R^2$, $R^3$, $R^4$, $R^5$ have the meanings given above for formula (I) is oxidized with one equivalent of an oxidizing agent to give the optically active sulfoxides (III) (n=1) or oxidized with two equivalents of an oxidizing agent to give the sulfones (IV) (n=2).

The sulfones of the formula (IV) can also be obtained from the optically active sulfoxides of the formula (III), where the sulfoxides of the formula (III) are oxidized using one equivalent of an oxidizing agent, giving the sulfones of the formula (IV).

The oxidizing agents which can be used for this reaction are not subject to any particular restrictions, it being possible in general to use all oxidizing agents which are capable of oxidizing corresponding sulfur compounds to sulfoxide compounds or sulfone compounds.

Suitable oxidizing agents for preparing the optically active sulfoxides (n=1) are inorganic peroxides such as, for example, hydrogen peroxide, sodium metaperiodate, optionally in the presence of a catalyst such as, for example, ruthenium(III) chloride, organic peroxides such as, for example, tert-butyl hydroperoxide or organic peracids such as peracetic acid or, preferably, 3-chloro-perbenzoic acid. The reaction can be carried out in halogenated hydrocarbons, for example dichloromethane, 1,2-dichloroethane, an alcohol, such as, for example, methanol, or in dimethylformamide, acetonitrile, water or acetic acid, or in a mixture of the solvents mentioned above. The reaction is carried out in a temperature range of between −80 and 120° C., preferably between −20 and 50° C. Such processes are known in the literature and described, for example, in J. Org. Chem., 58 (1993) 2791, J. Org. Chem., 68 (2003) 3849 and J. Heterocyclic Chem., 15 (1978) 1361.

Oxidizing agents suitable for preparing the sulfones (n=2) are, for example, hydrogen peroxide, organic peroxides such as, for example, tert-butyl hydroperoxide or organic peracids such as peracetic acid or, preferably, 3-chloroperbenzoic acid.

The enantioselective synthesis of chiral sulfoxides of the formula (III) in optically enriched or pure form can be carried out from thio compounds of the formula (II) using methods as described, for example, in Chem. Rev., 103 (2003) 3651-3705 and in the literature cited therein, and Adv. Synth. Catal., 347 (2005) 19-31 and in the literature cited therein. In each individual case, the absolute configuration of the product depends on the structure of the optically active catalyst.

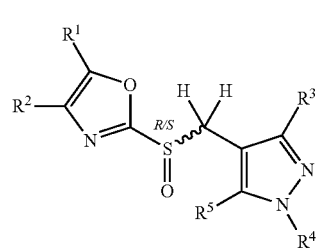

Compounds of the formula (III) consist of a mixture of the respective enantiomers (III-S) and (III-R), which are chiral at the sulfoxide function,

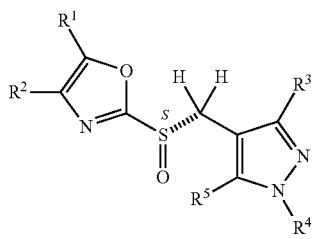

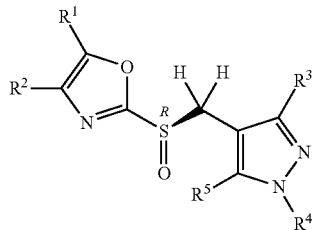

where the radicals $R^1$, $R^2$, $R^3$, $R^4$, $R^5$ have the meaning given above for formula (I).

Suitable for preparing enantiomers of the formula (III) are, in addition to enantioselective syntheses, also customary methods for the separation of racemates (cf. textbooks of stereochemistry).

Racemic mixtures, for example of optically active sulfoxides of the formula (III), can be separated by known processes. Such methods for the separation of racemates are described in textbooks of stereochemistry, for example in "Basic Organic Stereochemistry" (Eds.: Eliel, Ernest L.; Wilen, Samuel H.; Doyle, Michael P.; 2001; John Wiley & Sons) and "Stereochemistry of Organic Compounds" (Eds.: Eliel, Ernest L.; Wilen, Samuel H.; Mander, Lewis N.; 1994; John Wiley & Sons). Suitable for this purpose are, for example, adduct formation with an optically active auxiliary, separation of the diastereomeric adducts into the corresponding diastereomers, for example by crystallization, chromatographic methods, especially column chromatography and high pressure liquid chromatography, distillation, if appropriate under reduced pressure, extraction and other methods and subsequent cleavage of the diastereomers to afford the enantiomers. Suitable for preparative amounts or on an industrial scale are processes such as the crystallization of diastereomeric salts which can be obtained from the compounds (III) using optically active acids and, if appropriate, provided that acidic groups are present, using optically active bases. Optically active acids which are suitable for racemate separation by crystallization of diastereomeric salts are, for example, camphorsulfonic acid, camphoric acid, bromocamphorsulfonic acid, quinic acid, tartaric acid, dibenzoyltartaric acid and other analogous acids; suitable optically active bases are, for example, quinine, cinchonine, quinidine, brucine, 1-phenylethylamine and other analogous bases.

The crystallizations are then in most cases carried out in aqueous or aqueous-organic solvents, where the diastereomer which is less soluble precipitates first, if appropriate after seeding. One enantiomer of the compound of the formula (III) is then liberated from the precipitated salt, or the other is liberated from the crystals, by acidification or using a base.

Furthermore, racemates can be separated chromatographically using chiral stationary phases. Such enantiomer separations can be carried out in the mg to 100 kg range using preparative HPLC units operated batch-wise or continuously.

The preparation of the thioethers of the formula (II) which serve as starting material for the preparation of the sulfoxides of the formula (III) or the sulfones of the formula (IV) is described below under processes b.), c.), d.), e.), f.), g.) and h.).

b.) To prepare a thioether of the formula (II),

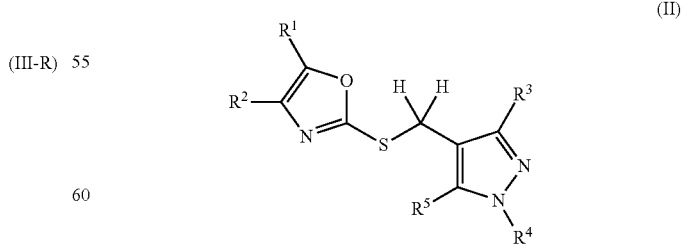

in which $R^1$, $R^2$, $R^3$, $R^4$, $R^5$ have the meanings given above for formula (I), for example, a 2-mercaptooxazole or an oxazole-2(3H)-thione or a salt thereof, preferably an alkali metal or alkaline earth metal salt of the formula (V),

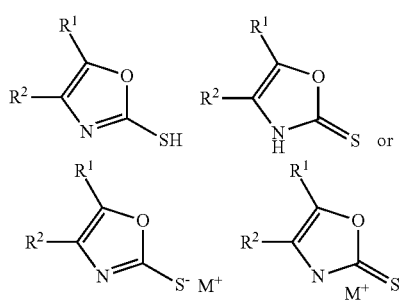

M = alkali metal, alkaline earth metal in which $R^1$, $R^2$ have the meanings given above for formula (I), is reacted with a (1H-pyrazol-4-ylmethyl) derivative of the formula (VI)

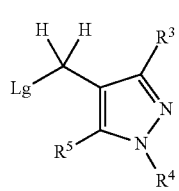

(VI)

in which $R^3$, $R^4$, $R^5$ have the meanings given above for formula (I) and Lg is a leaving group, in the presence of a suitable alkali metal or alkaline earth metal base, for example potassium carbonate or sodium hydride, or an organic base such as, for example, 1,8-diazabicyclo(5.4.0)undec-7-ene (DBU), in a suitable solvent, for example dimethylformamide, tetrahydrofuran, ethanol, or preferably acetonitrile, in a temperature range between 0 and 100° C., and if appropriate under an atmosphere of an inert gas, for example nitrogen.

Analogous reactions for converting 2-mercaptooxazoles or oxazole-2(3H)-thiones or salts thereof have been described in the literature, for example in DE 26 25 229 A, WO 99/52874 A, WO 01/66529 A, WO 95/24403 A, Bradsher, C. K.; Jones, W. J. Jr; J. Org. Chem. 32, 2079 (1967).

Instead of the mercapto compounds mentioned or the salt thereof, it is also possible to use mercaptan formers, such as, for example, isothiuronium salts.

Preferred leaving groups Lg are chlorine, bromine, iodine or sulfonate groups, such as methane, trifluoromethane, ethane, benzene or toluenesulfonate.

The 2-mercaptooxazole derivatives or oxazole-2(3H) thiones or the corresponding salts of the 2-mercaptooxazole derivatives or oxazole-2(3H)-thiones of the formula (V) employed in process b.) are known to the person skilled in the art, and some of them are commercially available or can be prepared by processes known to the person skilled in the art, for example as described in a) Science of Synthesis, Houben-Weyl (Methods of Molecular Transformations), Category 2, Volume 11, Ed. E. Schaumann; b) Houben-Weyl (Methoden der organische Chemie [Methods of Organic Chemistry]), Volume E8a, Hetarene III-part 1, Ed. E. Schaumann; c) Can. J. Chem., Vol. 50, 3082-3083 (1972); d) WO 2003/006442 A.

The (1H-pyrazol-4-ylmethyl) derivatives of the formula (VI) employed in process b.) are known to the person skilled in the art or available commercially or can be prepared by processes known to the person skilled in the art (see, for example: a) Communications de la Faculté des Sciences de l'Université d'Ankara, Series B: Chemistry and Chemical Engineering (1996), 41(1-2), 87-94; b) WO 2004/013106 A; c) WO 2006/024820 A).

c.) Alternatively, the preparation of a thioether of the formula (II),

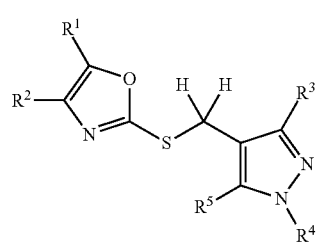

(II)

in which $R^1$, $R^2$, $R^3$, $R^4$, $R^5$ have the meanings given above for formula (I), can take place by reacting an oxazole derivative of the formula (VII),

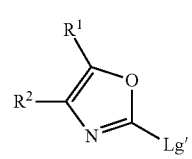

(VII)

in which $R^1$, $R^2$ have the meanings given above for formula (I) and Lg' is a leaving group, suitable leaving groups being inter alia fluorine, chlorine, bromine, iodine, sulfide, sulfoxide or sulfonate groups, with a [(1H-pyrazol-4-ylmethyl)]imidothio-carbamate salt of the formula (VIII)

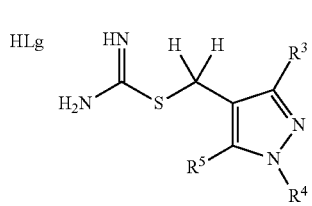

(VIII)

in which $R^3$, $R^4$, $R^5$ have the meanings given above for formula (I), Lg is a leaving group, in a one-pot process in the presence of an aqueous alkali metal or alkaline earth metal base.

The reaction is represented in a general manner by the equation below:

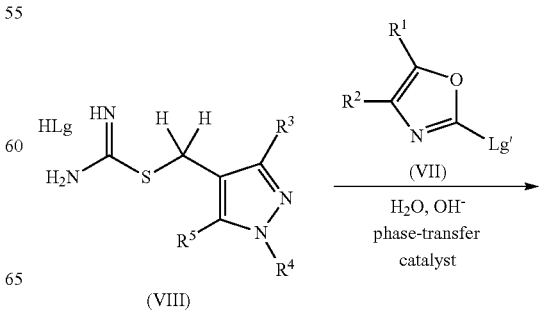

-continued

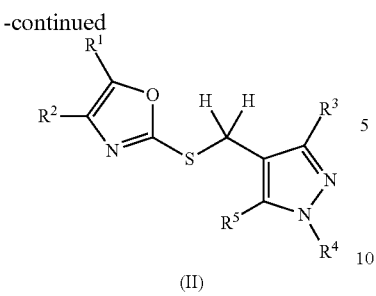

(II)

The oxazole derivatives of the formula (VII) employed in process c.) are known to the person skilled in the art or available commercially or can be prepared by processes known to the person skilled in the art (as described, for example, in "Science of Synthesis", Houben-Weyl (Methods of Molecular Transformations), Category 2, Volume 11, Ed. E. Schaumann; DE 26 25 229 A).

The use of imidothiocarbamate salts (isothiuronium salts) in the sense of a one-pot reaction for hydrolyzing the imidothiocarbamate salt (isothiuronium salt) and the reaction of the mercaptan intermediate in an exchange reaction are described in another reaction scheme, for example, in DE 39 42 946, WO 2006/024820 A and WO 2006/037945 A, and under use of phase-transfer catalysis in WO 2007/003294 A and WO 2007/003295 A.

Compounds of the formula (VIII) can be obtained by reacting an alkylating agent of the formula (VI) in which $R^3$, $R^4$, $R^5$ have the meanings given above for formula (I) and Lg is a leaving group with thiourea.

The preparation of the imidothiocarbamate salts (VIII) by reaction of a (1H-pyrazol-4-yl)methylating agent of the formula (VI) with thiourea is carried out by known processes (such as, for example, by the process described in DD 152557), advantageously by reaction with an equimolar amount of thiourea and optionally in the presence of an alkali metal iodide, for example sodium iodide or potassium iodide, in an inert solvent such as a lower alcohol, for example methanol, ethanol or isopropanol; a hydrocarbon, for example benzene or toluene; a halogenated hydrocarbon, for example dichloromethane or chloroform; or an ether derivative, for example methyl tert-butyl ether, tetrahydrofuran or dioxane, at temperatures between 0 and 150° C., preferably between 20 and 100° C.

In the process according to the invention, the compounds of the imidothiocarbamate salts of the formula (VIII), which in many cases are obtained by crystallization, are generally reacted without any further purification steps under vigorous stirring with equimolar amounts of the oxazole derivatives of the formula (VII) under phase-transfer conditions.

Here, the reaction is advantageously carried out in a two-phase system where, in addition to an aqueous strongly basic alkali metal or alkaline earth metal hydroxide solution, preferably sodium hydroxide or potassium hydroxide, with at least two equivalents of the base, the organic phase is an inert solvent such as tetrahydrofuran, diethyl ether, acetonitrile, pentane, hexane, benzene, toluene, xylene, chlorobenzene, dichloromethane, chloroform, carbon tetrachloride, nitrobenzene or mixtures of these solvents.

It is also possible to use a slightly subequimolar amount of the respectively more valuable starting material of the formula (VIII) or of the formula (VII).

Suitable phase-transfer catalysts are quaternary ammonium or phosphonium salts and also crown ethers, cryptands or polyethylene glycols. Examples of such catalysts can be found, for example, in W. P. Weber, G. W. Gokel; Phase Transfer Catalysis in Organic Synthesis, Springer-Verlag, Berlin 1977 or E. V. Dehmlow, S. S. Dehmlow, Phase Transfer Catalysis, Second Ed. Verlag Chemie, Weinheim 1983.

The reactants and the catalyst are preferably stirred vigorously at temperatures of from 20 to 100° C. under an atmosphere of protective gas.

The mercaptan intermediate, formed under the reaction conditions, of the formula (IX) in which $R^3$, $R^4$, $R^5$ have the meaning given above for formula (I)

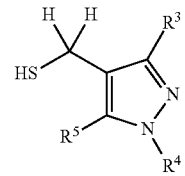

(IX)

immediately reacts in situ with the oxazole derivative of the formula (VII).

d.) Alternatively, thioethers of the formula (II) in which $R^1$, $R^2$, $R^3$, $R^4$, $R^5$ have the meanings given above for formula (I)

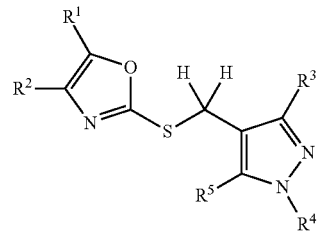

(II)

can be prepared by reacting an oxazole derivative of the formula (VII)

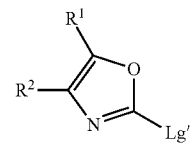

(VII)

in which $R^1$, $R^2$ have the meanings given above for formula (I) and Lg' is a leaving group, suitable leaving groups being chlorine, bromine or methylsulfonyl groups, inter alia, with a (1H-pyrazol-4-ylmethyl)imidothiocarbamate salt (isothiuronium salt) of the formula (VIII)

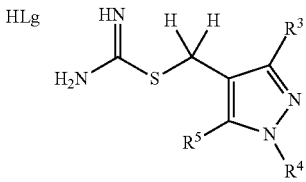

(VIII)

in which $R^3$, $R^4$, $R^5$ have the meanings given above for formula (I), Lg is a leaving group, in a one-pot process in the presence of an alkali metal or alkaline earth metal carbonate base and a solvent such as an alcohol.

The reaction is represented in a general manner by the equation below:

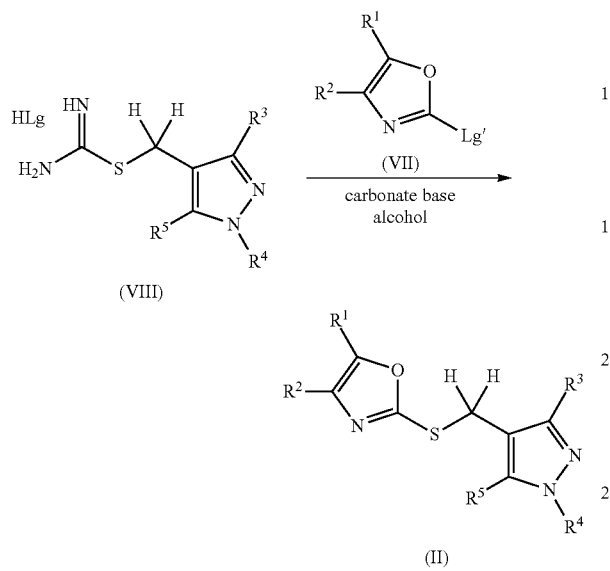

Compounds of the formula (VIII) can be obtained by reacting an alkylating agent of the formula (VI) in which $R^3, R^4, R^5$ have the meanings given above for formula (I) and Lg is a leaving group with thiourea, as described in process c.) above.

In the process according to the invention, the imidothiocarbamate salts (isothiuronium salts) of the formula (VIII) are generally reacted without any further purification steps under vigorous stirring with a slight excess of the oxazole derivatives of the formula (VII) and with a slight excess of a carbonate base, for example potassium carbonate, sodium carbonate or potassium bicarbonate, or a hydroxide, for example potassium hydroxide, or an alkoxide, for example a sodium alkoxide, in an alcohol, for example ethanol, an ether, for example 1,4-dioxane, tetrahydrofuran, a polar solvent such as, for example, water, dimethylformamide or a mixture of these solvents in a temperature range between 20 and 200° C., preferably between 50 and 150° C., optionally under an atmosphere of an inert gas, for example nitrogen, or in a microwave apparatus.

The imidothiocarbamate salts (isothiuronium salts) of the formula (VIII) can also be reacted further in situ, without isolation.

Here, the reaction is advantageously carried out in an alcohol, preferably ethanol, using at least 1.1 equivalents of the base, preferably potassium carbonate ($K_2CO_3$).

Such processes are known in the literature and described, for example, in WO 2006/024820 A, WO 2001/012613 A and WO 2006/123088 A.

The oxazole derivatives of the formula (VII) employed in process d.) are known to the person skilled in the art or available commercially, or they can be prepared by processes known to the person skilled in the art [see, for example, Science of Synthesis, Houben-Weyl (Methods of Molecular Transformations), Category 2, Volume 11, Ed. E. Schaumann].

e.) Alternatively, a thioether of the formula (II),

in which $R^1, R^2, R^3, R^4, R^5$ have the meanings given above for formula (I), can be prepared by reacting an oxazole derivative of the formula (VII),

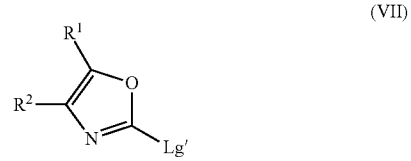

in which $R^1, R^2$ have the meanings given above for formula (I) and Lg' is a leaving group, suitable leaving groups LG' being fluorine, chlorine, bromine or sulfonate groups, inter alia, with a 1H-pyrazol-4-ylmethyl mercaptan of the formula (IX),

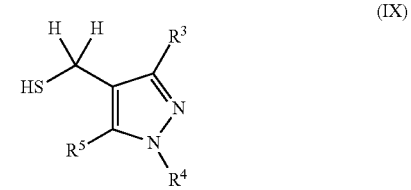

in which $R^3, R^4, R^5$ have the meaning given above for formula (I), in the presence of an alkali metal or alkaline earth metal base, for example potassium carbonate or sodium hydride, or an organic base, for example preferably 1,8-diazabicyclo (5.4.0)undec-7-ene (DBU), optionally in a solvent, for example dimethylformamide, tetrahydrofuran, ethanol, or preferably acetonitrile, in a temperature range between 0 and 100° C., and optionally under an atmosphere of an inert gas, for example nitrogen.

Some of the processes are known from the literature and are described, for example, in WO 2006/024820 A, WO 2001/012613 A and WO 2006/123088 A.

Nucleophilic substitutions at oxazole derivatives have been described in the literature, for example, in Yamanaka, H.; Ohba, S.; Sakamoto, T.; Heterocycles (1990), 31(6), 1115-27.

The oxazole derivatives of the formula (VII) employed in process e.) are known to the person skilled in the art or available commercially or can be prepared by processes known to the person skilled in the art [see, for example, Science of Synthesis, Houben-Weyl (Methods of Molecular Transformations), Category 2, Volume 11, Ed. E. Schaumann].

The mercaptans of the formula (IX) employed in process e.) are known to the person skilled in the art (see, for example, WO 2004/013106 A) or can be prepared analogously to processes, known to the person skilled in the art, for preparing mercaptans.

f.) Thioethers of the formula (II) in which $R^2$, $R^3$, $R^4$, $R^5$ have the meanings given above for formula (I) and $R^1$ represents halogen or nitro

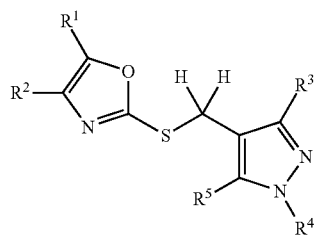
(II)

can be prepared, for example, by reacting an oxazole derivative of the formula (X),

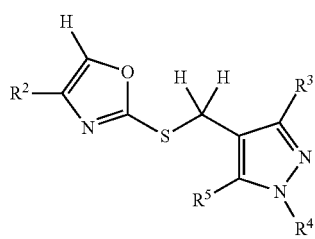
(X)

in which $R^2$, $R^3$, $R^4$, $R^5$ have the meanings given above for formula (I). The reaction is represented in a general manner by the equation below:

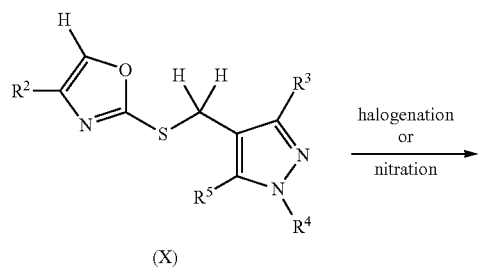

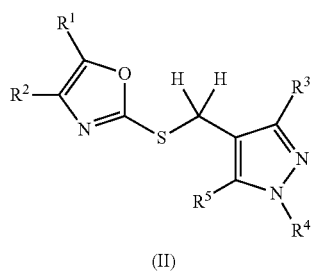
(II)

The compounds of the formula (X) are treated with a halogenating agent such as, for example, halogen, such as chlorine, bromine, iodine or a halosuccinimide, such as N-chlorosuccinimide (NCS), N-bromosuccinimide (NBS), N-iodosuccinimide (NIS) or for nitro with a nitrating agent such as, for example, nitrating acid prepared from sulfuric acid and nitric acid, and reacted in suitable solvents such as chlorinated hydrocarbons, for example carbon tetrachloride, dichloromethane, 1,2-dichloroethane or dimethylformamide to give compounds of the formula (II).

The analogous thioether derivatives of the formula (X) employed in process f.) can be prepared by processes known to the person skilled in the art (see, for example: DE 26 25 229 A, WO 99/52874 A, WO 01/66529 A, WO 95/24403 A; or by the processes mentioned above under b.), c.), d.), e.).

g.) Thioethers of the formula (II) in which $R^1$, $R^2$, $R^3$, $R^4$, $R^5$ have the meanings given above for formula (I)

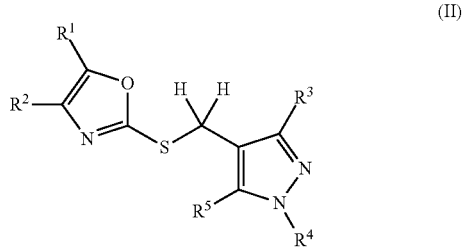
(II)

can be prepared, for example, by reacting an oxazole derivative of the formula (XI),

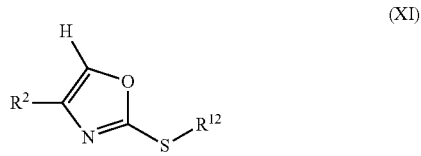
(XI)

prepared from an oxazole derivative of the formula (V) by reaction with an alkylating agent $R^{12}Lg'$, in which $R^2$ has the meanings given above for formula (I); $R^{12}$ is preferably ($C_1$-$C_6$)-alkyl which is unsubstituted or substituted by one or more identical or different radicals from the halogen group, and particularly preferably is methyl or ethyl, and Lg' is a leaving group, suitable leaving groups being chlorine, bromine or methylsulfonyl groups, inter alia, in the presence of a strong base and an alkylating agent $R^1Lg'$, in which $R^1$ has the meaning given above for formula (I), according to the equation

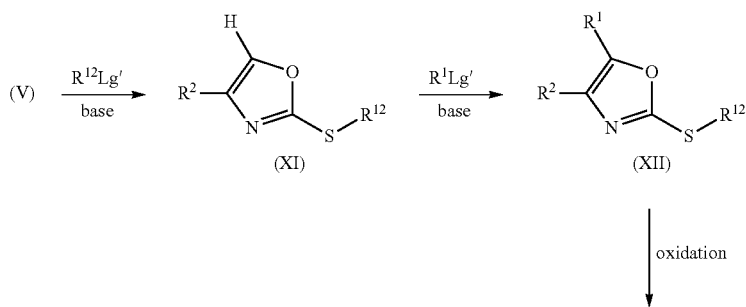

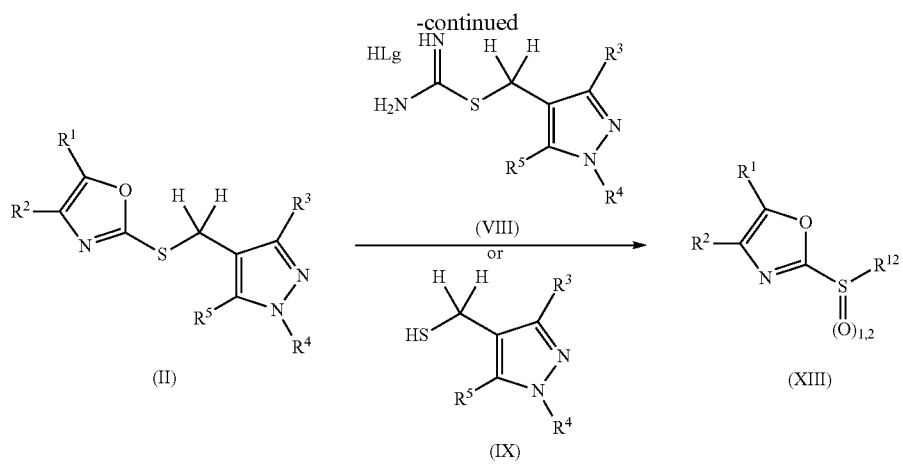

in which $R^1, R^2, R^3, R^4, R^5$ have the meanings given above for formula (I) and Lg or Lg' is a leaving group, suitable leaving groups being, inter alia, fluorine, chlorine, bromine, iodine or sulfonate groups such as methane-, trifluoromethane-, ethane-, phenyl- or toluenesulfonate, and $R^{12}$ preferably has the meaning given above.

The strong base used can be lithium diisopropylamide (LDA), lithium tetramethylpiperidine (LTMP), lithium hexamethyldisilazane (LHMDS), preferably LDA, which can be prepared by processes known to the person skilled in the art. Hexamethylphosphoric triamide (HMPT), for example, can be used as cosolvent.

Inert solvents such as hydrocarbons such as, for example, hexane, heptane, cyclohexane, aromatic hydrocarbons such as, for example, benzene, ethers such as, for example, diethyl ether, methyl tert-butyl ether (MTBE), tetrahydrofuran and dioxane, preferably tetrahydrofuran, serve as solvents. The solvents mentioned above can also be used as mixtures.

In this reaction, the compounds of the formula (XI) and the base or the alkylating agent $R^1Lg'$ are preferably employed in amount of 0.9 to 1.5 mol of the latter per mole of the former. The reaction is preferably carried out in a temperature range between –90° C. and the boiling point of the solvent. The reaction time is not subject to any restriction; in general, the reactions will have gone to completion after 1 to 24 h.

For preparing the sulfones and sulfoxides of the compounds of the formula (II) in which $R^1, R^2, R^3, R^4, R^5$ have the meanings given above for formula (I), it is possible to use the method given under a).

In particular in the case that $R^1$ is fluorine, preference is given to using reagents for electrophilic fluorination, such as, for example, 1-chloromethyl-4-fluoro-1,4-diazabi-cyclo[2,2,2]octane bistetrafluoroborate (F-TEDA-BF4, Select-Fluor™), N-fluorobenzenesulfonimide (NFBS or NFSi), N-fluoro-o-benzenedisulfonimide (NFOBS), 1-fluoro-4-hydroxy-1,4-diazoniabicyclo[2.2.2]octane bis(tetrafluoroborate) (NFTh, AccuFluor™) and others, as described in "Modern Fluoroorganic Chemistry", 2004, Wiley-VCH Verlag, Ed. P. Kirsch.

The 2-mercaptooxazole derivatives or oxazole-2(3H)-thiones or the corresponding salts of the 2-mercaptooxazole derivatives or oxazole-2(3H)-thione derivatives of the formula (V) employed in process g.) are known to the person skilled in the art or available commercially or can be prepared by processes known to the person skilled in the art, for example as described in Science of Synthesis, Houben-Weyl (Methods of Molecular Transformations), Category 2, Volume 11, Ed. E. Schaumann.

Analogously to processes known to the person skilled in the art, it is possible to deprotonate oxazole derivatives (XI) regioselectively in the 5-position. Analogous reactions using an alkyl base such as buthyllithium have been described in the literature, for example in Boger, D. L. et al; *J. Med. Chem.* (2007) 50 (33), 1058-1068 and Molinski, T. F. et al. *J. Org. Chem.* (1998) 63, 551-555, and using tort-butyllithium and a copper salt in Marino, J. P.; Nguyen, N. *Tet. Lett.* (2003) 44, 7395-7398 and the literature cited therein.

The oxazole derivatives of the formula (XI) employed in process g.) can be prepared, for example, according to process b.) by reacting a 2-mercaptooxazole derivative or oxazole-2(3H)-thione derivative of the formula (V) with an alkylating agent $R^{12}Lg'$ or according to processes known to the person skilled in the art [see, for example, Science of Synthesis, Houben-Weyl (Methods of Molecular Transformations), Category 2, Volume 11, Ed. E. Schaumann], or they are commercially available.

The compounds of the formula (XIII) mentioned in process g.) can be prepared from the compounds of the formula (XII) by oxidation according to process a) above or by processes known to the person skilled in the art. In turn, the compounds of the formula (XIII) can be reacted by the above process c.) or d.) with (1H-pyrazol-4-ylmethyl) imidothiocarbamate salts (VIII) or with (1H-pyrazol-4-ylmethyl) mercaptans of the formula (IX) according to the above process e.) to give compounds of type (II).

h.) Thioethers of the formula (II) in which $R^1, R^2, R^3, R^4, R^5$ have the meanings given above for formula (I)

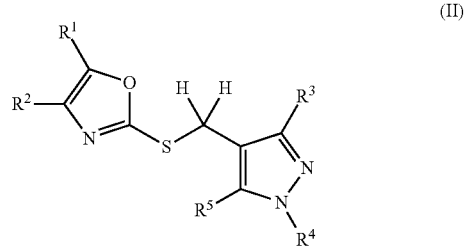

(II)

can also be prepared, for example, by reacting a (1H-pyrazol-4-ylmethyl) disulfide derivative of the formula (XV) with 2-aminooxazoles of the formula (XIV) and a diazotizing agent, as shown in the equation below

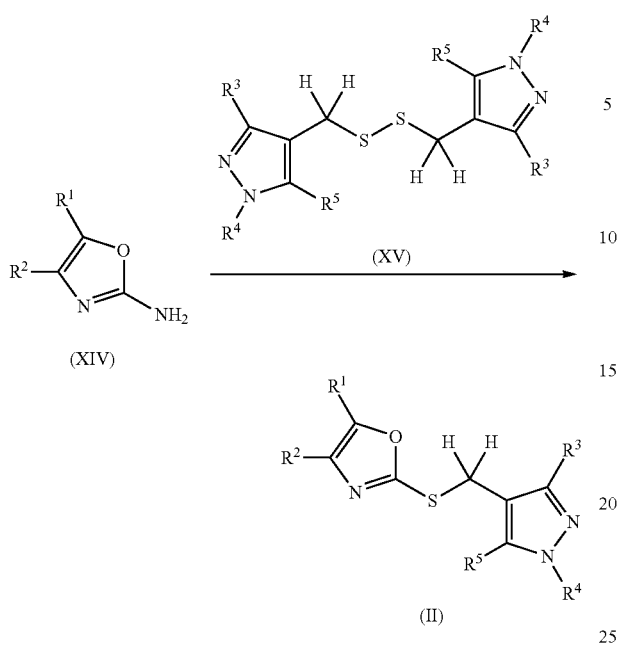

(XIV)  (XV)

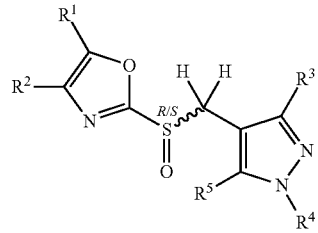

(II)

in which $R^1$, $R^2$, $R^3$, $R^4$, $R^5$ have the meanings given above for formula (I).

The (1H-pyrazol-4-ylmethyl) disulfides of the formula (XV) are reacted with a diazotizing agent and a 2-aminooxazole derivative of the formula (XIV) in a suitable solvent to give compounds of the formula (II).

Suitable solvents are reaction-inert solvents such as, for example, hydrocarbons, such as hexane, heptane, cyclohexane, aromatic hydrocarbons such as benzene, chlorobenzene, toluene, xylene, halogenated hydrocarbons such as, for example, dichloromethane, dichloroethane, chloroform and carbon tetrachloride, esters such as, for example, ethyl acetate and methyl acetate, ethers such as, for example, diethyl ether, methyl tert-butyl ether, dioxane, nitriles such as acetonitrile, alcohols such as, for example, methanol, ethanol, isopropyl alcohol, amides such as, for example, N,N-dimethylformamide, and sulfoxides such as, for example, dimethyl sulfoxide.

The diazotizing agent may, for example, be a nitrite ester such as isoamyl nitrite or a nitrite salt such as, for example, sodium nitrite. The molar ratios can be chosen as desired; equimolar amounts of heteroarylalkyl disulfides and diazotizing agents are preferred. The reaction is preferably carried out at a temperature between −20° C. and the boiling point of the chosen solvent and is gone to completion after a period of from 0.1 to 40 hours.

The diazotization of a 2-aminooxazole derivative of the formula (XIV) is described, for example, in Hodgetts, K. J.; Kershaw, M. T. *Org. Lett.* (2002), 4(17), 2905-2907.

The oxazole derivatives of the formula (XIV) employed in process h.) are known to the person skilled in the art or available commercially, or they can be prepared by processes known to the person skilled in the art (see Science of Synthesis, Houben-Weyl (Methods of Molecular Transformations), Category 2, Volume 11, Ed. E. Schaumann).

The 1H-pyrazol-4-ylmethyl disulfides of the formula (XV) can be prepared by processes known to the person skilled in the art, for example as in Gladysz, J. A., Wong, V. K., Jick, B. S.; Tetrahedron (1979) 35, 2329.

Preferred leaving groups Lg are halogens, for example chlorine, bromine, iodine, or alkyl- or arylsulfonyl groups, such as methyl-, ethyl-, phenyl- or tolylsulfonyl, or a haloalkylsulfonyl group, such as trifluoromethyl, or nitro; however, preference is given to chlorine and methylsulfonyl.

Preferred leaving groups Lg' are halogens, for example chlorine, bromine, iodine, or alkyl- or arylsulfonyl groups, such as methyl-, ethyl-, phenyl- or tolylsulfonyl, or a haloalkylsulfonyl group, such as trifluoromethyl, or nitro; however, preference is given to chlorine and methylsulfonyl.

A preferred group $R^{12}$ is $(C_1-C_6)$-alkyl which is unsubstituted or optionally substituted by one or more identical or different radicals from the halogen group, particularly preferably methyl or ethyl.

The present compounds of the formula (III)

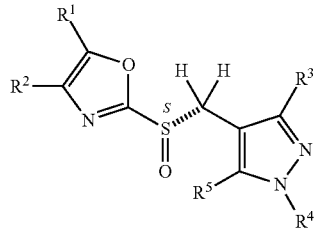

(III)

consist of a mixture of the respective chiral entantiomers (III-S) and (III-R):

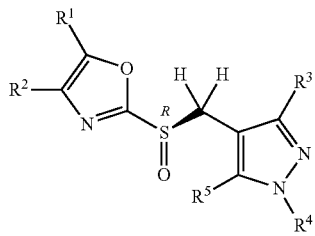

(III-S)

(III-R)

Thus, they have a chiral sulfur atom which, in the structure shown above, is illustrated by the marker (R/S). According to the rules of Cahn, Ingold and Prelog (CIP rules), this sulfur atom can have either an (R) configuration or an (S) configuration.

The present invention encompasses compounds of the formula (III) both with (S) and with (R) configuration, i.e. the present invention encompasses the compounds of the formula (III) in which the sulfur atom in question has
(1) an (R) configuration; or
(2) an (S) configuration.

In addition, the scope of the present invention also encompasses
(3) any mixtures of compounds of the formula (III) having an (R) configuration (compounds of the formula (III-(R)) with compounds of the formula (III) having an (S) configuration (compounds of the formula (III-(S)).

The present invention embraces racemic compounds of the formula (III), i.e. where the compounds of the formula (III) having the (S) configuration (compounds of the formula (III-S)) are, compared to the (R) configuration (compounds of the formula (III-R)), present as a 1:1 mixture (stereochemical purity 50%).

However, within the context of the present invention, preference is also given to compounds of the formula (III) having (S) configuration (compounds of the formula (III-S)) as compared to the (R) configuration (compounds of the formula (III-R)) having a stereochemical purity of in general from more than 50% to 100%, preferably from 60 to 100%, in particular from 80 to 100%, very particularly from 90 to 100%, especially from 95 to 100%, where the particular (S) compound is preferably present with an enantioselectivity of in each case more than 50% ee, preferably 60 to 100% ee, in particular 80 to 100% ee, very particularly 90 to 100% ee, most preferably 95 to 100% ee, based on the total content of (S) compound in question.

In the context of the present invention, preference is furthermore also given to compounds of the formula (III) having the (R) configuration (compounds of the formula (III-R)) as compared to the (S) configuration (compounds of the formula (III-R)) having a stereochemical purity of in general from more than 50% to 100%, preferably from 60 to 100%, in particular from 80 to 100%, very particularly from 90 to 100%, especially from 95 to 100%, where the respective (R) compound is preferably present in an enantioselectivity of in each case more than 50% ee, preferably from 60 to 100% ee, in particular from 80 to 100% ee, very particularly from 90 to 100% ee, most preferably from 95 to 100% ee, based on the total content of the respective (S) compound.

Accordingly, the present invention also relates to compounds of the formula (III) in which the stereochemical configuration at the sulfur atom (S) marked by (*) is of a stereochemical purity of from 60 to 100% (S), preferably from 80 to 100% (S), in particular from 90 to 100% (S), very particularly from 95 to 100% (S).

Depending on the type and attachment of the substituents, the compounds of the formula (III) may contain further centers of chirality in addition to the sulfur atom marked (*) in formula (III), in which case they are then present as stereoisomers. The formula (III) encompasses all possible stereoisomers defined by their specific spatial form, such as enantiomers, diastereomers, Z and E isomers. If, for example, one or more alkenyl groups are present, there may be diastereomers (Z and E isomers). If, for example, one or more asymmetric carbon atoms are present, there may be enantiomers and diastereomers. Stereoisomers may be obtained from the mixtures resulting from the preparation using customary separation methods, for example by chromatographic separation techniques. It is also possible to prepare stereoisomers selectively by using stereoselective reactions employing optically active starting materials and/or auxiliaries. Accordingly, the invention also relates to all stereoisomers embraced by the formula (III) but not shown in their specific stereoform, and to their mixtures.

If, for example, one or more alkenyl groups are present, there may be diastereomers (Z and E isomers).

If, for example, one or more asymmetric carbon atoms are present, there may be enantiomers and diastereomers.

Such stereoisomers may be obtained from the mixtures resulting from the preparation using customary separation methods, for example by chromatographic separation techniques. It is also possible to prepare stereoisomers selectively by using stereoselective reactions employing optically active starting materials and/or auxiliaries. Accordingly, the invention also relates to all stereoisomers embraced by the formula (I) but not shown in their specific stereoform, and to their mixtures.

In the context of the present invention, acid addition salts of the compounds of the formula (I) can also be used. The following acids are suitable for preparing the acid addition salts of the compounds of the formula (I): hydrohalic acids, such as hydrochloric acid or hydrobromic acid, furthermore phosphoric acid, nitric acid, sulfuric acid, mono- or bifunctional carboxylic acids and hydroxycarboxylic acids, such as acetic acid, maleic acid, succinic acid, fumaric acid, tartaric acid, citric acid, salicylic acid, sorbic acid, or lactic acid, and also sulfonic acids, such as p-toluenesulfonic acid and 1,5-naphthalenedisulfonic acid. The acid addition compounds of the formula (I) can be obtained in a simple manner by the customary methods for forming salts, for example by dissolving a compound of the formula (I) in a suitable organic solvent, such as, for example, methanol, acetone, methylene chloride or benzene, and adding the acid at temperatures of from 0 to 100° C., and they can be isolated in a known manner, for example by filtration, and, if appropriate, purified by washing with an inert organic solvent.

The base addition salts of the compounds of the formula (I) are preferably prepared in inert polar solvents, such as, for example, water, methanol or acetone, at temperatures of from 0 to 100° C. Examples of bases which are suitable for the preparation of the salts according to the invention are alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide or potassium tert-butoxide, or ammonia, ethanolamine or quaternary ammonium hydroxide of the formula [NRR'R''R''']$^+$ OH$^-$.

Collections of compounds of the formula (I) and/or their salts which can be synthesized in accordance with the above-mentioned reactions can also be prepared in a parallelized manner, which can be effected manually or in a partly or fully automated manner. Here, it is possible for example to automate the procedure of the reaction, the work-up or the purification of the products or intermediates. In total, this is understood as meaning a procedure as described for example by D. Tiebes in Combinatorial Chemistry—Synthesis, Analysis, Screening (Editor Günther Jung), Wiley 1999, on pages 1 to 34.

A number of commercially available apparatuses can be used for the parallelized reaction procedure and work-up, for example Calpyso reaction blocks from Barnstead International, Dubuque, Iowa 52004-0797, USA, or reaction stations from Radleys, Shirehill, Saffron Walden, Essex, CB 11 3AZ, England or MultiPROBE Automated Workstations from Perkin Elmar, Waltham, Mass. 02451, USA. Chromatographic apparatuses, for example from ISCO, Inc., 4700 Superior Street, Lincoln, Nebr. 68504, USA, are available, inter alia, for the parallelized purification of compounds of the formula (I) and their salts or of intermediates generated in the course of the preparation.

The apparatuses listed lead to a modular procedure in which the individual passes are automated, but manual operations must be carried out between the passes. This can be circumvented by the use of partly or fully integrated automation systems, where the relevant automation modules are operated by, for example, robots. Such automation systems can be obtained for example from Caliper, Hopkinton, Mass. 01748, USA.

The performance of individual, or a plurality of, synthesis steps can be aided by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the formula (I) and their salts can be effected fully or in part by solid-phase-supported methods. For this purpose, individual intermediates, or all intermediates, of the synthesis or of a synthesis adapted to the relevant procedure are bound to a synthesis resin. Solid-phase-supported synthesis methods are described sufficiently in the specialist literature, for example Barry A. Bunin in "The Combinatorial Index", Academic Press, 1998 and Combinatorial Chemistry—Synthesis, Analysis, Screening (Editor Günther Jung), Wiley, 1999. The use of solid-phase-supported synthesis methods permits a series of protocols known from the literature, which, again, can be carried out manually or in an automated manner. For example, the reactions can be carried out by means of IRORI technology in microreactors from Nexus Biosystems, 12140 Community Road, Poway, Calif. 92064, USA.

Carrying out individual or a plurality of synthesis steps, both on a solid and in the liquid phase, can be aided by the use of microwave technology. A series of experimental protocols are described in the specialist literature, for example in Microwaves in Organic and Medicinal Chemistry (Editors C. O. Kappe and A. Stadler), Wiley, 2005.

The preparation in accordance with the processes described herein generates compounds of the formula (I) and their salts in the form of substance collections, which are referred to as libraries. The present invention also relates to libraries which comprise at least two compounds of the formula (I) and their salts.

On account of their herbicidal and plant growth regulatory properties, the active compounds can also be used for controlling harmful plants in crops of known plants or genetically modified plants which are yet to be developed. As a rule, the transgenic plants are distinguished by particularly advantageous properties, for example by resistances to certain pesticides, primarily certain herbicides, resistances to plant diseases or pathogens of plant diseases, such as certain insects or microorganisms such as fungi, bacteria or viruses. Other particular properties relate, for example, to the harvested material with respect to quantity, quality, storability, composition and specific ingredients. For example, transgenic plants with increased starch content or modified quality of the starch or those with a different fatty acid composition of the harvested material are known. Further particular properties can lie in a tolerance or resistance to abiotic stress factors, for example heat, cold, drought, salt and ultraviolet radiation.

Preference is given to using the compounds of the formula (I) according to the invention or their salts in economically important transgenic crops of useful plants and ornamental plants, for example of cereals such as wheat, barley, rye, oats, millet, rice, manioc and corn, or else crops of sugarbeet, cotton, soybean, rapeseed, potatoes, tomatoes, peas and other vegetable varieties.

Preferably, the compounds of the formula (I) can be used as herbicides in crops of useful plants which are resistant to, or have been rendered genetically resistant to, the phytotoxic effects of the herbicides.

Conventional ways of producing new plants which have modified properties compared to existing plants consist, for example, in classic cultivation methods and the generation of mutants. Alternatively, new plants with modified properties can be produced using genetic engineering methods (see e.g. EP 0221044, EP 0131624). For example, in several cases the following have been described genetic modifications of crop plants for the purpose of modifying the starch synthesized in the plants (e.g. WO 92/011376 A, WO 92/014827 A, WO 91/019806 A), transgenic crop plants which are resistant to certain herbicides of the glufosinate type (cf. e.g. EP 0 242 236 A, EP 0 242 246 A) or of the glyphosate type (WO 92/000377 A) or of the sulfonylurea type (EP 0 257 993 A, U.S. Pat. No. 5,013,659) or to combinations or mixtures of these herbicides through "gene stacking", such as transgenic crop plants e.g. corn or soybean with the tradename or the name Optimum™ GAT™ (glyphosate ALS tolerant), transgenic crop plants, for example cotton, with the ability to produce *Bacillus thuringiensis* toxins (Bt toxins) which make the plants resistant to certain pests (EP 0 142 924 A, EP 0 193 259 A), transgenic crop plants with a modified fatty acid composition (WO 91/013972 A), genetically modified crop plants with new ingredients or secondary substances, e.g. new phytoalexins, which bring about increased resistance to disease (EP 0 309 862 A, EP 0 464 461 A), genetically modified plants with reduced photorespiration which have higher yields and higher stress tolerance (EP 0 305 398 A), transgenic crop plants which produce pharmaceutically or diagnostically important proteins ("molecular pharming"), transgenic crop plants distinguished by higher yields or better quality, transgenic crop plants distinguished by combinations e.g. of the aforementioned new properties ("gene stacking").

Numerous molecular biological techniques with which new transgenic plants with modified properties can be produced are known in principle; see e.g. I. Potrykus and G. Spangenberg (eds.) Gene Transfer to Plants, Springer Lab Manual (1995), Springer Verlag Berlin, Heidelberg or Christou, "Trends in Plant Science" 1 (1996) 423-431.

For genetic manipulations of this kind, nucleic acid molecules which permit a mutagenesis or a sequence modification by recombination of DNA sequences can be introduced into plasmids. For example, with the help of standard methods, it is possible to carry out base exchanges, to remove part sequences or to add natural or synthetic sequences. For joining the DNA fragments to one another, adaptors or linkers may be added to the fragments, see e.g. Sambrook et al., 1989, Molecular Cloning, A Laboratory Manual, 2nd edition, Cold Spring Harbor Laboratory Press, Cold Spring Harbor, N.Y.; or Winnacker "Gene and Klone [Genes and Clones]", VCH Weinheim 2nd edition, 1996.

The preparation of plant cells with reduced activity of a gene product can be achieved, for example, through the expression of at least one corresponding antisense-RNA, a sense-RNA to achieve a cosuppression effect or the expression of at least one correspondingly constructed ribozyme which specifically cleaves transcripts of the aforementioned gene product.

To this end, it is possible to use firstly DNA molecules which encompass the entire coding sequence of a gene product including any flanking sequences which may be present, and also DNA molecules which only encompass parts of the coding sequence, it being necessary for these parts to be long enough to bring about an antisense effect in the cells. Also possible is the use of DNA sequences which have a high degree of homology to the coding sequences of a gene product but are not entirely identical thereto.

During the expression of nucleic acid molecules in plants, the synthesized protein can be localized in any compartment of the plant cell. However, in order to achieve localization in a certain compartment, it is possible, for example, to link the coding region with DNA sequences which ensure localization in a certain compartment. Sequences of this type are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The expression of the nucleic acid molecules can also take place in the organelles of the plant cells.

The transgenic plant cells can be regenerated by known techniques to give whole plants. In principle, the transgenic plants may be plants of any desired plant species, i.e. either monocotyledonous or dicotyledonous plants.

Transgenic plants are thus obtainable which have modified properties as a result of overexpression, suppression or inhibition of homologous (=natural) genes or gene sequences or expression of heterologous (=foreign) genes or gene sequences.

It is preferred to employ the compounds (I) according to the invention in transgenic crops which are resistant to growth regulators such as, for example, 2,4 D, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosates, glufosinates or benzoylisoxazoles and analogous active compounds or against any combinations of these active compounds.

The compounds according to the invention can be particularly preferably used in transgenic crop plants which are resistant to a combination of glyphosates and glufosinates, glyphosates and sulfonylureas or imidazolinones. The compounds according to the invention can very particularly preferably be used in transgenic crop plants such as e.g. corn or soybean with the tradename or the name Optimum™ GAT™ (glyphosate ALS tolerant).

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicides and plant growth-regulating compositions which comprise the compounds according to the invention.

The compounds of the formula (I) can be formulated in various ways according to which biological and/or physico-chemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to prepare combinations with other pesticidally active compounds, such as, for example, insecticides, acaricides, herbicides, fungicides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To prepare the wettable powders, the active herbicidal ingredients are ground finely, for example in customary apparatus such as hammer mills, blower mills and air-jet mills, and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active compound onto adsorptive granulated inert material or by applying active compound concentrates by means of adhesives, for example polyvinyl alcohol, sodium polyacrylate or else mineral oils, onto the surface of carriers such as sand, kaolinites or of granulated inert material. It is also possible to granulate suitable active compounds in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 if; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of active compound of the formula (I).

In wettable powders, the active compound concentration is, for example, from about 10 to 90% by weight; the remainder to 100% by weight consists of customary formulation constituents. In the case of emulsifiable concentrates, the active compound concentration may be from about 1 to 90% by weight, preferably from 5 to 80% by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In water-dispersible granules, the active compound content depends partly on whether the active compound is present in solid or liquid form and which granulation assistants, fillers, etc. are used. In the granules dispersible in water, the content of active compound is, for example, between 1 and 95% by weight, preferably between 10 and 80% by weight.

In addition, the specified active compound formulations optionally comprise the adhesives, wetting agents, dispersants, emulsifiers, penetration agents, preservatives, antifreezes and solvents, fillers, carriers and colorants, antifoams, evaporation inhibitors and agents which influence the pH and the viscosity that are customary in each case.

The compounds of the formula (I) or their salts can be used as such or combined in the form of their preparations (formulations) with other pesticidally active substances, such as, for example, insecticides, acaricides, nematicides, herbicides, fungicides, safeners, fertilizers and/or growth regulators, e.g. as ready mix or as tank mixes.

Combination partners which can be used for the compounds of the formula (I) according to the invention in mixture formulations or in the tank mix are, for example, known active compounds which are based on an inhibition of, for example, acetolactate synthase, acetyl-coenzyme-A-carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as described, for example, in Weed Research 26 (1986) 441-445 or "The Pesticide Manual", 14th edition, The British Crop Protection Council and the Royal Soc. of Chemistry, 2003 and literature cited therein. Known herbicides or plant growth regulators which can be combined with the compounds according to the invention are, for example, the following active compounds (the compounds are designated either with the "common name" in accordance with the International Organization for Standardization (ISO) or with the chemical name or with the code number) and always encompass all of the application forms such as acids, salts, esters and isomers such as stereoisomers and optical isomers. Here, by way of example, one and sometimes also more application forms are specified:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzosfluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachior, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPIC, esprocarb, ethaifluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochior, propoxycarbazone, propoxycarbazone-sodium, propyzamide, prosulfalin, prosulfocarb, prosulfuron, prynachlor, pyraclonil, pyraflufen, pyraflufen-ethyl, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

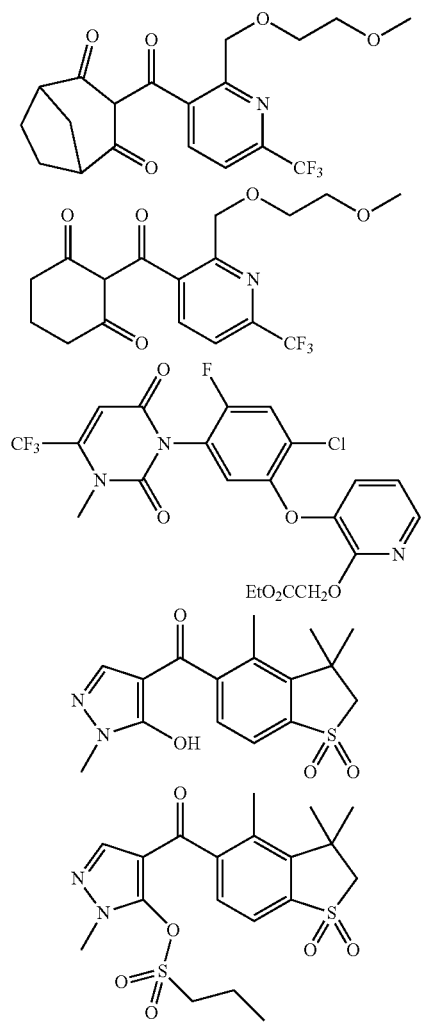

Of particular interest is the selective control of harmful plants in crops of useful plants and ornamental plants. Although the compounds of the formula (I) according to the invention already have very good to adequate selectivity in many crops, it is in principle possible, in some crops and primarily also in the case of mixtures with other herbicides which are less selective, for phytotoxicities on the crop plants to occur. In this connection, combinations of compounds of the formula (I) according to the invention are of particular interest which comprise the compounds of the formula (I) or their combinations with other herbicides or pesticides and safeners. The safeners which are used in an antidotically effective content reduce the phytotoxic side-effects of the herbicides/pesticides used, e.g. in economically important crops such as cereals (wheat, barley, rye, corn, rice, millet), sugarbeet, sugarcane, rapeseed, cotton and soybean, preferably cereals. The following groups of compounds are suitable, for example, as safeners for the compounds (I) alone or else in their combinations with further pesticides:

S1) Compounds of the Formula (S1),

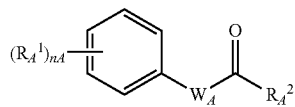
(S1)

where the symbols and indices have the following meanings:

$n_A$ is a natural number from 0 to 5, preferably 0 to 3;

$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group of the partially unsaturated or aromatic five-ring heterocycles having 1 to 3 heteroring atoms from the group consisting of N and O, where at least one N atom and at most one O atom is present in the ring, preferably a radical from the group $(W_A^1)$ to $(W_A^4)$,

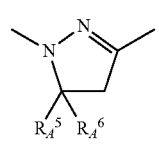
($W_A^1$)

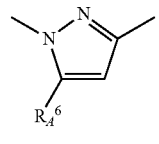
($W_A^2$)

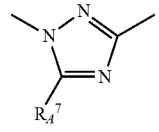
($W_A^3$)

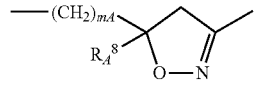
($W_A^4$)

$m_A$ is 0 or 1;

$R_A^2$ is $OR_A^3$, $SR_A^3$ or $NR_A^3R_A^4$ or a saturated or unsaturated 3- to 7-membered heterocycle with at least one N atom and up to 3 heteroatoms, preferably from the group consisting of O and S, which is bonded to the carbonyl group in (S1) via the N atom and is unsubstituted or substituted by radicals from the group consisting of $(C_1-C_4)$-alkyl, $(C_1-C_4)$-alkoxy or optionally substituted phenyl, preferably a radical of the formula $OR_A^3$, $NHR_A^4$ or $N(CH_3)_2$, in particular of the formula $OR_A^3$;

$R_A^3$ is hydrogen or an unsubstituted or substituted aliphatic hydrocarbon radical, preferably having in total 1 to 18 carbon atoms;

$R_A^4$ is hydrogen, $(C_1-C_6)$-alkyl, $(C_1-C_6)$-alkoxy or substituted or unsubstituted phenyl;

$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$, in which $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different, hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;

b) derivatives of dichlorophenylpyrazolecarboxylic acid (S1$^b$), preferably corn-pounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;

c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;

d) compounds of the triazolecarboxylic acid type (S1$^d$), preferably compounds such as fenchlorazole(-ethyl), i.e. ethyl 1-(2,4-dichlorophenyl)-5-trichloro-methyl-(1H)-1,2,4-triazole-3-carboxylate (S1-7), and related compounds, as described in EP-A-174 562 and EP-A-346 620;

e) compounds of the 5-benzyl- or 5-phenyl-2-isoxazoline-3-carboxylic acid type or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazoline-carboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or of the ethyl 5-(4-fluorophenyl)-5-phenyl-2-isoxazoline-3-carboxylate type (S1-13), as described in the patent application WO-A-95/07897.

S2) Quinoline Derivatives of the Formula (S2),

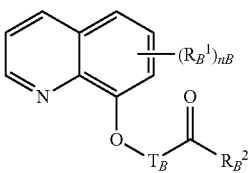
(S2)

where the symbols and indices have the following meanings:
$R_B^1$ is halogen, $(C_1-C_4)$-alkyl, $(C_1-C_4)$-alkoxy, nitro or $(C_1-C_4)$-haloalkyl;
$n_B$ is a natural number from 0 to 5, preferably 0 to 3;
$R_B^2$ is $OR_B^3$, $SR_B^3$ or $NR_B^3R_B^4$ or a saturated or unsaturated 3- to 7-membered heterocycle having at least one N atom and up to 3 heteroatoms, preferably from the group consisting of O and S, which is joined to the carbonyl group in (S2) via the N atom and is unsubstituted or substituted by radicals from the group consisting of $(C_1-C_4)$-alkyl, $(C_1-C_4)$-alkoxy or optionally substituted phenyl, preferably a radical of the formula $OR_B^3$, $NHR_B^4$ or $N(CH_3)_2$, in particular of the formula $OR_B^3$;
$R_B^3$ is hydrogen or an unsubstituted or substituted aliphatic hydrocarbon radical, preferably having in total 1 to 18 carbon atoms;
$R_B^4$ is hydrogen, $(C_1-C_6)$-alkyl, $(C_1-C_6)$-alkoxy or substituted or unsubstituted phenyl;
$T_B$ is a ($C_1$ or $C_2$)-alkanediyl chain which is unsubstituted or substituted by one or two $(C_1-C_4)$-alkyl radicals or by [$(C_1-C_3)$-alkoxy]carbonyl;
preferably:
a) compounds of the 8-quinolinoxyacetic acid type ($S2^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminum, iron, ammonium, quaternary ammonium, sulfonium or phosphonium salts, as described in WO-A-2002/34048;
b) compounds of the (5-chloro-8-quinolinoxy)malonic acid type ($S2^b$), preferably compounds such as diethyl (5-chloro-8-quinolinoxy)malonate, diallyl (5-chloro-8-quinolinoxy)malonate, methyl ethyl (5-chloro-8-quinolinoxy)-malonate and related compounds, as described in EP-A-0 582 198.
S3) Compounds of the Formula (S3)

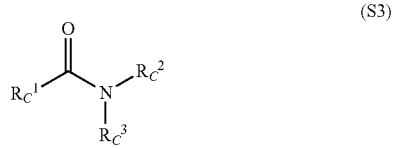

(S3)

where the symbols and indices have the following meanings:
$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are identical or different, hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ form together a substituted or unsubstituted heterocyclic ring, preferably an oxazolidine, thiazolidine, piperidine, morpholine, hexahydropyrimidine or benzoxazine ring;
preferably:
active compounds of the dichloroacetamide type, which are often used as pre-emergence safeners (soil-acting safeners), such as, for example,
"dichlormid" (N,N-diallyl-2,2-dichloroacetamide) (S3-1),
"R-29148" (3-dichloroacetyl-2,2,5-trimethyl-1,3-oxazolidine) from Stauffer (S3-2),
"R-28725" (3-dichloroacetyl-2,2-dimethyl-1,3-oxazolidine) from Stauffer (S3-3),
"benoxacor" (4-dichloroacetyl-3,4-dihydro-3-methyl-2H-1,4-benzoxazine) (S3-4),
"PPG-1292" (N-allyl-N-[(1,3-dioxolan-2-yl)methyl]dichloroacetamide) from PPG Industries (S3-5),
"DKA-24" (N-allyl-N-[(allylaminocarbonyl)methyl]dichloroacetamide) from Sagro-Chem (S3-6),
"AD-67" or "MON 4660" (3-dichloroacetyl-1-oxa-3-azaspiro[4,5]decane) from Nitrokemia or Monsanto (S3-7),
"TI-35" (1-dichloroacetylazepane) from TRI-Chemical RT (S3-8),
"diclonon" (dicyclonone) or "BAS145138" or "LAB145138" (S3-9) (3-dichloroacetyl-2,5,5-trimethyl-1,3-diazabicyclo[4.3.0]nonane) from BASF,
"furilazole" or "MON 13900" ((RS)-3-dichloroacetyl-5-(2-furyl)-2,2-dimethyl-oxazolidine) (S3-10); and also its (R)-isomer (S3-11).
S4) N-Acylsulfonamides of the Formula (S4) and their Salts,

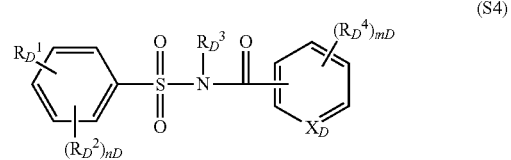

(S4)

in which the symbols and indices have the following meanings:
$X_D$ is CH or N;
$R_D^1$ is $CO-NR_D^5R_D^6$ or $NHCO-R_D^7$;
$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;
$R_D^3$ is hydrogen, $(C_1-C_4)$-alkyl, $(C_2-C_4)$-alkenyl or $(C_2-C_4)$-alkynyl;
$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkyl-sulfinyl, $(C_1-C_4)$-alkylsulfonyl, $(C_1-C_4)$-alkoxycarbonyl or $(C_1-C_4)$-alkylcarbonyl;
$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl comprising $v_D$ heteroatoms from the group consisting of nitrogen, oxygen and sulfur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
$R_D^6$ is hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxyl, $(C_1-C_4)$-alkyl, $(C_1-C_4)$-alkoxy and $(C_1-C_4)$-alkylthio, or $R_D^5$ and $R_D^6$ together with the nitrogen atom carrying them form a pyrrolidinyl or piperidinyl radical;

$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;

$n_D$ is 0, 1 or 2;

$m_D$ is 1 or 2;

$v_D$ is 0, 1, 2 or 3;

of which preference is given to compounds of the N-acylsulfonamide type, for example of the following formula (S4$^a$), which are known, for example, from WO-A-97/45016

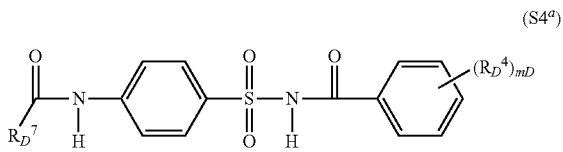

(S4$^a$)

in which $R_D^7$ is $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;

$R_D^4$ is halogen, $(C_1-C_4)$-alkyl, $(C_1-C_4)$-alkoxy, $CF_3$;

$m_D$ is 1 or 2;

$v_D$ is 0, 1, 2 or 3;

and acylsulfamoylbenzamides, e.g. of the following formula (S4$^b$), which are known, for example, from WO-A-99/16744,

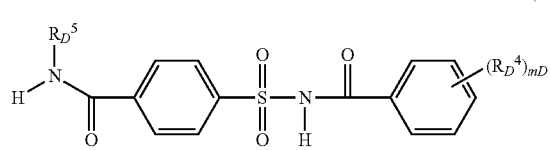

(S4$^b$)

e.g. those in which $R_D^5$=cyclopropyl and $(R_D^4)$=2-OMe ("cyprosulfamide", S4-1), $R_D^5$=cyclopropyl and $(R_D^4)$=5-Cl-2-OMe (S4-2), $R_D^5$=ethyl and $(R_D^4)$=2-OMe (S4-3), $R_D^5$=isopropyl and $(R_D^4)$=5-Cl-2-OMe (S4-4) and $R_D^5$=isopropyl and $(R_D^4)$=2-OMe (S4-5), and compounds of the N-acylsulfamoylphenylurea type of the formula (S4$^c$), which are known, for example, from EP-A-365484,

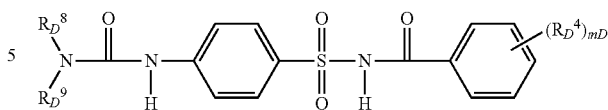

(S4$^c$)

in which $R_D^8$ and $R_D^9$, independently of one another, are hydrogen, $(C_1-C_8)$-alkyl, $(C_3-C_8)$-cycloalkyl, $(C_3-C_6)$-alkenyl, $(C_3-C_6)$-alkynyl, $R_D^4$ is halogen, $(C_1-C_4)$-alkyl, $(C_1-C_4)$-alkoxy, $CF_3$ $m_D$ is 1 or 2;

for example

1-[4-(N-2-methoxybenzoylsulfamoyl)phenyl]-3-methylurea,

1-[4-(N-2-methoxybenzoylsulfamoyl)phenyl]-3,3-dimethylurea,

1-[4-(N-4,5-dimethylbenzoylsulfamoyl)phenyl]-3-methylurea.

S5) Active compounds from the class of hydroxyaromatics and aromatic-aliphatic carboxylic acid derivatives (S5), e.g. ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), e.g. 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydro-quinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the Formula (S7), as Described in WO-A-1998/38856

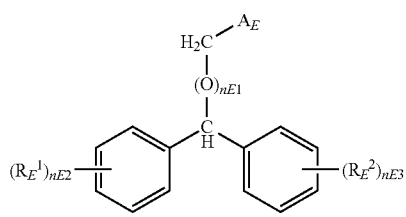

(S7)

in which the symbols and the indices have the following meanings:

$R_E^1$, $R_E^2$ independently of one another are halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;

$A_E$ is $COOR_E^3$ or $COSR_E^4$ $R_E^3$, $R_E^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium, $n_E^1$ is 0 or 1

$n_E^2$, $n_E^3$ independently of one another are 0, 1 or 2, preferably:

diphenylmethoxyacetic acid, ethyl diphenylmethoxyacetate, methyl diphenylmethoxyacetate (CAS Reg. No. 41858-19-9) (S7-1).

S8) Compounds of the Formula (S8), as Described in WO-A-98/27049

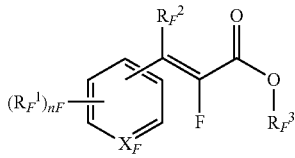

in which
$X_F$ is CH or N,
$n_F$ if $X_F$=N, is an integer from 0 to 4 and
  if $X_F$=CH, is an integer from 0 to 5,
$R_F^1$ is halogen, $(C_1$-$C_4)$-alkyl, $(C_1$-$C_4)$-haloalkyl, $(C_1$-$C_4)$-alkoxy, $(C_1$-$C_4)$-haloalkoxy, nitro, $(C_1$-$C_4)$-alkylthio, $(C_1$-$C_4)$-alkylsulfonyl, $(C_1$-$C_4)$-alkoxycarbonyl, optionally substituted phenyl, optionally substituted phenoxy,
$R_F^2$ is hydrogen or $(C_1$-$C_4)$-alkyl,
$R_F^3$ is hydrogen, $(C_1$-$C_8)$-alkyl, $(C_2$-$C_4)$-alkenyl, $(C_2$-$C_4)$-alkynyl, or aryl, where each of the aforementioned C-containing radicals is unsubstituted or substituted by one or more, preferably up to three, identical or different radicals from the group consisting of halogen and alkoxy, or salts thereof,
preferably compounds in which
$X_F$ is CH,
$n_F$ is an integer from 0 to 2,
$R_F^1$ is halogen, $(C_1$-$C_4)$-alkyl, $(C_1$-$C_4)$-haloalkyl, $(C_1$-$C_4)$-alkoxy, $(C_1$-$C_4)$-haloalkoxy,
$R_F^2$ is hydrogen or $(C_1$-$C_4)$-alkyl,
$R_F^3$ is hydrogen, $(C_1$-$C_8)$-alkyl, $(C_2$-$C_4)$-alkenyl, $(C_2$-$C_4)$-alkynyl, or aryl, where each of the aforementioned C-containing radicals is unsubstituted or substituted by one or more, preferably up to three, identical or different radicals from the group consisting of halogen and alkoxy, or salts thereof.

S9) Active Compounds from the Class of the 3-(5-tetrazolylcarbonyl)-2-quinolones (S9), e.g.
  1,2-dihydro-4-hydroxy-1-ethyl-3-(5-tetrazolylcarbonyl)-2-quinolone (CAS Reg. No. 219479-18-2), 1,2-dihydro-4-hydroxy-1-methyl-3-(5-tetrazolylcarbonyl)-2-quinolone (CAS Reg. No. 95855-00-8), as described in WO-A-1999/000020.

S10) Compounds of the Formulae (S10$^a$) or (S10$^b$)
  as described in WO-A-2007/023719 and WO-A-2007/023764

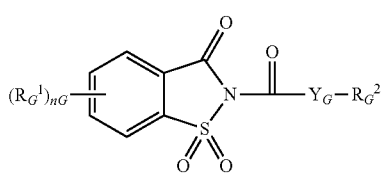

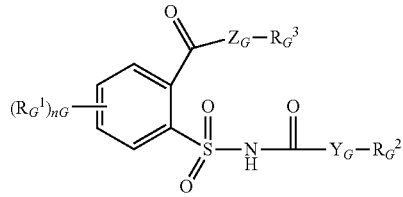

in which
$R_G^1$ is halogen, $(C_1$-$C_4)$-alkyl, methoxy, nitro, cyano, $CF_3$, $OCF_3$
$Y_G$, $Z_G$ independently of one another are O or S,
$n_G$ is an integer from 0 to 4,
$R_G^2$ is $(C_1$-$C_{16})$-alkyl, $(C_2$-$C_6)$-alkenyl, $(C_3$-$C_6)$-cycloalkyl, aryl; benzyl, halobenzyl,
$R_G^3$ is hydrogen or $(C_1$-$C_6)$-alkyl.

S11) Active Compounds of the Oxyimino Compound Type (S11), which are Known as Seed Dressings, Such as, for Example,
  "oxabetrinil" ((Z)-1,3-dioxolan-2-ylmethoxyimino(phenyl)acetonitrile) (S11-1), which is known as seed dressing safener for millet against metolachlor damage,
  "fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and
  "cyometrinil" or "CGA-43089" ((Z)-cyanomethoxyimino(phenyl)acetonitrile) (S11-3), which is known as seed dressing safener for millet against metolachlor damage.

S12) Active compounds from the class of the isothiochromanones (S12), such as, for example, methyl [(3-oxo-1H-2-benzothiopyran-4(3H)-ylidene)methoxy]acetate (CAS Reg. No. 205121-04-6) (S12-1) and related compounds from WO-A-1998/13361.

S13) One or More Compounds from Group (S13):
  "naphthalic anhydride" (1,8-naphthalenedicarboxylic anhydride) (S13-1), which is known as seed dressing safener for corn against thiocarbamate herbicide damage,
  "fenclorim" (4,6-dichloro-2-phenylpyrimidine) (S13-2), which is known as safener for pretilachlor in sown rice,
  "flurazole" (benzyl 2-chloro-4-trifluoromethyl-1,3-thiazole-5-carboxylate) (S13-3), which is known as seed dressing safener for millet against alachlor and metolachlor damage,
  "CL 304415" (CAS Reg. No. 31541-57-8) (4-carboxy-3,4-dihydro-2H-1-benzopyran-4-acetic acid), (S13-4) from American Cyanamid, which is known as safener for corn against imidazolinone damage,
  "MG 191" (CAS Reg. No. 96420-72-3) (2-dichloromethyl-2-methyl-1,3-dioxolane) (S13-5) from Nitrokemia, which is known as safener for corn,
  "MG-838" (CAS Reg. No. 133993-74-5) (2-propenyl 1-oxa-4-azaspiro[4.5]decane-4-carbodithioate) (S13-6) from Nitrokemia,
  "disulfoton" (O,O-diethyl S-2-ethylthioethyl phosphorodithioate) (S13-7),
  "dietholate" (O,O-diethyl O-phenyl phosphorothioate) (S13-8),
  "mephenate" (4-chlorophenyl methylcarbamate) (S13-9).

S14) Active compounds which, besides a herbicidal effect against harmful plants, also have safener effect on crop plants such as rice, such as, for example, "dimepiperate" or "MY-93" (S-1-methyl-1-phenylethyl piperidine-1-carbothioate), which is known as safener for rice against molinate herbicide damage, "daimuron" or "SK 23" (1-(1-methyl-1-phenylethyl)-3-p-tolylurea), which is known as safener for rice against imazosulfuron herbicide damage, "cumyluron"="JC-940" (3-(2-chlorophenylmethyl)-1-(1-methyl-1-phenyl-ethyl)urea, see JP-A-60087254), which is known as safener for rice against some herbicide damage, "methoxyphenone" or "NK 049" (3,3'-dimethyl-4-methoxybenzophenone), which is known as safener for rice against some herbicide damage, "CSB" (1-bromo-4-(chloromethylsulfonyl)benzene) from Kumiai, (CAS Reg. No. 54091-06-4), which is known as safener against some herbicide damage in rice.

S15) Active compounds which are primarily used as herbicides, but also have safener effect on crop plants, for example (2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Some of the safeners are already known as herbicides and thus, besides the herbicidal effect in respect of harmful plants, at the same time also develop a protective effect in respect of the crop plants.

The weight ratios of herbicide (mixture) to safener generally depend on the application rate of herbicide and the effectiveness of the particular safener and can vary within wide limits, for example in the range from 200:1 to 1:200, preferably 100:1 to 1:100, in particular 20:1 to 1:20. The safeners can be formulated analogously to the compounds of the formula (I) or mixtures thereof with further herbicides/pesticides and can be provided and applied as ready mix or tank mix with the herbicides.

For use, the formulations present in standard commercial form are, if appropriate, diluted in the usual manner, e.g. in the case of wettable powders, emulsifiable concentrates, dispersions and water-dispersible granules by means of water. Dust-like preparations, soil and scatter granules, and also sprayable solutions are usually no longer diluted with further inert substances prior to use.

The required application rate of the compounds of the formula (I) varies inter alia with the external conditions such as temperature, humidity, the type of herbicide used. It can fluctuate within wide limits, e.g. between 0.001 and 10.0 kg/ha or more of active substance, but is preferably between 0.005 and 5 kg/ha.

The present invention is illustrated in more detail by reference to the examples below, although these do not limit the invention in any way.

SYNTHESIS EXAMPLES

A number of synthesis examples of compounds of the formula (I) or their salts are described in an exemplary manner below.

2-({[5-(Difluoromethoxy)-1-methyl-3-(trifluoromethyl)-1H-pyrazol-4-yl]methyl}sulfanyl)-1,3-oxazole (Ex. 49)

1,3-Oxazole-2(3H)-thione (2.960 g, 29 mmol; prepared as described in WO 2003/006442 A) is initially charged in 50 ml of acetonitrile. With ice-bath cooling, 1,8-diazabicyclo(5.4.0)undec-7-ene (DBU, 4.81 ml, 32 mmol) is added dropwise. The mixture is stirred at 25° C. for 30 minutes. A solution of 4-(bromomethyl)-5-(difluoromethoxy)-1-methyl-3-(trifluoromethyl)-1H-pyrazole (9.045 g, 29 mmol) dissolved in acetonitrile is added dropwise. The mixture is stirred at 25° C. for a further 4 hours and allowed to stand overnight. For work-up, the reaction mixture is added to water and extracted twice with dichloromethane, and the extracts are then washed with water and finally with saturated NaCl solution. The combined organic phases are dried over magnesium sulfate, filtered off and concentrated. The crude product is purified chromatographically (heptan:ethyl acetate, gradient 10:0 to 7:3). This gives 7.6 g of product (74.9% of theory).

NMR (CDCl$_3$, 400 MHz): 3.82 (s, 3H, CH$_3$); 4.32 (s, 2H, SCH$_2$); 6.75 (t, 1H, OCHF$_2$); 7.11 (br s, 1H); 7.68 (br s, 1H).

2-({[5-(Difluoromethoxy)-1-methyl-3-(trifluoromethyl)-1H-pyrazol-4-yl]methyl}sulfinyl)-1,3-oxazole (Ex. 50)

Under an atmosphere of argon, 2-({[5-(difluoromethoxy)-1-methyl-3-(trifluoromethyl)-1H-pyrazol-4-yl]methyl}sulfanyl)-1,3-oxazole (2.00 g, 6 mmol) is initially charged in 333 ml of dichloromethane. With stirring and ice-cooling, 3-chloroperbenzoic acid (1.362 g, 6 mmol, 77% pure) is then added a little at a time, and the mixture is stirred at 0° C. for a further 6 hours. For work-up, the reaction mixture is extracted twice with 2-molar sodium hydroxide solution and then washed with water and finally with saturated NaCl solution. The combined organic phases are dried over magnesium sulfate, filtered off and concentrated. The crude product is purified chromatographically (heptane:ethyl acetate, gradient 10:0 to 6:4). This gives 1.98 g of product (89.7% of theory).

NMR (CDCl$_3$, 400 MHz): 3.86 (s, 3H, CH$_3$); 4.36 (d, 1H, S(O)CH$_2$); 4.49 (d, 1H, S(O)CH$_2$); 6.97 (dd, 1H, OCHF$_2$); 7.39 (br s, 1H); 7.93 (br s, 1H).

2-[(S)-{[5-(Difluoromethoxy)-1-methyl-3-(trifluoromethyl)-1H-pyrazol-4-yl]methyl}sulfinyl]-1,3-oxazole (Ex. 2285) and 2-[(R)-{[5-(difluoromethoxy)-1-methyl-3-(trifluoromethyl)-1H-pyrazol-4-yl]methyl}sulfinyl]-1,3-oxazole (Ex. 3041)

The racemic 2-({[5-(difluoromethoxy)-1-methyl-3-(trifluoromethyl)-1H-pyrazol-4-yl]methyl}sulfinyl)-1,3-oxazole (0.5 g, 99% pure) obtained is separated into the enantiomers by preparative chiral HPLC (column: Chiralpak® IC; mobile phase: n-heptane/2-propanol 80:20; flow rate: 90 ml/min; column temperature: 25° C.). This gives 0.2 g (40% of theory) of 2-[(S)-{[5-(difluoromethoxy)-1-methyl-3-(trifluoromethyl)-1H-pyrazol-4-yl]methyl}sulfinyl]-1,3-oxazole ($R_t$=8.129 min, $[\alpha]^D$=−126.1°) and 0.2 g (40% of theory) of 2-[(R)-{[5-(difluoromethoxy)-1-methyl-3-(trifluoromethyl)-1H-pyrazol-4-yl]methyl}sulfinyl]-1,3-oxazole ($R_t$=10.286 min, $[\alpha]^D$=+123.3°).

The absolute configuration of 2-[(S)-{[5-(difluoromethoxy)-1-methyl-3-(trifluoromethyl)-1H-pyrazol-4-yl]methyl}sulfinyl]-1,3-oxazole was confirmed by X-ray structural analysis.

Retention times ($R_t$, in minutes) and enantiomeric ratios (ee) of chiral compounds were determined by analytical chiral HPLC [Chiralpak® IC column (250×4.6 mm, particle size 10 μm), temperature 25° C., flow rate 1 ml/min, n-heptane/2-propanol 80:20 v/v].

Racemates or enantiomeric mixtures were separated into the respective enantiomers by preparative chiral HPLC [Chiralpak® IC column (250×50 mm, particle size 20 μm), temperature 25° C., flow rate 90 ml/min, n-heptane/2-propanol 80:20 v/v].

2-({[5-(Difluoromethoxy)-1-methyl-3-(trifluoromethyl)-1H-pyrazol-4-yl]methyl}sulfonyl)-1,3-oxazole (Ex. 51)

Under an atmosphere of argon, 2-({[5-(difluoromethoxy)-1-methyl-3-(trifluoromethyl)-1H-pyrazol-4-yl]methyl}sulfanyl)-1,3-oxazole (0.30 g, 1 mmol) is initially charged in 50 ml of dichloromethane. With stirring and ice-cooling, 3-chloroperbenzoic acid (0.449 g, 2 mmol, 77% pure) is then added a little at a time, and the mixture is stirred at 25° C. for a further 3 hours and allowed to stand overnight. A further 100 mg of 3-chloroperbenzoic acid are added, and stirring at 25° C. is continued for 4 hours. For work-up, the reaction mixture is washed twice with 2-molar sodium hydroxide solution, then with water and finally with saturated NaCl solution. The combined organic phases are dried over magnesium sulfate, filtered off and concentrated. The crude product is purified by preparative HPLC (reverse phase). This gives 0.097 g of product (28% of theory).

NMR (CDCl$_3$, 400 MHz): 3.87 (s, 3H, CH$_3$); 4.59 (s, 2H, S(O)$_2$CH$_2$); 6.84 (t, 1H, OCHF$_2$); 7.4 (br s, 1H); 7.89 (br s, 1H).

5-Bromo-2-({[5-(difluoromethoxy)-1-methyl-3-(trifluoromethyl)-1H-pyrazol-4-yl]methyl}sulfanyl)-1,3-oxazole (Ex. 787)

a) Preparation of 2-({[5-(difluoromethoxy)-1-methyl-3-(trifluoromethyl)-1H-pyrazol-4-yl]methyl}sulfanyl)-1,3-oxazole [according to Can. J. Chem., Vol. 50, 3082-3083 (1972)]

Under an atmosphere of argon, dihydroxyfumaric acid (5.00 g, 34 mmol) is added a little at a time to water (20 ml) at a temperature of 60° C. (evolution of gas). The mixture is stirred at 60° C. until the evolution of gas has ceased (about 1 h; solution 1). Potassium thiocyanate (3.282 g, 34 mmol) is initially charged in ethanol (25 ml). At 0° C., concentrated hydrochloric acid (4 ml, 4.76 g, 48 mmol) is added dropwise, and the mixture is stirred at 25° C. for 1 hour. The precipitated potassium chloride formed is filtered off with suction, the filtrate is slowly added dropwise to solution 1 at room temperature and the mixture is then stirred at reflux for another 12 hours. The reaction solution is concentrated, and acetonitrile (50 ml) is added to the aqueous residue. Initially potassium carbonate (7.00 g, 51 mmol) and then 4-(bromomethyl)-5-(difluoromethoxy)-1-methyl-3-(trifluoromethyl)-1H-pyrazole (5.218 g, 17 mmol) are added, and the mixture is stirred at 60° C. for a further 7 hours. For work-up, the reaction mixture is added to water and extracted twice with ethyl acetate, and the extracts are then washed with water and finally with saturated NaCl solution. The combined organic phases are dried over magnesium sulfate, filtered off and concentrated. The crude product is purified chromatographically (heptane:ethyl acetate, gradient 10:0 to 7:3). This gives 3.09 g of product (26.4% of theory).

b) Preparation of 5-bromo-2-({[5-(difluoromethoxy)-1-methyl-3-(trifluoromethyl)-1H-pyrazol-4-yl]methyl}sulfanyl)-1,3-oxazole 2-({[5-(Difluoromethoxy)-1-methyl-3-(trifluoromethyl)-1H-pyrazol-4-yl]methyl}sulfanyl)-1,3-oxazole (1.24 g, 4 mmol) is initially charged in 20 ml of dimethylformamide. N-Bromosuccinimide (0.892 g, 5 mmol) is then added a little at a time with stirring. The mixture is stirred at 40° C. for a further 6 hours. For work-up, the reaction mixture is added to water and extracted twice with dichloromethane, and the extracts are then washed with water and finally with saturated NaCl solution. The combined organic phases are dried over magnesium sulfate, filtered off and concentrated. The crude product is purified chromatographically (heptane:ethyl acetate, gradient 10:0 to 7:3). This gives 0.70 g of product (43.2% of theory).

NMR (CDCl$_3$, 400 MHz): 3.81 (s, 3H, CH$_3$); 4.28 (s, 2H, SCH$_2$); 6.71 (t, 1H, OCHF$_2$); 6.98 (s, 1H).

5-Chloro-2-({[5-(difluoromethoxy)-1-methyl-3-(trifluoromethyl)-1H-pyrazol-4-yl]methyl}sulfanyl)-1,3-oxazole (Ex. 541)

2-({[5-(Difluoromethoxy)-1-methyl-3-(trifluoromethyl)-1H-pyrazol-4-yl]methyl}sulfanyl)-1,3-oxazole (1.02 g, 3 mmol) is initially charged in 15 ml of dimethylformamide. N-Chlorosuccinimide (0.550 g, 4 mmol) is then added a little at a time with stirring. The mixture is stirred at 40° C. for a further 4 hours. For work-up, the reaction mixture is added to water and extracted twice with dichloromethane, and the extracts are then washed with water and finally with saturated NaCl solution. The combined organic phases are dried over magnesium sulfate, filtered off and concentrated. The crude product is purified chromatographically (heptane:ethyl acetate, gradient 10:0 to 7:3). This gives 0.45 g of product (35.9% of theory).

NMR (CDCl$_3$, 400 MHz): 3.80 (s, 3H, CH$_3$); 4.28 (s, 2H, SCH$_2$); 6.69 (t, 1H, OCHF$_2$); 6.88 (s, 1H).

5-Iodo-2-({[5-(difluoromethoxy)-1-methyl-3-(trifluoromethyl)-1H-pyrazol-4-yl]methyl}sulfanyl)-1,3-oxazole (Ex. 1033)

2-({[5-(Difluoromethoxy)-1-methyl-3-(trifluoromethyl)-1H-pyrazol-4-yl]methyl}sulfanyl)-1,3-oxazole (0.700 g, 2 mmol) is initially charged in 10 ml of dimethylformamide. N-Iodosuccinimide (0.750 g, 3.3 mmol) is then added a little at a time with stirring. The mixture is stirred at 40° C. for a further 16 hours. For work-up, the reaction mixture is added to water and extracted twice with dichloromethane, and the extracts are then washed with water and finally with saturated NaCl solution. The combined organic phases are dried over magnesium sulfate, filtered off and concentrated. The crude product is purified chromatographically (heptane:ethyl acetate, gradient 10:0 to 8:2). This gives 0.25 g of product (24.5% of theory).

NMR (CDCl$_3$, 400 MHz): 3.80 (s, 3H, CH$_3$); 4.29 (s, 2H, SCH$_2$); 6.70 (t, 1H, OCHF$_2$); 7.11 (s, 1H).

2-({[5-(Chloro)-1-methyl-3-(trifluoromethyl)-1H-pyrazol-4-yl]methyl}sulfanyl)-1, oxazole (Ex. 34)

a) Preparation of 2-(methylsulfonyl)-1,3-oxazole

Under an atmosphere of protective gas, 1,3-oxazole-2(3H)-thione (1.00 g, 10 mmol; prepared as described in WO 2003/006442 A) is initially charged in 20 ml of acetonitrile. Iodomethane (1.544 g, 0.677 ml, 11 mmol) is added dropwise, then potassium carbonate (1.503 ml, 11 mmol) is added. The mixture is stirred at 25° C. for 6 hours. For work-up, the reaction mixture is added to water and extracted twice with dichloromethane (100 ml), and the extract is then washed with water and finally with saturated NaCl solution. The combined organic phases are dried over magnesium sulfate, filtered off and directly reacted further. With stirring and ice-cooling, 3-chloro-perbenzoic acid (5.100 g, 23 mmol, 77% pure) is then added a little at a time to this solution in dichloromethane, and the mixture is stirred at 25° C. for a further 6 hours and then allowed to stand overnight. For work-up, the reaction mixture is washed twice with 2-molar sodium hydroxide solution, then with water and finally with saturated NaCl solution. The combined organic phases are dried over magnesium sulfate, filtered off and concentrated. This gives 0.820 g of product (50.7% of theory).

NMR (CDCl$_3$, 400 MHz): 3.35 (s, 3H, CH$_3$); 7.38 (br s, 1H); 7.88 (br s, 1H).

b) Preparation of 2-({[5-(chloro)-1-methyl-3-(trifluoromethyl)-1H-pyrazol-4-yl]methyl}sulfanyl)-1,3-oxazole

[5-Chloro-1-methyl-3-(trifluoromethyl)-1H-pyrazol-4-yl]methyl imidothiocarbamate hydrobromide (1.934 g, 5 mmol) is added to a vigorously stirred mixture consisting of 50 ml of toluene and 50% strength aqueous sodium hydroxide solution (21 g), and the mixture is stirred vigorously for a further 1.5 hours. Tetra-n-butylammonium bromide (0.494 g, 2 mmol) and 2-(methylsulfonyl)-1,3-oxazole (0.805 g, 5 mmol) are then added, and the mixture is stirred vigorously at 25° C. for a further 6 hours. For work-up, the reaction solution is added to water and extracted with toluene. The combined organic phases are dried and concentrated. This gives 1.290 g of product (75.2% of theory).

NMR (CDCl$_3$, 400 MHz): 3.89 (s, 3H, CH$_3$); 4.33 (s, 2H, SCH$_2$); 7.12 (br s, 1H); 7.68 (br s, 1H).

The compounds described in Tables 1-3 below are obtained in accordance with or analogously to the synthesis examples described above.

In the tables:

| | |
|---|---|
| Me = | methyl |
| Et = | ethyl |
| Ph = | phenyl |
| Pr = | n-propyl |
| cPr = | cyclopropyl |
| iPr = | isopropyl |
| tBu = | tert-butyl |
| cPen = | cyclopentyl |

TABLE 1

Compounds of the formula (I)

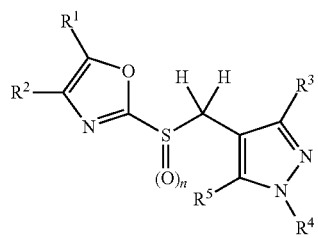

| Ex. No. | R$^1$ | R$^2$ | R$^3$ | R$^4$ | R$^5$ | n |
|---|---|---|---|---|---|---|
| 1. | H | H | CF$_3$ | Ph | Cl | 0 |
| 2. | H | H | CF$_3$ | Ph | Cl | 1 |
| 3. | H | H | CF$_3$ | Ph | Cl | 2 |
| 4. | H | H | CF$_3$ | tBu | Cl | 0 |
| 5. | H | H | CF$_3$ | tBu | Cl | 1 |
| 6. | H | H | CF$_3$ | tBu | Cl | 2 |
| 7. | H | H | CF$_3$ | CHF$_2$ | Cl | 0 |
| 8. | H | H | CF$_3$ | CHF$_2$ | Cl | 1 |
| 9. | H | H | CF$_3$ | CHF$_2$ | Cl | 2 |
| 10. | H | H | Cl | CHF$_2$ | CF$_3$ | 0 |
| 11. | H | H | Cl | CHF$_2$ | CF$_3$ | 1 |
| 12. | H | H | Cl | CHF$_2$ | CF$_3$ | 2 |
| 13. | H | H | CF$_3$ | Me | OMe | 0 |
| 14. | H | H | CF$_3$ | Me | OMe | 1 |
| 15. | H | H | CF$_3$ | Me | OMe | 2 |
| 16. | H | H | CF$_3$ | Me | CN | 0 |
| 17. | H | H | CF$_3$ | Me | CN | 1 |
| 18. | H | H | CF$_3$ | Me | CN | 2 |
| 19. | H | H | Cl | Et | Cl | 0 |
| 20. | H | H | Cl | Et | Cl | 1 |
| 21. | H | H | Cl | Et | Cl | 2 |
| 22. | H | H | CHF$_2$ | Me | Cl | 0 |
| 23. | H | H | CHF$_2$ | Me | Cl | 1 |
| 24. | H | H | CHF$_2$ | Me | Cl | 2 |
| 25. | H | H | Me | Me | Me | 0 |
| 26. | H | H | Me | Me | Me | 1 |
| 27. | H | H | Me | Me | Me | 2 |
| 28. | H | H | Me | Me | Cl | 0 |
| 29. | H | H | Me | Me | Cl | 1 |
| 30. | H | H | Me | Me | Cl | 2 |
| 31. | H | H | Cl | Me | Cl | 0 |
| 32. | H | H | Cl | Me | Cl | 1 |
| 33. | H | H | Cl | Me | Cl | 2 |
| 34. | H | H | CF$_3$ | Me | Cl | 0 |
| 35. | H | H | CF$_3$ | Me | Cl | 1 |
| 36. | H | H | CF$_3$ | Me | Cl | 2 |
| 37. | H | H | Cl | Me | CF$_3$ | 0 |
| 38. | H | H | Cl | Me | CF$_3$ | 1 |
| 39. | H | H | Cl | Me | CF$_3$ | 2 |
| 40. | H | H | CF$_3$ | Me | F | 0 |
| 41. | H | H | CF$_3$ | Me | F | 1 |
| 42. | H | H | CF$_3$ | Me | F | 2 |
| 43. | H | H | OMe | Me | CF$_3$ | 0 |
| 44. | H | H | OMe | Me | CF$_3$ | 1 |
| 45. | H | H | OMe | Me | CF$_3$ | 2 |
| 46. | H | H | CF$_3$ | Me | OEt | 0 |
| 47. | H | H | CF$_3$ | Me | OEt | 1 |
| 48. | H | H | CF$_3$ | Me | OEt | 2 |
| 49. | H | H | CF$_3$ | Me | OCHF$_2$ | 0 |
| 50. | H | H | CF$_3$ | Me | OCHF$_2$ | 1 |
| 51. | H | H | CF$_3$ | Me | OCHF$_2$ | 2 |
| 52. | H | H | OCHF$_2$ | Me | CF$_3$ | 0 |
| 53. | H | H | OCHF$_2$ | Me | CF$_3$ | 1 |
| 54. | H | H | OCHF$_2$ | Me | CF$_3$ | 2 |
| 55. | H | H | CF$_3$ | Me | OCH$_2$CHF$_2$ | 0 |
| 56. | H | H | CF$_3$ | Me | OCH$_2$CHF$_2$ | 1 |
| 57. | H | H | CF$_3$ | Me | OCH$_2$CHF$_2$ | 2 |
| 58. | H | H | CF$_3$ | Me | OCH$_2$CF$_3$ | 0 |
| 59. | H | H | CF$_3$ | Me | OCH$_2$CF$_3$ | 1 |
| 60. | H | H | CF$_3$ | Me | OCH$_2$CF$_3$ | 2 |
| 61. | H | H | CF$_3$ | Me | OCH$_2$CN | 0 |
| 62. | H | H | CF$_3$ | Me | OCH$_2$CN | 1 |

TABLE 1-continued

Compounds of the formula (I)

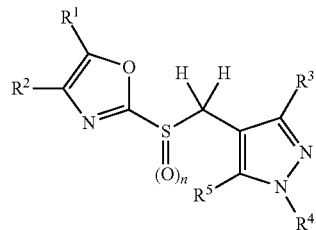

(I)

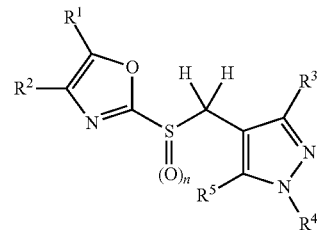

(I)

| Ex. No. | R¹ | R² | R³ | R⁴ | R⁵ | n |
|---|---|---|---|---|---|---|
| 63. | H | H | CF₃ | Me | OCH₂CN | 2 |
| 64. | H | H | CF₃ | Me | SO₂Me | 0 |
| 65. | H | H | CF₃ | Me | SO₂Me | 1 |
| 66. | H | H | CF₃ | Me | SO₂Me | 2 |
| 67. | H | H | CF₃ | Me | SEt | 0 |
| 68. | H | H | CF₃ | Me | SEt | 1 |
| 69. | H | H | CF₃ | Me | SEt | 2 |
| 70. | H | H | CF₃ | Me | Me | 0 |
| 71. | H | H | CF₃ | Me | Me | 1 |
| 72. | H | H | CF₃ | Me | Me | 2 |
| 73. | H | H | CF₃ | Me | Et | 0 |
| 74. | H | H | CF₃ | Me | Et | 1 |
| 75. | H | H | CF₃ | Me | Et | 2 |
| 76. | H | H | CF₃ | Et | Cl | 0 |
| 77. | H | H | CF₃ | Et | Cl | 1 |
| 78. | H | H | CF₃ | Et | Cl | 2 |
| 79. | H | H | Cl | Et | CF₃ | 0 |
| 80. | H | H | Cl | Et | CF₃ | 1 |
| 81. | H | H | Cl | Et | CF₃ | 2 |
| 82. | H | H | CF₃ | iPr | Cl | 0 |
| 83. | H | H | CF₃ | iPr | Cl | 1 |
| 84. | H | H | CF₃ | iPr | Cl | 2 |
| 85. | H | H | Cl | iPr | CF₃ | 0 |
| 86. | H | H | Cl | iPr | CF₃ | 1 |
| 87. | H | H | Cl | iPr | CF₃ | 2 |
| 88. | H | H | CF₃ | tBu | Cl | 0 |
| 89. | H | H | CF₃ | tBu | Cl | 1 |
| 90. | H | H | CF₃ | tBu | Cl | 2 |
| 91. | H | H | Cl | tBu | CF₃ | 0 |
| 92. | H | H | Cl | tBu | CF₃ | 1 |
| 93. | H | H | Cl | tBu | CF₃ | 2 |
| 94. | H | H | CF₃ | cPen | Cl | 0 |
| 95. | H | H | CF₃ | cPen | Cl | 1 |
| 96. | H | H | CF₃ | cPen | Cl | 2 |
| 97. | H | H | Cl | cPen | CF₃ | 0 |
| 98. | H | H | Cl | cPen | CF₃ | 1 |
| 99. | H | H | Cl | cPen | CF₃ | 2 |
| 100. | H | H | CF₃ | CH₂cPr | Cl | 0 |
| 101. | H | H | CF₃ | CH₂cPr | Cl | 1 |
| 102. | H | H | CF₃ | CH₂cPr | Cl | 2 |
| 103. | H | H | Cl | CH₂cPr | CF₃ | 0 |
| 104. | H | H | Cl | CH₂cPr | CF₃ | 1 |
| 105. | H | H | Cl | CH₂cPr | CF₃ | 2 |
| 106. | H | H | CF₃ | CH₂CH=CH₂ | Cl | 0 |
| 107. | H | H | CF₃ | CH₂CH=CH₂ | Cl | 1 |
| 108. | H | H | CF₃ | CH₂CH=CH₂ | Cl | 2 |
| 109. | H | H | Cl | CH₂CH=CH₂ | CF₃ | 0 |
| 110. | H | H | Cl | CH₂CH=CH₂ | CF₃ | 1 |
| 111. | H | H | Cl | CH₂CH=CH₂ | CF₃ | 2 |
| 112. | H | H | CF₃ | CHF₂ | OMe | 0 |
| 113. | H | H | CF₃ | CHF₂ | OMe | 1 |
| 114. | H | H | CF₃ | CHF₂ | OMe | 2 |
| 115. | H | OMe | CHF₂ | CF₃ | | 0 |
| 116. | H | OMe | CHF₂ | CF₃ | | 1 |
| 117. | H | OMe | CHF₂ | CF₃ | | 2 |
| 118. | H | H | CF₃ | CH₂CF₃ | Cl | 0 |
| 119. | H | H | CF₃ | CH₂CF₃ | Cl | 1 |
| 120. | H | H | CF₃ | CH₂CF₃ | Cl | 2 |
| 121. | H | H | Cl | CH₂CF₃ | CF₃ | 0 |
| 122. | H | H | Cl | CH₂CF₃ | CF₃ | 1 |
| 123. | H | H | Cl | CH₂CF₃ | CF₃ | 2 |
| 124. | H | H | CF₃ | CH₂OMe | Cl | 0 |
| 125. | H | H | CF₃ | CH₂OMe | Cl | 1 |
| 126. | H | H | CF₃ | CH₂OMe | Cl | 2 |
| 127. | H | H | Cl | CH₂OMe | CF₃ | 0 |
| 128. | H | H | Cl | CH₂OMe | CF₃ | 1 |
| 129. | H | H | Cl | CH₂OMe | CF₃ | 2 |
| 130. | H | H | CF₃ | CH₂CN | Cl | 0 |
| 131. | H | H | CF₃ | CH₂CN | Cl | 1 |
| 132. | H | H | CF₃ | CH₂CN | Cl | 2 |
| 133. | H | H | Me | Ph | Me | 0 |
| 134. | H | H | Me | Ph | Me | 1 |
| 135. | H | H | Me | Ph | Me | 2 |
| 136. | H | H | Me | Ph | Cl | 0 |
| 137. | H | H | Me | Ph | Cl | 1 |
| 138. | H | H | Me | Ph | Cl | 2 |
| 139. | H | H | Et | Ph | Cl | 0 |
| 140. | H | H | Et | Ph | Cl | 1 |
| 141. | H | H | Et | Ph | Cl | 2 |
| 142. | H | H | Pr | Ph | Cl | 0 |
| 143. | H | H | Pr | Ph | Cl | 1 |
| 144. | H | H | Pr | Ph | Cl | 2 |
| 145. | H | H | iPr | Ph | Cl | 0 |
| 146. | H | H | iPr | Ph | Cl | 1 |
| 147. | H | H | iPr | Ph | Cl | 2 |
| 148. | H | H | CF₃ | Ph | Cl | 0 |
| 149. | H | H | CF₃ | Ph | Cl | 1 |
| 150. | H | H | CF₃ | Ph | Cl | 2 |
| 151. | H | H | CF₃ | Ph | Me | 0 |
| 152. | H | H | CF₃ | Ph | Me | 1 |
| 153. | H | H | CF₃ | Ph | Me | 2 |
| 154. | H | H | CF₃ | Ph | CF₃ | 0 |
| 155. | H | H | CF₃ | Ph | CF₃ | 1 |
| 156. | H | H | CF₃ | Ph | CF₃ | 2 |
| 157. | H | H | CF₃ | Ph | F | 0 |
| 158. | H | H | CF₃ | Ph | F | 1 |
| 159. | H | H | CF₃ | Ph | F | 2 |
| 160. | H | H | CF₃ | Ph | OMe | 0 |
| 161. | H | H | CF₃ | Ph | OMe | 1 |
| 162. | H | H | CF₃ | Ph | OMe | 2 |
| 163. | H | H | CF₃ | Ph | OEt | 0 |
| 164. | H | H | CF₃ | Ph | OEt | 1 |
| 165. | H | H | CF₃ | Ph | OEt | 2 |
| 166. | H | H | CF₃ | Ph | OCHF₂ | 0 |
| 167. | H | H | CF₃ | Ph | OCHF₂ | 1 |
| 168. | H | H | CF₃ | Ph | OCHF₂ | 2 |
| 169. | H | H | CF₃ | Ph | CN | 0 |
| 170. | H | H | CF₃ | Ph | CN | 1 |
| 171. | H | H | CF₃ | Ph | CN | 2 |
| 172. | H | H | CF₃ | Ph(4-Cl) | Cl | 0 |
| 173. | H | H | CF₃ | Ph(4-Cl) | Cl | 1 |
| 174. | H | H | CF₃ | Ph(4-Cl) | Cl | 2 |
| 175. | H | H | Me | Me | OCH₂CF₃ | 0 |
| 176. | H | H | Me | Me | OCH₂CF₃ | 1 |
| 177. | H | H | Me | Me | OCH₂CF₃ | 2 |
| 178. | H | H | CF₃ | Me | 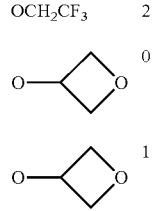 | 0 |
| 179. | H | H | CF₃ | Me | 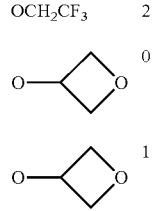 | 1 |

TABLE 1-continued

Compounds of the formula (I)

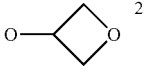

| Ex. No. | R¹ | R² | R³ | R⁴ | R⁵ | n |
|---|---|---|---|---|---|---|
| 180. | H | H | $CF_3$ | Me | (oxetane) | 2 |
| 181. | H | H | $CF_3$ | Me | H | 0 |
| 182. | H | H | $CF_3$ | Me | H | 1 |
| 183. | H | H | $CF_3$ | Me | H | 2 |
| 184. | H | H | $CF_3$ | Me | $OCH_2CH_2OMe$ | 0 |
| 185. | H | H | $CF_3$ | Me | $OCH_2CH_2OMe$ | 1 |
| 186. | H | H | $CF_3$ | Me | $OCH_2CH_2OMe$ | 2 |
| 187. | H | H | $CF_3$ | Me | SMe | 0 |
| 188. | H | H | $CF_3$ | Me | SMe | 1 |
| 189. | H | H | $CF_3$ | Me | SMe | 2 |
| 190. | H | H | $CF_3$ | Me | $OCH_2CH_2CH_2F$ | 0 |
| 191. | H | H | $CF_3$ | Me | $OCH_2CH_2CH_2F$ | 1 |
| 192. | H | H | $CF_3$ | Me | $OCH_2CH_2CH_2F$ | 2 |
| 193. | H | H | $CF_3$ | Me | $OCH(CH_2F)_2$ | 0 |
| 194. | H | H | $CF_3$ | Me | $OCH(CH_2F)_2$ | 1 |
| 195. | H | H | $CF_3$ | Me | $OCH(CH_2F)_2$ | 2 |
| 196. | H | H | $CF_3$ | Me | $OCH_2CF_2CHF_2$ | 0 |
| 197. | H | H | $CF_3$ | Me | $OCH_2CF_2CHF_2$ | 1 |
| 198. | H | H | $CF_3$ | Me | $OCH_2CF_2CHF_2$ | 2 |
| 199. | H | H | $CF_3$ | Me | $OCH_2CF=CH_2$ | 0 |
| 200. | H | H | $CF_3$ | Me | $OCH_2CF=CH_2$ | 1 |
| 201. | H | H | $CF_3$ | Me | $OCH_2CF=CH_2$ | 2 |
| 202. | H | H | $CF_3$ | Me | $OCH(Me)CF_3$ | 0 |
| 203. | H | H | $CF_3$ | Me | $OCH(Me)CF_3$ | 1 |
| 204. | H | H | $CF_3$ | Me | $OCH(Me)CF_3$ | 2 |
| 205. | H | H | $CF_3$ | Me | $OCH(Me)CH_2F$ | 0 |
| 206. | H | H | $CF_3$ | Me | $OCH(Me)CH_2F$ | 1 |
| 207. | H | H | $CF_3$ | Me | $OCH(Me)CH_2F$ | 2 |
| 208. | H | H | $OCH_2CF_3$ | Me | $CF_3$ | 0 |
| 209. | H | H | $OCH_2CF_3$ | Me | $CF_3$ | 1 |
| 210. | H | H | $OCH_2CF_3$ | Me | $CF_3$ | 2 |
| 211. | H | H | $OCH_2CF_3$ | Me | $CHF_2$ | 0 |
| 212. | H | H | $OCH_2CF_3$ | Me | $CHF_2$ | 1 |
| 213. | H | H | $OCH_2CF_3$ | Me | $CHF_2$ | 2 |
| 214. | H | H | $CHF_2$ | Me | $CHF_2$ | 0 |
| 215. | H | H | $CHF_2$ | Me | $CHF_2$ | 1 |
| 216. | H | H | $CHF_2$ | Me | $CHF_2$ | 2 |
| 217. | H | H | $CF_3$ | Me | $CHF_2$ | 0 |
| 218. | H | H | $CF_3$ | Me | $CHF_2$ | 1 |
| 219. | H | H | $CF_3$ | Me | $CHF_2$ | 2 |
| 220. | H | H | Cl | Me | $OCHF_2$ | 0 |
| 221. | H | H | Cl | Me | $OCHF_2$ | 1 |
| 222. | H | H | Cl | Me | $OCHF_2$ | 2 |
| 223. | H | H | Br | Me | $OCHF_2$ | 0 |
| 224. | H | H | Br | Me | $OCHF_2$ | 1 |
| 225. | H | H | Br | Me | $OCHF_2$ | 2 |
| 226. | H | H | Br | Me | $CF_3$ | 0 |
| 227. | H | H | Br | Me | $CF_3$ | 1 |
| 228. | H | H | Br | Me | $CF_3$ | 2 |
| 229. | H | H | $CF_3$ | Me | $CF_3$ | 0 |
| 230. | H | H | $CF_3$ | Me | $CF_3$ | 1 |
| 231. | H | H | $CF_3$ | Me | $CF_3$ | 2 |
| 232. | H | H | $CHF_2$ | Me | $CF_3$ | 0 |
| 233. | H | H | $CHF_2$ | Me | $CF_3$ | 1 |
| 234. | H | H | $CHF_2$ | Me | $CF_3$ | 2 |
| 235. | H | H | $CF_2CF_3$ | Me | $CF_3$ | 0 |
| 236. | H | H | $CF_2CF_3$ | Me | $CF_3$ | 1 |
| 237. | H | H | $CF_2CF_3$ | Me | $CF_3$ | 2 |
| 238. | H | H | $CF_3$ | Me | $CF_2CF_3$ | 0 |
| 239. | H | H | $CF_3$ | Me | $CF_2CF_3$ | 1 |
| 240. | H | H | $CF_3$ | Me | $CF_2CF_3$ | 2 |
| 241. | H | H | $CHF_2$ | Me | $OCH_2CF_3$ | 0 |
| 242. | H | H | $CHF_2$ | Me | $OCH_2CF_3$ | 1 |
| 243. | H | H | $CHF_2$ | Me | $OCH_2CF_3$ | 2 |
| 244. | H | H | $CHF_2$ | Me | $OCHF_2$ | 0 |
| 245. | H | H | $CHF_2$ | Me | $OCHF_2$ | 1 |
| 246. | H | H | $CHF_2$ | Me | $OCHF_2$ | 2 |
| 247. | F | H | $CF_3$ | Ph | Cl | 0 |
| 248. | F | H | $CF_3$ | Ph | Cl | 1 |
| 249. | F | H | $CF_3$ | Ph | Cl | 2 |
| 250. | F | H | $CF_3$ | tBu | Cl | 0 |
| 251. | F | H | $CF_3$ | tBu | Cl | 1 |
| 252. | F | H | $CF_3$ | tBu | Cl | 2 |
| 253. | F | H | $CF_3$ | $CHF_2$ | Cl | 0 |
| 254. | F | H | $CF_3$ | $CHF_2$ | Cl | 1 |
| 255. | F | H | $CF_3$ | $CHF_2$ | Cl | 2 |
| 256. | F | H | Cl | $CHF_2$ | $CF_3$ | 0 |
| 257. | F | H | Cl | $CHF_2$ | $CF_3$ | 1 |
| 258. | F | H | Cl | $CHF_2$ | $CF_3$ | 2 |
| 259. | F | H | $CF_3$ | Me | OMe | 0 |
| 260. | F | H | $CF_3$ | Me | OMe | 1 |
| 261. | F | H | $CF_3$ | Me | OMe | 2 |
| 262. | F | H | $CF_3$ | Me | CN | 0 |
| 263. | F | H | $CF_3$ | Me | CN | 1 |
| 264. | F | H | $CF_3$ | Me | CN | 2 |
| 265. | F | H | Cl | Et | Cl | 0 |
| 266. | F | H | Cl | Et | Cl | 1 |
| 267. | F | H | Cl | Et | Cl | 2 |
| 268. | F | H | $CHF_2$ | Me | Cl | 0 |
| 269. | F | H | $CHF_2$ | Me | Cl | 1 |
| 270. | F | H | $CHF_2$ | Me | Cl | 2 |
| 271. | F | H | Me | Me | Me | 0 |
| 272. | F | H | Me | Me | Me | 1 |
| 273. | F | H | Me | Me | Me | 2 |
| 274. | F | H | Me | Me | Cl | 0 |
| 275. | F | H | Me | Me | Cl | 1 |
| 276. | F | H | Me | Me | Cl | 2 |
| 277. | F | H | Cl | Me | Cl | 0 |
| 278. | F | H | Cl | Me | Cl | 1 |
| 279. | F | H | Cl | Me | Cl | 2 |
| 280. | F | H | $CF_3$ | Me | Cl | 0 |
| 281. | F | H | $CF_3$ | Me | Cl | 1 |
| 282. | F | H | $CF_3$ | Me | Cl | 2 |
| 283. | F | H | Cl | Me | $CF_3$ | 0 |
| 284. | F | H | Cl | Me | $CF_3$ | 1 |
| 285. | F | H | Cl | Me | $CF_3$ | 2 |
| 286. | F | H | $CF_3$ | Me | F | 0 |
| 287. | F | H | $CF_3$ | Me | F | 1 |
| 288. | F | H | $CF_3$ | Me | F | 2 |
| 289. | F | H | OMe | Me | $CF_3$ | 0 |
| 290. | F | H | OMe | Me | $CF_3$ | 1 |
| 291. | F | H | OMe | Me | $CF_3$ | 2 |
| 292. | F | H | $CF_3$ | Me | OEt | 0 |
| 293. | F | H | $CF_3$ | Me | OEt | 1 |
| 294. | F | H | $CF_3$ | Me | OEt | 2 |
| 295. | F | H | $CF_3$ | Me | $OCHF_2$ | 0 |
| 296. | F | H | $CF_3$ | Me | $OCHF_2$ | 1 |
| 297. | F | H | $CF_3$ | Me | $OCHF_2$ | 2 |
| 298. | F | H | $OCHF_2$ | Me | $CF_3$ | 0 |

TABLE 1-continued

Compounds of the formula (I)

| Ex. No. | R¹ | R² | R³ | R⁴ | R⁵ | n |
|---|---|---|---|---|---|---|
| 299. | F | H | OCHF$_2$ | Me | CF$_3$ | 1 |
| 300. | F | H | OCHF$_2$ | Me | CF$_3$ | 2 |
| 301. | F | H | CF$_3$ | Me | OCH$_2$CHF$_2$ | 0 |
| 302. | F | H | CF$_3$ | Me | OCH$_2$CHF$_2$ | 1 |
| 303. | F | H | CF$_3$ | Me | OCH$_2$CHF$_2$ | 2 |
| 304. | F | H | CF$_3$ | Me | OCH$_2$CF$_3$ | 0 |
| 305. | F | H | CF$_3$ | Me | OCH$_2$CF$_3$ | 1 |
| 306. | F | H | CF$_3$ | Me | OCH$_2$CF$_3$ | 2 |
| 307. | F | H | CF$_3$ | Me | OCH$_2$CN | 0 |
| 308. | F | H | CF$_3$ | Me | OCH$_2$CN | 1 |
| 309. | F | H | CF$_3$ | Me | OCH$_2$CN | 2 |
| 310. | F | H | CF$_3$ | Me | SO$_2$Me | 0 |
| 311. | F | H | CF$_3$ | Me | SO$_2$Me | 1 |
| 312. | F | H | CF$_3$ | Me | SO$_2$Me | 2 |
| 313. | F | H | CF$_3$ | Me | SEt | 0 |
| 314. | F | H | CF$_3$ | Me | SEt | 1 |
| 315. | F | H | CF$_3$ | Me | SEt | 2 |
| 316. | F | H | CF$_3$ | Me | Me | 0 |
| 317. | F | H | CF$_3$ | Me | Me | 1 |
| 318. | F | H | CF$_3$ | Me | Me | 2 |
| 319. | F | H | CF$_3$ | Me | Et | 0 |
| 320. | F | H | CF$_3$ | Me | Et | 1 |
| 321. | F | H | CF$_3$ | Me | Et | 2 |
| 322. | F | H | CF$_3$ | Et | Cl | 0 |
| 323. | F | H | CF$_3$ | Et | Cl | 1 |
| 324. | F | H | CF$_3$ | Et | Cl | 2 |
| 325. | F | H | Cl | Et | CF$_3$ | 0 |
| 326. | F | H | Cl | Et | CF$_3$ | 1 |
| 327. | F | H | Cl | Et | CF$_3$ | 2 |
| 328. | F | H | CF$_3$ | iPr | Cl | 0 |
| 329. | F | H | CF$_3$ | iPr | Cl | 1 |
| 330. | F | H | CF$_3$ | iPr | Cl | 2 |
| 331. | F | H | Cl | iPr | CF$_3$ | 0 |
| 332. | F | H | Cl | iPr | CF$_3$ | 1 |
| 333. | F | H | Cl | iPr | CF$_3$ | 2 |
| 334. | F | H | CF$_3$ | tBu | Cl | 0 |
| 335. | F | H | CF$_3$ | tBu | Cl | 1 |
| 336. | F | H | CF$_3$ | tBu | Cl | 2 |
| 337. | F | H | Cl | tBu | CF$_3$ | 0 |
| 338. | F | H | Cl | tBu | CF$_3$ | 1 |
| 339. | F | H | Cl | tBu | CF$_3$ | 2 |
| 340. | F | H | CF$_3$ | cPen | Cl | 0 |
| 341. | F | H | CF$_3$ | cPen | Cl | 1 |
| 342. | F | H | CF$_3$ | cPen | Cl | 2 |
| 343. | F | H | Cl | cPen | CF$_3$ | 0 |
| 344. | F | H | Cl | cPen | CF$_3$ | 1 |
| 345. | F | H | Cl | cPen | CF$_3$ | 2 |
| 346. | F | H | CF$_3$ | CH$_2$cPr | Cl | 0 |
| 347. | F | H | CF$_3$ | CH$_2$cPr | Cl | 1 |
| 348. | F | H | CF$_3$ | CH$_2$cPr | Cl | 2 |
| 349. | F | H | Cl | CH$_2$cPr | CF$_3$ | 0 |
| 350. | F | H | Cl | CH$_2$cPr | CF$_3$ | 1 |
| 351. | F | H | Cl | CH$_2$cPr | CF$_3$ | 2 |
| 352. | F | H | CF$_3$ | CH$_2$CH=CH$_2$ | Cl | 0 |
| 353. | F | H | CF$_3$ | CH$_2$CH=CH$_2$ | Cl | 1 |
| 354. | F | H | CF$_3$ | CH$_2$CH=CH$_2$ | Cl | 2 |
| 355. | F | H | Cl | CH$_2$CH=CH$_2$ | CF$_3$ | 0 |
| 356. | F | H | Cl | CH$_2$CH=CH$_2$ | CF$_3$ | 1 |
| 357. | F | H | Cl | CH$_2$CH=CH$_2$ | CF$_3$ | 2 |
| 358. | F | H | CF$_3$ | CHF$_2$ | OMe | 0 |
| 359. | F | H | CF$_3$ | CHF$_2$ | OMe | 1 |
| 360. | F | H | CF$_3$ | CHF$_2$ | OMe | 2 |
| 361. | F | H | OMe | CHF$_2$ | CF$_3$ | 0 |
| 362. | F | H | OMe | CHF$_2$ | CF$_3$ | 1 |
| 363. | F | H | OMe | CHF$_2$ | CF$_3$ | 2 |
| 364. | F | H | CF$_3$ | CH$_2$CF$_3$ | Cl | 0 |
| 365. | F | H | CF$_3$ | CH$_2$CF$_3$ | Cl | 1 |
| 366. | F | H | CF$_3$ | CH$_2$CF$_3$ | Cl | 2 |
| 367. | F | H | Cl | CH$_2$CF$_3$ | CF$_3$ | 0 |
| 368. | F | H | Cl | CH$_2$CF$_3$ | CF$_3$ | 1 |
| 369. | F | H | Cl | CH$_2$CF$_3$ | CF$_3$ | 2 |
| 370. | F | H | CF$_3$ | CH$_2$OMe | Cl | 0 |
| 371. | F | H | CF$_3$ | CH$_2$OMe | Cl | 1 |
| 372. | F | H | CF$_3$ | CH$_2$OMe | Cl | 2 |
| 373. | F | H | Cl | CH$_2$OMe | CF$_3$ | 0 |
| 374. | F | H | Cl | CH$_2$OMe | CF$_3$ | 1 |
| 375. | F | H | Cl | CH$_2$OMe | CF$_3$ | 2 |
| 376. | F | H | CF$_3$ | CH$_2$CN | Cl | 0 |
| 377. | F | H | CF$_3$ | CH$_2$CN | Cl | 1 |
| 378. | F | H | CF$_3$ | CH$_2$CN | Cl | 2 |
| 379. | F | H | Me | Ph | Me | 0 |
| 380. | F | H | Me | Ph | Me | 1 |
| 381. | F | H | Me | Ph | Me | 2 |
| 382. | F | H | Me | Ph | Cl | 0 |
| 383. | F | H | Me | Ph | Cl | 1 |
| 384. | F | H | Me | Ph | Cl | 2 |
| 385. | F | H | Et | Ph | Cl | 0 |
| 386. | F | H | Et | Ph | Cl | 1 |
| 387. | F | H | Et | Ph | Cl | 2 |
| 388. | F | H | Pr | Ph | Cl | 0 |
| 389. | F | H | Pr | Ph | Cl | 1 |
| 390. | F | H | Pr | Ph | Cl | 2 |
| 391. | F | H | iPr | Ph | Cl | 0 |
| 392. | F | H | iPr | Ph | Cl | 1 |
| 393. | F | H | iPr | Ph | Cl | 2 |
| 394. | F | H | CF$_3$ | Ph | Cl | 0 |
| 395. | F | H | CF$_3$ | Ph | Cl | 1 |
| 396. | F | H | CF$_3$ | Ph | Cl | 2 |
| 397. | F | H | CF$_3$ | Ph | Me | 0 |
| 398. | F | H | CF$_3$ | Ph | Me | 1 |
| 399. | F | H | CF$_3$ | Ph | Me | 2 |
| 400. | F | H | CF$_3$ | Ph | CF$_3$ | 0 |
| 401. | F | H | CF$_3$ | Ph | CF$_3$ | 1 |
| 402. | F | H | CF$_3$ | Ph | CF$_3$ | 2 |
| 403. | F | H | CF$_3$ | Ph | F | 0 |
| 404. | F | H | CF$_3$ | Ph | F | 1 |
| 405. | F | H | CF$_3$ | Ph | F | 2 |
| 406. | F | H | CF$_3$ | Ph | OMe | 0 |
| 407. | F | H | CF$_3$ | Ph | OMe | 1 |
| 408. | F | H | CF$_3$ | Ph | OMe | 2 |
| 409. | F | H | CF$_3$ | Ph | OEt | 0 |
| 410. | F | H | CF$_3$ | Ph | OEt | 1 |
| 411. | F | H | CF$_3$ | Ph | OEt | 2 |
| 412. | F | H | CF$_3$ | Ph | OCHF$_2$ | 0 |
| 413. | F | H | CF$_3$ | Ph | OCHF$_2$ | 1 |
| 414. | F | H | CF$_3$ | Ph | OCHF$_2$ | 2 |
| 415. | F | H | CF$_3$ | Ph | CN | 0 |
| 416. | F | H | CF$_3$ | Ph | CN | 1 |
| 417. | F | H | CF$_3$ | Ph | CN | 2 |
| 418. | F | H | CF$_3$ | Ph(4-Cl) | Cl | 0 |
| 419. | F | H | CF$_3$ | Ph(4-Cl) | Cl | 1 |
| 420. | F | H | CF$_3$ | Ph(4-Cl) | Cl | 2 |
| 421. | F | H | Me | Me | OCH$_2$CF$_3$ | 0 |
| 422. | F | H | Me | Me | OCH$_2$CF$_3$ | 1 |

TABLE 1-continued

Compounds of the formula (I)

| Ex. No. | R¹ | R² | R³ | R⁴ | R⁵ | n |
|---|---|---|---|---|---|---|
| 423. | F | H | Me | Me | OCH$_2$CF$_3$ | 2 |
| 424. | F | H | CF$_3$ | Me |  | 0 |
| 425. | F | H | CF$_3$ | Me |  | 1 |
| 426. | F | H | CF$_3$ | Me |  | 2 |
| 427. | F | H | CF$_3$ | Me | H | 0 |
| 428. | F | H | CF$_3$ | Me | H | 1 |
| 429. | F | H | CF$_3$ | Me | H | 2 |
| 430. | F | H | CF$_3$ | Me | OCH$_2$CH$_2$OMe | 0 |
| 431. | F | H | CF$_3$ | Me | OCH$_2$CH$_2$OMe | 1 |
| 432. | F | H | CF$_3$ | Me | OCH$_2$CH$_2$OMe | 2 |
| 433. | F | H | CF$_3$ | Me | SMe | 0 |
| 434. | F | H | CF$_3$ | Me | SMe | 1 |
| 435. | F | H | CF$_3$ | Me | SMe | 2 |
| 436. | F | H | CF$_3$ | Me | OCH$_2$CH$_2$CH$_2$F | 0 |
| 437. | F | H | CF$_3$ | Me | OCH$_2$CH$_2$CH$_2$F | 1 |
| 438. | F | H | CF$_3$ | Me | OCH$_2$CH$_2$CH$_2$F | 2 |
| 439. | F | H | CF$_3$ | Me | OCH(CH$_2$F)$_2$ | 0 |
| 440. | F | H | CF$_3$ | Me | OCH(CH$_2$F)$_2$ | 1 |
| 441. | F | H | CF$_3$ | Me | OCH(CH$_2$F)$_2$ | 2 |
| 442. | F | H | CF$_3$ | Me | OCH$_2$CF$_2$CHF$_2$ | 0 |
| 443. | F | H | CF$_3$ | Me | OCH$_2$CF$_2$CHF$_2$ | 1 |
| 444. | F | H | CF$_3$ | Me | OCH$_2$CF$_2$CHF$_2$ | 2 |
| 445. | F | H | CF$_3$ | Me | OCH$_2$CF=CH$_2$ | 0 |
| 446. | F | H | CF$_3$ | Me | OCH$_2$CF=CH$_2$ | 1 |
| 447. | F | H | CF$_3$ | Me | OCH$_2$CF=CH$_2$ | 2 |
| 448. | F | H | CF$_3$ | Me | OCH(Me)CF$_3$ | 0 |
| 449. | F | H | CF$_3$ | Me | OCH(Me)CF$_3$ | 1 |
| 450. | F | H | CF$_3$ | Me | OCH(Me)CF$_3$ | 2 |
| 451. | F | H | CF$_3$ | Me | OCH(Me)CH$_2$F | 0 |
| 452. | F | H | CF$_3$ | Me | OCH(Me)CH$_2$F | 1 |
| 453. | F | H | CF$_3$ | Me | OCH(Me)CH$_2$F | 2 |
| 454. | F | H | OCH$_2$CF$_3$ | Me | CF$_3$ | 0 |
| 455. | F | H | OCH$_2$CF$_3$ | Me | CF$_3$ | 1 |
| 456. | F | H | OCH$_2$CF$_3$ | Me | CF$_3$ | 2 |
| 457. | F | H | OCH$_2$CF$_3$ | Me | CHF$_2$ | 0 |
| 458. | F | H | OCH$_2$CF$_3$ | Me | CHF$_2$ | 1 |
| 459. | F | H | OCH$_2$CF$_3$ | Me | CHF$_2$ | 2 |
| 460. | F | H | CHF$_2$ | Me | CHF$_2$ | 0 |
| 461. | F | H | CHF$_2$ | Me | CHF$_2$ | 1 |
| 462. | F | H | CHF$_2$ | Me | CHF$_2$ | 2 |
| 463. | F | H | CF$_3$ | Me | CHF$_2$ | 0 |
| 464. | F | H | CF$_3$ | Me | CHF$_2$ | 1 |
| 465. | F | H | CF$_3$ | Me | CHF$_2$ | 2 |
| 466. | F | H | Cl | Me | OCHF$_2$ | 0 |
| 467. | F | H | Cl | Me | OCHF$_2$ | 1 |
| 468. | F | H | Cl | Me | OCHF$_2$ | 2 |
| 469. | F | H | Br | Me | OCHF$_2$ | 0 |
| 470. | F | H | Br | Me | OCHF$_2$ | 1 |
| 471. | F | H | Br | Me | OCHF$_2$ | 2 |
| 472. | F | H | Br | Me | CF$_3$ | 0 |
| 473. | F | H | Br | Me | CF$_3$ | 1 |
| 474. | F | H | Br | Me | CF$_3$ | 2 |
| 475. | F | H | CF$_3$ | Me | CF$_3$ | 0 |
| 476. | F | H | CF$_3$ | Me | CF$_3$ | 1 |
| 477. | F | H | CF$_3$ | Me | CF$_3$ | 2 |
| 478. | F | H | CHF$_2$ | Me | CF$_3$ | 0 |
| 479. | F | H | CHF$_2$ | Me | CF$_3$ | 1 |
| 480. | F | H | CHF$_2$ | Me | CF$_3$ | 2 |
| 481. | F | H | CF$_2$CF$_3$ | Me | CF$_3$ | 0 |
| 482. | F | H | CF$_2$CF$_3$ | Me | CF$_3$ | 1 |
| 483. | F | H | CF$_2$CF$_3$ | Me | CF$_3$ | 2 |
| 484. | F | H | CF$_3$ | Me | CF$_2$CF$_3$ | 0 |
| 485. | F | H | CF$_3$ | Me | CF$_2$CF$_3$ | 1 |
| 486. | F | H | CF$_3$ | Me | CF$_2$CF$_3$ | 2 |
| 487. | F | H | CHF$_2$ | Me | OCH$_2$CF$_3$ | 0 |
| 488. | F | H | CHF$_2$ | Me | OCH$_2$CF$_3$ | 1 |
| 489. | F | H | CHF$_2$ | Me | OCH$_2$CF$_3$ | 2 |
| 490. | F | H | CHF$_2$ | Me | OCHF$_2$ | 0 |
| 491. | F | H | CHF$_2$ | Me | OCHF$_2$ | 1 |
| 492. | F | H | CHF$_2$ | Me | OCHF$_2$ | 2 |
| 493. | Cl | H | CF$_3$ | Ph | Cl | 0 |
| 494. | Cl | H | CF$_3$ | Ph | Cl | 1 |
| 495. | Cl | H | CF$_3$ | Ph | Cl | 2 |
| 496. | Cl | H | CF$_3$ | tBu | Cl | 0 |
| 497. | Cl | H | CF$_3$ | tBu | Cl | 1 |
| 498. | Cl | H | CF$_3$ | tBu | Cl | 2 |
| 499. | Cl | H | CF$_3$ | CHF$_2$ | Cl | 0 |
| 500. | Cl | H | CF$_3$ | CHF$_2$ | Cl | 1 |
| 501. | Cl | H | CF$_3$ | CHF$_2$ | Cl | 2 |
| 502. | Cl | H | Cl | CHF$_2$ | CF$_3$ | 0 |
| 503. | Cl | H | Cl | CHF$_2$ | CF$_3$ | 1 |
| 504. | Cl | H | Cl | CHF$_2$ | CF$_3$ | 2 |
| 505. | Cl | H | CF$_3$ | Me | OMe | 0 |
| 506. | Cl | H | CF$_3$ | Me | OMe | 1 |
| 507. | Cl | H | CF$_3$ | Me | OMe | 2 |
| 508. | Cl | H | CF$_3$ | Me | CN | 0 |
| 509. | Cl | H | CF$_3$ | Me | CN | 1 |
| 510. | Cl | H | CF$_3$ | Me | CN | 2 |
| 511. | Cl | H | Cl | Et | Cl | 0 |
| 512. | Cl | H | Cl | Et | Cl | 1 |
| 513. | Cl | H | Cl | Et | Cl | 2 |
| 514. | Cl | H | CHF$_2$ | Me | Cl | 0 |
| 515. | Cl | H | CHF$_2$ | Me | Cl | 1 |
| 516. | Cl | H | CHF$_2$ | Me | Cl | 2 |
| 517. | Cl | H | Me | Me | Me | 0 |
| 518. | Cl | H | Me | Me | Me | 1 |
| 519. | Cl | H | Me | Me | Me | 2 |
| 520. | Cl | H | Me | Me | Cl | 0 |
| 521. | Cl | H | Me | Me | Cl | 1 |
| 522. | Cl | H | Me | Me | Cl | 2 |
| 523. | Cl | H | Cl | Me | Cl | 0 |
| 524. | Cl | H | Cl | Me | Cl | 1 |
| 525. | Cl | H | Cl | Me | Cl | 2 |
| 526. | Cl | H | CF$_3$ | Me | Cl | 0 |
| 527. | Cl | H | CF$_3$ | Me | Cl | 1 |
| 528. | Cl | H | CF$_3$ | Me | Cl | 2 |
| 529. | Cl | H | Cl | Me | CF$_3$ | 0 |
| 530. | Cl | H | Cl | Me | CF$_3$ | 1 |
| 531. | Cl | H | Cl | Me | CF$_3$ | 2 |
| 532. | Cl | H | CF$_3$ | Me | F | 0 |
| 533. | Cl | H | CF$_3$ | Me | F | 1 |
| 534. | Cl | H | CF$_3$ | Me | F | 2 |
| 535. | Cl | H | OMe | Me | CF$_3$ | 0 |

TABLE 1-continued

Compounds of the formula (I)

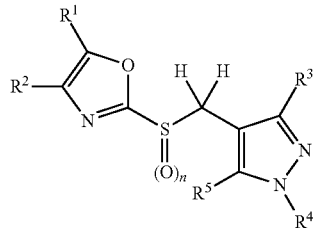
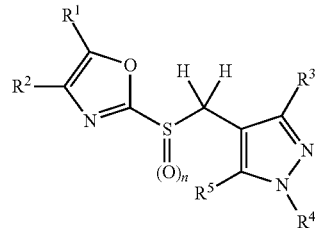

| Ex. No. | R¹ | R² | R³ | R⁴ | R⁵ | n |
|---|---|---|---|---|---|---|
| 536. | Cl | H | OMe | Me | CF$_3$ | 1 |
| 537. | Cl | H | OMe | Me | CF$_3$ | 2 |
| 538. | Cl | H | CF$_3$ | Me | OEt | 0 |
| 539. | Cl | H | CF$_3$ | Me | OEt | 1 |
| 540. | Cl | H | CF$_3$ | Me | OEt | 2 |
| 541. | Cl | H | CF$_3$ | Me | OCHF$_2$ | 0 |
| 542. | Cl | H | CF$_3$ | Me | OCHF$_2$ | 1 |
| 543. | Cl | H | CF$_3$ | Me | OCHF$_2$ | 2 |
| 544. | Cl | H | OCHF$_2$ | Me | CF$_3$ | 0 |
| 545. | Cl | H | OCHF$_2$ | Me | CF$_3$ | 1 |
| 546. | Cl | H | OCHF$_2$ | Me | CF$_3$ | 2 |
| 547. | Cl | H | CF$_3$ | Me | OCH$_2$CHF$_2$ | 0 |
| 548. | Cl | H | CF$_3$ | Me | OCH$_2$CHF$_2$ | 1 |
| 549. | Cl | H | CF$_3$ | Me | OCH$_2$CHF$_2$ | 2 |
| 550. | Cl | H | CF$_3$ | Me | OCH$_2$CF$_3$ | 0 |
| 551. | Cl | H | CF$_3$ | Me | OCH$_2$CF$_3$ | 1 |
| 552. | Cl | H | CF$_3$ | Me | OCH$_2$CF$_3$ | 2 |
| 553. | Cl | H | CF$_3$ | Me | OCH$_2$CN | 0 |
| 554. | Cl | H | CF$_3$ | Me | OCH$_2$CN | 1 |
| 555. | Cl | H | CF$_3$ | Me | OCH$_2$CN | 2 |
| 556. | Cl | H | CF$_3$ | Me | SO$_2$Me | 0 |
| 557. | Cl | H | CF$_3$ | Me | SO$_2$Me | 1 |
| 558. | Cl | H | CF$_3$ | Me | SO$_2$Me | 2 |
| 559. | Cl | H | CF$_3$ | Me | SEt | 0 |
| 560. | Cl | H | CF$_3$ | Me | SEt | 1 |
| 561. | Cl | H | CF$_3$ | Me | SEt | 2 |
| 562. | Cl | H | CF$_3$ | Me | Me | 0 |
| 563. | Cl | H | CF$_3$ | Me | Me | 1 |
| 564. | Cl | H | CF$_3$ | Me | Me | 2 |
| 565. | Cl | H | CF$_3$ | Me | Et | 0 |
| 566. | Cl | H | CF$_3$ | Me | Et | 1 |
| 567. | Cl | H | CF$_3$ | Me | Et | 2 |
| 568. | Cl | H | CF$_3$ | Et | Cl | 0 |
| 569. | Cl | H | CF$_3$ | Et | Cl | 1 |
| 570. | Cl | H | CF$_3$ | Et | Cl | 2 |
| 571. | Cl | H | Cl | Et | CF$_3$ | 0 |
| 572. | Cl | H | Cl | Et | CF$_3$ | 1 |
| 573. | Cl | H | Cl | Et | CF$_3$ | 2 |
| 574. | Cl | H | CF$_3$ | iPr | Cl | 0 |
| 575. | Cl | H | CF$_3$ | iPr | Cl | 1 |
| 576. | Cl | H | CF$_3$ | iPr | Cl | 2 |
| 577. | Cl | H | Cl | iPr | CF$_3$ | 0 |
| 578. | Cl | H | Cl | iPr | CF$_3$ | 1 |
| 579. | Cl | H | Cl | iPr | CF$_3$ | 2 |
| 580. | Cl | H | CF$_3$ | tBu | Cl | 0 |
| 581. | Cl | H | CF$_3$ | tBu | Cl | 1 |
| 582. | Cl | H | CF$_3$ | tBu | Cl | 2 |
| 583. | Cl | H | Cl | tBu | CF$_3$ | 0 |
| 584. | Cl | H | Cl | tBu | CF$_3$ | 1 |
| 585. | Cl | H | Cl | tBu | CF$_3$ | 2 |
| 586. | Cl | H | CF$_3$ | cPen | Cl | 0 |
| 587. | Cl | H | CF$_3$ | cPen | Cl | 1 |
| 588. | Cl | H | CF$_3$ | cPen | Cl | 2 |
| 589. | Cl | H | Cl | cPen | CF$_3$ | 0 |
| 590. | Cl | H | Cl | cPen | CF$_3$ | 1 |
| 591. | Cl | H | Cl | cPen | CF$_3$ | 2 |
| 592. | Cl | H | CF$_3$ | CH$_2$cPr | Cl | 0 |
| 593. | Cl | H | CF$_3$ | CH$_2$cPr | Cl | 1 |
| 594. | Cl | H | CF$_3$ | CH$_2$cPr | Cl | 2 |
| 595. | Cl | H | Cl | CH$_2$cPr | CF$_3$ | 0 |
| 596. | Cl | H | Cl | CH$_2$cPr | CF$_3$ | 1 |
| 597. | Cl | H | Cl | CH$_2$cPr | CF$_3$ | 2 |
| 598. | Cl | H | CF$_3$ | CH$_2$CH=CH$_2$ | Cl | 0 |
| 599. | Cl | H | CF$_3$ | CH$_2$CH=CH$_2$ | Cl | 1 |
| 600. | Cl | H | CF$_3$ | CH$_2$CH=CH$_2$ | Cl | 2 |
| 601. | Cl | H | Cl | CH$_2$CH=CH$_2$ | CF$_3$ | 0 |
| 602. | Cl | H | Cl | CH$_2$CH=CH$_2$ | CF$_3$ | 1 |
| 603. | Cl | H | Cl | CH$_2$CH=CH$_2$ | CF$_3$ | 2 |
| 604. | Cl | H | CF$_3$ | CHF$_2$ | OMe | 0 |
| 605. | Cl | H | CF$_3$ | CHF$_2$ | OMe | 1 |
| 606. | Cl | H | CF$_3$ | CHF$_2$ | OMe | 2 |
| 607. | Cl | H | OMe | CHF$_2$ | CF$_3$ | 0 |
| 608. | Cl | H | OMe | CHF$_2$ | CF$_3$ | 1 |
| 609. | Cl | H | OMe | CHF$_2$ | CF$_3$ | 2 |
| 610. | Cl | H | CF$_3$ | CH$_2$CF$_3$ | Cl | 0 |
| 611. | Cl | H | CF$_3$ | CH$_2$CF$_3$ | Cl | 1 |
| 612. | Cl | H | CF$_3$ | CH$_2$CF$_3$ | Cl | 2 |
| 613. | Cl | H | Cl | CH$_2$CF$_3$ | CF$_3$ | 0 |
| 614. | Cl | H | Cl | CH$_2$CF$_3$ | CF$_3$ | 1 |
| 615. | Cl | H | Cl | CH$_2$CF$_3$ | CF$_3$ | 2 |
| 616. | Cl | H | CF$_3$ | CH$_2$OMe | Cl | 0 |
| 617. | Cl | H | CF$_3$ | CH$_2$OMe | Cl | 1 |
| 618. | Cl | H | CF$_3$ | CH$_2$OMe | Cl | 2 |
| 619. | Cl | H | Cl | CH$_2$OMe | CF$_3$ | 0 |
| 620. | Cl | H | Cl | CH$_2$OMe | CF$_3$ | 1 |
| 621. | Cl | H | Cl | CH$_2$OMe | CF$_3$ | 2 |
| 622. | Cl | H | CF$_3$ | CH$_2$CN | Cl | 0 |
| 623. | Cl | H | CF$_3$ | CH$_2$CN | Cl | 1 |
| 624. | Cl | H | CF$_3$ | CH$_2$CN | Cl | 2 |
| 625. | Cl | H | Me | Ph | Me | 0 |
| 626. | Cl | H | Me | Ph | Me | 1 |
| 627. | Cl | H | Me | Ph | Me | 2 |
| 628. | Cl | H | Me | Ph | Cl | 0 |
| 629. | Cl | H | Me | Ph | Cl | 1 |
| 630. | Cl | H | Me | Ph | Cl | 2 |
| 631. | Cl | H | Et | Ph | Cl | 0 |
| 632. | Cl | H | Et | Ph | Cl | 1 |
| 633. | Cl | H | Et | Ph | Cl | 2 |
| 634. | Cl | H | Pr | Ph | Cl | 0 |
| 635. | Cl | H | Pr | Ph | Cl | 1 |
| 636. | Cl | H | Pr | Ph | Cl | 2 |
| 637. | Cl | H | iPr | Ph | Cl | 0 |
| 638. | Cl | H | iPr | Ph | Cl | 1 |
| 639. | Cl | H | iPr | Ph | Cl | 2 |
| 640. | Cl | H | CF$_3$ | Ph | Cl | 0 |
| 641. | Cl | H | CF$_3$ | Ph | Cl | 1 |
| 642. | Cl | H | CF$_3$ | Ph | Cl | 2 |
| 643. | Cl | H | CF$_3$ | Ph | Me | 0 |
| 644. | Cl | H | CF$_3$ | Ph | Me | 1 |
| 645. | Cl | H | CF$_3$ | Ph | Me | 2 |
| 646. | Cl | H | CF$_3$ | Ph | CF$_3$ | 0 |
| 647. | Cl | H | CF$_3$ | Ph | CF$_3$ | 1 |
| 648. | Cl | H | CF$_3$ | Ph | CF$_3$ | 2 |
| 649. | Cl | H | CF$_3$ | Ph | F | 0 |
| 650. | Cl | H | CF$_3$ | Ph | F | 1 |
| 651. | Cl | H | CF$_3$ | Ph | F | 2 |
| 652. | Cl | H | CF$_3$ | Ph | OMe | 0 |
| 653. | Cl | H | CF$_3$ | Ph | OMe | 1 |
| 654. | Cl | H | CF$_3$ | Ph | OMe | 2 |
| 655. | Cl | H | CF$_3$ | Ph | OEt | 0 |
| 656. | Cl | H | CF$_3$ | Ph | OEt | 1 |
| 657. | Cl | H | CF$_3$ | Ph | OEt | 2 |
| 658. | Cl | H | CF$_3$ | Ph | OCHF$_2$ | 0 |
| 659. | Cl | H | CF$_3$ | Ph | OCHF$_2$ | 1 |

TABLE 1-continued

Compounds of the formula (I)

| Ex. No. | R¹ | R² | R³ | R⁴ | R⁵ | n |
|---|---|---|---|---|---|---|
| 660. | Cl | H | $CF_3$ | Ph | $OCHF_2$ | 2 |
| 661. | Cl | H | $CF_3$ | Ph | CN | 0 |
| 662. | Cl | H | $CF_3$ | Ph | CN | 1 |
| 663. | Cl | H | $CF_3$ | Ph | CN | 2 |
| 664. | Cl | H | $CF_3$ | Ph(4-Cl) | Cl | 0 |
| 665. | Cl | H | $CF_3$ | Ph(4-Cl) | Cl | 1 |
| 666. | Cl | H | $CF_3$ | Ph(4-Cl) | Cl | 2 |
| 667. | Cl | H | Me | Me | $OCH_2CF_3$ | 0 |
| 668. | Cl | H | Me | Me | $OCH_2CF_3$ | 1 |
| 669. | Cl | H | Me | Me | $OCH_2CF_3$ | 2 |
| 670. | Cl | H | $CF_3$ | Me |  | 0 |
| 671. | Cl | H | $CF_3$ | Me |  | 1 |
| 672. | Cl | H | $CF_3$ | Me |  | 2 |
| 673. | Cl | H | $CF_3$ | Me | H | 0 |
| 674. | Cl | H | $CF_3$ | Me | H | 1 |
| 675. | Cl | H | $CF_3$ | Me | H | 2 |
| 676. | Cl | H | $CF_3$ | Me | $OCH_2CH_2OMe$ | 0 |
| 677. | Cl | H | $CF_3$ | Me | $OCH_2CH_2OMe$ | 1 |
| 678. | Cl | H | $CF_3$ | Me | $OCH_2CH_2OMe$ | 2 |
| 679. | Cl | H | $CF_3$ | Me | SMe | 0 |
| 680. | Cl | H | $CF_3$ | Me | SMe | 1 |
| 681. | Cl | H | $CF_3$ | Me | SMe | 2 |
| 682. | Cl | H | $CF_3$ | Me | $OCH_2CH_2CH_2F$ | 0 |
| 683. | Cl | H | $CF_3$ | Me | $OCH_2CH_2CH_2F$ | 1 |
| 684. | Cl | H | $CF_3$ | Me | $OCH_2CH_2CH_2F$ | 2 |
| 685. | Cl | H | $CF_3$ | Me | $OCH(CH_2F)_2$ | 0 |
| 686. | Cl | H | $CF_3$ | Me | $OCH(CH_2F)_2$ | 1 |
| 687. | Cl | H | $CF_3$ | Me | $OCH(CH_2F)_2$ | 2 |
| 688. | Cl | H | $CF_3$ | Me | $OCH_2CF_2CHF_2$ | 0 |
| 689. | Cl | H | $CF_3$ | Me | $OCH_2CF_2CHF_2$ | 1 |
| 690. | Cl | H | $CF_3$ | Me | $OCH_2CF_2CHF_2$ | 2 |
| 691. | Cl | H | $CF_3$ | Me | $OCH_2CF=CH_2$ | 0 |
| 692. | Cl | H | $CF_3$ | Me | $OCH_2CF=CH_2$ | 1 |
| 693. | Cl | H | $CF_3$ | Me | $OCH_2CF=CH_2$ | 2 |
| 694. | Cl | H | $CF_3$ | Me | $OCH(Me)CF_3$ | 0 |
| 695. | Cl | H | $CF_3$ | Me | $OCH(Me)CF_3$ | 1 |
| 696. | Cl | H | $CF_3$ | Me | $OCH(Me)CF_3$ | 2 |
| 697. | Cl | H | $CF_3$ | Me | $OCH(Me)CH_2F$ | 0 |
| 698. | Cl | H | $CF_3$ | Me | $OCH(Me)CH_2F$ | 1 |
| 699. | Cl | H | $CF_3$ | Me | $OCH(Me)CH_2F$ | 2 |
| 700. | Cl | H | $OCH_2CF_3$ | Me | $CF_3$ | 0 |
| 701. | Cl | H | $OCH_2CF_3$ | Me | $CF_3$ | 1 |
| 702. | Cl | H | $OCH_2CF_3$ | Me | $CF_3$ | 2 |
| 703. | Cl | H | $OCH_2CF_3$ | Me | $CHF_2$ | 0 |
| 704. | Cl | H | $OCH_2CF_3$ | Me | $CHF_2$ | 1 |
| 705. | Cl | H | $OCH_2CF_3$ | Me | $CHF_2$ | 2 |
| 706. | Cl | H | $CHF_2$ | Me | $CHF_2$ | 0 |
| 707. | Cl | H | $CHF_2$ | Me | $CHF_2$ | 1 |
| 708. | Cl | H | $CHF_2$ | Me | $CHF_2$ | 2 |
| 709. | Cl | H | $CF_3$ | Me | $CHF_2$ | 0 |
| 710. | Cl | H | $CF_3$ | Me | $CHF_2$ | 1 |
| 711. | Cl | H | $CF_3$ | Me | $CHF_2$ | 2 |
| 712. | Cl | H | Cl | Me | $OCHF_2$ | 0 |
| 713. | Cl | H | Cl | Me | $OCHF_2$ | 1 |
| 714. | Cl | H | Cl | Me | $OCHF_2$ | 2 |
| 715. | Cl | H | Br | Me | $OCHF_2$ | 0 |
| 716. | Cl | H | Br | Me | $OCHF_2$ | 1 |
| 717. | Cl | H | Br | Me | $OCHF_2$ | 2 |
| 718. | Cl | H | Br | Me | $CF_3$ | 0 |
| 719. | Cl | H | Br | Me | $CF_3$ | 1 |
| 720. | Cl | H | Br | Me | $CF_3$ | 2 |
| 721. | Cl | H | $CF_3$ | Me | $CF_3$ | 0 |
| 722. | Cl | H | $CF_3$ | Me | $CF_3$ | 1 |
| 723. | Cl | H | $CF_3$ | Me | $CF_3$ | 2 |
| 724. | Cl | H | $CHF_2$ | Me | $CF_3$ | 0 |
| 725. | Cl | H | $CHF_2$ | Me | $CF_3$ | 1 |
| 726. | Cl | H | $CHF_2$ | Me | $CF_3$ | 2 |
| 727. | Cl | H | $CF_2CF_3$ | Me | $CF_3$ | 0 |
| 728. | Cl | H | $CF_2CF_3$ | Me | $CF_3$ | 1 |
| 729. | Cl | H | $CF_2CF_3$ | Me | $CF_3$ | 2 |
| 730. | Cl | H | $CF_3$ | Me | $CF_2CF_3$ | 0 |
| 731. | Cl | H | $CF_3$ | Me | $CF_2CF_3$ | 1 |
| 732. | Cl | H | $CF_3$ | Me | $CF_2CF_3$ | 2 |
| 733. | Cl | H | $CHF_2$ | Me | $OCH_2CF_3$ | 0 |
| 734. | Cl | H | $CHF_2$ | Me | $OCH_2CF_3$ | 1 |
| 735. | Cl | H | $CHF_2$ | Me | $OCH_2CF_3$ | 2 |
| 736. | Cl | H | $CHF_2$ | Me | $OCHF_2$ | 0 |
| 737. | Cl | H | $CHF_2$ | Me | $OCHF_2$ | 1 |
| 738. | Cl | H | $CHF_2$ | Me | $OCHF_2$ | 2 |
| 739. | Br | H | $CF_3$ | Ph | Cl | 0 |
| 740. | Br | H | $CF_3$ | Ph | Cl | 1 |
| 741. | Br | H | $CF_3$ | Ph | Cl | 2 |
| 742. | Br | H | $CF_3$ | tBu | Cl | 0 |
| 743. | Br | H | $CF_3$ | tBu | Cl | 1 |
| 744. | Br | H | $CF_3$ | tBu | Cl | 2 |
| 745. | Br | H | $CF_3$ | $CHF_2$ | Cl | 0 |
| 746. | Br | H | $CF_3$ | $CHF_2$ | Cl | 1 |
| 747. | Br | H | $CF_3$ | $CHF_2$ | Cl | 2 |
| 748. | Br | H | Cl | $CHF_2$ | $CF_3$ | 0 |
| 749. | Br | H | Cl | $CHF_2$ | $CF_3$ | 1 |
| 750. | Br | H | Cl | $CHF_2$ | $CF_3$ | 2 |
| 751. | Br | H | $CF_3$ | Me | OMe | 0 |
| 752. | Br | H | $CF_3$ | Me | OMe | 1 |
| 753. | Br | H | $CF_3$ | Me | OMe | 2 |
| 754. | Br | H | $CF_3$ | Me | CN | 0 |
| 755. | Br | H | $CF_3$ | Me | CN | 1 |
| 756. | Br | H | $CF_3$ | Me | CN | 2 |
| 757. | Br | H | Cl | Et | Cl | 0 |
| 758. | Br | H | Cl | Et | Cl | 1 |
| 759. | Br | H | Cl | Et | Cl | 2 |
| 760. | Br | H | $CHF_2$ | Me | Cl | 0 |
| 761. | Br | H | $CHF_2$ | Me | Cl | 1 |
| 762. | Br | H | $CHF_2$ | Me | Cl | 2 |
| 763. | Br | H | Me | Me | Me | 0 |
| 764. | Br | H | Me | Me | Me | 1 |
| 765. | Br | H | Me | Me | Me | 2 |
| 766. | Br | H | Me | Me | Cl | 0 |
| 767. | Br | H | Me | Me | Cl | 1 |
| 768. | Br | H | Me | Me | Cl | 2 |
| 769. | Br | H | Cl | Me | Cl | 0 |
| 770. | Br | H | Cl | Me | Cl | 1 |
| 771. | Br | H | Cl | Me | Cl | 2 |
| 772. | Br | H | $CF_3$ | Me | Cl | 0 |

TABLE 1-continued

Compounds of the formula (I)

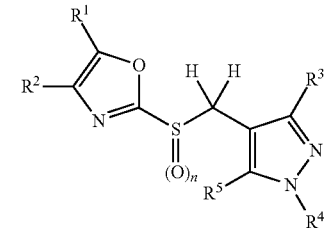

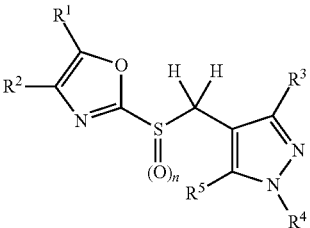

| Ex. No. | R¹ | R² | R³ | R⁴ | R⁵ | n |
|---|---|---|---|---|---|---|
| 773. | Br | H | CF₃ | Me | Cl | 1 |
| 774. | Br | H | CF₃ | Me | Cl | 2 |
| 775. | Br | H | Cl | Me | CF₃ | 0 |
| 776. | Br | H | Cl | Me | CF₃ | 1 |
| 777. | Br | H | Cl | Me | CF₃ | 2 |
| 778. | Br | H | CF₃ | Me | F | 0 |
| 779. | Br | H | CF₃ | Me | F | 1 |
| 780. | Br | H | CF₃ | Me | F | 2 |
| 781. | Br | H | OMe | Me | CF₃ | 0 |
| 782. | Br | H | OMe | Me | CF₃ | 1 |
| 783. | Br | H | OMe | Me | CF₃ | 2 |
| 784. | Br | H | CF₃ | Me | OEt | 0 |
| 785. | Br | H | CF₃ | Me | OEt | 1 |
| 786. | Br | H | CF₃ | Me | OEt | 2 |
| 787. | Br | H | CF₃ | Me | OCHF₂ | 0 |
| 788. | Br | H | CF₃ | Me | OCHF₂ | 1 |
| 789. | Br | H | CF₃ | Me | OCHF₂ | 2 |
| 790. | Br | H | OCHF₂ | Me | CF₃ | 0 |
| 791. | Br | H | OCHF₂ | Me | CF₃ | 1 |
| 792. | Br | H | OCHF₂ | Me | CF₃ | 2 |
| 793. | Br | H | CF₃ | Me | OCH₂CHF₂ | 0 |
| 794. | Br | H | CF₃ | Me | OCH₂CHF₂ | 1 |
| 795. | Br | H | CF₃ | Me | OCH₂CHF₂ | 2 |
| 796. | Br | H | CF₃ | Me | OCH₂CF₃ | 0 |
| 797. | Br | H | CF₃ | Me | OCH₂CF₃ | 1 |
| 798. | Br | H | CF₃ | Me | OCH₂CF₃ | 2 |
| 799. | Br | H | CF₃ | Me | OCH₂CN | 0 |
| 800. | Br | H | CF₃ | Me | OCH₂CN | 1 |
| 801. | Br | H | CF₃ | Me | OCH₂CN | 2 |
| 802. | Br | H | CF₃ | Me | SO₂Me | 0 |
| 803. | Br | H | CF₃ | Me | SO₂Me | 1 |
| 804. | Br | H | CF₃ | Me | SO₂Me | 2 |
| 805. | Br | H | CF₃ | Me | SEt | 0 |
| 806. | Br | H | CF₃ | Me | SEt | 1 |
| 807. | Br | H | CF₃ | Me | SEt | 2 |
| 808. | Br | H | CF₃ | Me | Me | 0 |
| 809. | Br | H | CF₃ | Me | Me | 1 |
| 810. | Br | H | CF₃ | Me | Me | 2 |
| 811. | Br | H | CF₃ | Me | Et | 0 |
| 812. | Br | H | CF₃ | Me | Et | 1 |
| 813. | Br | H | CF₃ | Me | Et | 2 |
| 814. | Br | H | CF₃ | Et | Cl | 0 |
| 815. | Br | H | CF₃ | Et | Cl | 1 |
| 816. | Br | H | CF₃ | Et | Cl | 2 |
| 817. | Br | H | Cl | Et | CF₃ | 0 |
| 818. | Br | H | Cl | Et | CF₃ | 1 |
| 819. | Br | H | Cl | Et | CF₃ | 2 |
| 820. | Br | H | CF₃ | iPr | Cl | 0 |
| 821. | Br | H | CF₃ | iPr | Cl | 1 |
| 822. | Br | H | CF₃ | iPr | Cl | 2 |
| 823. | Br | H | Cl | iPr | CF₃ | 0 |
| 824. | Br | H | Cl | iPr | CF₃ | 1 |
| 825. | Br | H | Cl | iPr | CF₃ | 2 |
| 826. | Br | H | CF₃ | tBu | Cl | 0 |
| 827. | Br | H | CF₃ | tBu | Cl | 1 |
| 828. | Br | H | CF₃ | tBu | Cl | 2 |
| 829. | Br | H | Cl | tBu | CF₃ | 0 |
| 830. | Br | H | Cl | tBu | CF₃ | 1 |
| 831. | Br | H | Cl | tBu | CF₃ | 2 |
| 832. | Br | H | CF₃ | cPen | Cl | 0 |
| 833. | Br | H | CF₃ | cPen | Cl | 1 |
| 834. | Br | H | CF₃ | cPen | Cl | 2 |
| 835. | Br | H | Cl | cPen | CF₃ | 0 |
| 836. | Br | H | Cl | cPen | CF₃ | 1 |
| 837. | Br | H | Cl | cPen | CF₃ | 2 |
| 838. | Br | H | CF₃ | CH₂cPr | Cl | 0 |
| 839. | Br | H | CF₃ | CH₂cPr | Cl | 1 |
| 840. | Br | H | CF₃ | CH₂cPr | Cl | 2 |
| 841. | Br | H | Cl | CH₂cPr | CF₃ | 0 |
| 842. | Br | H | Cl | CH₂cPr | CF₃ | 1 |
| 843. | Br | H | Cl | CH₂cPr | CF₃ | 2 |
| 844. | Br | H | CF₃ | CH₂CH=CH₂ | Cl | 0 |
| 845. | Br | H | CF₃ | CH₂CH=CH₂ | Cl | 1 |
| 846. | Br | H | CF₃ | CH₂CH=CH₂ | Cl | 2 |
| 847. | Br | H | Cl | CH₂CH=CH₂ | CF₃ | 0 |
| 848. | Br | H | Cl | CH₂CH=CH₂ | CF₃ | 1 |
| 849. | Br | H | Cl | CH₂CH=CH₂ | CF₃ | 2 |
| 850. | Br | H | CF₃ | CHF₂ | OMe | 0 |
| 851. | Br | H | CF₃ | CHF₂ | OMe | 1 |
| 852. | Br | H | CF₃ | CHF₂ | OMe | 2 |
| 853. | Br | H | OMe | CHF₂ | CF₃ | 0 |
| 854. | Br | H | OMe | CHF₂ | CF₃ | 1 |
| 855. | Br | H | OMe | CHF₂ | CF₃ | 2 |
| 856. | Br | H | CF₃ | CH₂CF₃ | Cl | 0 |
| 857. | Br | H | CF₃ | CH₂CF₃ | Cl | 1 |
| 858. | Br | H | CF₃ | CH₂CF₃ | Cl | 2 |
| 859. | Br | H | Cl | CH₂CF₃ | CF₃ | 0 |
| 860. | Br | H | Cl | CH₂CF₃ | CF₃ | 1 |
| 861. | Br | H | Cl | CH₂CF₃ | CF₃ | 2 |
| 862. | Br | H | CF₃ | CH₂OMe | Cl | 0 |
| 863. | Br | H | CF₃ | CH₂OMe | Cl | 1 |
| 864. | Br | H | CF₃ | CH₂OMe | Cl | 2 |
| 865. | Br | H | Cl | CH₂OMe | CF₃ | 0 |
| 866. | Br | H | Cl | CH₂OMe | CF₃ | 1 |
| 867. | Br | H | Cl | CH₂OMe | CF₃ | 2 |
| 868. | Br | H | CF₃ | CH₂CN | Cl | 0 |
| 869. | Br | H | CF₃ | CH₂CN | Cl | 1 |
| 870. | Br | H | CF₃ | CH₂CN | Cl | 2 |
| 871. | Br | H | Me | Ph | Me | 0 |
| 872. | Br | H | Me | Ph | Me | 1 |
| 873. | Br | H | Me | Ph | Me | 2 |
| 874. | Br | H | Me | Ph | Cl | 0 |
| 875. | Br | H | Me | Ph | Cl | 1 |
| 876. | Br | H | Me | Ph | Cl | 2 |
| 877. | Br | H | Et | Ph | Cl | 0 |
| 878. | Br | H | Et | Ph | Cl | 1 |
| 879. | Br | H | Et | Ph | Cl | 2 |
| 880. | Br | H | Pr | Ph | Cl | 0 |
| 881. | Br | H | Pr | Ph | Cl | 1 |
| 882. | Br | H | Pr | Ph | Cl | 2 |
| 883. | Br | H | iPr | Ph | Cl | 0 |
| 884. | Br | H | iPr | Ph | Cl | 1 |
| 885. | Br | H | iPr | Ph | Cl | 2 |
| 886. | Br | H | CF₃ | Ph | Cl | 0 |
| 887. | Br | H | CF₃ | Ph | Cl | 1 |
| 888. | Br | H | CF₃ | Ph | Cl | 2 |
| 889. | Br | H | CF₃ | Ph | Me | 0 |
| 890. | Br | H | CF₃ | Ph | Me | 1 |
| 891. | Br | H | CF₃ | Ph | Me | 2 |
| 892. | Br | H | CF₃ | Ph | CF₃ | 0 |
| 893. | Br | H | CF₃ | Ph | CF₃ | 1 |
| 894. | Br | H | CF₃ | Ph | CF₃ | 2 |
| 895. | Br | H | CF₃ | Ph | F | 0 |
| 896. | Br | H | CF₃ | Ph | F | 1 |

TABLE 1-continued

Compounds of the formula (I)

| Ex. No. | R¹ | R² | R³ | R⁴ | R⁵ | n |
|---|---|---|---|---|---|---|
| 897. | Br | H | $CF_3$ | Ph | F | 2 |
| 898. | Br | H | $CF_3$ | Ph | OMe | 0 |
| 899. | Br | H | $CF_3$ | Ph | OMe | 1 |
| 900. | Br | H | $CF_3$ | Ph | OMe | 2 |
| 901. | Br | H | $CF_3$ | Ph | OEt | 0 |
| 902. | Br | H | $CF_3$ | Ph | OEt | 1 |
| 903. | Br | H | $CF_3$ | Ph | OEt | 2 |
| 904. | Br | H | $CF_3$ | Ph | $OCHF_2$ | 0 |
| 905. | Br | H | $CF_3$ | Ph | $OCHF_2$ | 1 |
| 906. | Br | H | $CF_3$ | Ph | $OCHF_2$ | 2 |
| 907. | Br | H | $CF_3$ | Ph | CN | 0 |
| 908. | Br | H | $CF_3$ | Ph | CN | 1 |
| 909. | Br | H | $CF_3$ | Ph | CN | 2 |
| 910. | Br | H | $CF_3$ | Ph(4-Cl) | Cl | 0 |
| 911. | Br | H | $CF_3$ | Ph(4-Cl) | Cl | 1 |
| 912. | Br | H | $CF_3$ | Ph(4-Cl) | Cl | 2 |
| 913. | Br | H | Me | Me | $OCH_2CF_3$ | 0 |
| 914. | Br | H | Me | Me | $OCH_2CF_3$ | 1 |
| 915. | Br | H | Me | Me | $OCH_2CF_3$ | 2 |
| 916. | Br | H | $CF_3$ | Me |  | 0 |
| 917. | Br | H | $CF_3$ | Me |  | 1 |
| 918. | Br | H | $CF_3$ | Me |  | 2 |
| 919. | Br | H | $CF_3$ | Me | H | 0 |
| 920. | Br | H | $CF_3$ | Me | H | 1 |
| 921. | Br | H | $CF_3$ | Me | H | 2 |
| 922. | Br | H | $CF_3$ | Me | $OCH_2CH_2OMe$ | 0 |
| 923. | Br | H | $CF_3$ | Me | $OCH_2CH_2OMe$ | 1 |
| 924. | Br | H | $CF_3$ | Me | $OCH_2CH_2OMe$ | 2 |
| 925. | Br | H | $CF_3$ | Me | SMe | 0 |
| 926. | Br | H | $CF_3$ | Me | SMe | 1 |
| 927. | Br | H | $CF_3$ | Me | SMe | 2 |
| 928. | Br | H | $CF_3$ | Me | $OCH_2CH_2CH_2F$ | 0 |
| 929. | Br | H | $CF_3$ | Me | $OCH_2CH_2CH_2F$ | 1 |
| 930. | Br | H | $CF_3$ | Me | $OCH_2CH_2CH_2F$ | 2 |
| 931. | Br | H | $CF_3$ | Me | $OCH(CH_2F)_2$ | 0 |
| 932. | Br | H | $CF_3$ | Me | $OCH(CH_2F)_2$ | 1 |
| 933. | Br | H | $CF_3$ | Me | $OCH(CH_2F)_2$ | 2 |
| 934. | Br | H | $CF_3$ | Me | $OCH_2CF_2CHF_2$ | 0 |
| 935. | Br | H | $CF_3$ | Me | $OCH_2CF_2CHF_2$ | 1 |
| 936. | Br | H | $CF_3$ | Me | $OCH_2CF_2CHF_2$ | 2 |
| 937. | Br | H | $CF_3$ | Me | $OCH_2CF=CH_2$ | 0 |
| 938. | Br | H | $CF_3$ | Me | $OCH_2CF=CH_2$ | 1 |
| 939. | Br | H | $CF_3$ | Me | $OCH_2CF=CH_2$ | 2 |
| 940. | Br | H | $CF_3$ | Me | $OCH(Me)CF_3$ | 0 |
| 941. | Br | H | $CF_3$ | Me | $OCH(Me)CF_3$ | 1 |
| 942. | Br | H | $CF_3$ | Me | $OCH(Me)CF_3$ | 2 |
| 943. | Br | H | $CF_3$ | Me | $OCH(Me)CH_2F$ | 0 |
| 944. | Br | H | $CF_3$ | Me | $OCH(Me)CH_2F$ | 1 |
| 945. | Br | H | $CF_3$ | Me | $OCH(Me)CH_2F$ | 2 |
| 946. | Br | H | $OCH_2CF_3$ | Me | $CF_3$ | 0 |
| 947. | Br | H | $OCH_2CF_3$ | Me | $CF_3$ | 1 |
| 948. | Br | H | $OCH_2CF_3$ | Me | $CF_3$ | 2 |
| 949. | Br | H | $OCH_2CF_3$ | Me | $CHF_2$ | 0 |
| 950. | Br | H | $OCH_2CF_3$ | Me | $CHF_2$ | 1 |
| 951. | Br | H | $OCH_2CF_3$ | Me | $CHF_2$ | 2 |
| 952. | Br | H | $CHF_2$ | Me | $CHF_2$ | 0 |
| 953. | Br | H | $CHF_2$ | Me | $CHF_2$ | 1 |
| 954. | Br | H | $CHF_2$ | Me | $CHF_2$ | 2 |
| 955. | Br | H | $CF_3$ | Me | $CHF_2$ | 0 |
| 956. | Br | H | $CF_3$ | Me | $CHF_2$ | 1 |
| 957. | Br | H | $CF_3$ | Me | $CHF_2$ | 2 |
| 958. | Br | H | Cl | Me | $OCHF_2$ | 0 |
| 959. | Br | H | Cl | Me | $OCHF_2$ | 1 |
| 960. | Br | H | Cl | Me | $OCHF_2$ | 2 |
| 961. | Br | H | Br | Me | $OCHF_2$ | 0 |
| 962. | Br | H | Br | Me | $OCHF_2$ | 1 |
| 963. | Br | H | Br | Me | $OCHF_2$ | 2 |
| 964. | Br | H | Br | Me | $CF_3$ | 0 |
| 965. | Br | H | Br | Me | $CF_3$ | 1 |
| 966. | Br | H | Br | Me | $CF_3$ | 2 |
| 967. | Br | H | $CF_3$ | Me | $CF_3$ | 0 |
| 968. | Br | H | $CF_3$ | Me | $CF_3$ | 1 |
| 969. | Br | H | $CF_3$ | Me | $CF_3$ | 2 |
| 970. | Br | H | $CHF_2$ | Me | $CF_3$ | 0 |
| 971. | Br | H | $CHF_2$ | Me | $CF_3$ | 1 |
| 972. | Br | H | $CHF_2$ | Me | $CF_3$ | 2 |
| 973. | Br | H | $CF_2CF_3$ | Me | $CF_3$ | 0 |
| 974. | Br | H | $CF_2CF_3$ | Me | $CF_3$ | 1 |
| 975. | Br | H | $CF_2CF_3$ | Me | $CF_3$ | 2 |
| 976. | Br | H | $CF_3$ | Me | $CF_2CF_3$ | 0 |
| 977. | Br | H | $CF_3$ | Me | $CF_2CF_3$ | 1 |
| 978. | Br | H | $CF_3$ | Me | $CF_2CF_3$ | 2 |
| 979. | Br | H | $CHF_2$ | Me | $OCH_2CF_3$ | 0 |
| 980. | Br | H | $CHF_2$ | Me | $OCH_2CF_3$ | 1 |
| 981. | Br | H | $CHF_2$ | Me | $OCH_2CF_3$ | 2 |
| 982. | Br | H | $CHF_2$ | Me | $OCHF_2$ | 0 |
| 983. | Br | H | $CHF_2$ | Me | $OCHF_2$ | 1 |
| 984. | Br | H | $CHF_2$ | Me | $OCHF_2$ | 2 |
| 985. | I | H | $CF_3$ | Ph | Cl | 0 |
| 986. | I | H | $CF_3$ | Ph | Cl | 1 |
| 987. | I | H | $CF_3$ | Ph | Cl | 2 |
| 988. | I | H | $CF_3$ | tBu | Cl | 0 |
| 989. | I | H | $CF_3$ | tBu | Cl | 1 |
| 990. | I | H | $CF_3$ | tBu | Cl | 2 |
| 991. | I | H | $CF_3$ | $CHF_2$ | Cl | 0 |
| 992. | I | H | $CF_3$ | $CHF_2$ | Cl | 1 |
| 993. | I | H | $CF_3$ | $CHF_2$ | Cl | 2 |
| 994. | I | H | Cl | $CHF_2$ | $CF_3$ | 0 |
| 995. | I | H | Cl | $CHF_2$ | $CF_3$ | 1 |
| 996. | I | H | Cl | $CHF_2$ | $CF_3$ | 2 |
| 997. | I | H | $CF_3$ | Me | OMe | 0 |
| 998. | I | H | $CF_3$ | Me | OMe | 1 |
| 999. | I | H | $CF_3$ | Me | OMe | 2 |
| 1000. | I | H | $CF_3$ | Me | CN | 0 |
| 1001. | I | H | $CF_3$ | Me | CN | 1 |
| 1002. | I | H | $CF_3$ | Me | CN | 2 |
| 1003. | I | H | Cl | Et | Cl | 0 |
| 1004. | I | H | Cl | Et | Cl | 1 |
| 1005. | I | H | Cl | Et | Cl | 2 |
| 1006. | I | H | $CHF_2$ | Me | Cl | 0 |
| 1007. | I | H | $CHF_2$ | Me | Cl | 1 |
| 1008. | I | H | $CHF_2$ | Me | Cl | 2 |
| 1009. | I | H | Me | Me | Me | 0 |

TABLE 1-continued

Compounds of the formula (I)

(I)

| Ex. No. | R¹ | R² | R³ | R⁴ | R⁵ | n |
|---|---|---|---|---|---|---|
| 1010. | I | H | Me | Me | Me | 1 |
| 1011. | I | H | Me | Me | Me | 2 |
| 1012. | I | H | Me | Me | Cl | 0 |
| 1013. | I | H | Me | Me | Cl | 1 |
| 1014. | I | H | Me | Me | Cl | 2 |
| 1015. | I | H | Cl | Me | Cl | 0 |
| 1016. | I | H | Cl | Me | Cl | 1 |
| 1017. | I | H | Cl | Me | Cl | 2 |
| 1018. | I | H | CF₃ | Me | Cl | 0 |
| 1019. | I | H | CF₃ | Me | Cl | 1 |
| 1020. | I | H | CF₃ | Me | Cl | 2 |
| 1021. | I | H | Cl | Me | CF₃ | 0 |
| 1022. | I | H | Cl | Me | CF₃ | 1 |
| 1023. | I | H | Cl | Me | CF₃ | 2 |
| 1024. | I | H | CF₃ | Me | F | 0 |
| 1025. | I | H | CF₃ | Me | F | 1 |
| 1026. | I | H | CF₃ | Me | F | 2 |
| 1027. | I | H | OMe | Me | CF₃ | 0 |
| 1028. | I | H | OMe | Me | CF₃ | 1 |
| 1029. | I | H | OMe | Me | CF₃ | 2 |
| 1030. | I | H | CF₃ | Me | OEt | 0 |
| 1031. | I | H | CF₃ | Me | OEt | 1 |
| 1032. | I | H | CF₃ | Me | OEt | 2 |
| 1033. | I | H | CF₃ | Me | OCHF₂ | 0 |
| 1034. | I | H | CF₃ | Me | OCHF₂ | 1 |
| 1035. | I | H | CF₃ | Me | OCHF₂ | 2 |
| 1036. | I | H | OCHF₂ | Me | CF₃ | 0 |
| 1037. | I | H | OCHF₂ | Me | CF₃ | 1 |
| 1038. | I | H | OCHF₂ | Me | CF₃ | 2 |
| 1039. | I | H | CF₃ | Me | OCH₂CHF₂ | 0 |
| 1040. | I | H | CF₃ | Me | OCH₂CHF₂ | 1 |
| 1041. | I | H | CF₃ | Me | OCH₂CHF₂ | 2 |
| 1042. | I | H | CF₃ | Me | OCH₂CF₃ | 0 |
| 1043. | I | H | CF₃ | Me | OCH₂CF₃ | 1 |
| 1044. | I | H | CF₃ | Me | OCH₂CF₃ | 2 |
| 1045. | I | H | CF₃ | Me | OCH₂CN | 0 |
| 1046. | I | H | CF₃ | Me | OCH₂CN | 1 |
| 1047. | I | H | CF₃ | Me | OCH₂CN | 2 |
| 1048. | I | H | CF₃ | Me | SO₂Me | 0 |
| 1049. | I | H | CF₃ | Me | SO₂Me | 1 |
| 1050. | I | H | CF₃ | Me | SO₂Me | 2 |
| 1051. | I | H | CF₃ | Me | SEt | 0 |
| 1052. | I | H | CF₃ | Me | SEt | 1 |
| 1053. | I | H | CF₃ | Me | SEt | 2 |
| 1054. | I | H | CF₃ | Me | Me | 0 |
| 1055. | I | H | CF₃ | Me | Me | 1 |
| 1056. | I | H | CF₃ | Me | Me | 2 |
| 1057. | I | H | CF₃ | Me | Et | 0 |
| 1058. | I | H | CF₃ | Me | Et | 1 |
| 1059. | I | H | CF₃ | Me | Et | 2 |
| 1060. | I | H | CF₃ | Et | Cl | 0 |
| 1061. | I | H | CF₃ | Et | Cl | 1 |
| 1062. | I | H | CF₃ | Et | Cl | 2 |
| 1063. | I | H | Cl | Et | CF₃ | 0 |
| 1064. | I | H | Cl | Et | CF₃ | 1 |
| 1065. | I | H | Cl | Et | CF₃ | 2 |
| 1066. | I | H | CF₃ | iPr | Cl | 0 |
| 1067. | I | H | CF₃ | iPr | Cl | 1 |
| 1068. | I | H | CF₃ | iPr | Cl | 2 |
| 1069. | I | H | Cl | iPr | CF₃ | 0 |
| 1070. | I | H | Cl | iPr | CF₃ | 1 |
| 1071. | I | H | Cl | iPr | CF₃ | 2 |
| 1072. | I | H | CF₃ | tBu | Cl | 0 |
| 1073. | I | H | CF₃ | tBu | Cl | 1 |
| 1074. | I | H | CF₃ | tBu | Cl | 2 |
| 1075. | I | H | Cl | tBu | CF₃ | 0 |
| 1076. | I | H | Cl | tBu | CF₃ | 1 |
| 1077. | I | H | Cl | tBu | CF₃ | 2 |
| 1078. | I | H | CF₃ | cPen | Cl | 0 |
| 1079. | I | H | CF₃ | cPen | Cl | 1 |
| 1080. | I | H | CF₃ | cPen | Cl | 2 |
| 1081. | I | H | Cl | cPen | CF₃ | 0 |
| 1082. | I | H | Cl | cPen | CF₃ | 1 |
| 1083. | I | H | Cl | cPen | CF₃ | 2 |
| 1084. | I | H | CF₃ | CH₂cPr | Cl | 0 |
| 1085. | I | H | CF₃ | CH₂cPr | Cl | 1 |
| 1086. | I | H | CF₃ | CH₂cPr | Cl | 2 |
| 1087. | I | H | Cl | CH₂cPr | CF₃ | 0 |
| 1088. | I | H | Cl | CH₂cPr | CF₃ | 1 |
| 1089. | I | H | Cl | CH₂cPr | CF₃ | 2 |
| 1090. | I | H | CF₃ | CH₂CH=CH₂ | Cl | 0 |
| 1091. | I | H | CF₃ | CH₂CH=CH₂ | Cl | 1 |
| 1092. | I | H | CF₃ | CH₂CH=CH₂ | Cl | 2 |
| 1093. | I | H | Cl | CH₂CH=CH₂ | CF₃ | 0 |
| 1094. | I | H | Cl | CH₂CH=CH₂ | CF₃ | 1 |
| 1095. | I | H | Cl | CH₂CH=CH₂ | CF₃ | 2 |
| 1096. | I | H | CF₃ | CHF₂ | OMe | 0 |
| 1097. | I | H | CF₃ | CHF₂ | OMe | 1 |
| 1098. | I | H | CF₃ | CHF₂ | OMe | 2 |
| 1099. | I | H | OMe | CHF₂ | CF₃ | 0 |
| 1100. | I | H | OMe | CHF₂ | CF₃ | 1 |
| 1101. | I | H | OMe | CHF₂ | CF₃ | 2 |
| 1102. | I | H | CF₃ | CH₂CF₃ | Cl | 0 |
| 1103. | I | H | CF₃ | CH₂CF₃ | Cl | 1 |
| 1104. | I | H | CF₃ | CH₂CF₃ | Cl | 2 |
| 1105. | I | H | Cl | CH₂CF₃ | CF₃ | 0 |
| 1106. | I | H | Cl | CH₂CF₃ | CF₃ | 1 |
| 1107. | I | H | Cl | CH₂CF₃ | CF₃ | 2 |
| 1108. | I | H | CF₃ | CH₂OMe | Cl | 0 |
| 1109. | I | H | CF₃ | CH₂OMe | Cl | 1 |
| 1110. | I | H | CF₃ | CH₂OMe | Cl | 2 |
| 1111. | I | H | Cl | CH₂OMe | CF₃ | 0 |
| 1112. | I | H | Cl | CH₂OMe | CF₃ | 1 |
| 1113. | I | H | Cl | CH₂OMe | CF₃ | 2 |
| 1114. | I | H | CF₃ | CH₂CN | Cl | 0 |
| 1115. | I | H | CF₃ | CH₂CN | Cl | 1 |
| 1116. | I | H | CF₃ | CH₂CN | Cl | 2 |
| 1117. | I | H | Me | Ph | Me | 0 |
| 1118. | I | H | Me | Ph | Me | 1 |
| 1119. | I | H | Me | Ph | Me | 2 |
| 1120. | I | H | Me | Ph | Cl | 0 |
| 1121. | I | H | Me | Ph | Cl | 1 |
| 1122. | I | H | Me | Ph | Cl | 2 |
| 1123. | I | H | Et | Ph | Cl | 0 |
| 1124. | I | H | Et | Ph | Cl | 1 |
| 1125. | I | H | Et | Ph | Cl | 2 |
| 1126. | I | H | Pr | Ph | Cl | 0 |
| 1127. | I | H | Pr | Ph | Cl | 1 |
| 1128. | I | H | Pr | Ph | Cl | 2 |
| 1129. | I | H | iPr | Ph | Cl | 0 |
| 1130. | I | H | iPr | Ph | Cl | 1 |
| 1131. | I | H | iPr | Ph | Cl | 2 |
| 1132. | I | H | CF₃ | Ph | Cl | 0 |
| 1133. | I | H | CF₃ | Ph | Cl | 1 |

TABLE 1-continued

Compounds of the formula (I)

| Ex. No. | R¹ | R² | R³ | R⁴ | R⁵ | n |
|---|---|---|---|---|---|---|
| 1134. | I | H | $CF_3$ | Ph | Cl | 2 |
| 1135. | I | H | $CF_3$ | Ph | Me | 0 |
| 1136. | I | H | $CF_3$ | Ph | Me | 1 |
| 1137. | I | H | $CF_3$ | Ph | Me | 2 |
| 1138. | I | H | $CF_3$ | Ph | $CF_3$ | 0 |
| 1139. | I | H | $CF_3$ | Ph | $CF_3$ | 1 |
| 1140. | I | H | $CF_3$ | Ph | $CF_3$ | 2 |
| 1141. | I | H | $CF_3$ | Ph | F | 0 |
| 1142. | I | H | $CF_3$ | Ph | F | 1 |
| 1143. | I | H | $CF_3$ | Ph | F | 2 |
| 1144. | I | H | $CF_3$ | Ph | OMe | 0 |
| 1145. | I | H | $CF_3$ | Ph | OMe | 1 |
| 1146. | I | H | $CF_3$ | Ph | OMe | 2 |
| 1147. | I | H | $CF_3$ | Ph | OEt | 0 |
| 1148. | I | H | $CF_3$ | Ph | OEt | 1 |
| 1149. | I | H | $CF_3$ | Ph | OEt | 2 |
| 1150. | I | H | $CF_3$ | Ph | $OCHF_2$ | 0 |
| 1151. | I | H | $CF_3$ | Ph | $OCHF_2$ | 1 |
| 1152. | I | H | $CF_3$ | Ph | $OCHF_2$ | 2 |
| 1153. | I | H | $CF_3$ | Ph | CN | 0 |
| 1154. | I | H | $CF_3$ | Ph | CN | 1 |
| 1155. | I | H | $CF_3$ | Ph | CN | 2 |
| 1156. | I | H | $CF_3$ | Ph(4-Cl) | Cl | 0 |
| 1157. | I | H | $CF_3$ | Ph(4-Cl) | Cl | 1 |
| 1158. | I | H | $CF_3$ | Ph(4-Cl) | Cl | 2 |
| 1159. | I | H | Me | Me | $OCH_2CF_3$ | 0 |
| 1160. | I | H | Me | Me | $OCH_2CF_3$ | 1 |
| 1161. | I | H | Me | Me | $OCH_2CF_3$ | 2 |
| 1162. | I | H | $CF_3$ | Me | oxetan-3-yloxy | 0 |
| 1163. | I | H | $CF_3$ | Me | oxetan-3-yloxy | 1 |
| 1164. | I | H | $CF_3$ | Me | oxetan-3-yloxy | 2 |
| 1165. | I | H | $CF_3$ | Me | H | 0 |
| 1166. | I | H | $CF_3$ | Me | H | 1 |
| 1167. | I | H | $CF_3$ | Me | H | 2 |
| 1168. | I | H | $CF_3$ | Me | $OCH_2CH_2OMe$ | 0 |
| 1169. | I | H | $CF_3$ | Me | $OCH_2CH_2OMe$ | 1 |
| 1170. | I | H | $CF_3$ | Me | $OCH_2CH_2OMe$ | 2 |
| 1171. | I | H | $CF_3$ | Me | SMe | 0 |
| 1172. | I | H | $CF_3$ | Me | SMe | 1 |
| 1173. | I | H | $CF_3$ | Me | SMe | 2 |
| 1174. | I | H | $CF_3$ | Me | $OCH_2CH_2CH_2F$ | 0 |
| 1175. | I | H | $CF_3$ | Me | $OCH_2CH_2CH_2F$ | 1 |
| 1176. | I | H | $CF_3$ | Me | $OCH_2CH_2CH_2F$ | 2 |
| 1177. | I | H | $CF_3$ | Me | $OCH(CH_2F)_2$ | 0 |
| 1178. | I | H | $CF_3$ | Me | $OCH(CH_2F)_2$ | 1 |
| 1179. | I | H | $CF_3$ | Me | $OCH(CH_2F)_2$ | 2 |
| 1180. | I | H | $CF_3$ | Me | $OCH_2CF_2CHF_2$ | 0 |
| 1181. | I | H | $CF_3$ | Me | $OCH_2CF_2CHF_2$ | 1 |
| 1182. | I | H | $CF_3$ | Me | $OCH_2CF_2CHF_2$ | 2 |
| 1183. | I | H | $CF_3$ | Me | $OCH_2CF=CH_2$ | 0 |
| 1184. | I | H | $CF_3$ | Me | $OCH_2CF=CH_2$ | 1 |
| 1185. | I | H | $CF_3$ | Me | $OCH_2CF=CH_2$ | 2 |
| 1186. | I | H | $CF_3$ | Me | $OCH(Me)CF_3$ | 0 |
| 1187. | I | H | $CF_3$ | Me | $OCH(Me)CF_3$ | 1 |
| 1188. | I | H | $CF_3$ | Me | $OCH(Me)CF_3$ | 2 |
| 1189. | I | H | $CF_3$ | Me | $OCH(Me)CH_2F$ | 0 |
| 1190. | I | H | $CF_3$ | Me | $OCH(Me)CH_2F$ | 1 |
| 1191. | I | H | $CF_3$ | Me | $OCH(Me)CH_2F$ | 2 |
| 1192. | I | H | $OCH_2CF_3$ | Me | $CF_3$ | 0 |
| 1193. | I | H | $OCH_2CF_3$ | Me | $CF_3$ | 1 |
| 1194. | I | H | $OCH_2CF_3$ | Me | $CF_3$ | 2 |
| 1195. | I | H | $OCH_2CF_3$ | Me | $CHF_2$ | 0 |
| 1196. | I | H | $OCH_2CF_3$ | Me | $CHF_2$ | 1 |
| 1197. | I | H | $OCH_2CF_3$ | Me | $CHF_2$ | 2 |
| 1198. | I | H | $CHF_2$ | Me | $CHF_2$ | 0 |
| 1199. | I | H | $CHF_2$ | Me | $CHF_2$ | 1 |
| 1200. | I | H | $CHF_2$ | Me | $CHF_2$ | 2 |
| 1201. | I | H | $CF_3$ | Me | $CHF_2$ | 0 |
| 1202. | I | H | $CF_3$ | Me | $CHF_2$ | 1 |
| 1203. | I | H | $CF_3$ | Me | $CHF_2$ | 2 |
| 1204. | I | H | Cl | Me | $OCHF_2$ | 0 |
| 1205. | I | H | Cl | Me | $OCHF_2$ | 1 |
| 1206. | I | H | Cl | Me | $OCHF_2$ | 2 |
| 1207. | I | H | Br | Me | $OCHF_2$ | 0 |
| 1208. | I | H | Br | Me | $OCHF_2$ | 1 |
| 1209. | I | H | Br | Me | $OCHF_2$ | 2 |
| 1210. | I | H | Br | Me | $CF_3$ | 0 |
| 1211. | I | H | Br | Me | $CF_3$ | 1 |
| 1212. | I | H | Br | Me | $CF_3$ | 2 |
| 1213. | I | H | $CF_3$ | Me | $CF_3$ | 0 |
| 1214. | I | H | $CF_3$ | Me | $CF_3$ | 1 |
| 1215. | I | H | $CF_3$ | Me | $CF_3$ | 2 |
| 1216. | I | H | $CHF_2$ | Me | $CF_3$ | 0 |
| 1217. | I | H | $CHF_2$ | Me | $CF_3$ | 1 |
| 1218. | I | H | $CHF_2$ | Me | $CF_3$ | 2 |
| 1219. | I | H | $CF_2CF_3$ | Me | $CF_3$ | 0 |
| 1220. | I | H | $CF_2CF_3$ | Me | $CF_3$ | 1 |
| 1221. | I | H | $CF_2CF_3$ | Me | $CF_3$ | 2 |
| 1222. | I | H | $CF_3$ | Me | $CF_2CF_3$ | 0 |
| 1223. | I | H | $CF_3$ | Me | $CF_2CF_3$ | 1 |
| 1224. | I | H | $CF_3$ | Me | $CF_2CF_3$ | 2 |
| 1225. | I | H | $CHF_2$ | Me | $OCH_2CF_3$ | 0 |
| 1226. | I | H | $CHF_2$ | Me | $OCH_2CF_3$ | 1 |
| 1227. | I | H | $CHF_2$ | Me | $OCH_2CF_3$ | 2 |
| 1228. | I | H | $CHF_2$ | Me | $OCHF_2$ | 0 |
| 1229. | I | H | $CHF_2$ | Me | $OCHF_2$ | 1 |
| 1230. | I | H | $CHF_2$ | Me | $OCHF_2$ | 2 |
| 1231. | H | F | $CF_3$ | Ph | Cl | 0 |
| 1232. | H | F | $CF_3$ | Ph | Cl | 1 |
| 1233. | H | F | $CF_3$ | Ph | Cl | 2 |
| 1234. | H | F | $CF_3$ | tBu | Cl | 0 |
| 1235. | H | F | $CF_3$ | tBu | Cl | 1 |
| 1236. | H | F | $CF_3$ | tBu | Cl | 2 |
| 1237. | H | F | $CF_3$ | $CHF_2$ | Cl | 0 |
| 1238. | H | F | $CF_3$ | $CHF_2$ | Cl | 1 |
| 1239. | H | F | $CF_3$ | $CHF_2$ | Cl | 2 |
| 1240. | H | F | Cl | $CHF_2$ | $CF_3$ | 0 |
| 1241. | H | F | Cl | $CHF_2$ | $CF_3$ | 1 |
| 1242. | H | F | Cl | $CHF_2$ | $CF_3$ | 2 |
| 1243. | H | F | $CF_3$ | Me | OMe | 0 |
| 1244. | H | F | $CF_3$ | Me | OMe | 1 |
| 1245. | H | F | $CF_3$ | Me | OMe | 2 |
| 1246. | H | F | $CF_3$ | Me | CN | 0 |

TABLE 1-continued

Compounds of the formula (I)

| Ex. No. | R¹ | R² | R³ | R⁴ | R⁵ | n |
|---|---|---|---|---|---|---|
| 1247. | H | F | CF$_3$ | Me | CN | 1 |
| 1248. | H | F | CF$_3$ | Me | CN | 2 |
| 1249. | H | F | Cl | Et | Cl | 0 |
| 1250. | H | F | Cl | Et | Cl | 1 |
| 1251. | H | F | Cl | Et | Cl | 2 |
| 1252. | H | F | CHF$_2$ | Me | Cl | 0 |
| 1253. | H | F | CHF$_2$ | Me | Cl | 1 |
| 1254. | H | F | CHF$_2$ | Me | Cl | 2 |
| 1255. | H | F | Me | Me | Me | 0 |
| 1256. | H | F | Me | Me | Me | 1 |
| 1257. | H | F | Me | Me | Me | 2 |
| 1258. | H | F | Me | Me | Cl | 0 |
| 1259. | H | F | Me | Me | Cl | 1 |
| 1260. | H | F | Me | Me | Cl | 2 |
| 1261. | H | F | Cl | Me | Cl | 0 |
| 1262. | H | F | Cl | Me | Cl | 1 |
| 1263. | H | F | Cl | Me | Cl | 2 |
| 1264. | H | F | CF$_3$ | Me | Cl | 0 |
| 1265. | H | F | CF$_3$ | Me | Cl | 1 |
| 1266. | H | F | CF$_3$ | Me | Cl | 2 |
| 1267. | H | F | Cl | Me | CF$_3$ | 0 |
| 1268. | H | F | Cl | Me | CF$_3$ | 1 |
| 1269. | H | F | Cl | Me | CF$_3$ | 2 |
| 1270. | H | F | CF$_3$ | Me | F | 0 |
| 1271. | H | F | CF$_3$ | Me | F | 1 |
| 1272. | H | F | CF$_3$ | Me | F | 2 |
| 1273. | H | F | OMe | Me | CF$_3$ | 0 |
| 1274. | H | F | OMe | Me | CF$_3$ | 1 |
| 1275. | H | F | OMe | Me | CF$_3$ | 2 |
| 1276. | H | F | CF$_3$ | Me | OEt | 0 |
| 1277. | H | F | CF$_3$ | Me | OEt | 1 |
| 1278. | H | F | CF$_3$ | Me | OEt | 2 |
| 1279. | H | F | CF$_3$ | Me | OCHF$_2$ | 0 |
| 1280. | H | F | CF$_3$ | Me | OCHF$_2$ | 1 |
| 1281. | H | F | CF$_3$ | Me | OCHF$_2$ | 2 |
| 1282. | H | F | OCHF$_2$ | Me | CF$_3$ | 0 |
| 1283. | H | F | OCHF$_2$ | Me | CF$_3$ | 1 |
| 1284. | H | F | OCHF$_2$ | Me | CF$_3$ | 2 |
| 1285. | H | F | CF$_3$ | Me | OCH$_2$CHF$_2$ | 0 |
| 1286. | H | F | CF$_3$ | Me | OCH$_2$CHF$_2$ | 1 |
| 1287. | H | F | CF$_3$ | Me | OCH$_2$CHF$_2$ | 2 |
| 1288. | H | F | CF$_3$ | Me | OCH$_2$CF$_3$ | 0 |
| 1289. | H | F | CF$_3$ | Me | OCH$_2$CF$_3$ | 1 |
| 1290. | H | F | CF$_3$ | Me | OCH$_2$CF$_3$ | 2 |
| 1291. | H | F | CF$_3$ | Me | OCH$_2$CN | 0 |
| 1292. | H | F | CF$_3$ | Me | OCH$_2$CN | 1 |
| 1293. | H | F | CF$_3$ | Me | OCH$_2$CN | 2 |
| 1294. | H | F | CF$_3$ | Me | SO$_2$Me | 0 |
| 1295. | H | F | CF$_3$ | Me | SO$_2$Me | 1 |
| 1296. | H | F | CF$_3$ | Me | SO$_2$Me | 2 |
| 1297. | H | F | CF$_3$ | Me | SEt | 0 |
| 1298. | H | F | CF$_3$ | Me | SEt | 1 |
| 1299. | H | F | CF$_3$ | Me | SEt | 2 |
| 1300. | H | F | CF$_3$ | Me | Me | 0 |
| 1301. | H | F | CF$_3$ | Me | Me | 1 |
| 1302. | H | F | CF$_3$ | Me | Me | 2 |
| 1303. | H | F | CF$_3$ | Me | Et | 0 |
| 1304. | H | F | CF$_3$ | Me | Et | 1 |
| 1305. | H | F | CF$_3$ | Me | Et | 2 |
| 1306. | H | F | CF$_3$ | Et | Cl | 0 |
| 1307. | H | F | CF$_3$ | Et | Cl | 1 |
| 1308. | H | F | CF$_3$ | Et | Cl | 2 |
| 1309. | H | F | Cl | Et | CF$_3$ | 0 |
| 1310. | H | F | Cl | Et | CF$_3$ | 1 |
| 1311. | H | F | Cl | Et | CF$_3$ | 2 |
| 1312. | H | F | CF$_3$ | iPr | Cl | 0 |
| 1313. | H | F | CF$_3$ | iPr | Cl | 1 |
| 1314. | H | F | CF$_3$ | iPr | Cl | 2 |
| 1315. | H | F | Cl | iPr | CF$_3$ | 0 |
| 1316. | H | F | Cl | iPr | CF$_3$ | 1 |
| 1317. | H | F | Cl | iPr | CF$_3$ | 2 |
| 1318. | H | F | CF$_3$ | tBu | Cl | 0 |
| 1319. | H | F | CF$_3$ | tBu | Cl | 1 |
| 1320. | H | F | CF$_3$ | tBu | Cl | 2 |
| 1321. | H | F | Cl | tBu | CF$_3$ | 0 |
| 1322. | H | F | Cl | tBu | CF$_3$ | 1 |
| 1323. | H | F | Cl | tBu | CF$_3$ | 2 |
| 1324. | H | F | CF$_3$ | cPen | Cl | 0 |
| 1325. | H | F | CF$_3$ | cPen | Cl | 1 |
| 1326. | H | F | CF$_3$ | cPen | Cl | 2 |
| 1327. | H | F | Cl | cPen | CF$_3$ | 0 |
| 1328. | H | F | Cl | cPen | CF$_3$ | 1 |
| 1329. | H | F | Cl | cPen | CF$_3$ | 2 |
| 1330. | H | F | CF$_3$ | CH$_2$cPr | Cl | 0 |
| 1331. | H | F | CF$_3$ | CH$_2$cPr | Cl | 1 |
| 1332. | H | F | CF$_3$ | CH$_2$cPr | Cl | 2 |
| 1333. | H | F | Cl | CH$_2$cPr | CF$_3$ | 0 |
| 1334. | H | F | Cl | CH$_2$cPr | CF$_3$ | 1 |
| 1335. | H | F | Cl | CH$_2$cPr | CF$_3$ | 2 |
| 1336. | H | F | CF$_3$ | CH$_2$CH=CH$_2$ | Cl | 0 |
| 1337. | H | F | CF$_3$ | CH$_2$CH=CH$_2$ | Cl | 1 |
| 1338. | H | F | CF$_3$ | CH$_2$CH=CH$_2$ | Cl | 2 |
| 1339. | H | F | Cl | CH$_2$CH=CH$_2$ | CF$_3$ | 0 |
| 1340. | H | F | Cl | CH$_2$CH=CH$_2$ | CF$_3$ | 1 |
| 1341. | H | F | Cl | CH$_2$CH=CH$_2$ | CF$_3$ | 2 |
| 1342. | H | F | CF$_3$ | CHF$_2$ | OMe | 0 |
| 1343. | H | F | CF$_3$ | CHF$_2$ | OMe | 1 |
| 1344. | H | F | CF$_3$ | CHF$_2$ | OMe | 2 |
| 1345. | H | F | OMe | CHF$_2$ | CF$_3$ | 0 |
| 1346. | H | F | OMe | CHF$_2$ | CF$_3$ | 1 |
| 1347. | H | F | OMe | CHF$_2$ | CF$_3$ | 2 |
| 1348. | H | F | CF$_3$ | CH$_2$CF$_3$ | Cl | 0 |
| 1349. | H | F | CF$_3$ | CH$_2$CF$_3$ | Cl | 1 |
| 1350. | H | F | CF$_3$ | CH$_2$CF$_3$ | Cl | 2 |
| 1351. | H | F | Cl | CH$_2$CF$_3$ | CF$_3$ | 0 |
| 1352. | H | F | Cl | CH$_2$CF$_3$ | CF$_3$ | 1 |
| 1353. | H | F | Cl | CH$_2$CF$_3$ | CF$_3$ | 2 |
| 1354. | H | F | CF$_3$ | CH$_2$OMe | Cl | 0 |
| 1355. | H | F | CF$_3$ | CH$_2$OMe | Cl | 1 |
| 1356. | H | F | CF$_3$ | CH$_2$OMe | Cl | 2 |
| 1357. | H | F | Cl | CH$_2$OMe | CF$_3$ | 0 |
| 1358. | H | F | Cl | CH$_2$OMe | CF$_3$ | 1 |
| 1359. | H | F | Cl | CH$_2$OMe | CF$_3$ | 2 |
| 1360. | H | F | CF$_3$ | CH$_2$CN | Cl | 0 |
| 1361. | H | F | CF$_3$ | CH$_2$CN | Cl | 1 |
| 1362. | H | F | CF$_3$ | CH$_2$CN | Cl | 2 |
| 1363. | H | F | Me | Ph | Me | 0 |
| 1364. | H | F | Me | Ph | Me | 1 |
| 1365. | H | F | Me | Ph | Me | 2 |
| 1366. | H | F | Me | Ph | Cl | 0 |
| 1367. | H | F | Me | Ph | Cl | 1 |
| 1368. | H | F | Me | Ph | Cl | 2 |
| 1369. | H | F | Et | Ph | Cl | 0 |
| 1370. | H | F | Et | Ph | Cl | 1 |

TABLE 1-continued

Compounds of the formula (I)

| Ex. No. | R¹ | R² | R³ | R⁴ | R⁵ | n |
|---|---|---|---|---|---|---|
| 1371. | H | F | Et | Ph | Cl | 2 |
| 1372. | H | F | Pr | Ph | Cl | 0 |
| 1373. | H | F | Pr | Ph | Cl | 1 |
| 1374. | H | F | Pr | Ph | Cl | 2 |
| 1375. | H | F | iPr | Ph | Cl | 0 |
| 1376. | H | F | iPr | Ph | Cl | 1 |
| 1377. | H | F | iPr | Ph | Cl | 2 |
| 1378. | H | F | $CF_3$ | Ph | Cl | 0 |
| 1379. | H | F | $CF_3$ | Ph | Cl | 1 |
| 1380. | H | F | $CF_3$ | Ph | Cl | 2 |
| 1381. | H | F | $CF_3$ | Ph | Me | 0 |
| 1382. | H | F | $CF_3$ | Ph | Me | 1 |
| 1383. | H | F | $CF_3$ | Ph | Me | 2 |
| 1384. | H | F | $CF_3$ | Ph | $CF_3$ | 0 |
| 1385. | H | F | $CF_3$ | Ph | $CF_3$ | 1 |
| 1386. | H | F | $CF_3$ | Ph | $CF_3$ | 2 |
| 1387. | H | F | $CF_3$ | Ph | F | 0 |
| 1388. | H | F | $CF_3$ | Ph | F | 1 |
| 1389. | H | F | $CF_3$ | Ph | F | 2 |
| 1390. | H | F | $CF_3$ | Ph | OMe | 0 |
| 1391. | H | F | $CF_3$ | Ph | OMe | 1 |
| 1392. | H | F | $CF_3$ | Ph | OMe | 2 |
| 1393. | H | F | $CF_3$ | Ph | OEt | 0 |
| 1394. | H | F | $CF_3$ | Ph | OEt | 1 |
| 1395. | H | F | $CF_3$ | Ph | OEt | 2 |
| 1396. | H | F | $CF_3$ | Ph | $OCHF_2$ | 0 |
| 1397. | H | F | $CF_3$ | Ph | $OCHF_2$ | 1 |
| 1398. | H | F | $CF_3$ | Ph | $OCHF_2$ | 2 |
| 1399. | H | F | $CF_3$ | Ph | CN | 0 |
| 1400. | H | F | $CF_3$ | Ph | CN | 1 |
| 1401. | H | F | $CF_3$ | Ph | CN | 2 |
| 1402. | H | F | $CF_3$ | Ph(4-Cl) | Cl | 0 |
| 1403. | H | F | $CF_3$ | Ph(4-Cl) | Cl | 1 |
| 1404. | H | F | $CF_3$ | Ph(4-Cl) | Cl | 2 |
| 1405. | H | F | Me | Me | $OCH_2CF_3$ | 0 |
| 1406. | H | F | Me | Me | $OCH_2CF_3$ | 1 |
| 1407. | H | F | Me | Me | $OCH_2CF_3$ | 2 |
| 1408. | H | F | $CF_3$ | Me | oxetanyl-O | 0 |
| 1409. | H | F | $CF_3$ | Me | oxetanyl-O | 1 |
| 1410. | H | F | $CF_3$ | Me | oxetanyl-O | 2 |
| 1411. | H | F | $CF_3$ | Me | H | 0 |
| 1412. | H | F | $CF_3$ | Me | H | 1 |
| 1413. | H | F | $CF_3$ | Me | H | 2 |
| 1414. | H | F | $CF_3$ | Me | $OCH_2CH_2OMe$ | 0 |
| 1415. | H | F | $CF_3$ | Me | $OCH_2CH_2OMe$ | 1 |
| 1416. | H | F | $CF_3$ | Me | $OCH_2CH_2OMe$ | 2 |
| 1417. | H | F | $CF_3$ | Me | SMe | 0 |
| 1418. | H | F | $CF_3$ | Me | SMe | 1 |
| 1419. | H | F | $CF_3$ | Me | SMe | 2 |
| 1420. | H | F | $CF_3$ | Me | $OCH_2CH_2CH_2F$ | 0 |
| 1421. | H | F | $CF_3$ | Me | $OCH_2CH_2CH_2F$ | 1 |
| 1422. | H | F | $CF_3$ | Me | $OCH_2CH_2CH_2F$ | 2 |
| 1423. | H | F | $CF_3$ | Me | $OCH(CH_2F)_2$ | 0 |
| 1424. | H | F | $CF_3$ | Me | $OCH(CH_2F)_2$ | 1 |
| 1425. | H | F | $CF_3$ | Me | $OCH(CH_2F)_2$ | 2 |
| 1426. | H | F | $CF_3$ | Me | $OCH_2CF_2CHF_2$ | 0 |
| 1427. | H | F | $CF_3$ | Me | $OCH_2CF_2CHF_2$ | 1 |
| 1428. | H | F | $CF_3$ | Me | $OCH_2CF_2CHF_2$ | 2 |
| 1429. | H | F | $CF_3$ | Me | $OCH_2CF=CH_2$ | 0 |
| 1430. | H | F | $CF_3$ | Me | $OCH_2CF=CH_2$ | 1 |
| 1431. | H | F | $CF_3$ | Me | $OCH_2CF=CH_2$ | 2 |
| 1432. | H | F | $CF_3$ | Me | $OCH(Me)CF_3$ | 0 |
| 1433. | H | F | $CF_3$ | Me | $OCH(Me)CF_3$ | 1 |
| 1434. | H | F | $CF_3$ | Me | $OCH(Me)CF_3$ | 2 |
| 1435. | H | F | $CF_3$ | Me | $OCH(Me)CH_2F$ | 0 |
| 1436. | H | F | $CF_3$ | Me | $OCH(Me)CH_2F$ | 1 |
| 1437. | H | F | $CF_3$ | Me | $OCH(Me)CH_2F$ | 2 |
| 1438. | H | F | $OCH_2CF_3$ | Me | $CF_3$ | 0 |
| 1439. | H | F | $OCH_2CF_3$ | Me | $CF_3$ | 1 |
| 1440. | H | F | $OCH_2CF_3$ | Me | $CF_3$ | 2 |
| 1441. | H | F | $OCH_2CF_3$ | Me | $CHF_2$ | 0 |
| 1442. | H | F | $OCH_2CF_3$ | Me | $CHF_2$ | 1 |
| 1443. | H | F | $OCH_2CF_3$ | Me | $CHF_2$ | 2 |
| 1444. | H | F | $CHF_2$ | Me | $CHF_2$ | 0 |
| 1445. | H | F | $CHF_2$ | Me | $CHF_2$ | 1 |
| 1446. | H | F | $CHF_2$ | Me | $CHF_2$ | 2 |
| 1447. | H | F | $CF_3$ | Me | $CHF_2$ | 0 |
| 1448. | H | F | $CF_3$ | Me | $CHF_2$ | 1 |
| 1449. | H | F | $CF_3$ | Me | $CHF_2$ | 2 |
| 1450. | H | F | Cl | Me | $OCHF_2$ | 0 |
| 1451. | H | F | Cl | Me | $OCHF_2$ | 1 |
| 1452. | H | F | Cl | Me | $OCHF_2$ | 2 |
| 1453. | H | F | Br | Me | $OCHF_2$ | 0 |
| 1454. | H | F | Br | Me | $OCHF_2$ | 1 |
| 1455. | H | F | Br | Me | $OCHF_2$ | 2 |
| 1456. | H | F | Br | Me | $CF_3$ | 0 |
| 1457. | H | F | Br | Me | $CF_3$ | 1 |
| 1458. | H | F | Br | Me | $CF_3$ | 2 |
| 1459. | H | Cl | $CF_3$ | tBu | Cl | 0 |
| 1460. | H | Cl | $CF_3$ | tBu | Cl | 1 |
| 1461. | H | Cl | $CF_3$ | tBu | Cl | 2 |
| 1462. | H | Cl | $CF_3$ | $CHF_2$ | Cl | 0 |
| 1463. | H | Cl | $CF_3$ | $CHF_2$ | Cl | 1 |
| 1464. | H | Cl | $CF_3$ | $CHF_2$ | Cl | 2 |
| 1465. | H | Cl | Cl | $CHF_2$ | $CF_3$ | 0 |
| 1466. | H | Cl | Cl | $CHF_2$ | $CF_3$ | 1 |
| 1467. | H | Cl | Cl | $CHF_2$ | $CF_3$ | 2 |
| 1468. | H | Cl | $CF_3$ | Me | OMe | 0 |
| 1469. | H | Cl | $CF_3$ | Me | OMe | 1 |
| 1470. | H | Cl | $CF_3$ | Me | OMe | 2 |
| 1471. | H | Cl | $CF_3$ | Me | CN | 0 |
| 1472. | H | Cl | $CF_3$ | Me | CN | 1 |
| 1473. | H | Cl | $CF_3$ | Me | CN | 2 |
| 1474. | H | Cl | $CHF_2$ | Me | Cl | 0 |
| 1475. | H | Cl | $CHF_2$ | Me | Cl | 1 |
| 1476. | H | Cl | $CHF_2$ | Me | Cl | 2 |
| 1477. | H | Cl | Me | Me | Me | 0 |
| 1478. | H | Cl | Me | Me | Me | 1 |
| 1479. | H | Cl | Me | Me | Me | 2 |
| 1480. | H | Cl | Me | Me | Cl | 0 |
| 1481. | H | Cl | Me | Me | Cl | 1 |
| 1482. | H | Cl | Me | Me | Cl | 2 |
| 1483. | H | Cl | $CF_3$ | Me | Cl | 0 |

TABLE 1-continued

Compounds of the formula (I)

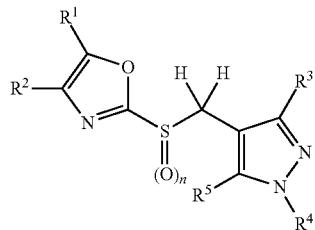

(I)

| Ex. No. | R¹ | R² | R³ | R⁴ | R⁵ | n |
|---|---|---|---|---|---|---|
| 1484. | H | Cl | CF₃ | Me | Cl | 1 |
| 1485. | H | Cl | CF₃ | Me | Cl | 2 |
| 1486. | H | Cl | Cl | Me | CF₃ | 0 |
| 1487. | H | Cl | Cl | Me | CF₃ | 1 |
| 1488. | H | Cl | Cl | Me | CF₃ | 2 |
| 1489. | H | Cl | CF₃ | Me | F | 0 |
| 1490. | H | Cl | CF₃ | Me | F | 1 |
| 1491. | H | Cl | CF₃ | Me | F | 2 |
| 1492. | H | Cl | OMe | Me | CF₃ | 0 |
| 1493. | H | Cl | OMe | Me | CF₃ | 1 |
| 1494. | H | Cl | OMe | Me | CF₃ | 2 |
| 1495. | H | Cl | CF₃ | Me | OCHF₂ | 0 |
| 1496. | H | Cl | CF₃ | Me | OCHF₂ | 1 |
| 1497. | H | Cl | CF₃ | Me | OCHF₂ | 2 |
| 1498. | H | Cl | OCHF₂ | Me | CF₃ | 0 |
| 1499. | H | Cl | OCHF₂ | Me | CF₃ | 1 |
| 1500. | H | Cl | OCHF₂ | Me | CF₃ | 2 |
| 1501. | H | Cl | CF₃ | Me | OCH₂CHF₂ | 0 |
| 1502. | H | Cl | CF₃ | Me | OCH₂CHF₂ | 1 |
| 1503. | H | Cl | CF₃ | Me | OCH₂CHF₂ | 2 |
| 1504. | H | Cl | CF₃ | Me | OCH₂CF₃ | 0 |
| 1505. | H | Cl | CF₃ | Me | OCH₂CF₃ | 1 |
| 1506. | H | Cl | CF₃ | Me | OCH₂CF₃ | 2 |
| 1507. | H | Cl | CF₃ | Me | SO₂Me | 0 |
| 1508. | H | Cl | CF₃ | Me | SO₂Me | 1 |
| 1509. | H | Cl | CF₃ | Me | SO₂Me | 2 |
| 1510. | H | Cl | CF₃ | Me | SEt | 0 |
| 1511. | H | Cl | CF₃ | Me | SEt | 1 |
| 1512. | H | Cl | CF₃ | Me | SEt | 2 |
| 1513. | H | Cl | CF₃ | Et | Cl | 0 |
| 1514. | H | Cl | CF₃ | Et | Cl | 1 |
| 1515. | H | Cl | CF₃ | Et | Cl | 2 |
| 1516. | H | Cl | CF₃ | iPr | Cl | 0 |
| 1517. | H | Cl | CF₃ | iPr | Cl | 1 |
| 1518. | H | Cl | CF₃ | iPr | Cl | 2 |
| 1519. | H | Cl | CF₃ | tBu | Cl | 0 |
| 1520. | H | Cl | CF₃ | tBu | Cl | 1 |
| 1521. | H | Cl | CF₃ | tBu | Cl | 2 |
| 1522. | H | Cl | Cl | tBu | CF₃ | 0 |
| 1523. | H | Cl | Cl | tBu | CF₃ | 1 |
| 1524. | H | Cl | Cl | tBu | CF₃ | 2 |
| 1525. | H | Cl | CF₃ | cPen | Cl | 0 |
| 1526. | H | Cl | CF₃ | cPen | Cl | 1 |
| 1527. | H | Cl | CF₃ | cPen | Cl | 2 |
| 1528. | H | Cl | CF₃ | CHF₂ | OMe | 0 |
| 1529. | H | Cl | CF₃ | CHF₂ | OMe | 1 |
| 1530. | H | Cl | CF₃ | CHF₂ | OMe | 2 |
| 1531. | H | Cl | CF₃ | CH₂CF₃ | Cl | 0 |
| 1532. | H | Cl | CF₃ | CH₂CF₃ | Cl | 1 |
| 1533. | H | Cl | CF₃ | CH₂CF₃ | Cl | 2 |
| 1534. | H | Cl | CF₃ | Ph | OCHF₂ | 0 |
| 1535. | H | Cl | CF₃ | Ph | OCHF₂ | 1 |
| 1536. | H | Cl | CF₃ | Ph | OCHF₂ | 2 |
| 1537. | H | Cl | CF₃ | Ph | Cl | 0 |
| 1538. | H | Cl | CF₃ | Ph | Cl | 1 |
| 1539. | H | Cl | CF₃ | Ph | Cl | 2 |
| 1540. | H | Cl | Me | Me | OCH₂CF₃ | 0 |
| 1541. | H | Cl | Me | Me | OCH₂CF₃ | 1 |
| 1542. | H | Cl | Me | Me | OCH₂CF₃ | 2 |

TABLE 1-continued

Compounds of the formula (I)

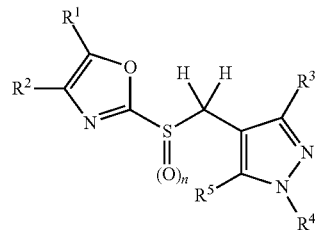

(I)

| Ex. No. | R¹ | R² | R³ | R⁴ | R⁵ | n |
|---|---|---|---|---|---|---|
| 1543. | H | Cl | CF₃ | Me | (oxetane) | 0 |
| 1544. | H | Cl | CF₃ | Me | (oxetane) | 1 |
| 1545. | H | Cl | CF₃ | Me | (oxetane) | 2 |
| 1546. | H | Cl | CF₃ | Me | H | 0 |
| 1547. | H | Cl | CF₃ | Me | H | 1 |
| 1548. | H | Cl | CF₃ | Me | H | 2 |
| 1549. | H | Cl | CF₃ | Me | OCH₂CH₂OMe | 0 |
| 1550. | H | Cl | CF₃ | Me | OCH₂CH₂OMe | 1 |
| 1551. | H | Cl | CF₃ | Me | OCH₂CH₂OMe | 2 |
| 1552. | H | Cl | CF₃ | Me | SMe | 0 |
| 1553. | H | Cl | CF₃ | Me | SMe | 1 |
| 1554. | H | Cl | CF₃ | Me | SMe | 2 |
| 1555. | H | Cl | CF₃ | Me | OCH₂CH₂CH₂F | 0 |
| 1556. | H | Cl | CF₃ | Me | OCH₂CH₂CH₂F | 1 |
| 1557. | H | Cl | CF₃ | Me | OCH₂CH₂CH₂F | 2 |
| 1558. | H | Cl | CF₃ | Me | OCH(CH₂F)₂ | 0 |
| 1559. | H | Cl | CF₃ | Me | OCH(CH₂F)₂ | 1 |
| 1560. | H | Cl | CF₃ | Me | OCH(CH₂F)₂ | 2 |
| 1561. | H | Cl | CF₃ | Me | OCH₂CF₂CHF₂ | 0 |
| 1562. | H | Cl | CF₃ | Me | OCH₂CF₂CHF₂ | 1 |
| 1563. | H | Cl | CF₃ | Me | OCH₂CF₂CHF₂ | 2 |
| 1564. | H | Cl | CF₃ | Me | OCH₂CF=CH₂ | 0 |
| 1565. | H | Cl | CF₃ | Me | OCH₂CF=CH₂ | 1 |
| 1566. | H | Cl | CF₃ | Me | OCH₂CF=CH₂ | 2 |
| 1567. | H | Cl | CF₃ | Me | OCH(Me)CF₃ | 0 |
| 1568. | H | Cl | CF₃ | Me | OCH(Me)CF₃ | 1 |
| 1569. | H | Cl | CF₃ | Me | OCH(Me)CF₃ | 2 |
| 1570. | H | Cl | CF₃ | Me | OCH(Me)CH₂F | 0 |
| 1571. | H | Cl | CF₃ | Me | OCH(Me)CH₂F | 1 |
| 1572. | H | Cl | CF₃ | Me | OCH(Me)CH₂F | 2 |
| 1573. | H | Cl | OCH₂CF₃ | Me | CF₃ | 0 |
| 1574. | H | Cl | OCH₂CF₃ | Me | CF₃ | 1 |
| 1575. | H | Cl | OCH₂CF₃ | Me | CF₃ | 2 |
| 1576. | H | Cl | OCH₂CF₃ | Me | CHF₂ | 0 |
| 1577. | H | Cl | OCH₂CF₃ | Me | CHF₂ | 1 |
| 1578. | H | Cl | OCH₂CF₃ | Me | CHF₂ | 2 |
| 1579. | H | Cl | CHF₂ | Me | CHF₂ | 0 |
| 1580. | H | Cl | CHF₂ | Me | CHF₂ | 1 |
| 1581. | H | Cl | CHF₂ | Me | CHF₂ | 2 |
| 1582. | H | Cl | CF₃ | Me | CHF₂ | 0 |
| 1583. | H | Cl | CF₃ | Me | CHF₂ | 1 |
| 1584. | H | Cl | CF₃ | Me | CHF₂ | 2 |
| 1585. | H | Cl | Cl | Me | OCHF₂ | 0 |
| 1586. | H | Cl | Cl | Me | OCHF₂ | 1 |
| 1587. | H | Cl | Cl | Me | OCHF₂ | 2 |
| 1588. | H | Cl | Br | Me | OCHF₂ | 0 |
| 1589. | H | Cl | Br | Me | OCHF₂ | 1 |
| 1590. | H | Cl | Br | Me | OCHF₂ | 2 |
| 1591. | H | Cl | Br | Me | CF₃ | 0 |
| 1592. | H | Cl | Br | Me | CF₃ | 1 |
| 1593. | H | Cl | Br | Me | CF₃ | 2 |
| 1594. | H | Br | CF₃ | tBu | Cl | 0 |

TABLE 1-continued

Compounds of the formula (I)

| Ex. No. | R¹ | R² | R³ | R⁴ | R⁵ | n |
|---|---|---|---|---|---|---|
| 1595. | H | Br | $CF_3$ | tBu | Cl | 1 |
| 1596. | H | Br | $CF_3$ | tBu | Cl | 2 |
| 1597. | H | Br | $CF_3$ | $CHF_2$ | Cl | 0 |
| 1598. | H | Br | $CF_3$ | $CHF_2$ | Cl | 1 |
| 1599. | H | Br | $CF_3$ | $CHF_2$ | Cl | 2 |
| 1600. | H | Br | Cl | $CHF_2$ | $CF_3$ | 0 |
| 1601. | H | Br | Cl | $CHF_2$ | $CF_3$ | 1 |
| 1602. | H | Br | Cl | $CHF_2$ | $CF_3$ | 2 |
| 1603. | H | Br | $CF_3$ | Me | OMe | 0 |
| 1604. | H | Br | $CF_3$ | Me | OMe | 1 |
| 1605. | H | Br | $CF_3$ | Me | OMe | 2 |
| 1606. | H | Br | $CF_3$ | Me | CN | 0 |
| 1607. | H | Br | $CF_3$ | Me | CN | 1 |
| 1608. | H | Br | $CF_3$ | Me | CN | 2 |
| 1609. | H | Br | $CHF_2$ | Me | Cl | 0 |
| 1610. | H | Br | $CHF_2$ | Me | Cl | 1 |
| 1611. | H | Br | $CHF_2$ | Me | Cl | 2 |
| 1612. | H | Br | Me | Me | Me | 0 |
| 1613. | H | Br | Me | Me | Me | 1 |
| 1614. | H | Br | Me | Me | Me | 2 |
| 1615. | H | Br | Me | Me | Cl | 0 |
| 1616. | H | Br | Me | Me | Cl | 1 |
| 1617. | H | Br | Me | Me | Cl | 2 |
| 1618. | H | Br | $CF_3$ | Me | Cl | 0 |
| 1619. | H | Br | $CF_3$ | Me | Cl | 1 |
| 1620. | H | Br | $CF_3$ | Me | Cl | 2 |
| 1621. | H | Br | Cl | Me | $CF_3$ | 0 |
| 1622. | H | Br | Cl | Me | $CF_3$ | 1 |
| 1623. | H | Br | Cl | Me | $CF_3$ | 2 |
| 1624. | H | Br | $CF_3$ | Me | F | 0 |
| 1625. | H | Br | $CF_3$ | Me | F | 1 |
| 1626. | H | Br | $CF_3$ | Me | F | 2 |
| 1627. | H | Br | OMe | Me | $CF_3$ | 0 |
| 1628. | H | Br | OMe | Me | $CF_3$ | 1 |
| 1629. | H | Br | OMe | Me | $CF_3$ | 2 |
| 1630. | H | Br | $CF_3$ | Me | $OCHF_2$ | 0 |
| 1631. | H | Br | $CF_3$ | Me | $OCHF_2$ | 1 |
| 1632. | H | Br | $CF_3$ | Me | $OCHF_2$ | 2 |
| 1633. | H | Br | $OCHF_2$ | Me | $CF_3$ | 0 |
| 1634. | H | Br | $OCHF_2$ | Me | $CF_3$ | 1 |
| 1635. | H | Br | $OCHF_2$ | Me | $CF_3$ | 2 |
| 1636. | H | Br | $CF_3$ | Me | $OCH_2CHF_2$ | 0 |
| 1637. | H | Br | $CF_3$ | Me | $OCH_2CHF_2$ | 1 |
| 1638. | H | Br | $CF_3$ | Me | $OCH_2CHF_2$ | 2 |
| 1639. | H | Br | $CF_3$ | Me | $OCH_2CF_3$ | 0 |
| 1640. | H | Br | $CF_3$ | Me | $OCH_2CF_3$ | 1 |
| 1641. | H | Br | $CF_3$ | Me | $OCH_2CF_3$ | 2 |
| 1642. | H | Br | $CF_3$ | Me | $SO_2Me$ | 0 |
| 1643. | H | Br | $CF_3$ | Me | $SO_2Me$ | 1 |
| 1644. | H | Br | $CF_3$ | Me | $SO_2Me$ | 2 |
| 1645. | H | Br | $CF_3$ | Me | SEt | 0 |
| 1646. | H | Br | $CF_3$ | Me | SEt | 1 |
| 1647. | H | Br | $CF_3$ | Me | SEt | 2 |
| 1648. | H | Br | $CF_3$ | Et | Cl | 0 |
| 1649. | H | Br | $CF_3$ | Et | Cl | 1 |
| 1650. | H | Br | $CF_3$ | Et | Cl | 2 |
| 1651. | H | Br | $CF_3$ | iPr | Cl | 0 |
| 1652. | H | Br | $CF_3$ | iPr | Cl | 1 |
| 1653. | H | Br | $CF_3$ | iPr | Cl | 2 |
| 1654. | H | Br | $CF_3$ | tBu | Cl | 0 |
| 1655. | H | Br | $CF_3$ | tBu | Cl | 1 |
| 1656. | H | Br | $CF_3$ | tBu | Cl | 2 |
| 1657. | H | Br | Cl | tBu | $CF_3$ | 0 |
| 1658. | H | Br | Cl | tBu | $CF_3$ | 1 |
| 1659. | H | Br | Cl | tBu | $CF_3$ | 2 |
| 1660. | H | Br | $CF_3$ | cPen | Cl | 0 |
| 1661. | H | Br | $CF_3$ | cPen | Cl | 1 |
| 1662. | H | Br | $CF_3$ | cPen | Cl | 2 |
| 1663. | H | Br | $CF_3$ | $CHF_2$ | OMe | 0 |
| 1664. | H | Br | $CF_3$ | $CHF_2$ | OMe | 1 |
| 1665. | H | Br | $CF_3$ | $CHF_2$ | OMe | 2 |
| 1666. | H | Br | $CF_3$ | $CH_2CF_3$ | Cl | 0 |
| 1667. | H | Br | $CF_3$ | $CH_2CF_3$ | Cl | 1 |
| 1668. | H | Br | $CF_3$ | $CH_2CF_3$ | Cl | 2 |
| 1669. | H | Br | $CF_3$ | Ph | $OCHF_2$ | 0 |
| 1670. | H | Br | $CF_3$ | Ph | $OCHF_2$ | 1 |
| 1671. | H | Br | $CF_3$ | Ph | $OCHF_2$ | 2 |
| 1672. | H | Br | $CF_3$ | Ph | Cl | 0 |
| 1673. | H | Br | $CF_3$ | Ph | Cl | 1 |
| 1674. | H | Br | $CF_3$ | Ph | Cl | 2 |
| 1675. | H | Br | Me | Me | $OCH_2CF_3$ | 0 |
| 1676. | H | Br | Me | Me | $OCH_2CF_3$ | 1 |
| 1677. | H | Br | Me | Me | $OCH_2CF_3$ | 2 |
| 1678. | H | Br | $CF_3$ | Me | oxetanyl | 0 |
| 1679. | H | Br | $CF_3$ | Me | oxetanyl | 1 |
| 1680. | H | Br | $CF_3$ | Me | oxetanyl | 2 |
| 1681. | H | Br | $CF_3$ | Me | H | 0 |
| 1682. | H | Br | $CF_3$ | Me | H | 1 |
| 1683. | H | Br | $CF_3$ | Me | H | 2 |
| 1684. | H | Br | $CF_3$ | Me | $OCH_2CH_2OMe$ | 0 |
| 1685. | H | Br | $CF_3$ | Me | $OCH_2CH_2OMe$ | 1 |
| 1686. | H | Br | $CF_3$ | Me | $OCH_2CH_2OMe$ | 2 |
| 1687. | H | Br | $CF_3$ | Me | SMe | 0 |
| 1688. | H | Br | $CF_3$ | Me | SMe | 1 |
| 1689. | H | Br | $CF_3$ | Me | SMe | 2 |
| 1690. | H | Br | $CF_3$ | Me | $OCH_2CH_2CH_2F$ | 0 |
| 1691. | H | Br | $CF_3$ | Me | $OCH_2CH_2CH_2F$ | 1 |
| 1692. | H | Br | $CF_3$ | Me | $OCH_2CH_2CH_2F$ | 2 |
| 1693. | H | Br | $CF_3$ | Me | $OCH(CH_2F)_2$ | 0 |
| 1694. | H | Br | $CF_3$ | Me | $OCH(CH_2F)_2$ | 1 |
| 1695. | H | Br | $CF_3$ | Me | $OCH(CH_2F)_2$ | 2 |
| 1696. | H | Br | $CF_3$ | Me | $OCH_2CF_2CHF_2$ | 0 |
| 1697. | H | Br | $CF_3$ | Me | $OCH_2CF_2CHF_2$ | 1 |
| 1698. | H | Br | $CF_3$ | Me | $OCH_2CF_2CHF_2$ | 2 |
| 1699. | H | Br | $CF_3$ | Me | $OCH_2CF{=}CH_2$ | 0 |
| 1700. | H | Br | $CF_3$ | Me | $OCH_2CF{=}CH_2$ | 1 |
| 1701. | H | Br | $CF_3$ | Me | $OCH_2CF{=}CH_2$ | 2 |
| 1702. | H | Br | $CF_3$ | Me | $OCH(Me)CF_3$ | 0 |
| 1703. | H | Br | $CF_3$ | Me | $OCH(Me)CF_3$ | 1 |
| 1704. | H | Br | $CF_3$ | Me | $OCH(Me)CF_3$ | 2 |
| 1705. | H | Br | $CF_3$ | Me | $OCH(Me)CH_2F$ | 0 |
| 1706. | H | Br | $CF_3$ | Me | $OCH(Me)CH_2F$ | 1 |
| 1707. | H | Br | $CF_3$ | Me | $OCH(Me)CH_2F$ | 2 |

TABLE 1-continued

Compounds of the formula (I)

| Ex. No. | R¹ | R² | R³ | R⁴ | R⁵ | n |
|---|---|---|---|---|---|---|
| 1708. | H | Br | OCH$_2$CF$_3$ | Me | CF$_3$ | 0 |
| 1709. | H | Br | OCH$_2$CF$_3$ | Me | CF$_3$ | 1 |
| 1710. | H | Br | OCH$_2$CF$_3$ | Me | CF$_3$ | 2 |
| 1711. | H | Br | OCH$_2$CF$_3$ | Me | CHF$_2$ | 0 |
| 1712. | H | Br | OCH$_2$CF$_3$ | Me | CHF$_2$ | 1 |
| 1713. | H | Br | OCH$_2$CF$_3$ | Me | CHF$_2$ | 2 |
| 1714. | H | Br | CHF$_2$ | Me | CHF$_2$ | 0 |
| 1715. | H | Br | CHF$_2$ | Me | CHF$_2$ | 1 |
| 1716. | H | Br | CHF$_2$ | Me | CHF$_2$ | 2 |
| 1717. | H | Br | CF$_3$ | Me | CHF$_2$ | 0 |
| 1718. | H | Br | CF$_3$ | Me | CHF$_2$ | 1 |
| 1719. | H | Br | CF$_3$ | Me | CHF$_2$ | 2 |
| 1720. | H | Br | Cl | Me | OCHF$_2$ | 0 |
| 1721. | H | Br | Cl | Me | OCHF$_2$ | 1 |
| 1722. | H | Br | Cl | Me | OCHF$_2$ | 2 |
| 1723. | H | Br | Br | Me | OCHF$_2$ | 0 |
| 1724. | H | Br | Br | Me | OCHF$_2$ | 1 |
| 1725. | H | Br | Br | Me | OCHF$_2$ | 2 |
| 1726. | H | Br | Br | Me | CF$_3$ | 0 |
| 1727. | H | Br | Br | Me | CF$_3$ | 1 |
| 1728. | H | Br | Br | Me | CF$_3$ | 2 |
| 1729. | Me | H | CF$_3$ | tBu | Cl | 0 |
| 1730. | Me | H | CF$_3$ | tBu | Cl | 1 |
| 1731. | Me | H | CF$_3$ | tBu | Cl | 2 |
| 1732. | Me | H | CF$_3$ | CHF$_2$ | Cl | 0 |
| 1733. | Me | H | CF$_3$ | CHF$_2$ | Cl | 1 |
| 1734. | Me | H | CF$_3$ | CHF$_2$ | Cl | 2 |
| 1735. | Me | H | Cl | CHF$_2$ | CF$_3$ | 0 |
| 1736. | Me | H | Cl | CHF$_2$ | CF$_3$ | 1 |
| 1737. | Me | H | Cl | CHF$_2$ | CF$_3$ | 2 |
| 1738. | Me | H | CF$_3$ | Me | OMe | 0 |
| 1739. | Me | H | CF$_3$ | Me | OMe | 1 |
| 1740. | Me | H | CF$_3$ | Me | OMe | 2 |
| 1741. | Me | H | CF$_3$ | Me | CN | 0 |
| 1742. | Me | H | CF$_3$ | Me | CN | 1 |
| 1743. | Me | H | CF$_3$ | Me | CN | 2 |
| 1744. | Me | H | CHF$_2$ | Me | Cl | 0 |
| 1745. | Me | H | CHF$_2$ | Me | Cl | 1 |
| 1746. | Me | H | CHF$_2$ | Me | Cl | 2 |
| 1747. | Me | H | Me | Me | Me | 0 |
| 1748. | Me | H | Me | Me | Me | 1 |
| 1749. | Me | H | Me | Me | Me | 2 |
| 1750. | Me | H | Me | Me | Cl | 0 |
| 1751. | Me | H | Me | Me | Cl | 1 |
| 1752. | Me | H | Me | Me | Cl | 2 |
| 1753. | Me | H | CF$_3$ | Me | Cl | 0 |
| 1754. | Me | H | CF$_3$ | Me | Cl | 1 |
| 1755. | Me | H | CF$_3$ | Me | Cl | 2 |
| 1756. | Me | H | Cl | Me | CF$_3$ | 0 |
| 1757. | Me | H | Cl | Me | CF$_3$ | 1 |
| 1758. | Me | H | Cl | Me | CF$_3$ | 2 |
| 1759. | Me | H | CF$_3$ | Me | F | 0 |
| 1760. | Me | H | CF$_3$ | Me | F | 1 |
| 1761. | Me | H | CF$_3$ | Me | F | 2 |
| 1762. | Me | H | OMe | Me | CF$_3$ | 0 |
| 1763. | Me | H | OMe | Me | CF$_3$ | 1 |
| 1764. | Me | H | OMe | Me | CF$_3$ | 2 |
| 1765. | Me | H | CF$_3$ | Me | OCHF$_2$ | 0 |
| 1766. | Me | H | CF$_3$ | Me | OCHF$_2$ | 1 |
| 1767. | Me | H | CF$_3$ | Me | OCHF$_2$ | 2 |
| 1768. | Me | H | OCHF$_2$ | Me | CF$_3$ | 0 |
| 1769. | Me | H | OCHF$_2$ | Me | CF$_3$ | 1 |

TABLE 1-continued

Compounds of the formula (I)

| Ex. No. | R¹ | R² | R³ | R⁴ | R⁵ | n |
|---|---|---|---|---|---|---|
| 1770. | Me | H | OCHF$_2$ | Me | CF$_3$ | 2 |
| 1771. | Me | H | CF$_3$ | Me | OCH$_2$CHF$_2$ | 0 |
| 1772. | Me | H | CF$_3$ | Me | OCH$_2$CHF$_2$ | 1 |
| 1773. | Me | H | CF$_3$ | Me | OCH$_2$CHF$_2$ | 2 |
| 1774. | Me | H | CF$_3$ | Me | OCH$_2$CF$_3$ | 0 |
| 1775. | Me | H | CF$_3$ | Me | OCH$_2$CF$_3$ | 1 |
| 1776. | Me | H | CF$_3$ | Me | OCH$_2$CF$_3$ | 2 |
| 1777. | Me | H | CF$_3$ | Me | SO$_2$Me | 0 |
| 1778. | Me | H | CF$_3$ | Me | SO$_2$Me | 1 |
| 1779. | Me | H | CF$_3$ | Me | SO$_2$Me | 2 |
| 1780. | Me | H | CF$_3$ | Me | SEt | 0 |
| 1781. | Me | H | CF$_3$ | Me | SEt | 1 |
| 1782. | Me | H | CF$_3$ | Me | SEt | 2 |
| 1783. | Me | H | CF$_3$ | Et | Cl | 0 |
| 1784. | Me | H | CF$_3$ | Et | Cl | 1 |
| 1785. | Me | H | CF$_3$ | Et | Cl | 2 |
| 1786. | Me | H | CF$_3$ | iPr | Cl | 0 |
| 1787. | Me | H | CF$_3$ | iPr | Cl | 1 |
| 1788. | Me | H | CF$_3$ | iPr | Cl | 2 |
| 1789. | Me | H | CF$_3$ | tBu | Cl | 0 |
| 1790. | Me | H | CF$_3$ | tBu | Cl | 1 |
| 1791. | Me | H | CF$_3$ | tBu | Cl | 2 |
| 1792. | Me | H | Cl | tBu | CF$_3$ | 0 |
| 1793. | Me | H | Cl | tBu | CF$_3$ | 1 |
| 1794. | Me | H | Cl | tBu | CF$_3$ | 2 |
| 1795. | Me | H | CF$_3$ | cPen | Cl | 0 |
| 1796. | Me | H | CF$_3$ | cPen | Cl | 1 |
| 1797. | Me | H | CF$_3$ | cPen | Cl | 2 |
| 1798. | Me | H | CF$_3$ | CHF$_2$ | OMe | 0 |
| 1799. | Me | H | CF$_3$ | CHF$_2$ | OMe | 1 |
| 1800. | Me | H | CF$_3$ | CHF$_2$ | OMe | 2 |
| 1801. | Me | H | CF$_3$ | CH$_2$CF$_3$ | Cl | 0 |
| 1802. | Me | H | CF$_3$ | CH$_2$CF$_3$ | Cl | 1 |
| 1803. | Me | H | CF$_3$ | CH$_2$CF$_3$ | Cl | 2 |
| 1804. | Me | H | CF$_3$ | Ph | OCHF$_2$ | 0 |
| 1805. | Me | H | CF$_3$ | Ph | OCHF$_2$ | 1 |
| 1806. | Me | H | CF$_3$ | Ph | OCHF$_2$ | 2 |
| 1807. | Me | H | CF$_3$ | Ph | Cl | 0 |
| 1808. | Me | H | CF$_3$ | Ph | Cl | 1 |
| 1809. | Me | H | CF$_3$ | Ph | Cl | 2 |
| 1810. | Me | H | Me | Me | OCH$_2$CF$_3$ | 0 |
| 1811. | Me | H | Me | Me | OCH$_2$CF$_3$ | 1 |
| 1812. | Me | H | Me | Me | OCH$_2$CF$_3$ | 2 |
| 1813. | Me | H | CF$_3$ | Me |  | 0 |
| 1814. | Me | H | CF$_3$ | Me |  | 1 |
| 1815. | Me | H | CF$_3$ | Me |  | 2 |
| 1816. | Me | H | CF$_3$ | Me | H | 0 |
| 1817. | Me | H | CF$_3$ | Me | H | 1 |
| 1818. | Me | H | CF$_3$ | Me | H | 2 |
| 1819. | Me | H | CF$_3$ | Me | OCH$_2$CH$_2$OMe | 0 |
| 1820. | Me | H | CF$_3$ | Me | OCH$_2$CH$_2$OMe | 1 |

TABLE 1-continued

Compounds of the formula (I)

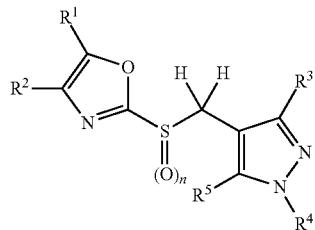

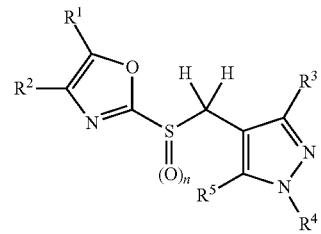

| Ex. No. | R¹ | R² | R³ | R⁴ | R⁵ | n |
|---|---|---|---|---|---|---|
| 1821. | Me | H | CF₃ | Me | OCH₂CH₂OMe | 2 |
| 1822. | Me | H | CF₃ | Me | SMe | 0 |
| 1823. | Me | H | CF₃ | Me | SMe | 1 |
| 1824. | Me | H | CF₃ | Me | SMe | 2 |
| 1825. | Me | H | CF₃ | Me | OCH₂CH₂CH₂F | 0 |
| 1826. | Me | H | CF₃ | Me | OCH₂CH₂CH₂F | 1 |
| 1827. | Me | H | CF₃ | Me | OCH₂CH₂CH₂F | 2 |
| 1828. | Me | H | CF₃ | Me | OCH(CH₂F)₂ | 0 |
| 1829. | Me | H | CF₃ | Me | OCH(CH₂F)₂ | 1 |
| 1830. | Me | H | CF₃ | Me | OCH(CH₂F)₂ | 2 |
| 1831. | Me | H | CF₃ | Me | OCH₂CF₂CHF₂ | 0 |
| 1832. | Me | H | CF₃ | Me | OCH₂CF₂CHF₂ | 1 |
| 1833. | Me | H | CF₃ | Me | OCH₂CF₂CHF₂ | 2 |
| 1834. | Me | H | CF₃ | Me | OCH₂CF=CH₂ | 0 |
| 1835. | Me | H | CF₃ | Me | OCH₂CF=CH₂ | 1 |
| 1836. | Me | H | CF₃ | Me | OCH₂CF=CH₂ | 2 |
| 1837. | Me | H | CF₃ | Me | OCH(Me)CF₃ | 0 |
| 1838. | Me | H | CF₃ | Me | OCH(Me)CF₃ | 1 |
| 1839. | Me | H | CF₃ | Me | OCH(Me)CF₃ | 2 |
| 1840. | Me | H | CF₃ | Me | OCH(Me)CH₂F | 0 |
| 1841. | Me | H | CF₃ | Me | OCH(Me)CH₂F | 1 |
| 1842. | Me | H | CF₃ | Me | OCH(Me)CH₂F | 2 |
| 1843. | Me | H | OCH₂CF₃ | Me | CF₃ | 0 |
| 1844. | Me | H | OCH₂CF₃ | Me | CF₃ | 1 |
| 1845. | Me | H | OCH₂CF₃ | Me | CF₃ | 2 |
| 1846. | Me | H | OCH₂CF₃ | Me | CHF₂ | 0 |
| 1847. | Me | H | OCH₂CF₃ | Me | CHF₂ | 1 |
| 1848. | Me | H | OCH₂CF₃ | Me | CHF₂ | 2 |
| 1849. | Me | H | CHF₂ | Me | CHF₂ | 0 |
| 1850. | Me | H | CHF₂ | Me | CHF₂ | 1 |
| 1851. | Me | H | CHF₂ | Me | CHF₂ | 2 |
| 1852. | Me | H | CF₃ | Me | CHF₂ | 0 |
| 1853. | Me | H | CF₃ | Me | CHF₂ | 1 |
| 1854. | Me | H | CF₃ | Me | CHF₂ | 2 |
| 1855. | Me | H | Cl | Me | OCHF₂ | 0 |
| 1856. | Me | H | Cl | Me | OCHF₂ | 1 |
| 1857. | Me | H | Cl | Me | OCHF₂ | 2 |
| 1858. | Me | H | Br | Me | OCHF₂ | 0 |
| 1859. | Me | H | Br | Me | OCHF₂ | 1 |
| 1860. | Me | H | Br | Me | OCHF₂ | 2 |
| 1861. | Me | H | Br | Me | CF₃ | 0 |
| 1862. | Me | H | Br | Me | CF₃ | 1 |
| 1863. | Me | H | Br | Me | CF₃ | 2 |
| 1864. | NO₂ | H | CF₃ | tBu | Cl | 0 |
| 1865. | NO₂ | H | CF₃ | tBu | Cl | 1 |
| 1866. | NO₂ | H | CF₃ | tBu | Cl | 2 |
| 1867. | NO₂ | H | CF₃ | CHF₂ | Cl | 0 |
| 1868. | NO₂ | H | CF₃ | CHF₂ | Cl | 1 |
| 1869. | NO₂ | H | CF₃ | CHF₂ | Cl | 2 |
| 1870. | NO₂ | H | Cl | CHF₂ | CF₃ | 0 |
| 1871. | NO₂ | H | Cl | CHF₂ | CF₃ | 1 |
| 1872. | NO₂ | H | Cl | CHF₂ | CF₃ | 2 |
| 1873. | NO₂ | H | CF₃ | Me | OMe | 0 |
| 1874. | NO₂ | H | CF₃ | Me | OMe | 1 |
| 1875. | NO₂ | H | CF₃ | Me | OMe | 2 |
| 1876. | NO₂ | H | CF₃ | Me | CN | 0 |
| 1877. | NO₂ | H | CF₃ | Me | CN | 1 |
| 1878. | NO₂ | H | CF₃ | Me | CN | 2 |
| 1879. | NO₂ | H | CHF₂ | Me | Cl | 0 |
| 1880. | NO₂ | H | CHF₂ | Me | Cl | 1 |
| 1881. | NO₂ | H | CHF₂ | Me | Cl | 2 |
| 1882. | NO₂ | H | Me | Me | Me | 0 |
| 1883. | NO₂ | H | Me | Me | Me | 1 |
| 1884. | NO₂ | H | Me | Me | Me | 2 |
| 1885. | NO₂ | H | Me | Me | Cl | 0 |
| 1886. | NO₂ | H | Me | Me | Cl | 1 |
| 1887. | NO₂ | H | Me | Me | Cl | 2 |
| 1888. | NO₂ | H | CF₃ | Me | Cl | 0 |
| 1889. | NO₂ | H | CF₃ | Me | Cl | 1 |
| 1890. | NO₂ | H | CF₃ | Me | Cl | 2 |
| 1891. | NO₂ | H | Cl | Me | CF₃ | 0 |
| 1892. | NO₂ | H | Cl | Me | CF₃ | 1 |
| 1893. | NO₂ | H | Cl | Me | CF₃ | 2 |
| 1894. | NO₂ | H | CF₃ | Me | F | 0 |
| 1895. | NO₂ | H | CF₃ | Me | F | 1 |
| 1896. | NO₂ | H | CF₃ | Me | F | 2 |
| 1897. | NO₂ | H | OMe | Me | CF₃ | 0 |
| 1898. | NO₂ | H | OMe | Me | CF₃ | 1 |
| 1899. | NO₂ | H | OMe | Me | CF₃ | 2 |
| 1900. | NO₂ | H | CF₃ | Me | OCHF₂ | 0 |
| 1901. | NO₂ | H | CF₃ | Me | OCHF₂ | 1 |
| 1902. | NO₂ | H | CF₃ | Me | OCHF₂ | 2 |
| 1903. | NO₂ | H | OCHF₂ | Me | CF₃ | 0 |
| 1904. | NO₂ | H | OCHF₂ | Me | CF₃ | 1 |
| 1905. | NO₂ | H | OCHF₂ | Me | CF₃ | 2 |
| 1906. | NO₂ | H | CF₃ | Me | OCH₂CHF₂ | 0 |
| 1907. | NO₂ | H | CF₃ | Me | OCH₂CHF₂ | 1 |
| 1908. | NO₂ | H | CF₃ | Me | OCH₂CHF₂ | 2 |
| 1909. | NO₂ | H | CF₃ | Me | OCH₂CF₃ | 0 |
| 1910. | NO₂ | H | CF₃ | Me | OCH₂CF₃ | 1 |
| 1911. | NO₂ | H | CF₃ | Me | OCH₂CF₃ | 2 |
| 1912. | NO₂ | H | CF₃ | Me | SO₂Me | 0 |
| 1913. | NO₂ | H | CF₃ | Me | SO₂Me | 1 |
| 1914. | NO₂ | H | CF₃ | Me | SO₂Me | 2 |
| 1915. | NO₂ | H | CF₃ | Me | SEt | 0 |
| 1916. | NO₂ | H | CF₃ | Me | SEt | 1 |
| 1917. | NO₂ | H | CF₃ | Me | SEt | 2 |
| 1918. | NO₂ | H | CF₃ | Et | Cl | 0 |
| 1919. | NO₂ | H | CF₃ | Et | Cl | 1 |
| 1920. | NO₂ | H | CF₃ | Et | Cl | 2 |
| 1921. | NO₂ | H | CF₃ | iPr | Cl | 0 |
| 1922. | NO₂ | H | CF₃ | iPr | Cl | 1 |
| 1923. | NO₂ | H | CF₃ | iPr | Cl | 2 |
| 1924. | NO₂ | H | CF₃ | tBu | Cl | 0 |
| 1925. | NO₂ | H | CF₃ | tBu | Cl | 1 |
| 1926. | NO₂ | H | CF₃ | tBu | Cl | 2 |
| 1927. | NO₂ | H | Cl | tBu | CF₃ | 0 |
| 1928. | NO₂ | H | Cl | tBu | CF₃ | 1 |
| 1929. | NO₂ | H | Cl | tBu | CF₃ | 2 |
| 1930. | NO₂ | H | CF₃ | cPen | Cl | 0 |
| 1931. | NO₂ | H | CF₃ | cPen | Cl | 1 |
| 1932. | NO₂ | H | CF₃ | cPen | Cl | 2 |
| 1933. | NO₂ | H | CF₃ | CHF₂ | OMe | 0 |
| 1934. | NO₂ | H | CF₃ | CHF₂ | OMe | 1 |
| 1935. | NO₂ | H | CF₃ | CHF₂ | OMe | 2 |
| 1936. | NO₂ | H | CF₃ | CH₂CF₃ | Cl | 0 |
| 1937. | NO₂ | H | CF₃ | CH₂CF₃ | Cl | 1 |
| 1938. | NO₂ | H | CF₃ | CH₂CF₃ | Cl | 2 |
| 1939. | NO₂ | H | CF₃ | Ph | OCHF₂ | 0 |
| 1940. | NO₂ | H | CF₃ | Ph | OCHF₂ | 1 |
| 1941. | NO₂ | H | CF₃ | Ph | OCHF₂ | 2 |
| 1942. | NO₂ | H | CF₃ | Ph | Cl | 0 |
| 1943. | NO₂ | H | CF₃ | Ph | Cl | 1 |
| 1944. | NO₂ | H | CF₃ | Ph | Cl | 2 |

TABLE 1-continued

Compounds of the formula (I)

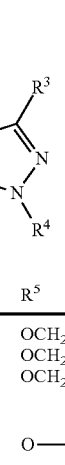

| Ex. No. | R¹ | R² | R³ | R⁴ | R⁵ | n |
|---|---|---|---|---|---|---|
| 1945. | $NO_2$ | H | Me | Me | $OCH_2CF_3$ | 0 |
| 1946. | $NO_2$ | H | Me | Me | $OCH_2CF_3$ | 1 |
| 1947. | $NO_2$ | H | Me | Me | $OCH_2CF_3$ | 2 |
| 1948. | $NO_2$ | H | $CF_3$ | Me |  | 0 |
| 1949. | $NO_2$ | H | $CF_3$ | Me |  | 1 |
| 1950. | $NO_2$ | H | $CF_3$ | Me |  | 2 |
| 1951. | $NO_2$ | H | $CF_3$ | Me | H | 0 |
| 1952. | $NO_2$ | H | $CF_3$ | Me | H | 1 |
| 1953. | $NO_2$ | H | $CF_3$ | Me | H | 2 |
| 1954. | $NO_2$ | H | $CF_3$ | Me | $OCH_2CH_2OMe$ | 0 |
| 1955. | $NO_2$ | H | $CF_3$ | Me | $OCH_2CH_2OMe$ | 1 |
| 1956. | $NO_2$ | H | $CF_3$ | Me | $OCH_2CH_2OMe$ | 2 |
| 1957. | $NO_2$ | H | $CF_3$ | Me | SMe | 0 |
| 1958. | $NO_2$ | H | $CF_3$ | Me | SMe | 1 |
| 1959. | $NO_2$ | H | $CF_3$ | Me | SMe | 2 |
| 1960. | $NO_2$ | H | $CF_3$ | Me | $OCH_2CH_2CH_2F$ | 0 |
| 1961. | $NO_2$ | H | $CF_3$ | Me | $OCH_2CH_2CH_2F$ | 1 |
| 1962. | $NO_2$ | H | $CF_3$ | Me | $OCH_2CH_2CH_2F$ | 2 |
| 1963. | $NO_2$ | H | $CF_3$ | Me | $OCH(CH_2F)_2$ | 0 |
| 1964. | $NO_2$ | H | $CF_3$ | Me | $OCH(CH_2F)_2$ | 1 |
| 1965. | $NO_2$ | H | $CF_3$ | Me | $OCH(CH_2F)_2$ | 2 |
| 1966. | $NO_2$ | H | $CF_3$ | Me | $OCH_2CF_2CHF_2$ | 0 |
| 1967. | $NO_2$ | H | $CF_3$ | Me | $OCH_2CF_2CHF_2$ | 1 |
| 1968. | $NO_2$ | H | $CF_3$ | Me | $OCH_2CF_2CHF_2$ | 2 |
| 1969. | $NO_2$ | H | $CF_3$ | Me | $OCH_2CF=CH_2$ | 0 |
| 1970. | $NO_2$ | H | $CF_3$ | Me | $OCH_2CF=CH_2$ | 1 |
| 1971. | $NO_2$ | H | $CF_3$ | Me | $OCH_2CF=CH_2$ | 2 |
| 1972. | $NO_2$ | H | $CF_3$ | Me | $OCH(Me)CF_3$ | 0 |
| 1973. | $NO_2$ | H | $CF_3$ | Me | $OCH(Me)CF_3$ | 1 |
| 1974. | $NO_2$ | H | $CF_3$ | Me | $OCH(Me)CF_3$ | 2 |
| 1975. | $NO_2$ | H | $CF_3$ | Me | $OCH(Me)CH_2F$ | 0 |
| 1976. | $NO_2$ | H | $CF_3$ | Me | $OCH(Me)CH_2F$ | 1 |
| 1977. | $NO_2$ | H | $CF_3$ | Me | $OCH(Me)CH_2F$ | 2 |
| 1978. | $NO_2$ | H | $OCH_2CF_3$ | Me | $CF_3$ | 0 |
| 1979. | $NO_2$ | H | $OCH_2CF_3$ | Me | $CF_3$ | 1 |
| 1980. | $NO_2$ | H | $OCH_2CF_3$ | Me | $CF_3$ | 2 |
| 1981. | $NO_2$ | H | $OCH_2CF_3$ | Me | $CHF_2$ | 0 |
| 1982. | $NO_2$ | H | $OCH_2CF_3$ | Me | $CHF_2$ | 1 |
| 1983. | $NO_2$ | H | $OCH_2CF_3$ | Me | $CHF_2$ | 2 |
| 1984. | $NO_2$ | H | $CHF_2$ | Me | $CHF_2$ | 0 |
| 1985. | $NO_2$ | H | $CHF_2$ | Me | $CHF_2$ | 1 |
| 1986. | $NO_2$ | H | $CHF_2$ | Me | $CHF_2$ | 2 |
| 1987. | $NO_2$ | H | $CF_3$ | Me | $CHF_2$ | 0 |
| 1988. | $NO_2$ | H | $CF_3$ | Me | $CHF_2$ | 1 |
| 1989. | $NO_2$ | H | $CF_3$ | Me | $CHF_2$ | 2 |
| 1990. | $NO_2$ | H | Cl | Me | $OCHF_2$ | 0 |
| 1991. | $NO_2$ | H | Cl | Me | $OCHF_2$ | 1 |
| 1992. | $NO_2$ | H | Cl | Me | $OCHF_2$ | 2 |
| 1993. | $NO_2$ | H | Br | Me | $OCHF_2$ | 0 |
| 1994. | $NO_2$ | H | Br | Me | $OCHF_2$ | 1 |
| 1995. | $NO_2$ | H | Br | Me | $OCHF_2$ | 2 |
| 1996. | $NO_2$ | H | Br | Me | $CF_3$ | 0 |
| 1997. | $NO_2$ | H | Br | Me | $CF_3$ | 1 |
| 1998. | $NO_2$ | H | Br | Me | $CF_3$ | 2 |
| 1999. | Cl | Cl | $CF_3$ | tBu | Cl | 0 |
| 2000. | Cl | Cl | $CF_3$ | tBu | Cl | 1 |
| 2001. | Cl | Cl | $CF_3$ | tBu | Cl | 2 |
| 2002. | Cl | Cl | $CF_3$ | $CHF_2$ | Cl | 0 |
| 2003. | Cl | Cl | $CF_3$ | $CHF_2$ | Cl | 1 |
| 2004. | Cl | Cl | $CF_3$ | $CHF_2$ | Cl | 2 |
| 2005. | Cl | Cl | Cl | $CHF_2$ | $CF_3$ | 0 |
| 2006. | Cl | Cl | Cl | $CHF_2$ | $CF_3$ | 1 |
| 2007. | Cl | Cl | Cl | $CHF_2$ | $CF_3$ | 2 |
| 2008. | Cl | Cl | $CF_3$ | Me | OMe | 0 |
| 2009. | Cl | Cl | $CF_3$ | Me | OMe | 1 |
| 2010. | Cl | Cl | $CF_3$ | Me | OMe | 2 |
| 2011. | Cl | Cl | $CF_3$ | Me | CN | 0 |
| 2012. | Cl | Cl | $CF_3$ | Me | CN | 1 |
| 2013. | Cl | Cl | $CF_3$ | Me | CN | 2 |
| 2014. | Cl | Cl | $CHF_2$ | Me | Cl | 0 |
| 2015. | Cl | Cl | $CHF_2$ | Me | Cl | 1 |
| 2016. | Cl | Cl | $CHF_2$ | Me | Cl | 2 |
| 2017. | Cl | Cl | Me | Me | Me | 0 |
| 2018. | Cl | Cl | Me | Me | Me | 1 |
| 2019. | Cl | Cl | Me | Me | Me | 2 |
| 2020. | Cl | Cl | Me | Me | Cl | 0 |
| 2021. | Cl | Cl | Me | Me | Cl | 1 |
| 2022. | Cl | Cl | Me | Me | Cl | 2 |
| 2023. | Cl | Cl | $CF_3$ | Me | Cl | 0 |
| 2024. | Cl | Cl | $CF_3$ | Me | Cl | 1 |
| 2025. | Cl | Cl | $CF_3$ | Me | Cl | 2 |
| 2026. | Cl | Cl | Cl | Me | $CF_3$ | 0 |
| 2027. | Cl | Cl | Cl | Me | $CF_3$ | 1 |
| 2028. | Cl | Cl | Cl | Me | $CF_3$ | 2 |
| 2029. | Cl | Cl | $CF_3$ | Me | F | 0 |
| 2030. | Cl | Cl | $CF_3$ | Me | F | 1 |
| 2031. | Cl | Cl | $CF_3$ | Me | F | 2 |
| 2032. | Cl | Cl | OMe | Me | $CF_3$ | 0 |
| 2033. | Cl | Cl | OMe | Me | $CF_3$ | 1 |
| 2034. | Cl | Cl | OMe | Me | $CF_3$ | 2 |
| 2035. | Cl | Cl | $CF_3$ | Me | $OCHF_2$ | 0 |
| 2036. | Cl | Cl | $CF_3$ | Me | $OCHF_2$ | 1 |
| 2037. | Cl | Cl | $CF_3$ | Me | $OCHF_2$ | 2 |
| 2038. | Cl | Cl | $OCHF_2$ | Me | $CF_3$ | 0 |
| 2039. | Cl | Cl | $OCHF_2$ | Me | $CF_3$ | 1 |
| 2040. | Cl | Cl | $OCHF_2$ | Me | $CF_3$ | 2 |
| 2041. | Cl | Cl | $CF_3$ | Me | $OCH_2CHF_2$ | 0 |
| 2042. | Cl | Cl | $CF_3$ | Me | $OCH_2CHF_2$ | 1 |
| 2043. | Cl | Cl | $CF_3$ | Me | $OCH_2CHF_2$ | 2 |
| 2044. | Cl | Cl | $CF_3$ | Me | $OCH_2CF_3$ | 0 |
| 2045. | Cl | Cl | $CF_3$ | Me | $OCH_2CF_3$ | 1 |
| 2046. | Cl | Cl | $CF_3$ | Me | $OCH_2CF_3$ | 2 |
| 2047. | Cl | Cl | $CF_3$ | Me | $SO_2Me$ | 0 |
| 2048. | Cl | Cl | $CF_3$ | Me | $SO_2Me$ | 1 |
| 2049. | Cl | Cl | $CF_3$ | Me | $SO_2Me$ | 2 |
| 2050. | Cl | Cl | $CF_3$ | Me | SEt | 0 |
| 2051. | Cl | Cl | $CF_3$ | Me | SEt | 1 |
| 2052. | Cl | Cl | $CF_3$ | Me | SEt | 2 |
| 2053. | Cl | Cl | $CF_3$ | Et | Cl | 0 |
| 2054. | Cl | Cl | $CF_3$ | Et | Cl | 1 |
| 2055. | Cl | Cl | $CF_3$ | Et | Cl | 2 |
| 2056. | Cl | Cl | $CF_3$ | iPr | Cl | 0 |
| 2057. | Cl | Cl | $CF_3$ | iPr | Cl | 1 |

TABLE 1-continued

Compounds of the formula (I)

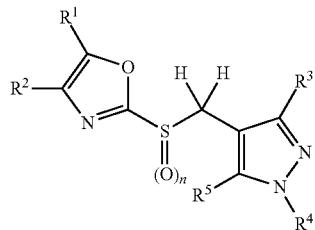
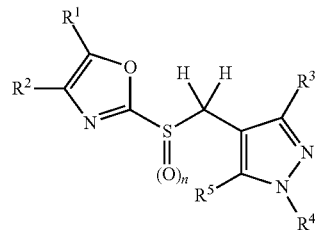

| Ex. No. | R¹ | R² | R³ | R⁴ | R⁵ | n |
|---|---|---|---|---|---|---|
| 2058. | Cl | Cl | $CF_3$ | iPr | Cl | 2 |
| 2059. | Cl | Cl | $CF_3$ | tBu | Cl | 0 |
| 2060. | Cl | Cl | $CF_3$ | tBu | Cl | 1 |
| 2061. | Cl | Cl | $CF_3$ | tBu | Cl | 2 |
| 2062. | Cl | Cl | Cl | tBu | $CF_3$ | 0 |
| 2063. | Cl | Cl | Cl | tBu | $CF_3$ | 1 |
| 2064. | Cl | Cl | Cl | tBu | $CF_3$ | 2 |
| 2065. | Cl | Cl | $CF_3$ | cPen | Cl | 0 |
| 2066. | Cl | Cl | $CF_3$ | cPen | Cl | 1 |
| 2067. | Cl | Cl | $CF_3$ | cPen | Cl | 2 |
| 2068. | Cl | Cl | $CF_3$ | $CHF_2$ | OMe | 0 |
| 2069. | Cl | Cl | $CF_3$ | $CHF_2$ | OMe | 1 |
| 2070. | Cl | Cl | $CF_3$ | $CHF_2$ | OMe | 2 |
| 2071. | Cl | Cl | $CF_3$ | $CH_2CF_3$ | Cl | 0 |
| 2072. | Cl | Cl | $CF_3$ | $CH_2CF_3$ | Cl | 1 |
| 2073. | Cl | Cl | $CF_3$ | $CH_2CF_3$ | Cl | 2 |
| 2074. | Cl | Cl | $CF_3$ | Ph | $OCHF_2$ | 0 |
| 2075. | Cl | Cl | $CF_3$ | Ph | $OCHF_2$ | 1 |
| 2076. | Cl | Cl | $CF_3$ | Ph | $OCHF_2$ | 2 |
| 2077. | Cl | Cl | $CF_3$ | Ph | Cl | 0 |
| 2078. | Cl | Cl | $CF_3$ | Ph | Cl | 1 |
| 2079. | Cl | Cl | $CF_3$ | Ph | Cl | 2 |
| 2080. | Cl | Cl | Me | Me | $OCH_2CF_3$ | 0 |
| 2081. | Cl | Cl | Me | Me | $OCH_2CF_3$ | 1 |
| 2082. | Cl | Cl | Me | Me | $OCH_2CF_3$ | 2 |
| 2083. | Cl | Cl | $CF_3$ | Me | oxetanyl | 0 |
| 2084. | Cl | Cl | $CF_3$ | Me | oxetanyl | 1 |
| 2085. | Cl | Cl | $CF_3$ | Me | oxetanyl | 2 |
| 2086. | Cl | Cl | $CF_3$ | Me | H | 0 |
| 2087. | Cl | Cl | $CF_3$ | Me | H | 1 |
| 2088. | Cl | Cl | $CF_3$ | Me | H | 2 |
| 2089. | Cl | Cl | $CF_3$ | Me | $OCH_2CH_2OMe$ | 0 |
| 2090. | Cl | Cl | $CF_3$ | Me | $OCH_2CH_2OMe$ | 1 |
| 2091. | Cl | Cl | $CF_3$ | Me | $OCH_2CH_2OMe$ | 2 |
| 2092. | Cl | Cl | $CF_3$ | Me | SMe | 0 |
| 2093. | Cl | Cl | $CF_3$ | Me | SMe | 1 |
| 2094. | Cl | Cl | $CF_3$ | Me | SMe | 2 |
| 2095. | Cl | Cl | $CF_3$ | Me | $OCH_2CH_2CH_2F$ | 0 |
| 2096. | Cl | Cl | $CF_3$ | Me | $OCH_2CH_2CH_2F$ | 1 |
| 2097. | Cl | Cl | $CF_3$ | Me | $OCH_2CH_2CH_2F$ | 2 |
| 2098. | Cl | Cl | $CF_3$ | Me | $OCH(CH_2F)_2$ | 0 |
| 2099. | Cl | Cl | $CF_3$ | Me | $OCH(CH_2F)_2$ | 1 |
| 2100. | Cl | Cl | $CF_3$ | Me | $OCH(CH_2F)_2$ | 2 |
| 2101. | Cl | Cl | $CF_3$ | Me | $OCH_2CF_2CHF_2$ | 0 |
| 2102. | Cl | Cl | $CF_3$ | Me | $OCH_2CF_2CHF_2$ | 1 |
| 2103. | Cl | Cl | $CF_3$ | Me | $OCH_2CF_2CHF_2$ | 2 |
| 2104. | Cl | Cl | $CF_3$ | Me | $OCH_2CF=CH_2$ | 0 |
| 2105. | Cl | Cl | $CF_3$ | Me | $OCH_2CF=CH_2$ | 1 |
| 2106. | Cl | Cl | $CF_3$ | Me | $OCH_2CF=CH_2$ | 2 |
| 2107. | Cl | Cl | $CF_3$ | Me | $OCH(Me)CF_3$ | 0 |
| 2108. | Cl | Cl | $CF_3$ | Me | $OCH(Me)CF_3$ | 1 |
| 2109. | Cl | Cl | $CF_3$ | Me | $OCH(Me)CF_3$ | 2 |
| 2110. | Cl | Cl | $CF_3$ | Me | $OCH(Me)CH_2F$ | 0 |
| 2111. | Cl | Cl | $CF_3$ | Me | $OCH(Me)CH_2F$ | 1 |
| 2112. | Cl | Cl | $CF_3$ | Me | $OCH(Me)CH_2F$ | 2 |
| 2113. | Cl | Cl | $OCH_2CF_3$ | Me | $CF_3$ | 0 |
| 2114. | Cl | Cl | $OCH_2CF_3$ | Me | $CF_3$ | 1 |
| 2115. | Cl | Cl | $OCH_2CF_3$ | Me | $CF_3$ | 2 |
| 2116. | Cl | Cl | $OCH_2CF_3$ | Me | $CHF_2$ | 0 |
| 2117. | Cl | Cl | $OCH_2CF_3$ | Me | $CHF_2$ | 1 |
| 2118. | Cl | Cl | $OCH_2CF_3$ | Me | $CHF_2$ | 2 |
| 2119. | Cl | Cl | $CHF_2$ | Me | $CHF_2$ | 0 |
| 2120. | Cl | Cl | $CHF_2$ | Me | $CHF_2$ | 1 |
| 2121. | Cl | Cl | $CHF_2$ | Me | $CHF_2$ | 2 |
| 2122. | Cl | Cl | $CF_3$ | Me | $CHF_2$ | 0 |
| 2123. | Cl | Cl | $CF_3$ | Me | $CHF_2$ | 1 |
| 2124. | Cl | Cl | $CF_3$ | Me | $CHF_2$ | 2 |
| 2125. | Cl | Cl | Cl | Me | $OCHF_2$ | 0 |
| 2126. | Cl | Cl | Cl | Me | $OCHF_2$ | 1 |
| 2127. | Cl | Cl | Cl | Me | $OCHF_2$ | 2 |
| 2128. | Cl | Cl | Br | Me | $OCHF_2$ | 0 |
| 2129. | Cl | Cl | Br | Me | $OCHF_2$ | 1 |
| 2130. | Cl | Cl | Br | Me | $OCHF_2$ | 2 |
| 2131. | Cl | Cl | Br | Me | $CF_3$ | 0 |
| 2132. | Cl | Cl | Br | Me | $CF_3$ | 1 |
| 2133. | Cl | Cl | Br | Me | $CF_3$ | 2 |
| 2134. | Cl | Me | $CF_3$ | tBu | Cl | 0 |
| 2135. | Cl | Me | $CF_3$ | tBu | Cl | 1 |
| 2136. | Cl | Me | $CF_3$ | tBu | Cl | 2 |
| 2137. | Cl | Me | $CF_3$ | $CHF_2$ | Cl | 0 |
| 2138. | Cl | Me | $CF_3$ | $CHF_2$ | Cl | 1 |
| 2139. | Cl | Me | $CF_3$ | $CHF_2$ | Cl | 2 |
| 2140. | Cl | Me | Cl | $CHF_2$ | $CF_3$ | 0 |
| 2141. | Cl | Me | Cl | $CHF_2$ | $CF_3$ | 1 |
| 2142. | Cl | Me | Cl | $CHF_2$ | $CF_3$ | 2 |
| 2143. | Cl | Me | $CF_3$ | Me | OMe | 0 |
| 2144. | Cl | Me | $CF_3$ | Me | OMe | 1 |
| 2145. | Cl | Me | $CF_3$ | Me | OMe | 2 |
| 2146. | Cl | Me | $CF_3$ | Me | CN | 0 |
| 2147. | Cl | Me | $CF_3$ | Me | CN | 1 |
| 2148. | Cl | Me | $CF_3$ | Me | CN | 2 |
| 2149. | Cl | Me | $CHF_2$ | Me | Cl | 0 |
| 2150. | Cl | Me | $CHF_2$ | Me | Cl | 1 |
| 2151. | Cl | Me | $CHF_2$ | Me | Cl | 2 |
| 2152. | Cl | Me | Me | Me | Me | 0 |
| 2153. | Cl | Me | Me | Me | Me | 1 |
| 2154. | Cl | Me | Me | Me | Me | 2 |
| 2155. | Cl | Me | Me | Me | Cl | 0 |
| 2156. | Cl | Me | Me | Me | Cl | 1 |
| 2157. | Cl | Me | Me | Me | Cl | 2 |
| 2158. | Cl | Me | $CF_3$ | Me | Cl | 0 |
| 2159. | Cl | Me | $CF_3$ | Me | Cl | 1 |
| 2160. | Cl | Me | $CF_3$ | Me | Cl | 2 |
| 2161. | Cl | Me | Cl | Me | $CF_3$ | 0 |
| 2162. | Cl | Me | Cl | Me | $CF_3$ | 1 |
| 2163. | Cl | Me | Cl | Me | $CF_3$ | 2 |
| 2164. | Cl | Me | $CF_3$ | Me | F | 0 |
| 2165. | Cl | Me | $CF_3$ | Me | F | 1 |
| 2166. | Cl | Me | $CF_3$ | Me | F | 2 |
| 2167. | Cl | Me | OMe | Me | $CF_3$ | 0 |
| 2168. | Cl | Me | OMe | Me | $CF_3$ | 1 |
| 2169. | Cl | Me | OMe | Me | $CF_3$ | 2 |
| 2170. | Cl | Me | $CF_3$ | Me | $OCHF_2$ | 0 |

TABLE 1-continued

Compounds of the formula (I)

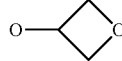

| Ex. No. | R¹ | R² | R³ | R⁴ | R⁵ | n |
|---|---|---|---|---|---|---|
| 2171. | Cl | Me | $CF_3$ | Me | $OCHF_2$ | 1 |
| 2172. | Cl | Me | $CF_3$ | Me | $OCHF_2$ | 2 |
| 2173. | Cl | Me | $OCHF_2$ | Me | $CF_3$ | 0 |
| 2174. | Cl | Me | $OCHF_2$ | Me | $CF_3$ | 1 |
| 2175. | Cl | Me | $OCHF_2$ | Me | $CF_3$ | 2 |
| 2176. | Cl | Me | $CF_3$ | Me | $OCH_2CHF_2$ | 0 |
| 2177. | Cl | Me | $CF_3$ | Me | $OCH_2CHF_2$ | 1 |
| 2178. | Cl | Me | $CF_3$ | Me | $OCH_2CHF_2$ | 2 |
| 2179. | Cl | Me | $CF_3$ | Me | $OCH_2CF_3$ | 0 |
| 2180. | Cl | Me | $CF_3$ | Me | $OCH_2CF_3$ | 1 |
| 2181. | Cl | Me | $CF_3$ | Me | $OCH_2CF_3$ | 2 |
| 2182. | Cl | Me | $CF_3$ | Me | $SO_2Me$ | 0 |
| 2183. | Cl | Me | $CF_3$ | Me | $SO_2Me$ | 1 |
| 2184. | Cl | Me | $CF_3$ | Me | $SO_2Me$ | 2 |
| 2185. | Cl | Me | $CF_3$ | Me | SEt | 0 |
| 2186. | Cl | Me | $CF_3$ | Me | SEt | 1 |
| 2187. | Cl | Me | $CF_3$ | Me | SEt | 2 |
| 2188. | Cl | Me | $CF_3$ | Et | Cl | 0 |
| 2189. | Cl | Me | $CF_3$ | Et | Cl | 1 |
| 2190. | Cl | Me | $CF_3$ | Et | Cl | 2 |
| 2191. | Cl | Me | $CF_3$ | iPr | Cl | 0 |
| 2192. | Cl | Me | $CF_3$ | iPr | Cl | 1 |
| 2193. | Cl | Me | $CF_3$ | iPr | Cl | 2 |
| 2194. | Cl | Me | $CF_3$ | tBu | Cl | 0 |
| 2195. | Cl | Me | $CF_3$ | tBu | Cl | 1 |
| 2196. | Cl | Me | $CF_3$ | tBu | Cl | 2 |
| 2197. | Cl | Me | Cl | tBu | $CF_3$ | 0 |
| 2198. | Cl | Me | Cl | tBu | $CF_3$ | 1 |
| 2199. | Cl | Me | Cl | tBu | $CF_3$ | 2 |
| 2200. | Cl | Me | $CF_3$ | cPen | Cl | 0 |
| 2201. | Cl | Me | $CF_3$ | cPen | Cl | 1 |
| 2202. | Cl | Me | $CF_3$ | cPen | Cl | 2 |
| 2203. | Cl | Me | $CF_3$ | $CHF_2$ | OMe | 0 |
| 2204. | Cl | Me | $CF_3$ | $CHF_2$ | OMe | 1 |
| 2205. | Cl | Me | $CF_3$ | $CHF_2$ | OMe | 2 |
| 2206. | Cl | Me | $CF_3$ | $CH_2CF_3$ | Cl | 0 |
| 2207. | Cl | Me | $CF_3$ | $CH_2CF_3$ | Cl | 1 |
| 2208. | Cl | Me | $CF_3$ | $CH_2CF_3$ | Cl | 2 |
| 2209. | Cl | Me | $CF_3$ | Ph | $OCHF_2$ | 0 |
| 2210. | Cl | Me | $CF_3$ | Ph | $OCHF_2$ | 1 |
| 2211. | Cl | Me | $CF_3$ | Ph | $OCHF_2$ | 2 |
| 2212. | Cl | Me | $CF_3$ | Ph | Cl | 0 |
| 2213. | Cl | Me | $CF_3$ | Ph | Cl | 1 |
| 2214. | Cl | Me | $CF_3$ | Ph | Cl | 2 |
| 2215. | Cl | Me | Me | Me | $OCH_2CF_3$ | 0 |
| 2216. | Cl | Me | Me | Me | $OCH_2CF_3$ | 1 |
| 2217. | Cl | Me | Me | Me | $OCH_2CF_3$ | 2 |
| 2218. | Cl | Me | $CF_3$ | Me | 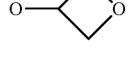 | 0 |
| 2219. | Cl | Me | $CF_3$ | Me | 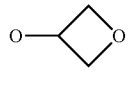 | 1 |
| 2220. | Cl | Me | $CF_3$ | Me | 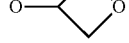 | 2 |
| 2221. | Cl | Me | $CF_3$ | Me | H | 0 |
| 2222. | Cl | Me | $CF_3$ | Me | H | 1 |
| 2223. | Cl | Me | $CF_3$ | Me | H | 2 |
| 2224. | Cl | Me | $CF_3$ | Me | $OCH_2CH_2OMe$ | 0 |
| 2225. | Cl | Me | $CF_3$ | Me | $OCH_2CH_2OMe$ | 1 |
| 2226. | Cl | Me | $CF_3$ | Me | $OCH_2CH_2OMe$ | 2 |
| 2227. | Cl | Me | $CF_3$ | Me | SMe | 0 |
| 2228. | Cl | Me | $CF_3$ | Me | SMe | 1 |
| 2229. | Cl | Me | $CF_3$ | Me | SMe | 2 |
| 2230. | Cl | Me | $CF_3$ | Me | $OCH_2CH_2CH_2F$ | 0 |
| 2231. | Cl | Me | $CF_3$ | Me | $OCH_2CH_2CH_2F$ | 1 |
| 2232. | Cl | Me | $CF_3$ | Me | $OCH_2CH_2CH_2F$ | 2 |
| 2233. | Cl | Me | $CF_3$ | Me | $OCH(CH_2F)_2$ | 0 |
| 2234. | Cl | Me | $CF_3$ | Me | $OCH(CH_2F)_2$ | 1 |
| 2235. | Cl | Me | $CF_3$ | Me | $OCH(CH_2F)_2$ | 2 |
| 2236. | Cl | Me | $CF_3$ | Me | $OCH_2CF_2CHF_2$ | 0 |
| 2237. | Cl | Me | $CF_3$ | Me | $OCH_2CF_2CHF_2$ | 1 |
| 2238. | Cl | Me | $CF_3$ | Me | $OCH_2CF_2CHF_2$ | 2 |
| 2239. | Cl | Me | $CF_3$ | Me | $OCH_2CF=CH_2$ | 0 |
| 2240. | Cl | Me | $CF_3$ | Me | $OCH_2CF=CH_2$ | 1 |
| 2241. | Cl | Me | $CF_3$ | Me | $OCH_2CF=CH_2$ | 2 |
| 2242. | Cl | Me | $CF_3$ | Me | $OCH(Me)CF_3$ | 0 |
| 2243. | Cl | Me | $CF_3$ | Me | $OCH(Me)CF_3$ | 1 |
| 2244. | Cl | Me | $CF_3$ | Me | $OCH(Me)CF_3$ | 2 |
| 2245. | Cl | Me | $CF_3$ | Me | $OCH(Me)CH_2F$ | 0 |
| 2246. | Cl | Me | $CF_3$ | Me | $OCH(Me)CH_2F$ | 1 |
| 2247. | Cl | Me | $CF_3$ | Me | $OCH(Me)CH_2F$ | 2 |
| 2248. | Cl | Me | $OCH_2CF_3$ | Me | $CF_3$ | 0 |
| 2249. | Cl | Me | $OCH_2CF_3$ | Me | $CF_3$ | 1 |
| 2250. | Cl | Me | $OCH_2CF_3$ | Me | $CF_3$ | 2 |
| 2251. | Cl | Me | $OCH_2CF_3$ | Me | $CHF_2$ | 0 |
| 2252. | Cl | Me | $OCH_2CF_3$ | Me | $CHF_2$ | 1 |
| 2253. | Cl | Me | $OCH_2CF_3$ | Me | $CHF_2$ | 2 |
| 2254. | Cl | Me | $CHF_2$ | Me | $CHF_2$ | 0 |
| 2255. | Cl | Me | $CHF_2$ | Me | $CHF_2$ | 1 |
| 2256. | Cl | Me | $CHF_2$ | Me | $CHF_2$ | 2 |
| 2257. | Cl | Me | $CF_3$ | Me | $CHF_2$ | 0 |
| 2258. | Cl | Me | $CF_3$ | Me | $CHF_2$ | 1 |
| 2259. | Cl | Me | $CF_3$ | Me | $CHF_2$ | 2 |
| 2260. | Cl | Me | Cl | Me | $OCHF_2$ | 0 |
| 2261. | Cl | Me | Cl | Me | $OCHF_2$ | 1 |
| 2262. | Cl | Me | Cl | Me | $OCHF_2$ | 2 |
| 2263. | Cl | Me | Br | Me | $OCHF_2$ | 0 |
| 2264. | Cl | Me | Br | Me | $OCHF_2$ | 1 |
| 2265. | Cl | Me | Br | Me | $OCHF_2$ | 2 |
| 2266. | Cl | Me | Br | Me | $CF_3$ | 0 |
| 2267. | Cl | Me | Br | Me | $CF_3$ | 1 |
| 2268. | Cl | Me | Br | Me | $CF_3$ | 2 |

NMR data of selected compounds of Table 1:

5-Chloro-2-({[5-(difluoromethoxy)-1-methyl-3-(trifluoromethyl)-1H-pyrazol-4-yl]methyl}sulfinyl)-1,3-oxazole Compound No. 542: NMR (CDCl$_3$, 400 MHz): 3.87 (s, 3H, CH$_3$); 4.38 (d, 1H, S(O)CH$_2$); 4.50 (d, 1H, S(O)CH$_2$); 6.92 (dd, 1H, OCHF$_2$); 7.16 (s, 1H).

5-Chloro-2-({[5-(difluoromethoxy)-1-methyl-3-(trifluoromethyl)-1H-pyrazol-4-yl]methyl}sulfonyl)-1,3-oxazole Compound No. 543: NMR (CDCl$_3$, 400 MHz): 3.88 (s, 3H, CH$_3$); 4.59 (s, 2H, S(O)$_2$CH$_2$); 6.81 (t, 1H, OCHF$_2$); 7.19 (s, 1H).

5-Bromo-2-({[5-(difluoromethoxy)-1-methyl-3-(trifluoromethyl)-1H-pyrazol-4-yl]methyl}sulfinyl)-1,3-oxazole Compound No. 788: NMR (CDCl$_3$, 400 MHz): 3.85 (s, 3H, CH$_3$); 4.38 (d, 1H, S(O)CH$_2$); 4.49 (d, 1H, S(O)CH$_2$); 6.91 (dd, 1H, OCHF$_2$); 7.24 (s, 1H).

5-Bromo-2-({[5-(difluoromethoxy)-1-methyl-3-(trifluoromethyl)-1H-pyrazol-4-yl]methyl}sulfonyl)-1,3-oxazole Compound No. 789: NMR (CDCl$_3$, 400 MHz): 3.88 (s, 3H, CH$_3$); 4.59 (s, 2H, S(O)$_2$CH$_2$); 6.81 (t, 1H, OCHF$_2$); 7.28 (s, 1H).

5-Iodo-2-({[5-(difluoromethoxy)-1-methyl-3-(trifluoromethyl)-1H-pyrazol-4-yl]methyl}sulfinyl)-1,3-oxazole Compound No. 1034: NMR (CDCl$_3$, 400 MHz): 3.85 (s, 3H, CH$_3$); 4.37 (d, 1H, S(O)CH$_2$); 4.48 (d, 1H, S(O)CH$_2$); 6.92 (dd, 1H, OCHF$_2$); 7.38 (s, 1H).

5-Iodo-2-({[5-(difluoromethoxy)-1-methyl-3-(trifluoromethyl)-1H-pyrazol-4-yl]methyl}sulfonyl)-1,3-oxazole Compound No. 1035: NMR (CDCl$_3$, 400 MHz): 3.88 (s, 3H, CH$_3$); 4.59 (s, 2H, S(O)$_2$CH$_2$); 6.81 (t, 1H, OCHF$_2$); 7.40 (s, 1H).

2-({[5-(Chloro)-1-methyl-3-(trifluoromethyl)-1H-pyrazol-4-yl]methyl}sulfinyl)-1,3-oxazole Compound No. 35: NMR (CDCl$_3$, 400 MHz): 4.00 (s, 3H, CH$_3$); 4.50 (br s, 2H, S(O)CH$_2$); 7.36 (br d, 1H); 7.91 (br d, 1H).

2-({[5-(Chloro)-1-methyl-3-(trifluoromethyl)-1H-pyrazol-4-yl]methyl}sulfonyl)-1,3-oxazole Compound No. 36: NMR (CDCl$_3$, 400 MHz): 3.20 (s, 3H, CH$_3$); 4.61 (s, 2H, S(O)$_2$CH$_2$); 7.40 (br d, 1H); 7.89 (br d, 1H).

2-({[3-(Difluoromethyl)-1-methyl-5-(2,2,2-trifluoroethoxy)-1H-pyrazol-4-yl]methyl}sulfinyl)-1,3-oxazole Compound No. 242: NMR (CDCl$_3$, 400 MHz): 3.75 (s, 3H, CH$_3$); 4.41 (d, 1H, S(O)CH$_2$); 4.51 (d, 1H, S(O)CH$_2$); 4.74 (dxq, 1H); 4.78 (dxq, 1H); 6.57 (t, 1H); 7.39 (br d, 1H); 7.93 (br d, 1H).

2-({[1-Methyl-3,5-bis(trifluoromethyl)-1H-pyrazol-4-yl]methyl}sulfinyl)-1,3-oxazole Compound No. 230: NMR (CDCl$_3$, 400 MHz): 4.09 (s, 3H, CH$_3$); 4.55 (d, 1H, S(O)CH$_2$); 4.66 (d, 1H, S(O)CH$_2$); 7.36 (br d, 1H); 7.93 (br d, 1H).

2-({[3-(Difluoromethyl)-1-methyl-5-(2,2,2-trifluoroethoxy)-1H-pyrazol-4-yl]methyl}sulfanyl)-1,3-oxazole Compound No. 241: NMR (CDCl$_3$, 400 MHz): 3.71 (s, 3H, CH$_3$); 4.39 (s, 2H, SCH$_2$); 4.63 (q, 2H); 5.60 (t, 1H); 7.11 (br d, 1H); 7.69 (br d, 1H).

2-({[3-(Difluoromethyl)-1-methyl-5-(2,2,2-trifluoroethoxy)-1H-pyrazol-4-yl]methyl}sulfonyl)-1,3-oxazole Compound No. 243: NMR (CDCl$_3$, 400 MHz): 3.78 (s, 3H, CH$_3$); 4.62 (s, 2H, S(O)$_2$CH$_2$); 4.69 (q, 2H); 6.54 (t, 1H); 7.39 (br d, 1H); 7.89 (br d, 1H).

2-({[1-Methyl-3,5-bis(trifluoromethyl)-1H-pyrazol-4-yl]methyl}sulfonyl)-1,3-oxazole Compound No. 231: NMR (CDCl$_3$, 400 MHz): 4.10 (s, 3H, CH$_3$); 4.26 (s, 2H, S(O)$_2$CH$_2$); 7.41 (br d, 1H); 7.89 (br d, 1H).

2-({[1-Methyl-3,5-bis(trifluoromethyl)-1H-pyrazol-4-yl]methyl}sulfanyl)-1,3-oxazole Compound No. 229: NMR (CDCl$_3$, 400 MHz): 4.05 (s, 3H, CH$_3$); 4.43 (s, 2H, SCH$_2$); 7.15 (br d, 1H); 7.69 (br d, 1H).

2-({[5-(Difluoromethyl)-1-methyl-3-(trifluoromethyl)-1H-pyrazol-4-yl]methyl}sulfanyl)-1,3-oxazole Compound No. 217: NMR (CDCl$_3$, 400 MHz): 4.02 (s, 3H, CH$_3$); 4.33 (s, 2H, SCH$_2$); 7.11 (br d, 1H); 7.31 (t, 1H); 7.65 (br d, 1H).

2-({[5-(Difluoromethyl)-1-methyl-3-(trifluoromethyl)-1H-pyrazol-4-yl]methyl}sulfinyl)-1,3-oxazole Compound No. 218: NMR (CDCl$_3$, 400 MHz): 4.10 (s, 3H, CH$_3$); 4.51 (d, 1H, S(O)CH$_2$); 4.56 (d, 1H, S(O)CH$_2$); 6.97 (t, 1H); 7.38 (br d, 1H); 7.90 (br d, 1H).

2-({[5-(Difluoromethyl)-1-methyl-3-(trifluoromethyl)-1H-pyrazol-4-yl]methyl}sulfonyl)-1,3-oxazole Compound No. 219: NMR (CDCl$_3$, 400 MHz): 4.10 (s, 3H, CH$_3$); 4.70 (s, 2H, S(O)$_2$CH$_2$); 7.02 (t, 1H); 7.39 (br d, 1H); 7.88 (br d, 1H).

2-({[1-Methyl-5-(2,2,2-trifluoroethoxy)-3-(trifluoromethyl)-1H-pyrazol-4-yl]methyl}sulfanyl)-1,3-oxazole Compound No. 58: NMR (CDCl$_3$, 400 MHz): 3.75 (s, 3H, CH$_3$); 4.36 (s, 2H, SCH$_2$); 4.67 (q, 2H); 7.12 (br d, 1H); 7.69 (br d, 1H).

2-({[1-Methyl-5-(2,2,2-trifluoroethoxy)-3-(trifluoromethyl)-1H-pyrazol-4-yl]methyl}sulfinyl)-1,3-oxazole Compound No. 59: NMR (CDCl₃, 400 MHz): 3.80 (s, 3H, CH₃); 4.31 (d, 1H, S(O)CH₂); 4.52 (d, 1H, S(O)CH₂); 4.76 (q, 1H); 4.78 (q, 1H); 7.40 (br d, 1H); 7.93 (br d, 1H).

2-({[1-Methyl-5-(2,2,2-trifluoroethoxy)-3-(trifluoromethyl)-1H-pyrazol-4-yl]methyl}sulfonyl)-1,3-oxazole Compound No. 60: NMR (CDCl₃, 400 MHz): 3.82 (s, 3H, CH₃); 4.60 (s, 2H, S(O)₂CH₂); 4.72 (q, 2H); 7.41 (br d, 1H); 7.90 (br d, 1H).

4-Chloro-2-({[5-(difluoromethoxy)-1-methyl-3-(trifluoromethyl)-1H-pyrazol-4-yl]methyl}sulfanyl)-1,3-oxazole Compound No. 1495: NMR (CDCl₃, 400 MHz): 3.80 (s, 3H, CH₃); 4.32 (s, 2H, SCH₂); 6.76 (t, 1H); 7.61 (br d, 1H).

4-Chloro-2-({[5-(difluoromethoxy)-1-methyl-3-(trifluoromethyl)-1H-pyrazol-4-yl]methyl}sulfinyl)-1,3-oxazole Compound No. 1496: NMR (CDCl₃, 400 MHz): 3.85 (s, 3H, CH₃); 4.39 (d, 1H, S(O)CH₂); 4.48 (d, 1H, S(O)CH₂); 6.90 (dxt, 1H); 7.82 (br d, 1H).

5-Chloro-2-({[5-(difluoromethoxy)-1-methyl-3-(trifluoromethyl)-1H-pyrazol-4-yl]methyl}sulfanyl)-4-methyl-1,3-oxazole Compound No. 2170: NMR (CDCl₃, 400 MHz): 2.09 (s, 3H, CH₃); 3.81 (s, 3H, CH₃); 4.25 (s, 2H, SCH₂); 6.74 (t, 1H).

TABLE 2

Compounds of the formula (III-S)

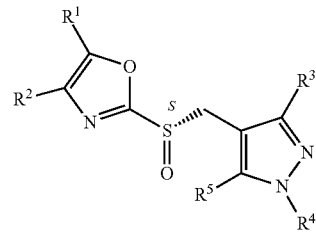

(III-S)

| Ex. No. | R¹ | R² | R³ | R⁴ | R⁵ |
|---|---|---|---|---|---|
| 2269. | H | H | CF₃ | Ph | Cl |
| 2270. | H | H | CF₃ | tBu | Cl |
| 2271. | H | H | CF₃ | CHF₂ | Cl |
| 2272. | H | H | Cl | CHF₂ | CF₃ |
| 2273. | H | H | CF₃ | Me | OMe |
| 2274. | H | H | CF₃ | Me | CN |
| 2275. | H | H | Cl | Et | Cl |
| 2276. | H | H | CHF₂ | Me | Cl |
| 2277. | H | H | Me | Me | Me |
| 2278. | H | H | Me | Me | Cl |
| 2279. | H | H | Cl | Me | Cl |
| 2280. | H | H | CF₃ | Me | Cl |
| 2281. | H | H | Cl | Me | CF₃ |
| 2282. | H | H | CF₃ | Me | F |
| 2283. | H | H | OMe | Me | CF₃ |
| 2284. | H | H | CF₃ | Me | OEt |
| 2285. | H | H | CF₃ | Me | OCHF₂ |
| 2286. | H | H | OCHF₂ | Me | CF₃ |
| 2287. | H | H | CF₃ | Me | OCH₂CHF₂ |
| 2288. | H | H | CF₃ | Me | OCH₂CF₃ |
| 2289. | H | H | CF₃ | Me | OCH₂CN |
| 2290. | H | H | CF₃ | Me | SO₂Me |
| 2291. | H | H | CF₃ | Me | SEt |
| 2292. | H | H | CF₃ | Me | Me |
| 2293. | H | H | CF₃ | Me | Et |
| 2294. | H | H | CF₃ | Et | Cl |
| 2295. | H | H | Cl | Et | CF₃ |
| 2296. | H | H | CF₃ | iPr | Cl |
| 2297. | H | H | Cl | iPr | CF₃ |
| 2298. | H | H | CF₃ | tBu | Cl |
| 2299. | H | H | Cl | tBu | CF₃ |
| 2300. | H | H | CF₃ | cPen | Cl |
| 2301. | H | H | Cl | cPen | CF₃ |
| 2302. | H | H | CF₃ | CH₂cPr | Cl |
| 2303. | H | H | Cl | CH₂cPr | CF₃ |
| 2304. | H | H | CF₃ | CH₂CH=CH₂ | Cl |
| 2305. | H | H | Cl | CH₂CH=CH₂ | CF₃ |
| 2306. | H | H | CF₃ | CHF₂ | OMe |
| 2307. | H | H | OMe | CHF₂ | CF₃ |
| 2308. | H | H | CF₃ | CH₂CF₃ | Cl |
| 2309. | H | H | Cl | CH₂CF₃ | CF₃ |
| 2310. | H | H | CF₃ | CH₂OMe | Cl |
| 2311. | H | H | Cl | CH₂OMe | CF₃ |
| 2312. | H | H | CF₃ | CH₂CN | Cl |
| 2313. | H | H | Me | Ph | Me |
| 2314. | H | H | Me | Ph | Cl |
| 2315. | H | H | Et | Ph | Cl |
| 2316. | H | H | Pr | Ph | Cl |
| 2317. | H | H | iPr | Ph | Cl |
| 2318. | H | H | CF₃ | Ph | Cl |
| 2319. | H | H | CF₃ | Ph | Me |
| 2320. | H | H | CF₃ | Ph | CF₃ |
| 2321. | H | H | CF₃ | Ph | F |
| 2322. | H | H | CF₃ | Ph | OMe |
| 2323. | H | H | CF₃ | Ph | OEt |
| 2324. | H | H | CF₃ | Ph | OCHF₂ |
| 2325. | H | H | CF₃ | Ph | CN |
| 2326. | H | H | CF₃ | Ph(4-Cl) | Cl |
| 2327. | H | H | Me | Me | OCH₂CF₃ |
| 2328. | H | H | CF₃ | Me | O–⬜–O |
| 2329. | H | H | CF₃ | Me | H |
| 2330. | H | H | CF₃ | Me | OCH₂CH₂OMe |
| 2331. | H | H | CF₃ | Me | SMe |
| 2332. | H | H | CF₃ | Me | OCH₂CH₂F |
| 2333. | H | H | CF₃ | Me | OCH(CH₂F)₂ |
| 2334. | H | H | CF₃ | Me | OCH₂CHF₂ |
| 2335. | H | H | CF₃ | Me | OCH₂CF=CH₂ |
| 2336. | H | H | CF₃ | Me | OCH(Me)CF₃ |
| 2337. | H | H | CF₃ | Me | OCH(Me)CH₂F |
| 2338. | H | H | OCH₂CF₃ | Me | CF₃ |
| 2339. | H | H | OCH₂CF₃ | Me | CHF₂ |
| 2340. | H | H | CHF₂ | Me | CHF₂ |
| 2341. | H | H | CF₃ | Me | CHF₂ |
| 2342. | H | H | Cl | Me | OCHF₂ |
| 2343. | H | H | Br | Me | OCHF₂ |

TABLE 2-continued

Compounds of the formula (III-S)

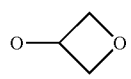

| Ex. No. | R¹ | R² | R³ | R⁴ | R⁵ |
|---|---|---|---|---|---|
| 2344. | H | H | Br | Me | $CF_3$ |
| 2345. | H | H | $CF_3$ | Me | $CF_3$ |
| 2346. | H | H | $CHF_2$ | Me | $CF_3$ |
| 2347. | H | H | $CF_2CF_3$ | Me | $CF_3$ |
| 2348. | H | H | $CF_3$ | Me | $CF_2CF_3$ |
| 2349. | H | H | $CHF_2$ | Me | $OCH_2CF_3$ |
| 2350. | H | H | $CHF_2$ | Me | $OCHF_2$ |
| 2351. | F | H | $CF_3$ | Ph | Cl |
| 2352. | F | H | $CF_3$ | tBu | Cl |
| 2353. | F | H | $CF_3$ | $CHF_2$ | Cl |
| 2354. | F | H | Cl | $CHF_2$ | $CF_3$ |
| 2355. | F | H | $CF_3$ | Me | OMe |
| 2356. | F | H | $CF_3$ | Me | CN |
| 2357. | F | H | Cl | Et | Cl |
| 2358. | F | H | $CHF_2$ | Me | Cl |
| 2359. | F | H | Me | Me | Me |
| 2360. | F | H | Me | Me | Cl |
| 2361. | F | H | Cl | Me | Cl |
| 2362. | F | H | $CF_3$ | Me | Cl |
| 2363. | F | H | Cl | Me | $CF_3$ |
| 2364. | F | H | $CF_3$ | Me | F |
| 2365. | F | H | OMe | Me | $CF_3$ |
| 2366. | F | H | $CF_3$ | Me | OEt |
| 2367. | F | H | $CF_3$ | Me | $OCHF_2$ |
| 2368. | F | H | $OCHF_2$ | Me | $CF_3$ |
| 2369. | F | H | $CF_3$ | Me | $OCH_2CHF_2$ |
| 2370. | F | H | $CF_3$ | Me | $OCH_2CF_3$ |
| 2371. | F | H | $CF_3$ | Me | $OCH_2CN$ |
| 2372. | F | H | $CF_3$ | Me | $SO_2Me$ |
| 2373. | F | H | $CF_3$ | Me | SEt |
| 2374. | F | H | $CF_3$ | Me | Me |
| 2375. | F | H | $CF_3$ | Me | Et |
| 2376. | F | H | $CF_3$ | Et | Cl |
| 2377. | F | H | Cl | Et | $CF_3$ |
| 2378. | F | H | $CF_3$ | iPr | Cl |
| 2379. | F | H | Cl | iPr | $CF_3$ |
| 2380. | F | H | $CF_3$ | tBu | Cl |
| 2381. | F | H | Cl | tBu | $CF_3$ |
| 2382. | F | H | $CF_3$ | cPen | Cl |
| 2383. | F | H | Cl | cPen | $CF_3$ |
| 2384. | F | H | $CF_3$ | $CH_2cPr$ | Cl |
| 2385. | F | H | Cl | $CH_2cPr$ | $CF_3$ |
| 2386. | F | H | $CF_3$ | $CH_2CH=CH_2$ | Cl |
| 2387. | F | H | Cl | $CH_2CH=CH_2$ | $CF_3$ |
| 2388. | F | H | $CF_3$ | $CHF_2$ | OMe |
| 2389. | F | H | OMe | $CHF_2$ | $CF_3$ |
| 2390. | F | H | $CF_3$ | $CH_2CF_3$ | Cl |
| 2391. | F | H | Cl | $CH_2CF_3$ | $CF_3$ |
| 2392. | F | H | $CF_3$ | $CH_2OMe$ | Cl |
| 2393. | F | H | Cl | $CH_2OMe$ | $CF_3$ |
| 2394. | F | H | $CF_3$ | $CH_2CN$ | Cl |
| 2395. | F | H | Me | Ph | Me |
| 2396. | F | H | Me | Ph | Cl |
| 2397. | F | H | Et | Ph | Cl |
| 2398. | F | H | Pr | Ph | Cl |
| 2399. | F | H | iPr | Ph | Cl |
| 2400. | F | H | $CF_3$ | Ph | Cl |
| 2401. | F | H | $CF_3$ | Ph | Me |
| 2402. | F | H | $CF_3$ | Ph | $CF_3$ |
| 2403. | F | H | $CF_3$ | Ph | F |
| 2404. | F | H | $CF_3$ | Ph | OMe |
| 2405. | F | H | $CF_3$ | Ph | OEt |
| 2406. | F | H | $CF_3$ | Ph | $OCHF_2$ |
| 2407. | F | H | $CF_3$ | Ph | CN |
| 2408. | F | H | $CF_3$ | Ph(4-Cl) | Cl |
| 2409. | F | H | Me | Me | $OCH_2CF_3$ |
| 2410. | F | H | $CF_3$ | Me | (oxetanyl) |
| 2411. | F | H | $CF_3$ | Me | H |
| 2412. | F | H | $CF_3$ | Me | $OCH_2CH_2OMe$ |
| 2413. | F | H | $CF_3$ | Me | SMe |
| 2414. | F | H | $CF_3$ | Me | $OCH_2CH_2CH_2F$ |
| 2415. | F | H | $CF_3$ | Me | $OCH(CH_2F)_2$ |
| 2416. | F | H | $CF_3$ | Me | $OCH_2CF_2CHF_2$ |
| 2417. | F | H | $CF_3$ | Me | $OCH_2CF=CH_2$ |
| 2418. | F | H | $CF_3$ | Me | $OCH(Me)CF_3$ |
| 2419. | F | H | $CF_3$ | Me | $OCH(Me)CH_2F$ |
| 2420. | F | H | $OCH_2CF_3$ | Me | $CF_3$ |
| 2421. | F | H | $OCH_2CF_3$ | Me | $CHF_2$ |
| 2422. | F | H | $CHF_2$ | Me | $CHF_2$ |
| 2423. | F | H | $CF_3$ | Me | $CHF_2$ |
| 2424. | F | H | Cl | Me | $OCHF_2$ |
| 2425. | F | H | Br | Me | $OCHF_2$ |
| 2426. | F | H | Br | Me | $CF_3$ |
| 2427. | F | H | $CF_3$ | Me | $CF_3$ |
| 2428. | F | H | $CHF_2$ | Me | $CF_3$ |
| 2429. | F | H | $CF_2CF_3$ | Me | $CF_3$ |
| 2430. | F | H | $CF_3$ | Me | $CF_2CF_3$ |
| 2431. | F | H | $CHF_2$ | Me | $OCH_2CF_3$ |
| 2432. | F | H | $CHF_2$ | Me | $OCHF_2$ |
| 2433. | Cl | H | $CF_3$ | Ph | Cl |
| 2434. | Cl | H | $CF_3$ | tBu | Cl |
| 2435. | Cl | H | $CF_3$ | $CHF_2$ | Cl |
| 2436. | Cl | H | Cl | $CHF_2$ | $CF_3$ |
| 2437. | Cl | H | $CF_3$ | Me | OMe |
| 2438. | Cl | H | $CF_3$ | Me | CN |
| 2439. | Cl | H | Cl | Et | Cl |
| 2440. | Cl | H | $CHF_2$ | Me | Cl |
| 2441. | Cl | H | Me | Me | Me |
| 2442. | Cl | H | Me | Me | Cl |
| 2443. | Cl | H | Cl | Me | Cl |
| 2444. | Cl | H | $CF_3$ | Me | Cl |
| 2445. | Cl | H | Cl | Me | $CF_3$ |
| 2446. | Cl | H | $CF_3$ | Me | F |
| 2447. | Cl | H | OMe | Me | $CF_3$ |
| 2448. | Cl | H | $CF_3$ | Me | OEt |
| 2449. | Cl | H | $CF_3$ | Me | $OCHF_2$ |
| 2450. | Cl | H | $OCHF_2$ | Me | $CF_3$ |
| 2451. | Cl | H | $CF_3$ | Me | $OCH_2CHF_2$ |
| 2452. | Cl | H | $CF_3$ | Me | $OCH_2CF_3$ |
| 2453. | Cl | H | $CF_3$ | Me | $OCH_2CN$ |
| 2454. | Cl | H | $CF_3$ | Me | $SO_2Me$ |
| 2455. | Cl | H | $CF_3$ | Me | SEt |
| 2456. | Cl | H | $CF_3$ | Me | Me |
| 2457. | Cl | H | $CF_3$ | Me | Et |
| 2458. | Cl | H | $CF_3$ | Et | Cl |
| 2459. | Cl | H | Cl | Et | $CF_3$ |
| 2460. | Cl | H | $CF_3$ | iPr | Cl |
| 2461. | Cl | H | Cl | iPr | $CF_3$ |
| 2462. | Cl | H | $CF_3$ | tBu | Cl |
| 2463. | Cl | H | Cl | tBu | $CF_3$ |
| 2464. | Cl | H | $CF_3$ | cPen | Cl |
| 2465. | Cl | H | Cl | cPen | $CF_3$ |

TABLE 2-continued

Compounds of the formula (III-S)

(III-S)

| Ex. No. | R¹ | R² | R³ | R⁴ | R⁵ |
|---|---|---|---|---|---|
| 2466. | Cl | H | $CF_3$ | $CH_2cPr$ | Cl |
| 2467. | Cl | H | Cl | $CH_2cPr$ | $CF_3$ |
| 2468. | Cl | H | $CF_3$ | $CH_2CH=CH_2$ | Cl |
| 2469. | Cl | H | Cl | $CH_2CH=CH_2$ | $CF_3$ |
| 2470. | Cl | H | $CF_3$ | $CHF_2$ | OMe |
| 2471. | Cl | H | OMe | $CHF_2$ | $CF_3$ |
| 2472. | Cl | H | $CF_3$ | $CH_2CF_3$ | Cl |
| 2473. | Cl | H | Cl | $CH_2CF_3$ | $CF_3$ |
| 2474. | Cl | H | $CF_3$ | $CH_2OMe$ | Cl |
| 2475. | Cl | H | Cl | $CH_2OMe$ | $CF_3$ |
| 2476. | Cl | H | $CF_3$ | $CH_2CN$ | Cl |
| 2477. | Cl | H | Me | Ph | Me |
| 2478. | Cl | H | Me | Ph | Cl |
| 2479. | Cl | H | Et | Ph | Cl |
| 2480. | Cl | H | Pr | Ph | Cl |
| 2481. | Cl | H | iPr | Ph | Cl |
| 2482. | Cl | H | $CF_3$ | Ph | Cl |
| 2483. | Cl | H | $CF_3$ | Ph | Me |
| 2484. | Cl | H | $CF_3$ | Ph | $CF_3$ |
| 2485. | Cl | H | $CF_3$ | Ph | F |
| 2486. | Cl | H | $CF_3$ | Ph | OMe |
| 2487. | Cl | H | $CF_3$ | Ph | OEt |
| 2488. | Cl | H | $CF_3$ | Ph | $OCHF_2$ |
| 2489. | Cl | H | $CF_3$ | Ph | CN |
| 2490. | Cl | H | $CF_3$ | Ph(4-Cl) | Cl |
| 2491. | Cl | H | Me | Me | $OCH_2CF_3$ |
| 2492. | Cl | H | $CF_3$ | Me | (oxetane) |
| 2493. | Cl | H | $CF_3$ | Me | H |
| 2494. | Cl | H | $CF_3$ | Me | $OCH_2CH_2OMe$ |
| 2495. | Cl | H | $CF_3$ | Me | SMe |
| 2496. | Cl | H | $CF_3$ | Me | $OCH_2CH_2CH_2F$ |
| 2497. | Cl | H | $CF_3$ | Me | $OCH(CH_2F)_2$ |
| 2498. | Cl | H | $CF_3$ | Me | $OCH_2CF_2CHF_2$ |
| 2499. | Cl | H | $CF_3$ | Me | $OCH_2CF=CH_2$ |
| 2500. | Cl | H | $CF_3$ | Me | $OCH(Me)CF_3$ |
| 2501. | Cl | H | $CF_3$ | Me | $OCH(Me)CH_2F$ |
| 2502. | Cl | H | $OCH_2CF_3$ | Me | $CF_3$ |
| 2503. | Cl | H | $OCH_2CF_3$ | Me | $CHF_2$ |
| 2504. | Cl | H | $CHF_2$ | Me | $CHF_2$ |
| 2505. | Cl | H | $CF_3$ | Me | $CHF_2$ |
| 2506. | Cl | H | Cl | Me | $OCHF_2$ |
| 2507. | Cl | H | Br | Me | $OCHF_2$ |
| 2508. | Cl | H | Br | Me | $CF_3$ |
| 2509. | Cl | H | $CF_3$ | Me | $CF_3$ |
| 2510. | Cl | H | $CHF_2$ | Me | $CF_3$ |
| 2511. | Cl | H | $CF_2CF_3$ | Me | $CF_3$ |
| 2512. | Cl | H | $CF_3$ | Me | $CF_2CF_3$ |
| 2513. | Cl | H | $CHF_2$ | Me | $OCH_2CF_3$ |
| 2514. | Cl | H | $CHF_2$ | Me | $OCHF_2$ |
| 2515. | Br | H | $CF_3$ | Ph | Cl |
| 2516. | Br | H | $CF_3$ | tBu | Cl |
| 2517. | Br | H | $CF_3$ | $CHF_2$ | Cl |
| 2518. | Br | H | Cl | $CHF_2$ | $CF_3$ |
| 2519. | Br | H | $CF_3$ | Me | OMe |
| 2520. | Br | H | $CF_3$ | Me | CN |
| 2521. | Br | H | Cl | Et | Cl |
| 2522. | Br | H | $CHF_2$ | Me | Cl |
| 2523. | Br | H | Me | Me | Me |
| 2524. | Br | H | Me | Me | Cl |
| 2525. | Br | H | Cl | Me | Cl |
| 2526. | Br | H | $CF_3$ | Me | Cl |
| 2527. | Br | H | Cl | Me | $CF_3$ |
| 2528. | Br | H | $CF_3$ | Me | F |
| 2529. | Br | H | OMe | Me | $CF_3$ |
| 2530. | Br | H | $CF_3$ | Me | OEt |
| 2531. | Br | H | $CF_3$ | Me | $OCHF_2$ |
| 2532. | Br | H | $OCHF_2$ | Me | $CF_3$ |
| 2533. | Br | H | $CF_3$ | Me | $OCH_2CHF_2$ |
| 2534. | Br | H | $CF_3$ | Me | $OCH_2CF_3$ |
| 2535. | Br | H | $CF_3$ | Me | $OCH_2CN$ |
| 2536. | Br | H | $CF_3$ | Me | $SO_2Me$ |
| 2537. | Br | H | $CF_3$ | Me | SEt |
| 2538. | Br | H | $CF_3$ | Me | Me |
| 2539. | Br | H | $CF_3$ | Me | Et |
| 2540. | Br | H | $CF_3$ | Et | Cl |
| 2541. | Br | H | Cl | Et | $CF_3$ |
| 2542. | Br | H | $CF_3$ | iPr | Cl |
| 2543. | Br | H | Cl | iPr | $CF_3$ |
| 2544. | Br | H | $CF_3$ | tBu | Cl |
| 2545. | Br | H | Cl | tBu | $CF_3$ |
| 2546. | Br | H | $CF_3$ | cPen | Cl |
| 2547. | Br | H | Cl | cPen | $CF_3$ |
| 2548. | Br | H | $CF_3$ | $CH_2cPr$ | Cl |
| 2549. | Br | H | Cl | $CH_2cPr$ | $CF_3$ |
| 2550. | Br | H | $CF_3$ | $CH_2CH=CH_2$ | Cl |
| 2551. | Br | H | Cl | $CH_2CH=CH_2$ | $CF_3$ |
| 2552. | Br | H | $CF_3$ | $CHF_2$ | OMe |
| 2553. | Br | H | OMe | $CHF_2$ | $CF_3$ |
| 2554. | Br | H | $CF_3$ | $CH_2CF_3$ | Cl |
| 2555. | Br | H | Cl | $CH_2CF_3$ | $CF_3$ |
| 2556. | Br | H | $CF_3$ | $CH_2OMe$ | Cl |
| 2557. | Br | H | Cl | $CH_2OMe$ | $CF_3$ |
| 2558. | Br | H | $CF_3$ | $CH_2CN$ | Cl |
| 2559. | Br | H | Me | Ph | Me |
| 2560. | Br | H | Me | Ph | Cl |
| 2561. | Br | H | Et | Ph | Cl |
| 2562. | Br | H | Pr | Ph | Cl |
| 2563. | Br | H | iPr | Ph | Cl |
| 2564. | Br | H | $CF_3$ | Ph | Cl |
| 2565. | Br | H | $CF_3$ | Ph | Me |
| 2566. | Br | H | $CF_3$ | Ph | $CF_3$ |
| 2567. | Br | H | $CF_3$ | Ph | F |
| 2568. | Br | H | $CF_3$ | Ph | OMe |
| 2569. | Br | H | $CF_3$ | Ph | OEt |
| 2570. | Br | H | $CF_3$ | Ph | $OCHF_2$ |
| 2571. | Br | H | $CF_3$ | Ph | CN |
| 2572. | Br | H | $CF_3$ | Ph(4-Cl) | Cl |
| 2573. | Br | H | Me | Me | $OCH_2CF_3$ |
| 2574. | Br | H | $CF_3$ | Me | (oxetane) |
| 2575. | Br | H | $CF_3$ | Me | H |
| 2576. | Br | H | $CF_3$ | Me | $OCH_2CH_2OMe$ |
| 2577. | Br | H | $CF_3$ | Me | SMe |
| 2578. | Br | H | $CF_3$ | Me | $OCH_2CH_2CH_2F$ |
| 2579. | Br | H | $CF_3$ | Me | $OCH(CH_2F)_2$ |
| 2580. | Br | H | $CF_3$ | Me | $OCH_2CF_2CHF_2$ |
| 2581. | Br | H | $CF_3$ | Me | $OCH_2CF=CH_2$ |
| 2582. | Br | H | $CF_3$ | Me | $OCH(Me)CF_3$ |
| 2583. | Br | H | $CF_3$ | Me | $OCH(Me)CH_2F$ |

TABLE 2-continued

Compounds of the formula (III-S)

| Ex. No. | R¹ | R² | R³ | R⁴ | R⁵ |
|---|---|---|---|---|---|
| 2584. | Br | H | $OCH_2CF_3$ | Me | $CF_3$ |
| 2585. | Br | H | $OCH_2CF_3$ | Me | $CHF_2$ |
| 2586. | Br | H | $CHF_2$ | Me | $CHF_2$ |
| 2587. | Br | H | $CF_3$ | Me | $CHF_2$ |
| 2588. | Br | H | Cl | Me | $OCHF_2$ |
| 2589. | Br | H | Br | Me | $OCHF_2$ |
| 2590. | Br | H | Br | Me | $CF_3$ |
| 2591. | Br | H | $CF_3$ | Me | $CF_3$ |
| 2592. | Br | H | $CHF_2$ | Me | $CF_3$ |
| 2593. | Br | H | $CF_2CF_3$ | Me | $CF_3$ |
| 2594. | Br | H | $CF_3$ | Me | $CF_2CF_3$ |
| 2595. | Br | H | $CHF_2$ | Me | $OCH_2CF_3$ |
| 2596. | Br | H | $CHF_2$ | Me | $OCHF_2$ |
| 2597. | I | H | $CF_3$ | Ph | Cl |
| 2598. | I | H | $CF_3$ | tBu | Cl |
| 2599. | I | H | $CF_3$ | $CHF_2$ | Cl |
| 2600. | I | H | Cl | $CHF_2$ | $CF_3$ |
| 2601. | I | H | $CF_3$ | Me | OMe |
| 2602. | I | H | $CF_3$ | Me | CN |
| 2603. | I | H | Cl | Et | Cl |
| 2604. | I | H | $CHF_2$ | Me | Cl |
| 2605. | I | H | Me | Me | Me |
| 2606. | I | H | Me | Me | Cl |
| 2607. | I | H | Cl | Me | Cl |
| 2608. | I | H | $CF_3$ | Me | Cl |
| 2609. | I | H | Cl | Me | $CF_3$ |
| 2610. | I | H | $CF_3$ | Me | F |
| 2611. | I | H | OMe | Me | $CF_3$ |
| 2612. | I | H | $CF_3$ | Me | OEt |
| 2613. | I | H | $CF_3$ | Me | $OCHF_2$ |
| 2614. | I | H | $OCHF_2$ | Me | $CF_3$ |
| 2615. | I | H | $CF_3$ | Me | $OCH_2CHF_2$ |
| 2616. | I | H | $CF_3$ | Me | $OCH_2CF_3$ |
| 2617. | I | H | $CF_3$ | Me | $OCH_2CN$ |
| 2618. | I | H | $CF_3$ | Me | $SO_2Me$ |
| 2619. | I | H | $CF_3$ | Me | SEt |
| 2620. | I | H | $CF_3$ | Me | Me |
| 2621. | I | H | $CF_3$ | Me | Et |
| 2622. | I | H | $CF_3$ | Et | Cl |
| 2623. | I | H | Cl | Et | $CF_3$ |
| 2624. | I | H | $CF_3$ | iPr | Cl |
| 2625. | I | H | Cl | iPr | $CF_3$ |
| 2626. | I | H | $CF_3$ | tBu | Cl |
| 2627. | I | H | Cl | tBu | $CF_3$ |
| 2628. | I | H | $CF_3$ | cPen | Cl |
| 2629. | I | H | Cl | cPen | $CF_3$ |
| 2630. | I | H | $CF_3$ | $CH_2cPr$ | Cl |
| 2631. | I | H | Cl | $CH_2cPr$ | $CF_3$ |
| 2632. | I | H | $CF_3$ | $CH_2CH=CH_2$ | Cl |
| 2633. | I | H | Cl | $CH_2CH=CH_2$ | $CF_3$ |
| 2634. | I | H | $CF_3$ | $CHF_2$ | OMe |
| 2635. | I | H | OMe | $CHF_2$ | $CF_3$ |
| 2636. | I | H | $CF_3$ | $CH_2CF_3$ | Cl |
| 2637. | I | H | Cl | $CH_2CF_3$ | $CF_3$ |
| 2638. | I | H | $CF_3$ | $CH_2OMe$ | Cl |
| 2639. | I | H | Cl | $CH_2OMe$ | $CF_3$ |
| 2640. | I | H | $CF_3$ | $CH_2CN$ | Cl |
| 2641. | I | H | Me | Ph | Me |
| 2642. | I | H | Me | Ph | Cl |
| 2643. | I | H | Et | Ph | Cl |
| 2644. | I | H | Pr | Ph | Cl |
| 2645. | I | H | iPr | Ph | Cl |
| 2646. | I | H | $CF_3$ | Ph | Cl |
| 2647. | I | H | $CF_3$ | Ph | Me |
| 2648. | I | H | $CF_3$ | Ph | $CF_3$ |
| 2649. | I | H | $CF_3$ | Ph | F |
| 2650. | I | H | $CF_3$ | Ph | OMe |
| 2651. | I | H | $CF_3$ | Ph | OEt |
| 2652. | I | H | $CF_3$ | Ph | $OCHF_2$ |
| 2653. | I | H | $CF_3$ | Ph | CN |
| 2654. | I | H | $CF_3$ | Ph(4-Cl) | Cl |
| 2655. | I | H | Me | Me | $OCH_2CF_3$ |
| 2656. | I | H | $CF_3$ | Me | oxetanyl |
| 2657. | I | H | $CF_3$ | Me | H |
| 2658. | I | H | $CF_3$ | Me | $OCH_2CH_2OMe$ |
| 2659. | I | H | $CF_3$ | Me | SMe |
| 2660. | I | H | $CF_3$ | Me | $OCH_2CH_2CH_2F$ |
| 2661. | I | H | $CF_3$ | Me | $OCH(CH_2F)_2$ |
| 2662. | I | H | $CF_3$ | Me | $OCH_2CF_2CHF_2$ |
| 2663. | I | H | $CF_3$ | Me | $OCH_2CF=CH_2$ |
| 2664. | I | H | $CF_3$ | Me | $OCH(Me)CF_3$ |
| 2665. | I | H | $CF_3$ | Me | $OCH(Me)CH_2F$ |
| 2666. | I | H | $OCH_2CF_3$ | Me | $CF_3$ |
| 2667. | I | H | $OCH_2CF_3$ | Me | $CHF_2$ |
| 2668. | I | H | $CHF_2$ | Me | $CHF_2$ |
| 2669. | I | H | $CF_3$ | Me | $CHF_2$ |
| 2670. | I | H | Cl | Me | $OCHF_2$ |
| 2671. | I | H | Br | Me | $OCHF_2$ |
| 2672. | I | H | Br | Me | $CF_3$ |
| 2673. | I | H | $CF_3$ | Me | $CF_3$ |
| 2674. | I | H | $CHF_2$ | Me | $CF_3$ |
| 2675. | I | H | $CF_2CF_3$ | Me | $CF_3$ |
| 2676. | I | H | $CF_3$ | Me | $CF_2CF_3$ |
| 2677. | I | H | $CHF_2$ | Me | $OCH_2CF_3$ |
| 2678. | I | H | $CHF_2$ | Me | $OCHF_2$ |
| 2679. | H | F | $CF_3$ | Ph | Cl |
| 2680. | H | F | $CF_3$ | tBu | Cl |
| 2681. | H | F | $CF_3$ | $CHF_2$ | Cl |
| 2682. | H | F | Cl | $CHF_2$ | $CF_3$ |
| 2683. | H | F | $CF_3$ | Me | OMe |
| 2684. | H | F | $CF_3$ | Me | CN |
| 2685. | H | F | Cl | Et | Cl |
| 2686. | H | F | $CHF_2$ | Me | Cl |
| 2687. | H | F | Me | Me | Me |
| 2688. | H | F | Me | Me | Cl |
| 2689. | H | F | Cl | Me | Cl |
| 2690. | H | F | $CF_3$ | Me | Cl |
| 2691. | H | F | Cl | Me | $CF_3$ |
| 2692. | H | F | $CF_3$ | Me | F |
| 2693. | H | F | OMe | Me | $CF_3$ |
| 2694. | H | F | $CF_3$ | Me | OEt |
| 2695. | H | F | $CF_3$ | Me | $OCHF_2$ |
| 2696. | H | F | $OCHF_2$ | Me | $CF_3$ |
| 2697. | H | F | $CF_3$ | Me | $OCH_2CHF_2$ |
| 2698. | H | F | $CF_3$ | Me | $OCH_2CF_3$ |
| 2699. | H | F | $CF_3$ | Me | $OCH_2CN$ |
| 2700. | H | F | $CF_3$ | Me | $SO_2Me$ |
| 2701. | H | F | $CF_3$ | Me | SEt |
| 2702. | H | F | $CF_3$ | Me | Me |
| 2703. | H | F | $CF_3$ | Me | Et |
| 2704. | H | F | $CF_3$ | Et | Cl |
| 2705. | H | F | Cl | Et | $CF_3$ |

TABLE 2-continued

Compounds of the formula (III-S)

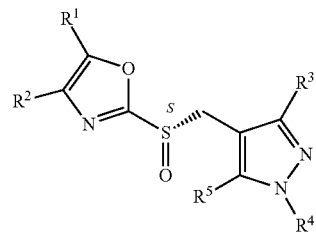

(III-S)

| Ex. No. | R¹ | R² | R³ | R⁴ | R⁵ |
|---|---|---|---|---|---|
| 2706. | H | F | CF₃ | iPr | Cl |
| 2707. | H | F | Cl | iPr | CF₃ |
| 2708. | H | F | CF₃ | tBu | Cl |
| 2709. | H | F | Cl | tBu | CF₃ |
| 2710. | H | F | CF₃ | cPen | Cl |
| 2711. | H | F | Cl | cPen | CF₃ |
| 2712. | H | F | CF₃ | CH₂cPr | Cl |
| 2713. | H | F | Cl | CH₂cPr | CF₃ |
| 2714. | H | F | CF₃ | CH₂CH=CH₂ | Cl |
| 2715. | H | F | Cl | CH₂CH=CH₂ | CF₃ |
| 2716. | H | F | CF₃ | CHF₂ | OMe |
| 2717. | H | F | OMe | CHF₂ | CF₃ |
| 2718. | H | F | CF₃ | CH₂CF₃ | Cl |
| 2719. | H | F | Cl | CH₂CF₃ | CF₃ |
| 2720. | H | F | CF₃ | CH₂OMe | Cl |
| 2721. | H | F | Cl | CH₂OMe | CF₃ |
| 2722. | H | F | CF₃ | CH₂CN | Cl |
| 2723. | H | F | Me | Ph | Me |
| 2724. | H | F | Me | Ph | Cl |
| 2725. | H | F | Et | Ph | Cl |
| 2726. | H | F | Pr | Ph | Cl |
| 2727. | H | F | iPr | Ph | Cl |
| 2728. | H | F | CF₃ | Ph | Cl |
| 2729. | H | F | CF₃ | Ph | Me |
| 2730. | H | F | CF₃ | Ph | CF₃ |
| 2731. | H | F | CF₃ | Ph | F |
| 2732. | H | F | CF₃ | Ph | OMe |
| 2733. | H | F | CF₃ | Ph | OEt |
| 2734. | H | F | CF₃ | Ph | OCHF₂ |
| 2735. | H | F | CF₃ | Ph | CN |
| 2736. | H | F | CF₃ | Ph(4-Cl) | Cl |
| 2737. | H | F | Me | Me | OCH₂CF₃ |
| 2738. | H | F | CF₃ | Me |  |
| 2739. | H | F | CF₃ | Me | H |
| 2740. | H | F | CF₃ | Me | OCH₂CH₂OMe |
| 2741. | H | F | CF₃ | Me | SMe |
| 2742. | H | F | CF₃ | Me | OCH₂CH₂CH₂F |
| 2743. | H | F | CF₃ | Me | OCH(CH₂F)₂ |
| 2744. | H | F | CF₃ | Me | OCH₂CF₂CHF₂ |
| 2745. | H | F | CF₃ | Me | OCH₂CF=CH₂ |
| 2746. | H | F | CF₃ | Me | OCH(Me)CF₃ |
| 2747. | H | F | CF₃ | Me | OCH(Me)CH₂F |
| 2748. | H | F | OCH₂CF₃ | Me | CF₃ |
| 2749. | H | F | OCH₂CF₃ | Me | CHF₂ |
| 2750. | H | F | CHF₂ | Me | CHF₂ |
| 2751. | H | F | CF₃ | Me | CHF₂ |
| 2752. | H | F | Cl | Me | OCHF₂ |
| 2753. | H | F | Br | Me | OCHF₂ |
| 2754. | H | F | Br | Me | CF₃ |
| 2755. | H | Cl | CF₃ | tBu | Cl |
| 2756. | H | Cl | CF₃ | CHF₂ | Cl |
| 2757. | H | Cl | Cl | CHF₂ | CF₃ |
| 2758. | H | Cl | CF₃ | Me | OMe |
| 2759. | H | Cl | CF₃ | Me | CN |
| 2760. | H | Cl | CHF₂ | Me | Cl |
| 2761. | H | Cl | Me | Me | Me |
| 2762. | H | Cl | Me | Me | Cl |
| 2763. | H | Cl | CF₃ | Me | Cl |
| 2764. | H | Cl | Cl | Me | CF₃ |
| 2765. | H | Cl | CF₃ | Me | F |
| 2766. | H | Cl | OMe | Me | CF₃ |
| 2767. | H | Cl | CF₃ | Me | OCHF₂ |
| 2768. | H | Cl | OCHF₂ | Me | CF₃ |
| 2769. | H | Cl | CF₃ | Me | OCH₂CHF₂ |
| 2770. | H | Cl | CF₃ | Me | OCH₂CF₃ |
| 2771. | H | Cl | CF₃ | Me | SO₂Me |
| 2772. | H | Cl | CF₃ | Me | SEt |
| 2773. | H | Cl | CF₃ | Et | Cl |
| 2774. | H | Cl | CF₃ | iPr | Cl |
| 2775. | H | Cl | CF₃ | tBu | Cl |
| 2776. | H | Cl | Cl | tBu | CF₃ |
| 2777. | H | Cl | CF₃ | cPen | Cl |
| 2778. | H | Cl | CF₃ | CHF₂ | OMe |
| 2779. | H | Cl | CF₃ | CH₂CF₃ | Cl |
| 2780. | H | Cl | CF₃ | Ph | OCHF₂ |
| 2781. | H | Cl | CF₃ | Ph | Cl |
| 2782. | H | Cl | Me | Me | OCH₂CF₃ |
| 2783. | H | Cl | CF₃ | Me | 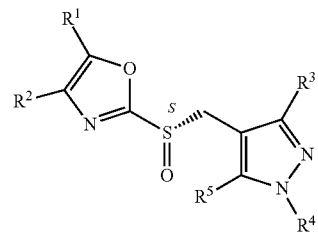 |
| 2784. | H | Cl | CF₃ | Me | H |
| 2785. | H | Cl | CF₃ | Me | OCH₂CH₂OMe |
| 2786. | H | Cl | CF₃ | Me | SMe |
| 2787. | H | Cl | CF₃ | Me | OCH₂CH₂CH₂F |
| 2788. | H | Cl | CF₃ | Me | OCH(CH₂F)₂ |
| 2789. | H | Cl | CF₃ | Me | OCH₂CF₂CHF₂ |
| 2790. | H | Cl | CF₃ | Me | OCH₂CF=CH₂ |
| 2791. | H | Cl | CF₃ | Me | OCH(Me)CF₃ |
| 2792. | H | Cl | CF₃ | Me | OCH(Me)CH₂F |
| 2793. | H | Cl | OCH₂CF₃ | Me | CF₃ |
| 2794. | H | Cl | OCH₂CF₃ | Me | CHF₂ |
| 2795. | H | Cl | CHF₂ | Me | CHF₂ |
| 2796. | H | Cl | CF₃ | Me | CHF₂ |
| 2797. | H | Cl | Cl | Me | OCHF₂ |
| 2798. | H | Cl | Br | Me | OCHF₂ |
| 2799. | H | Cl | Br | Me | CF₃ |
| 2800. | H | Br | CF₃ | tBu | Cl |
| 2801. | H | Br | CF₃ | CHF₂ | Cl |
| 2802. | H | Br | Cl | CHF₂ | CF₃ |
| 2803. | H | Br | CF₃ | Me | OMe |
| 2804. | H | Br | CF₃ | Me | CN |
| 2805. | H | Br | CHF₂ | Me | Cl |
| 2806. | H | Br | Me | Me | Me |
| 2807. | H | Br | Me | Me | Cl |
| 2808. | H | Br | CF₃ | Me | Cl |
| 2809. | H | Br | Cl | Me | CF₃ |
| 2810. | H | Br | CF₃ | Me | F |
| 2811. | H | Br | OMe | Me | CF₃ |
| 2812. | H | Br | CF₃ | Me | OCHF₂ |
| 2813. | H | Br | OCHF₂ | Me | CF₃ |
| 2814. | H | Br | CF₃ | Me | OCH₂CHF₂ |
| 2815. | H | Br | CF₃ | Me | OCH₂CF₃ |
| 2816. | H | Br | CF₃ | Me | SO₂Me |
| 2817. | H | Br | CF₃ | Me | SEt |
| 2818. | H | Br | CF₃ | Et | Cl |
| 2819. | H | Br | CF₃ | iPr | Cl |
| 2820. | H | Br | CF₃ | tBu | Cl |
| 2821. | H | Br | Cl | tBu | CF₃ |
| 2822. | H | Br | CF₃ | cPen | Cl |
| 2823. | H | Br | CF₃ | CHF₂ | OMe |

TABLE 2-continued

Compounds of the formula (III-S)

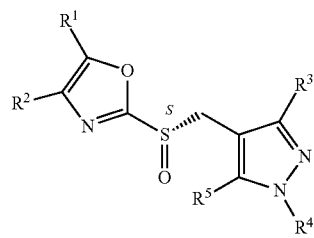

(III-S)

| Ex. No. | R¹ | R² | R³ | R⁴ | R⁵ |
|---|---|---|---|---|---|
| 2824. | H | Br | $CF_3$ | $CH_2CF_3$ | Cl |
| 2825. | H | Br | $CF_3$ | Ph | $OCHF_2$ |
| 2826. | H | Br | $CF_3$ | Ph | Cl |
| 2827. | H | Br | Me | Me | $OCH_2CF_3$ |
| 2828. | H | Br | $CF_3$ | Me | 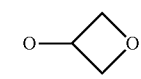 |
| 2829. | H | Br | $CF_3$ | Me | H |
| 2830. | H | Br | $CF_3$ | Me | $OCH_2CH_2OMe$ |
| 2831. | H | Br | $CF_3$ | Me | SMe |
| 2832. | H | Br | $CF_3$ | Me | $OCH_2CH_2CH_2F$ |
| 2833. | H | Br | $CF_3$ | Me | $OCH(CH_2F)_2$ |
| 2834. | H | Br | $CF_3$ | Me | $OCH_2CF_2CHF_2$ |
| 2835. | H | Br | $CF_3$ | Me | $OCH_2CF=CH_2$ |
| 2836. | H | Br | $CF_3$ | Me | $OCH(Me)CF_3$ |
| 2837. | H | Br | $CF_3$ | Me | $OCH(Me)CH_2F$ |
| 2838. | H | Br | $OCH_2CF_3$ | Me | $CF_3$ |
| 2839. | H | Br | $OCH_2CF_3$ | Me | $CHF_2$ |
| 2840. | H | Br | $CHF_2$ | Me | $CHF_2$ |
| 2841. | H | Br | $CF_3$ | Me | $CHF_2$ |
| 2842. | H | Br | Cl | Me | $OCHF_2$ |
| 2843. | H | Br | Br | Me | $OCHF_2$ |
| 2844. | H | Br | Br | Me | $CF_3$ |
| 2845. | Me | H | $CF_3$ | tBu | Cl |
| 2846. | Me | H | $CF_3$ | $CHF_2$ | Cl |
| 2847. | Me | H | Cl | $CHF_2$ | $CF_3$ |
| 2848. | Me | H | $CF_3$ | Me | OMe |
| 2849. | Me | H | $CF_3$ | Me | CN |
| 2850. | Me | H | $CHF_2$ | Me | Cl |
| 2851. | Me | H | Me | Me | Me |
| 2852. | Me | H | Me | Me | Cl |
| 2853. | Me | H | $CF_3$ | Me | Cl |
| 2854. | Me | H | Cl | Me | $CF_3$ |
| 2855. | Me | H | $CF_3$ | Me | F |
| 2856. | Me | H | OMe | Me | $CF_3$ |
| 2857. | Me | H | $CF_3$ | Me | $OCHF_2$ |
| 2858. | Me | H | $OCHF_2$ | Me | $CF_3$ |
| 2859. | Me | H | $CF_3$ | Me | $OCH_2CHF_2$ |
| 2860. | Me | H | $CF_3$ | Me | $OCH_2CF_3$ |
| 2861. | Me | H | $CF_3$ | Me | $SO_2Me$ |
| 2862. | Me | H | $CF_3$ | Me | SEt |
| 2863. | Me | H | $CF_3$ | Et | Cl |
| 2864. | Me | H | $CF_3$ | iPr | Cl |
| 2865. | Me | H | $CF_3$ | tBu | Cl |
| 2866. | Me | H | Cl | tBu | $CF_3$ |
| 2867. | Me | H | $CF_3$ | cPen | Cl |
| 2868. | Me | H | $CF_3$ | $CHF_2$ | OMe |
| 2869. | Me | H | $CF_3$ | $CH_2CF_3$ | Cl |
| 2870. | Me | H | $CF_3$ | Ph | $OCHF_2$ |
| 2871. | Me | H | $CF_3$ | Ph | Cl |
| 2872. | Me | H | Me | Me | $OCH_2CF_3$ |
| 2873. | Me | H | $CF_3$ | Me | 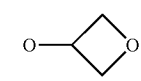 |
| 2874. | Me | H | $CF_3$ | Me | H |
| 2875. | Me | H | $CF_3$ | Me | $OCH_2CH_2OMe$ |
| 2876. | Me | H | $CF_3$ | Me | SMe |
| 2877. | Me | H | $CF_3$ | Me | $OCH_2CH_2CH_2F$ |
| 2878. | Me | H | $CF_3$ | Me | $OCH(CH_2F)_2$ |
| 2879. | Me | H | $CF_3$ | Me | $OCH_2CF_2CHF_2$ |
| 2880. | Me | H | $CF_3$ | Me | $OCH_2CF=CH_2$ |
| 2881. | Me | H | $CF_3$ | Me | $OCH(Me)CF_3$ |
| 2882. | Me | H | $CF_3$ | Me | $OCH(Me)CH_2F$ |
| 2883. | Me | H | $OCH_2CF_3$ | Me | $CF_3$ |
| 2884. | Me | H | $OCH_2CF_3$ | Me | $CHF_2$ |
| 2885. | Me | H | $CHF_2$ | Me | $CHF_2$ |
| 2886. | Me | H | $CF_3$ | Me | $CHF_2$ |
| 2887. | Me | H | Cl | Me | $OCHF_2$ |
| 2888. | Me | H | Br | Me | $OCHF_2$ |
| 2889. | Me | H | Br | Me | $CF_3$ |
| 2890. | $NO_2$ | H | $CF_3$ | tBu | Cl |
| 2891. | $NO_2$ | H | $CF_3$ | $CHF_2$ | Cl |
| 2892. | $NO_2$ | H | Cl | $CHF_2$ | $CF_3$ |
| 2893. | $NO_2$ | H | $CF_3$ | Me | OMe |
| 2894. | $NO_2$ | H | $CF_3$ | Me | CN |
| 2895. | $NO_2$ | H | $CHF_2$ | Me | Cl |
| 2896. | $NO_2$ | H | Me | Me | Me |
| 2897. | $NO_2$ | H | Me | Me | Cl |
| 2898. | $NO_2$ | H | $CF_3$ | Me | Cl |
| 2899. | $NO_2$ | H | Cl | Me | $CF_3$ |
| 2900. | $NO_2$ | H | $CF_3$ | Me | F |
| 2901. | $NO_2$ | H | OMe | Me | $CF_3$ |
| 2902. | $NO_2$ | H | $CF_3$ | Me | $OCHF_2$ |
| 2903. | $NO_2$ | H | $OCHF_2$ | Me | $CF_3$ |
| 2904. | $NO_2$ | H | $CF_3$ | Me | $OCH_2CHF_2$ |
| 2905. | $NO_2$ | H | $CF_3$ | Me | $OCH_2CF_3$ |
| 2906. | $NO_2$ | H | $CF_3$ | Me | $SO_2Me$ |
| 2907. | $NO_2$ | H | $CF_3$ | Me | SEt |
| 2908. | $NO_2$ | H | $CF_3$ | Et | Cl |
| 2909. | $NO_2$ | H | $CF_3$ | iPr | Cl |
| 2910. | $NO_2$ | H | $CF_3$ | tBu | Cl |
| 2911. | $NO_2$ | H | Cl | tBu | $CF_3$ |
| 2912. | $NO_2$ | H | $CF_3$ | cPen | Cl |
| 2913. | $NO_2$ | H | $CF_3$ | $CHF_2$ | OMe |
| 2914. | $NO_2$ | H | $CF_3$ | $CH_2CF_3$ | Cl |
| 2915. | $NO_2$ | H | $CF_3$ | Ph | $OCHF_2$ |
| 2916. | $NO_2$ | H | $CF_3$ | Ph | Cl |
| 2917. | $NO_2$ | H | Me | Me | $OCH_2CF_3$ |
| 2918. | $NO_2$ | H | $CF_3$ | Me | 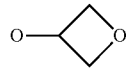 |
| 2919. | $NO_2$ | H | $CF_3$ | Me | H |
| 2920. | $NO_2$ | H | $CF_3$ | Me | $OCH_2CH_2OMe$ |
| 2921. | $NO_2$ | H | $CF_3$ | Me | SMe |
| 2922. | $NO_2$ | H | $CF_3$ | Me | $OCH_2CH_2CH_2F$ |
| 2923. | $NO_2$ | H | $CF_3$ | Me | $OCH(CH_2F)_2$ |
| 2924. | $NO_2$ | H | $CF_3$ | Me | $OCH_2CF_2CHF_2$ |
| 2925. | $NO_2$ | H | $CF_3$ | Me | $OCH_2CF=CH_2$ |
| 2926. | $NO_2$ | H | $CF_3$ | Me | $OCH(Me)CF_3$ |
| 2927. | $NO_2$ | H | $CF_3$ | Me | $OCH(Me)CH_2F$ |
| 2928. | $NO_2$ | H | $OCH_2CF_3$ | Me | $CF_3$ |
| 2929. | $NO_2$ | H | $OCH_2CF_3$ | Me | $CHF_2$ |
| 2930. | $NO_2$ | H | $CHF_2$ | Me | $CHF_2$ |
| 2931. | $NO_2$ | H | $CF_3$ | Me | $CHF_2$ |
| 2932. | $NO_2$ | H | Cl | Me | $OCHF_2$ |
| 2933. | $NO_2$ | H | Br | Me | $OCHF_2$ |
| 2934. | $NO_2$ | H | Br | Me | $CF_3$ |
| 2935. | Cl | Cl | $CF_3$ | tBu | Cl |
| 2936. | Cl | Cl | $CF_3$ | $CHF_2$ | Cl |

TABLE 2-continued

Compounds of the formula (III-S)

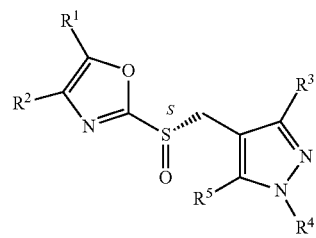

(III-S)

| Ex. No. | R¹ | R² | R³ | R⁴ | R⁵ |
|---|---|---|---|---|---|
| 2937. | Cl | Cl | Cl | CHF$_2$ | CF$_3$ |
| 2938. | Cl | Cl | CF$_3$ | Me | OMe |
| 2939. | Cl | Cl | CF$_3$ | Me | CN |
| 2940. | Cl | Cl | CHF$_2$ | Me | Cl |
| 2941. | Cl | Cl | Me | Me | Me |
| 2942. | Cl | Cl | Me | Me | Cl |
| 2943. | Cl | Cl | CF$_3$ | Me | Cl |
| 2944. | Cl | Cl | Cl | Me | CF$_3$ |
| 2945. | Cl | Cl | CF$_3$ | Me | F |
| 2946. | Cl | Cl | OMe | Me | CF$_3$ |
| 2947. | Cl | Cl | CF$_3$ | Me | OCHF$_2$ |
| 2948. | Cl | Cl | OCHF$_2$ | Me | CF$_3$ |
| 2949. | Cl | Cl | CF$_3$ | Me | OCH$_2$CHF$_2$ |
| 2950. | Cl | Cl | CF$_3$ | Me | OCH$_2$CF$_3$ |
| 2951. | Cl | Cl | CF$_3$ | Me | SO$_2$Me |
| 2952. | Cl | Cl | CF$_3$ | Me | SEt |
| 2953. | Cl | Cl | CF$_3$ | Et | Cl |
| 2954. | Cl | Cl | CF$_3$ | iPr | Cl |
| 2955. | Cl | Cl | CF$_3$ | tBu | Cl |
| 2956. | Cl | Cl | Cl | tBu | CF$_3$ |
| 2957. | Cl | Cl | CF$_3$ | cPen | Cl |
| 2958. | Cl | Cl | CF$_3$ | CHF$_2$ | OMe |
| 2959. | Cl | Cl | CF$_3$ | CH$_2$CF$_3$ | Cl |
| 2960. | Cl | Cl | CF$_3$ | Ph | OCHF$_2$ |
| 2961. | Cl | Cl | CF$_3$ | Ph | Cl |
| 2962. | Cl | Cl | Me | Me | OCH$_2$CF$_3$ |
| 2963. | Cl | Cl | CF$_3$ | Me | 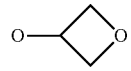 |
| 2964. | Cl | Cl | CF$_3$ | Me | H |
| 2965. | Cl | Cl | CF$_3$ | Me | OCH$_2$CH$_2$OMe |
| 2966. | Cl | Cl | CF$_3$ | Me | SMe |
| 2967. | Cl | Cl | CF$_3$ | Me | OCH$_2$CH$_2$CH$_2$F |
| 2968. | Cl | Cl | CF$_3$ | Me | OCH(CH$_2$F)$_2$ |
| 2969. | Cl | Cl | CF$_3$ | Me | OCH$_2$CF$_2$CHF$_2$ |
| 2970. | Cl | Cl | CF$_3$ | Me | OCH$_2$CF=CH$_2$ |
| 2971. | Cl | Cl | CF$_3$ | Me | OCH(Me)CF$_3$ |
| 2972. | Cl | Cl | CF$_3$ | Me | OCH(Me)CH$_2$F |
| 2973. | Cl | Cl | OCH$_2$CF$_3$ | Me | CF$_3$ |
| 2974. | Cl | Cl | OCH$_2$CF$_3$ | Me | CHF$_2$ |
| 2975. | Cl | Cl | CHF$_2$ | Me | CHF$_2$ |
| 2976. | Cl | Cl | CF$_3$ | Me | CHF$_2$ |
| 2977. | Cl | Cl | Cl | Me | OCHF$_2$ |
| 2978. | Cl | Cl | Br | Me | OCHF$_2$ |
| 2979. | Cl | Cl | Br | Me | CF$_3$ |
| 2980. | Cl | Me | CF$_3$ | tBu | Cl |
| 2981. | Cl | Me | CF$_3$ | CHF$_2$ | Cl |
| 2982. | Cl | Me | Cl | CHF$_2$ | CF$_3$ |
| 2983. | Cl | Me | CF$_3$ | Me | OMe |
| 2984. | Cl | Me | CF$_3$ | Me | CN |
| 2985. | Cl | Me | CHF$_2$ | Me | Cl |
| 2986. | Cl | Me | Me | Me | Me |
| 2987. | Cl | Me | Me | Me | Cl |
| 2988. | Cl | Me | CF$_3$ | Me | Cl |
| 2989. | Cl | Me | Cl | Me | CF$_3$ |
| 2990. | Cl | Me | CF$_3$ | Me | F |
| 2991. | Cl | Me | OMe | Me | CF$_3$ |
| 2992. | Cl | Me | CF$_3$ | Me | OCHF$_2$ |
| 2993. | Cl | Me | OCHF$_2$ | Me | CF$_3$ |
| 2994. | Cl | Me | CF$_3$ | Me | OCH$_2$CHF$_2$ |
| 2995. | Cl | Me | CF$_3$ | Me | OCH$_2$CF$_3$ |
| 2996. | Cl | Me | CF$_3$ | Me | SO$_2$Me |
| 2997. | Cl | Me | CF$_3$ | Me | SEt |
| 2998. | Cl | Me | CF$_3$ | Et | Cl |
| 2999. | Cl | Me | CF$_3$ | iPr | Cl |
| 3000. | Cl | Me | CF$_3$ | tBu | Cl |
| 3001. | Cl | Me | Cl | tBu | CF$_3$ |
| 3002. | Cl | Me | CF$_3$ | cPen | Cl |
| 3003. | Cl | Me | CF$_3$ | CHF$_2$ | OMe |
| 3004. | Cl | Me | CF$_3$ | CH$_2$CF$_3$ | Cl |
| 3005. | Cl | Me | CF$_3$ | Ph | OCHF$_2$ |
| 3006. | Cl | Me | CF$_3$ | Ph | Cl |
| 3007. | Cl | Me | Me | Me | OCH$_2$CF$_3$ |
| 3008. | Cl | Me | CF$_3$ | Me | 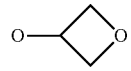 |
| 3009. | Cl | Me | CF$_3$ | Me | H |
| 3010. | Cl | Me | CF$_3$ | Me | OCH$_2$CH$_2$OMe |
| 3011. | Cl | Me | CF$_3$ | Me | SMe |
| 3012. | Cl | Me | CF$_3$ | Me | OCH$_2$CH$_2$CH$_2$F |
| 3013. | Cl | Me | CF$_3$ | Me | OCH(CH$_2$F)$_2$ |
| 3014. | Cl | Me | CF$_3$ | Me | OCH$_2$CF$_2$CHF$_2$ |
| 3015. | Cl | Me | CF$_3$ | Me | OCH$_2$CF=CH$_2$ |
| 3016. | Cl | Me | CF$_3$ | Me | OCH(Me)CF$_3$ |
| 3017. | Cl | Me | CF$_3$ | Me | OCH(Me)CH$_2$F |
| 3018. | Cl | Me | OCH$_2$CF$_3$ | Me | CF$_3$ |
| 3019. | Cl | Me | OCH$_2$CF$_3$ | Me | CHF$_2$ |
| 3020. | Cl | Me | CHF$_2$ | Me | CHF$_2$ |
| 3021. | Cl | Me | CF$_3$ | Me | CHF$_2$ |
| 3022. | Cl | Me | Cl | Me | OCHF$_2$ |
| 3023. | Cl | Me | Br | Me | OCHF$_2$ |
| 3024. | Cl | Me | Br | Me | CF$_3$ |

TABLE 3

Compounds of the formula (III-R)

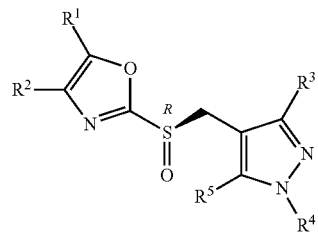

(III-R)

| Ex. No. | R¹ | R² | R³ | R⁴ | R⁵ |
|---|---|---|---|---|---|
| 3025. | H | H | CF$_3$ | Ph | Cl |
| 3026. | H | H | CF$_3$ | tBu | Cl |
| 3027. | H | H | CF$_3$ | CHF$_2$ | Cl |
| 3028. | H | H | Cl | CHF$_2$ | CF$_3$ |
| 3029. | H | H | CF$_3$ | Me | OMe |
| 3030. | H | H | CF$_3$ | Me | CN |
| 3031. | H | H | Cl | Et | Cl |

TABLE 3-continued

Compounds of the formula (III-R)

(III-R)

| Ex. No. | R¹ | R² | R³ | R⁴ | R⁵ |
|---|---|---|---|---|---|
| 3032. | H | H | CHF$_2$ | Me | Cl |
| 3033. | H | H | Me | Me | Me |
| 3034. | H | H | Me | Me | Cl |
| 3035. | H | H | Cl | Me | Cl |
| 3036. | H | H | CF$_3$ | Me | Cl |
| 3037. | H | H | Cl | Me | CF$_3$ |
| 3038. | H | H | CF$_3$ | Me | F |
| 3039. | H | H | OMe | Me | CF$_3$ |
| 3040. | H | H | CF$_3$ | Me | OEt |
| 3041. | H | H | CF$_3$ | Me | OCHF$_2$ |
| 3042. | H | H | OCHF$_2$ | Me | CF$_3$ |
| 3043. | H | H | CF$_3$ | Me | OCH$_2$CHF$_2$ |
| 3044. | H | H | CF$_3$ | Me | OCH$_2$CF$_3$ |
| 3045. | H | H | CF$_3$ | Me | OCH$_2$CN |
| 3046. | H | H | CF$_3$ | Me | SO$_2$Me |
| 3047. | H | H | CF$_3$ | Me | SEt |
| 3048. | H | H | CF$_3$ | Me | Me |
| 3049. | H | H | CF$_3$ | Me | Et |
| 3050. | H | H | CF$_3$ | Et | Cl |
| 3051. | H | H | Cl | Et | CF$_3$ |
| 3052. | H | H | CF$_3$ | iPr | Cl |
| 3053. | H | H | Cl | iPr | CF$_3$ |
| 3054. | H | H | CF$_3$ | tBu | Cl |
| 3055. | H | H | Cl | tBu | CF$_3$ |
| 3056. | H | H | CF$_3$ | cPen | Cl |
| 3057. | H | H | Cl | cPen | CF$_3$ |
| 3058. | H | H | CF$_3$ | CH$_2$cPr | Cl |
| 3059. | H | H | Cl | CH$_2$cPr | CF$_3$ |
| 3060. | H | H | CF$_3$ | CH$_2$CH=CH$_2$ | Cl |
| 3061. | H | H | Cl | CH$_2$CH=CH$_2$ | CF$_3$ |
| 3062. | H | H | CF$_3$ | CHF$_2$ | OMe |
| 3063. | H | H | OMe | CHF$_2$ | CF$_3$ |
| 3064. | H | H | CF$_3$ | CH$_2$CF$_3$ | Cl |
| 3065. | H | H | Cl | CH$_2$CF$_3$ | CF$_3$ |
| 3066. | H | H | CF$_3$ | CH$_2$OMe | Cl |
| 3067. | H | H | Cl | CH$_2$OMe | CF$_3$ |
| 3068. | H | H | CF$_3$ | CH$_2$CN | Cl |
| 3069. | H | H | Me | Ph | Me |
| 3070. | H | H | Me | Ph | Cl |
| 3071. | H | H | Et | Ph | Cl |
| 3072. | H | H | Pr | Ph | Cl |
| 3073. | H | H | iPr | Ph | Cl |
| 3074. | H | H | CF$_3$ | Ph | Cl |
| 3075. | H | H | CF$_3$ | Ph | Me |
| 3076. | H | H | CF$_3$ | Ph | CF$_3$ |
| 3077. | H | H | CF$_3$ | Ph | F |
| 3078. | H | H | CF$_3$ | Ph | OMe |
| 3079. | H | H | CF$_3$ | Ph | OEt |
| 3080. | H | H | CF$_3$ | Ph | OCHF$_2$ |
| 3081. | H | H | CF$_3$ | Ph | CN |
| 3082. | H | H | CF$_3$ | Ph(4-Cl) | Cl |
| 3083. | H | H | Me | Me | OCH$_2$CF$_3$ |
| 3084. | H | H | CF$_3$ | Me | oxetane-O |
| 3085. | H | H | CF$_3$ | Me | H |
| 3086. | H | H | CF$_3$ | Me | OCH$_2$CH$_2$OMe |
| 3087. | H | H | CF$_3$ | Me | SMe |
| 3088. | H | H | CF$_3$ | Me | OCH$_2$CH$_2$CH$_2$F |
| 3089. | H | H | CF$_3$ | Me | OCH(CH$_2$F)$_2$ |
| 3090. | H | H | CF$_3$ | Me | OCH$_2$CF$_2$CHF$_2$ |
| 3091. | H | H | CF$_3$ | Me | OCH$_2$CF=CH$_2$ |
| 3092. | H | H | CF$_3$ | Me | OCH(Me)CF$_3$ |
| 3093. | H | H | CF$_3$ | Me | OCH(Me)CH$_2$F |
| 3094. | H | H | OCH$_2$CF$_3$ | Me | CF$_3$ |
| 3095. | H | H | OCH$_2$CF$_3$ | Me | CHF$_2$ |
| 3096. | H | H | CHF$_2$ | Me | CHF$_2$ |
| 3097. | H | H | CF$_3$ | Me | CHF$_2$ |
| 3098. | H | H | Cl | Me | OCHF$_2$ |
| 3099. | H | H | Br | Me | OCHF$_2$ |
| 3100. | H | H | Br | Me | CF$_3$ |
| 3101. | H | H | CF$_3$ | Me | CF$_3$ |
| 3102. | H | H | CHF$_2$ | Me | CF$_3$ |
| 3103. | H | H | CF$_2$CF$_3$ | Me | CF$_3$ |
| 3104. | H | H | CF$_3$ | Me | CF$_2$CF$_3$ |
| 3105. | H | H | CHF$_2$ | Me | OCH$_2$CF$_3$ |
| 3106. | H | H | CHF$_2$ | Me | OCHF$_2$ |
| 3107. | F | H | CF$_3$ | Ph | Cl |
| 3108. | F | H | CF$_3$ | tBu | Cl |
| 3109. | F | H | CF$_3$ | CHF$_2$ | Cl |
| 3110. | F | H | Cl | CHF$_2$ | CF$_3$ |
| 3111. | F | H | CF$_3$ | Me | OMe |
| 3112. | F | H | CF$_3$ | Me | CN |
| 3113. | F | H | Cl | Et | Cl |
| 3114. | F | H | CHF$_2$ | Me | Cl |
| 3115. | F | H | Me | Me | Me |
| 3116. | F | H | Me | Me | Cl |
| 3117. | F | H | Cl | Me | Cl |
| 3118. | F | H | CF$_3$ | Me | Cl |
| 3119. | F | H | Cl | Me | CF$_3$ |
| 3120. | F | H | CF$_3$ | Me | F |
| 3121. | F | H | OMe | Me | CF$_3$ |
| 3122. | F | H | CF$_3$ | Me | OEt |
| 3123. | F | H | CF$_3$ | Me | OCHF$_2$ |
| 3124. | F | H | OCHF$_2$ | Me | CF$_3$ |
| 3125. | F | H | CF$_3$ | Me | OCH$_2$CHF$_2$ |
| 3126. | F | H | CF$_3$ | Me | OCH$_2$CF$_3$ |
| 3127. | F | H | CF$_3$ | Me | OCH$_2$CN |
| 3128. | F | H | CF$_3$ | Me | SO$_2$Me |
| 3129. | F | H | CF$_3$ | Me | SEt |
| 3130. | F | H | CF$_3$ | Me | Me |
| 3131. | F | H | CF$_3$ | Me | Et |
| 3132. | F | H | CF$_3$ | Et | Cl |
| 3133. | F | H | Cl | Et | CF$_3$ |
| 3134. | F | H | CF$_3$ | iPr | Cl |
| 3135. | F | H | Cl | iPr | CF$_3$ |
| 3136. | F | H | CF$_3$ | tBu | Cl |
| 3137. | F | H | Cl | tBu | CF$_3$ |
| 3138. | F | H | CF$_3$ | cPen | Cl |
| 3139. | F | H | Cl | cPen | CF$_3$ |
| 3140. | F | H | CF$_3$ | CH$_2$cPr | Cl |
| 3141. | F | H | Cl | CH$_2$cPr | CF$_3$ |
| 3142. | F | H | CF$_3$ | CH$_2$CH=CH$_2$ | Cl |
| 3143. | F | H | Cl | CH$_2$CH=CH$_2$ | CF$_3$ |
| 3144. | F | H | CF$_3$ | CHF$_2$ | OMe |
| 3145. | F | H | OMe | CHF$_2$ | CF$_3$ |
| 3146. | F | H | CF$_3$ | CH$_2$CF$_3$ | Cl |
| 3147. | F | H | Cl | CH$_2$CF$_3$ | CF$_3$ |
| 3148. | F | H | CF$_3$ | CH$_2$OMe | Cl |
| 3149. | F | H | Cl | CH$_2$OMe | CF$_3$ |
| 3150. | F | H | CF$_3$ | CH$_2$CN | Cl |
| 3151. | F | H | Me | Ph | Me |
| 3152. | F | H | Me | Ph | Cl |

TABLE 3-continued

Compounds of the formula (III-R)

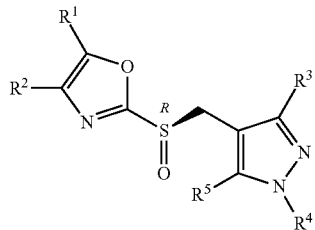

| Ex. No. | R¹ | R² | R³ | R⁴ | R⁵ |
|---|---|---|---|---|---|
| 3153. | F | H | Et | Ph | Cl |
| 3154. | F | H | Pr | Ph | Cl |
| 3155. | F | H | iPr | Ph | Cl |
| 3156. | F | H | CF₃ | Ph | Cl |
| 3157. | F | H | CF₃ | Ph | Me |
| 3158. | F | H | CF₃ | Ph | CF₃ |
| 3159. | F | H | CF₃ | Ph | F |
| 3160. | F | H | CF₃ | Ph | OMe |
| 3161. | F | H | CF₃ | Ph | OEt |
| 3162. | F | H | CF₃ | Ph | OCHF₂ |
| 3163. | F | H | CF₃ | Ph | CN |
| 3164. | F | H | CF₃ | Ph(4-Cl) | Cl |
| 3165. | F | H | Me | Me | OCH₂CF₃ |
| 3166. | F | H | CF₃ | Me | 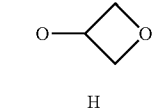 |
| 3167. | F | H | CF₃ | Me | H |
| 3168. | F | H | CF₃ | Me | OCH₂CH₂OMe |
| 3169. | F | H | CF₃ | Me | SMe |
| 3170. | F | H | CF₃ | Me | OCH₂CH₂CH₂F |
| 3171. | F | H | CF₃ | Me | OCH(CH₂F)₂ |
| 3172. | F | H | CF₃ | Me | OCH₂CF₂CHF₂ |
| 3173. | F | H | CF₃ | Me | OCH₂CF=CH₂ |
| 3174. | F | H | CF₃ | Me | OCH(Me)CF₃ |
| 3175. | F | H | CF₃ | Me | OCH(Me)CH₂F |
| 3176. | F | H | OCH₂CF₃ | Me | CF₃ |
| 3177. | F | H | OCH₂CF₃ | Me | CHF₂ |
| 3178. | F | H | CHF₂ | Me | CHF₂ |
| 3179. | F | H | CF₃ | Me | CHF₂ |
| 3180. | F | H | Cl | Me | OCHF₂ |
| 3181. | F | H | Br | Me | OCHF₂ |
| 3182. | F | H | Br | Me | CF₃ |
| 3183. | F | H | Cl | Me | CF₃ |
| 3184. | F | H | CHF₂ | Me | CF₃ |
| 3185. | F | H | CF₂CF₃ | Me | CF₃ |
| 3186. | F | H | CF₃ | Me | CF₂CF₃ |
| 3187. | F | H | CHF₂ | Me | OCH₂CF₃ |
| 3188. | F | H | CHF₂ | Me | OCHF₂ |
| 3189. | Cl | H | CF₃ | Ph | Cl |
| 3190. | Cl | H | CF₃ | tBu | Cl |
| 3191. | Cl | H | CF₃ | CHF₂ | Cl |
| 3192. | Cl | H | Cl | CHF₂ | CF₃ |
| 3193. | Cl | H | CF₃ | Me | OMe |
| 3194. | Cl | H | CF₃ | Me | CN |
| 3195. | Cl | H | Cl | Et | Cl |
| 3196. | Cl | H | CHF₂ | Me | Cl |
| 3197. | Cl | H | Me | Me | Me |
| 3198. | Cl | H | Me | Me | Cl |
| 3199. | Cl | H | Cl | Me | Cl |
| 3200. | Cl | H | CF₃ | Me | Cl |
| 3201. | Cl | H | Cl | Me | CF₃ |
| 3202. | Cl | H | CF₃ | Me | F |
| 3203. | Cl | H | OMe | Me | CF₃ |
| 3204. | Cl | H | CF₃ | Me | OEt |
| 3205. | Cl | H | CF₃ | Me | OCHF₂ |
| 3206. | Cl | H | OCHF₂ | Me | CF₃ |
| 3207. | Cl | H | CF₃ | Me | OCH₂CHF₂ |
| 3208. | Cl | H | CF₃ | Me | OCH₂CF₃ |
| 3209. | Cl | H | CF₃ | Me | OCH₂CN |
| 3210. | Cl | H | CF₃ | Me | SO₂Me |
| 3211. | Cl | H | CF₃ | Me | SEt |
| 3212. | Cl | H | CF₃ | Me | Me |
| 3213. | Cl | H | CF₃ | Me | Et |
| 3214. | Cl | H | CF₃ | Et | Cl |
| 3215. | Cl | H | Cl | Et | CF₃ |
| 3216. | Cl | H | CF₃ | iPr | Cl |
| 3217. | Cl | H | Cl | iPr | CF₃ |
| 3218. | Cl | H | CF₃ | tBu | Cl |
| 3219. | Cl | H | Cl | tBu | CF₃ |
| 3220. | Cl | H | CF₃ | cPen | Cl |
| 3221. | Cl | H | Cl | cPen | CF₃ |
| 3222. | Cl | H | CF₃ | CH₂cPr | Cl |
| 3223. | Cl | H | Cl | CH₂cPr | CF₃ |
| 3224. | Cl | H | CF₃ | CH₂CH=CH₂ | Cl |
| 3225. | Cl | H | Cl | CH₂CH=CH₂ | CF₃ |
| 3226. | Cl | H | CF₃ | CHF₂ | OMe |
| 3227. | Cl | H | OMe | CHF₂ | CF₃ |
| 3228. | Cl | H | CF₃ | CH₂CF₃ | Cl |
| 3229. | Cl | H | Cl | CH₂CF₃ | CF₃ |
| 3230. | Cl | H | CF₃ | CH₂OMe | Cl |
| 3231. | Cl | H | Cl | CH₂OMe | CF₃ |
| 3232. | Cl | H | CF₃ | CH₂CN | Cl |
| 3233. | Cl | H | Me | Ph | Me |
| 3234. | Cl | H | Me | Ph | Cl |
| 3235. | Cl | H | Et | Ph | Cl |
| 3236. | Cl | H | Pr | Ph | Cl |
| 3237. | Cl | H | iPr | Ph | Cl |
| 3238. | Cl | H | CF₃ | Ph | Cl |
| 3239. | Cl | H | CF₃ | Ph | Me |
| 3240. | Cl | H | CF₃ | Ph | CF₃ |
| 3241. | Cl | H | CF₃ | Ph | F |
| 3242. | Cl | H | CF₃ | Ph | OMe |
| 3243. | Cl | H | CF₃ | Ph | OEt |
| 3244. | Cl | H | CF₃ | Ph | OCHF₂ |
| 3245. | Cl | H | CF₃ | Ph | CN |
| 3246. | Cl | H | CF₃ | Ph(4-Cl) | Cl |
| 3247. | Cl | H | Me | Me | OCH₂CF₃ |
| 3248. | Cl | H | CF₃ | Me |  |
| 3249. | Cl | H | CF₃ | Me | H |
| 3250. | Cl | H | CF₃ | Me | OCH₂CH₂OMe |
| 3251. | Cl | H | CF₃ | Me | SMe |
| 3252. | Cl | H | CF₃ | Me | OCH₂CH₂CH₂F |
| 3253. | Cl | H | CF₃ | Me | OCH(CH₂F)₂ |
| 3254. | Cl | H | CF₃ | Me | OCH₂CF₂CHF₂ |
| 3255. | Cl | H | CF₃ | Me | OCH₂CF=CH₂ |
| 3256. | Cl | H | CF₃ | Me | OCH(Me)CF₃ |
| 3257. | Cl | H | CF₃ | Me | OCH(Me)CH₂F |
| 3258. | Cl | H | OCH₂CF₃ | Me | CF₃ |
| 3259. | Cl | H | OCH₂CF₃ | Me | CHF₂ |
| 3260. | Cl | H | CHF₂ | Me | CHF₂ |
| 3261. | Cl | H | CF₃ | Me | CHF₂ |
| 3262. | Cl | H | Cl | Me | OCHF₂ |
| 3263. | Cl | H | Br | Me | OCHF₂ |
| 3264. | Cl | H | Br | Me | CF₃ |
| 3265. | Cl | H | CF₃ | Me | CF₃ |
| 3266. | Cl | H | CHF₂ | Me | CF₃ |
| 3267. | Cl | H | CF₂CF₃ | Me | CF₃ |
| 3268. | Cl | H | CF₃ | Me | CF₂CF₃ |

TABLE 3-continued

Compounds of the formula (III-R)

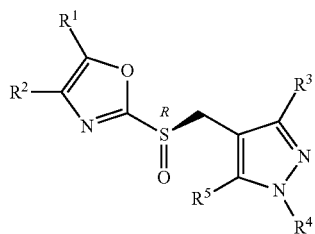

(III-R)

| Ex. No. | R¹ | R² | R³ | R⁴ | R⁵ |
|---|---|---|---|---|---|
| 3269. | Cl | H | CHF$_2$ | Me | OCH$_2$CF$_3$ |
| 3270. | Cl | H | CHF$_2$ | Me | OCHF$_2$ |
| 3271. | Br | H | CF$_3$ | Ph | Cl |
| 3272. | Br | H | CF$_3$ | tBu | Cl |
| 3273. | Br | H | CF$_3$ | CHF$_2$ | Cl |
| 3274. | Br | H | Cl | CHF$_2$ | CF$_3$ |
| 3275. | Br | H | CF$_3$ | Me | OMe |
| 3276. | Br | H | CF$_3$ | Me | CN |
| 3277. | Br | H | Cl | Et | Cl |
| 3278. | Br | H | CHF$_2$ | Me | Cl |
| 3279. | Br | H | Me | Me | Me |
| 3280. | Br | H | Me | Me | Cl |
| 3281. | Br | H | Cl | Me | Cl |
| 3282. | Br | H | CF$_3$ | Me | Cl |
| 3283. | Br | H | Cl | Me | CF$_3$ |
| 3284. | Br | H | CF$_3$ | Me | F |
| 3285. | Br | H | OMe | Me | CF$_3$ |
| 3286. | Br | H | CF$_3$ | Me | OEt |
| 3287. | Br | H | CF$_3$ | Me | OCHF$_2$ |
| 3288. | Br | H | OCHF$_2$ | Me | CF$_3$ |
| 3289. | Br | H | CF$_3$ | Me | OCH$_2$CHF$_2$ |
| 3290. | Br | H | CF$_3$ | Me | OCH$_2$CF$_3$ |
| 3291. | Br | H | CF$_3$ | Me | OCH$_2$CN |
| 3292. | Br | H | CF$_3$ | Me | SO$_2$Me |
| 3293. | Br | H | CF$_3$ | Me | SEt |
| 3294. | Br | H | CF$_3$ | Me | Me |
| 3295. | Br | H | CF$_3$ | Me | Et |
| 3296. | Br | H | CF$_3$ | Et | Cl |
| 3297. | Br | H | Cl | Et | CF$_3$ |
| 3298. | Br | H | CF$_3$ | iPr | Cl |
| 3299. | Br | H | Cl | iPr | CF$_3$ |
| 3300. | Br | H | CF$_3$ | tBu | Cl |
| 3301. | Br | H | Cl | tBu | CF$_3$ |
| 3302. | Br | H | CF$_3$ | cPen | Cl |
| 3303. | Br | H | Cl | cPen | CF$_3$ |
| 3304. | Br | H | CF$_3$ | CH$_2$cPr | Cl |
| 3305. | Br | H | Cl | CH$_2$cPr | CF$_3$ |
| 3306. | Br | H | CF$_3$ | CH$_2$CH=CH$_2$ | Cl |
| 3307. | Br | H | Cl | CH$_2$CH=CH$_2$ | CF$_3$ |
| 3308. | Br | H | CF$_3$ | CHF$_2$ | OMe |
| 3309. | Br | H | OMe | CHF$_2$ | CF$_3$ |
| 3310. | Br | H | CF$_3$ | CH$_2$CF$_3$ | Cl |
| 3311. | Br | H | Cl | CH$_2$CF$_3$ | CF$_3$ |
| 3312. | Br | H | CF$_3$ | CH$_2$OMe | Cl |
| 3313. | Br | H | Cl | CH$_2$OMe | CF$_3$ |
| 3314. | Br | H | CF$_3$ | CH$_2$CN | Cl |
| 3315. | Br | H | Me | Ph | Me |
| 3316. | Br | H | Me | Ph | Cl |
| 3317. | Br | H | Et | Ph | Cl |
| 3318. | Br | H | Pr | Ph | Cl |
| 3319. | Br | H | iPr | Ph | Cl |
| 3320. | Br | H | CF$_3$ | Ph | Cl |
| 3321. | Br | H | CF$_3$ | Ph | Me |
| 3322. | Br | H | CF$_3$ | Ph | CF$_3$ |
| 3323. | Br | H | CF$_3$ | Ph | F |
| 3324. | Br | H | CF$_3$ | Ph | OMe |
| 3325. | Br | H | CF$_3$ | Ph | OEt |
| 3326. | Br | H | CF3 | Ph | OCHF$_2$ |
| 3327. | Br | H | CF$_3$ | Ph | CN |
| 3328. | Br | H | CF$_3$ | Ph(4-Cl) | Cl |
| 3329. | Br | H | Me | Me | OCH$_2$CF$_3$ |
| 3330. | Br | H | CF$_3$ | Me | 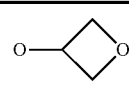 |
| 3331. | Br | H | CF$_3$ | Me | H |
| 3332. | Br | H | CF$_3$ | Me | OCH$_2$CH$_2$OMe |
| 3333. | Br | H | CF$_3$ | Me | SMe |
| 3334. | Br | H | CF$_3$ | Me | OCH$_2$CH$_2$CH$_2$F |
| 3335. | Br | H | CF$_3$ | Me | OCH(CH$_2$F)$_2$ |
| 3336. | Br | H | CF$_3$ | Me | OCH$_2$CF$_2$CHF$_2$ |
| 3337. | Br | H | CF$_3$ | Me | OCH$_2$CF=CH$_2$ |
| 3338. | Br | H | CF$_3$ | Me | OCH(Me)CF$_3$ |
| 3339. | Br | H | CF$_3$ | Me | OCH(Me)CH$_2$F |
| 3340. | Br | H | OCH$_2$CF$_3$ | Me | CF$_3$ |
| 3341. | Br | H | OCH$_2$CF$_3$ | Me | CHF$_2$ |
| 3342. | Br | H | CHF$_2$ | Me | CHF$_2$ |
| 3343. | Br | H | CF$_3$ | Me | CHF$_2$ |
| 3344. | Br | H | Cl | Me | OCHF$_2$ |
| 3345. | Br | H | Br | Me | OCHF$_2$ |
| 3346. | Br | H | Br | Me | CF$_3$ |
| 3347. | Br | H | CF$_3$ | Me | CF$_3$ |
| 3348. | Br | H | CHF$_2$ | Me | CF$_3$ |
| 3349. | Br | H | CF$_2$CF$_3$ | Me | CF$_3$ |
| 3350. | Br | H | CF$_3$ | Me | CF$_2$CF$_3$ |
| 3351. | Br | H | CHF$_2$ | Me | OCH$_2$CF$_3$ |
| 3352. | Br | H | CHF$_2$ | Me | OCHF$_2$ |
| 3353. | I | H | CF$_3$ | Ph | Cl |
| 3354. | I | H | CF$_3$ | tBu | Cl |
| 3355. | I | H | CF$_3$ | CHF$_2$ | Cl |
| 3356. | I | H | Cl | CHF$_2$ | CF$_3$ |
| 3357. | I | H | CF$_3$ | Me | OMe |
| 3358. | I | H | CF$_3$ | Me | CN |
| 3359. | I | H | Cl | Et | Cl |
| 3360. | I | H | CHF$_2$ | Me | Cl |
| 3361. | I | H | Me | Me | Me |
| 3362. | I | H | Me | Me | Cl |
| 3363. | I | H | Cl | Me | Cl |
| 3364. | I | H | CF$_3$ | Me | Cl |
| 3365. | I | H | Cl | Me | CF$_3$ |
| 3366. | I | H | CF$_3$ | Me | F |
| 3367. | I | H | OMe | Me | CF$_3$ |
| 3368. | I | H | CF$_3$ | Me | OEt |
| 3369. | I | H | CF$_3$ | Me | OCHF$_2$ |
| 3370. | I | H | OCHF$_2$ | Me | CF$_3$ |
| 3371. | I | H | CF$_3$ | Me | OCH$_2$CHF$_2$ |
| 3372. | I | H | CF$_3$ | Me | OCH$_2$CF$_3$ |
| 3373. | I | H | CF$_3$ | Me | OCH$_2$CN |
| 3374. | I | H | CF$_3$ | Me | SO$_2$Me |
| 3375. | I | H | CF$_3$ | Me | SEt |
| 3376. | I | H | CF$_3$ | Me | Me |
| 3377. | I | H | CF$_3$ | Me | Et |
| 3378. | I | H | CF$_3$ | Et | Cl |
| 3379. | I | H | Cl | Et | CF$_3$ |
| 3380. | I | H | CF$_3$ | iPr | Cl |
| 3381. | I | H | Cl | iPr | CF$_3$ |
| 3382. | I | H | CF$_3$ | tBu | Cl |
| 3383. | I | H | Cl | tBu | CF$_3$ |
| 3384. | I | H | CF$_3$ | cPen | Cl |
| 3385. | I | H | Cl | cPen | CF$_3$ |
| 3386. | I | H | CF$_3$ | CH$_2$cPr | Cl |
| 3387. | I | H | Cl | CH$_2$cPr | CF$_3$ |
| 3388. | I | H | CF$_3$ | CH$_2$CH=CH$_2$ | Cl |

TABLE 3-continued

Compounds of the formula (III-R)

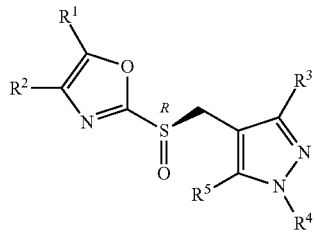

(III-R)

| Ex. No. | R¹ | R² | R³ | R⁴ | R⁵ |
|---|---|---|---|---|---|
| 3389. | I | H | Cl | CH₂CH=CH₂ | CF₃ |
| 3390. | I | H | CF₃ | CHF₂ | OMe |
| 3391. | I | H | OMe | CHF₂ | CF₃ |
| 3392. | I | H | CF₃ | CH₂CF₃ | Cl |
| 3393. | I | H | Cl | CH₂CF₃ | CF₃ |
| 3394. | I | H | CF₃ | CH₂OMe | Cl |
| 3395. | I | H | Cl | CH₂OMe | CF₃ |
| 3396. | I | H | CF₃ | CH₂CN | Cl |
| 3397. | I | H | Me | Ph | Me |
| 3398. | I | H | Me | Ph | Cl |
| 3399. | I | H | Et | Ph | Cl |
| 3400. | I | H | Pr | Ph | Cl |
| 3401. | I | H | iPr | Ph | Cl |
| 3402. | I | H | CF₃ | Ph | Cl |
| 3403. | I | H | CF₃ | Ph | Me |
| 3404. | I | H | CF₃ | Ph | CF₃ |
| 3405. | I | H | CF₃ | Ph | F |
| 3406. | I | H | CF₃ | Ph | OMe |
| 3407. | I | H | CF₃ | Ph | OEt |
| 3408. | I | H | CF₃ | Ph | OCHF₂ |
| 3409. | I | H | CF₃ | Ph | CN |
| 3410. | I | H | CF₃ | Ph(4-Cl) | Cl |
| 3411. | I | H | Me | Me | OCH₂CF₃ |
| 3412. | I | H | CF₃ | Me | 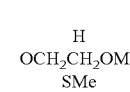 |
| 3413. | I | H | CF₃ | Me | H |
| 3414. | I | H | CF₃ | Me | OCH₂CH₂OMe |
| 3415. | I | H | CF₃ | Me | SMe |
| 3416. | I | H | CF₃ | Me | OCH₂CH₂F |
| 3417. | I | H | CF₃ | Me | OCH(CH₂F)₂ |
| 3418. | I | H | CF₃ | Me | OCH₂CF₂CHF₂ |
| 3419. | I | H | CF₃ | Me | OCH₂CF=CH₂ |
| 3420. | I | H | CF₃ | Me | OCH(Me)CF₃ |
| 3421. | I | H | CF₃ | Me | OCH(Me)CH₂F |
| 3422. | I | H | OCH₂CF₃ | Me | CF₃ |
| 3423. | I | H | OCH₂CF₃ | Me | CHF₂ |
| 3424. | I | H | CHF₂ | Me | CHF₂ |
| 3425. | I | H | CF₃ | Me | CHF₂ |
| 3426. | I | H | Cl | Me | OCHF₂ |
| 3427. | I | H | Br | Me | OCHF₂ |
| 3428. | I | H | Br | Me | CF₃ |
| 3429. | I | H | CF₃ | Me | CF₃ |
| 3430. | I | H | CHF₂ | Me | CF₃ |
| 3431. | I | H | CF₂CF₃ | Me | CF₃ |
| 3432. | I | H | CF₃ | Me | CF₂CF₃ |
| 3433. | I | H | CHF₂ | Me | OCH₂CF₃ |
| 3434. | I | H | CHF₂ | Me | OCHF₂ |
| 3435. | H | F | CF₃ | Ph | Cl |
| 3436. | H | F | CF₃ | tBu | Cl |
| 3437. | H | F | CF₃ | CHF₂ | Cl |
| 3438. | H | F | Cl | CHF₂ | CF₃ |
| 3439. | H | F | CF₃ | Me | OMe |
| 3440. | H | F | CF₃ | Me | CN |
| 3441. | H | F | Cl | Et | Cl |
| 3442. | H | F | CHF₂ | Me | Cl |
| 3443. | H | F | Me | Me | Me |
| 3444. | H | F | Me | Me | Cl |
| 3445. | H | F | Cl | Me | Cl |
| 3446. | H | F | CF₃ | Me | Cl |
| 3447. | H | F | Cl | Me | CF₃ |
| 3448. | H | F | CF₃ | Me | F |
| 3449. | H | F | OMe | Me | CF₃ |
| 3450. | H | F | CF₃ | Me | OEt |
| 3451. | H | F | CF₃ | Me | OCHF₂ |
| 3452. | H | F | OCHF₂ | Me | CF₃ |
| 3453. | H | F | CF₃ | Me | OCH₂CHF₂ |
| 3454. | H | F | CF₃ | Me | OCH₂CF₃ |
| 3455. | H | F | CF₃ | Me | OCH₂CN |
| 3456. | H | F | CF₃ | Me | SO₂Me |
| 3457. | H | F | CF₃ | Me | SEt |
| 3458. | H | F | CF₃ | Me | Me |
| 3459. | H | F | CF₃ | Me | Et |
| 3460. | H | F | CF₃ | Et | Cl |
| 3461. | H | F | Cl | Et | CF₃ |
| 3462. | H | F | CF₃ | iPr | Cl |
| 3463. | H | F | Cl | iPr | CF₃ |
| 3464. | H | F | CF₃ | tBu | Cl |
| 3465. | H | F | Cl | tBu | CF₃ |
| 3466. | H | F | CF₃ | cPen | Cl |
| 3467. | H | F | Cl | cPen | CF₃ |
| 3468. | H | F | CF₃ | CH₂cPr | Cl |
| 3469. | H | F | Cl | CH₂cPr | CF₃ |
| 3470. | H | F | CF₃ | CH₂CH=CH₂ | Cl |
| 3471. | H | F | Cl | CH₂CH=CH₂ | CF₃ |
| 3472. | H | F | CF₃ | CHF₂ | OMe |
| 3473. | H | F | OMe | CHF₂ | CF₃ |
| 3474. | H | F | CF₃ | CH₂CF₃ | Cl |
| 3475. | H | F | Cl | CH₂CF₃ | CF₃ |
| 3476. | H | F | CF₃ | CH₂OMe | Cl |
| 3477. | H | F | Cl | CH₂OMe | CF₃ |
| 3478. | H | F | CF₃ | CH₂CN | Cl |
| 3479. | H | F | Me | Ph | Me |
| 3480. | H | F | Me | Ph | Cl |
| 3481. | H | F | Et | Ph | Cl |
| 3482. | H | F | Pr | Ph | Cl |
| 3483. | H | F | iPr | Ph | Cl |
| 3484. | H | F | CF₃ | Ph | Cl |
| 3485. | H | F | CF₃ | Ph | Me |
| 3486. | H | F | CF₃ | Ph | CF₃ |
| 3487. | H | F | CF₃ | Ph | F |
| 3488. | H | F | CF₃ | Ph | OMe |
| 3489. | H | F | CF₃ | Ph | OEt |
| 3490. | H | F | CF₃ | Ph | OCHF₂ |
| 3491. | H | F | CF₃ | Ph | CN |
| 3492. | H | F | CF₃ | Ph(4-Cl) | Cl |
| 3493. | H | F | Me | Me | OCH₂CF₃ |
| 3494. | H | F | CF₃ | Me | 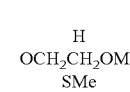 |
| 3495. | H | F | CF₃ | Me | H |
| 3496. | H | F | CF₃ | Me | OCH₂CH₂OMe |
| 3497. | H | F | CF₃ | Me | SMe |
| 3498. | H | F | CF₃ | Me | OCH₂CH₂F |
| 3499. | H | F | CF₃ | Me | OCH(CH₂F)₂ |
| 3500. | H | F | CF₃ | Me | OCH₂CF₂CHF₂ |
| 3501. | H | F | CF₃ | Me | OCH₂CF=CH₂ |
| 3502. | H | F | CF₃ | Me | OCH(Me)CF₃ |
| 3503. | H | F | CF₃ | Me | OCH(Me)CH₂F |
| 3504. | H | F | OCH₂CF₃ | Me | CF₃ |

TABLE 3-continued

Compounds of the formula (III-R)

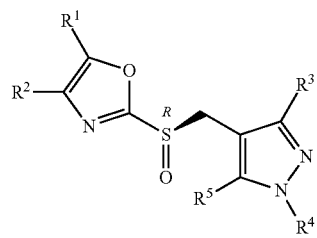

(III-R)

| Ex. No. | R¹ | R² | R³ | R⁴ | R⁵ |
|---|---|---|---|---|---|
| 3505. | H | F | OCH$_2$CF$_3$ | Me | CHF$_2$ |
| 3506. | H | F | CHF$_2$ | Me | CHF$_2$ |
| 3507. | H | F | CF$_3$ | Me | CHF$_2$ |
| 3508. | H | F | Cl | Me | OCHF$_2$ |
| 3509. | H | F | Br | Me | OCHF$_2$ |
| 3510. | H | F | Br | Me | CF$_3$ |
| 3511. | H | Cl | CF$_3$ | tBu | Cl |
| 3512. | H | Cl | CF$_3$ | CHF$_2$ | Cl |
| 3513. | H | Cl | Cl | CHF$_2$ | CF$_3$ |
| 3514. | H | Cl | CF$_3$ | Me | OMe |
| 3515. | H | Cl | CF$_3$ | Me | CN |
| 3516. | H | Cl | CHF$_2$ | Me | Cl |
| 3517. | H | Cl | Me | Me | Me |
| 3518. | H | Cl | Me | Me | Cl |
| 3519. | H | Cl | CF$_3$ | Me | Cl |
| 3520. | H | Cl | Cl | Me | CF$_3$ |
| 3521. | H | Cl | CF$_3$ | Me | F |
| 3522. | H | Cl | OMe | Me | CF$_3$ |
| 3523. | H | Cl | CF$_3$ | Me | OCHF$_2$ |
| 3524. | H | Cl | OCHF$_2$ | Me | CF$_3$ |
| 3525. | H | Cl | CF$_3$ | Me | OCH$_2$CHF$_2$ |
| 3526. | H | Cl | CF$_3$ | Me | OCH$_2$CF$_3$ |
| 3527. | H | Cl | CF$_3$ | Me | SO$_2$Me |
| 3528. | H | Cl | CF$_3$ | Me | SEt |
| 3529. | H | Cl | CF$_3$ | Et | Cl |
| 3530. | H | Cl | CF$_3$ | iPr | Cl |
| 3531. | H | Cl | CF$_3$ | tBu | Cl |
| 3532. | H | Cl | Cl | tBu | CF$_3$ |
| 3533. | H | Cl | CF$_3$ | cPen | Cl |
| 3534. | H | Cl | CHF$_2$ | CHF$_2$ | OMe |
| 3535. | H | Cl | CF$_3$ | CH$_2$CF$_3$ | Cl |
| 3536. | H | Cl | CF$_3$ | Ph | OCHF$_2$ |
| 3537. | H | Cl | CF$_3$ | Ph | Cl |
| 3538. | H | Cl | Me | Me | OCH$_2$CF$_3$ |
| 3539. | H | Cl | CF$_3$ | Me |  |
| 3540. | H | Cl | CF$_3$ | Me | H |
| 3541. | H | Cl | CF$_3$ | Me | OCH$_2$CH$_2$OMe |
| 3542. | H | Cl | CF$_3$ | Me | SMe |
| 3543. | H | Cl | CF$_3$ | Me | OCH$_2$CH$_2$F |
| 3544. | H | Cl | CF$_3$ | Me | OCH(CH$_2$F)$_2$ |
| 3545. | H | Cl | CF$_3$ | Me | OCH$_2$CF$_2$CHF$_2$ |
| 3546. | H | Cl | CF$_3$ | Me | OCH$_2$CF=CH$_2$ |
| 3547. | H | Cl | CF$_3$ | Me | OCH(Me)CF$_3$ |
| 3548. | H | Cl | CF$_3$ | Me | OCH(Me)CH$_2$F |
| 3549. | H | Cl | OCH$_2$CF$_3$ | Me | CF$_3$ |
| 3550. | H | Cl | OCH$_2$CF$_3$ | Me | CHF$_2$ |
| 3551. | H | Cl | CHF$_2$ | Me | CHF$_2$ |
| 3552. | H | Cl | CF$_3$ | Me | CHF$_2$ |
| 3553. | H | Cl | Cl | Me | OCHF$_2$ |
| 3554. | H | Cl | Br | Me | OCHF$_2$ |
| 3555. | H | Cl | Br | Me | CF$_3$ |
| 3556. | H | Br | CF$_3$ | tBu | Cl |
| 3557. | H | Br | CF$_3$ | CHF$_2$ | Cl |
| 3558. | H | Br | Cl | CHF$_2$ | CF$_3$ |
| 3559. | H | Br | CF$_3$ | Me | OMe |
| 3560. | H | Br | CF$_3$ | Me | CN |
| 3561. | H | Br | CHF$_2$ | Me | Cl |
| 3562. | H | Br | Me | Me | Me |
| 3563. | H | Br | Me | Me | Cl |
| 3564. | H | Br | CF$_3$ | Me | Cl |
| 3565. | H | Br | Cl | Me | CF$_3$ |
| 3566. | H | Br | CF$_3$ | Me | F |
| 3567. | H | Br | OMe | Me | CF$_3$ |
| 3568. | H | Br | CF$_3$ | Me | OCHF$_2$ |
| 3569. | H | Br | OCHF$_2$ | Me | CF$_3$ |
| 3570. | H | Br | CF$_3$ | Me | OCH$_2$CHF$_2$ |
| 3571. | H | Br | CF$_3$ | Me | OCH$_2$CF$_3$ |
| 3572. | H | Br | CF$_3$ | Me | SO$_2$Me |
| 3573. | H | Br | CF$_3$ | Me | SEt |
| 3574. | H | Br | CF$_3$ | Et | Cl |
| 3575. | H | Br | CF$_3$ | iPr | Cl |
| 3576. | H | Br | CF$_3$ | tBu | Cl |
| 3577. | H | Br | Cl | tBu | CF$_3$ |
| 3578. | H | Br | CF$_3$ | cPen | Cl |
| 3579. | H | Br | CF$_3$ | CHF$_2$ | OMe |
| 3580. | H | Br | CF$_3$ | CH$_2$CF$_3$ | Cl |
| 3581. | H | Br | CF$_3$ | Ph | OCHF$_2$ |
| 3582. | H | Br | CF$_3$ | Ph | Cl |
| 3583. | H | Br | Me | Me | OCH$_2$CF$_3$ |
| 3584. | H | Br | CF$_3$ | Me | 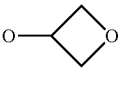 |
| 3585. | H | Br | CF$_3$ | Me | H |
| 3586. | H | Br | CF$_3$ | Me | OCH$_2$CH$_2$OMe |
| 3587. | H | Br | CF$_3$ | Me | SMe |
| 3588. | H | Br | CF$_3$ | Me | OCH$_2$CH$_2$F |
| 3589. | H | Br | CF$_3$ | Me | OCH(CH$_2$F)$_2$ |
| 3590. | H | Br | CF$_3$ | Me | OCH$_2$CF$_2$CHF$_2$ |
| 3591. | H | Br | CF$_3$ | Me | OCH$_2$CF=CH$_2$ |
| 3592. | H | Br | CF$_3$ | Me | OCH(Me)CF$_3$ |
| 3593. | H | Br | CF$_3$ | Me | OCH(Me)CH$_2$F |
| 3594. | H | Br | OCH$_2$CF$_3$ | Me | CF$_3$ |
| 3595. | H | Br | OCH$_2$CF$_3$ | Me | CHF$_2$ |
| 3596. | H | Br | CHF$_2$ | Me | CHF$_2$ |
| 3597. | H | Br | CF$_3$ | Me | CHF$_2$ |
| 3598. | H | Br | Cl | Me | OCHF$_2$ |
| 3599. | H | Br | Br | Me | OCHF$_2$ |
| 3600. | H | Br | Br | Me | CF$_3$ |
| 3601. | Me | H | CF$_3$ | tBu | Cl |
| 3602. | Me | H | CF$_3$ | CHF$_2$ | Cl |
| 3603. | Me | H | Cl | CHF$_2$ | CF$_3$ |
| 3604. | Me | H | CF$_3$ | Me | OMe |
| 3605. | Me | H | CF$_3$ | Me | CN |
| 3606. | Me | H | CHF$_2$ | Me | Cl |
| 3607. | Me | H | Me | Me | Me |
| 3608. | Me | H | Me | Me | Cl |
| 3609. | Me | H | CF$_3$ | Me | Cl |
| 3610. | Me | H | Cl | Me | CF$_3$ |
| 3611. | Me | H | CF$_3$ | Me | F |
| 3612. | Me | H | OMe | Me | CF$_3$ |
| 3613. | Me | H | CF$_3$ | Me | OCHF$_2$ |
| 3614. | Me | H | OCHF$_2$ | Me | CF$_3$ |
| 3615. | Me | H | CF$_3$ | Me | OCH$_2$CHF$_2$ |
| 3616. | Me | H | CF$_3$ | Me | OCH$_2$CF$_3$ |
| 3617. | Me | H | CF$_3$ | Me | SO$_2$Me |
| 3618. | Me | H | CF$_3$ | Me | SEt |
| 3619. | Me | H | CF$_3$ | Et | Cl |
| 3620. | Me | H | CF$_3$ | iPr | Cl |

TABLE 3-continued

Compounds of the formula (III-R)

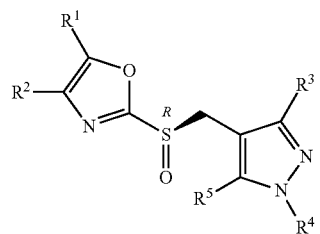

(III-R)

| Ex. No. | R¹ | R² | R³ | R⁴ | R⁵ |
|---|---|---|---|---|---|
| 3621. | Me | H | CF$_3$ | tBu | Cl |
| 3622. | Me | H | Cl | tBu | CF$_3$ |
| 3623. | Me | H | CF$_3$ | cPen | Cl |
| 3624. | Me | H | CF$_3$ | CHF$_2$ | OMe |
| 3625. | Me | H | CF$_3$ | CH$_2$CF$_3$ | Cl |
| 3626. | Me | H | CF$_3$ | Ph | OCHF$_2$ |
| 3627. | Me | H | CF$_3$ | Ph | Cl |
| 3628. | Me | H | Me | Me | OCH$_2$CF$_3$ |
| 3629. | Me | H | CF$_3$ | Me | 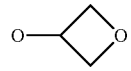 |
| 3630. | Me | H | CF$_3$ | Me | H |
| 3631. | Me | H | CF$_3$ | Me | OCH$_2$CH$_2$OMe |
| 3632. | Me | H | CF$_3$ | Me | SMe |
| 3633. | Me | H | CF$_3$ | Me | OCH$_2$CH$_2$CH$_2$F |
| 3634. | Me | H | CF$_3$ | Me | OCH(CH$_2$F)$_2$ |
| 3635. | Me | H | CF$_3$ | Me | OCH$_2$CF$_2$CHF$_2$ |
| 3636. | Me | H | CF$_3$ | Me | OCH$_2$CF=CH$_2$ |
| 3637. | Me | H | CF$_3$ | Me | OCH(Me)CF$_3$ |
| 3638. | Me | H | CF$_3$ | Me | OCH(Me)CH$_2$F |
| 3639. | Me | H | OCH$_2$CF$_3$ | Me | CF$_3$ |
| 3640. | Me | H | OCH$_2$CF$_3$ | Me | CHF$_2$ |
| 3641. | Me | H | CHF$_2$ | Me | CHF$_2$ |
| 3642. | Me | H | CF$_3$ | Me | CHF$_2$ |
| 3643. | Me | H | Cl | Me | OCHF$_2$ |
| 3644. | Me | H | Br | Me | OCHF$_2$ |
| 3645. | Me | H | Br | Me | CF$_3$ |
| 3646. | NO$_2$ | H | CF$_3$ | tBu | Cl |
| 3647. | NO$_2$ | H | CF$_3$ | CHF$_2$ | Cl |
| 3648. | NO$_2$ | H | Cl | CHF$_2$ | CF$_3$ |
| 3649. | NO$_2$ | H | CF$_3$ | Me | OMe |
| 3650. | NO$_2$ | H | CF$_3$ | Me | CN |
| 3651. | NO$_2$ | H | CHF$_2$ | Me | Cl |
| 3652. | NO$_2$ | H | Me | Me | Me |
| 3653. | NO$_2$ | H | Me | Me | Cl |
| 3654. | NO$_2$ | H | CF$_3$ | Me | Cl |
| 3655. | NO$_2$ | H | Cl | Me | CF$_3$ |
| 3656. | NO$_2$ | H | CF$_3$ | Me | F |
| 3657. | NO$_2$ | H | OMe | Me | CF$_3$ |
| 3658. | NO$_2$ | H | CF$_3$ | Me | OCHF$_2$ |
| 3659. | NO$_2$ | H | OCHF$_2$ | Me | CF$_3$ |
| 3660. | NO$_2$ | H | CF$_3$ | Me | OCH$_2$CHF$_2$ |
| 3661. | NO$_2$ | H | CF$_3$ | Me | OCH$_2$CF$_3$ |
| 3662. | NO$_2$ | H | CF$_3$ | Me | SO$_2$Me |
| 3663. | NO$_2$ | H | CF$_3$ | Me | SEt |
| 3664. | NO$_2$ | H | CF$_3$ | Et | Cl |
| 3665. | NO$_2$ | H | CF$_3$ | iPr | Cl |
| 3666. | NO$_2$ | H | CF$_3$ | tBu | Cl |
| 3667. | NO$_2$ | H | Cl | tBu | CF$_3$ |
| 3668. | NO$_2$ | H | CF$_3$ | cPen | Cl |
| 3669. | NO$_2$ | H | CF$_3$ | CHF$_2$ | OMe |
| 3670. | NO$_2$ | H | CF$_3$ | CH$_2$CF$_3$ | Cl |
| 3671. | NO$_2$ | H | CF$_3$ | Ph | OCHF$_2$ |
| 3672. | NO$_2$ | H | CF$_3$ | Ph | Cl |
| 3673. | NO$_2$ | H | Me | Me | OCH$_2$CF$_3$ |
| 3674. | NO$_2$ | H | CF$_3$ | Me | 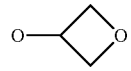 |
| 3675. | NO$_2$ | H | CF$_3$ | Me | H |
| 3676. | NO$_2$ | H | CF$_3$ | Me | OCH$_2$CH$_2$OMe |
| 3677. | NO$_2$ | H | CF$_3$ | Me | SMe |
| 3678. | NO$_2$ | H | CF$_3$ | Me | OCH$_2$CH$_2$CH$_2$F |
| 3679. | NO$_2$ | H | CF$_3$ | Me | OCH(CH$_2$F)$_2$ |
| 3680. | NO$_2$ | H | CF$_3$ | Me | OCH$_2$CF$_2$CHF$_2$ |
| 3681. | NO$_2$ | H | CF$_3$ | Me | OCH$_2$CF=CH$_2$ |
| 3682. | NO$_2$ | H | CF$_3$ | Me | OCH(Me)CF$_3$ |
| 3683. | NO$_2$ | H | CF$_3$ | Me | OCH(Me)CH$_2$F |
| 3684. | NO$_2$ | H | OCH$_2$CF$_3$ | Me | CF$_3$ |
| 3685. | NO$_2$ | H | OCH$_2$CF$_3$ | Me | CHF$_2$ |
| 3686. | NO$_2$ | H | CHF$_2$ | Me | CHF$_2$ |
| 3687. | NO$_2$ | H | CF$_3$ | Me | CHF$_2$ |
| 3688. | NO$_2$ | H | Cl | Me | OCHF$_2$ |
| 3689. | NO$_2$ | H | Br | Me | OCHF$_2$ |
| 3690. | NO$_2$ | H | Br | Me | CF$_3$ |
| 3691. | Cl | Cl | CF$_3$ | tBu | Cl |
| 3692. | Cl | Cl | CF$_3$ | CHF$_2$ | Cl |
| 3693. | Cl | Cl | Cl | CHF$_2$ | CF$_3$ |
| 3694. | Cl | Cl | CF$_3$ | Me | OMe |
| 3695. | Cl | Cl | CF$_3$ | Me | CN |
| 3696. | Cl | Cl | CHF$_2$ | Me | Cl |
| 3697. | Cl | Cl | Me | Me | Me |
| 3698. | Cl | Cl | Me | Me | Cl |
| 3699. | Cl | Cl | CF$_3$ | Me | Cl |
| 3700. | Cl | Cl | Cl | Me | CF$_3$ |
| 3701. | Cl | Cl | CF$_3$ | Me | F |
| 3702. | Cl | Cl | OMe | Me | CF$_3$ |
| 3703. | Cl | Cl | CF$_3$ | Me | OCHF$_2$ |
| 3704. | Cl | Cl | OCHF$_2$ | Me | CF$_3$ |
| 3705. | Cl | Cl | CF$_3$ | Me | OCH$_2$CHF$_2$ |
| 3706. | Cl | Cl | CF$_3$ | Me | OCH$_2$CF$_3$ |
| 3707. | Cl | Cl | CF$_3$ | Me | SO$_2$Me |
| 3708. | Cl | Cl | CF$_3$ | Me | SEt |
| 3709. | Cl | Cl | CF$_3$ | Et | Cl |
| 3710. | Cl | Cl | CF$_3$ | iPr | Cl |
| 3711. | Cl | Cl | CF$_3$ | tBu | Cl |
| 3712. | Cl | Cl | Cl | tBu | CF$_3$ |
| 3713. | Cl | Cl | CF$_3$ | cPen | Cl |
| 3714. | Cl | Cl | CF$_3$ | CHF$_2$ | OMe |
| 3715. | Cl | Cl | CF$_3$ | CH$_2$CF$_3$ | Cl |
| 3716. | Cl | Cl | CF$_3$ | Ph | OCHF$_2$ |
| 3717. | Cl | Cl | CF$_3$ | Ph | Cl |
| 3718. | Cl | Cl | Me | Me | OCH$_2$CF$_3$ |
| 3719. | Cl | Cl | CF$_3$ | Me | 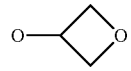 |
| 3720. | Cl | Cl | CF$_3$ | Me | H |
| 3721. | Cl | Cl | CF$_3$ | Me | OCH$_2$CH$_2$OMe |
| 3722. | Cl | Cl | CF$_3$ | Me | SMe |
| 3723. | Cl | Cl | CF$_3$ | Me | OCH$_2$CH$_2$CH$_2$F |
| 3724. | Cl | Cl | CF$_3$ | Me | OCH(CH$_2$F)$_2$ |
| 3725. | Cl | Cl | CF$_3$ | Me | OCH$_2$CF$_2$CHF$_2$ |
| 3726. | Cl | Cl | CF$_3$ | Me | OCH$_2$CF=CH$_2$ |
| 3727. | Cl | Cl | CF$_3$ | Me | OCH(Me)CF$_3$ |
| 3728. | Cl | Cl | CF$_3$ | Me | OCH(Me)CH$_2$F |
| 3729. | Cl | Cl | OCH$_2$CF$_3$ | Me | CF$_3$ |
| 3730. | Cl | Cl | OCH$_2$CF$_3$ | Me | CHF$_2$ |
| 3731. | Cl | Cl | CHF$_2$ | Me | CHF$_2$ |
| 3732. | Cl | Cl | CF$_3$ | Me | CHF$_2$ |

TABLE 3-continued

Compounds of the formula (III-R)

(III-R)

| Ex. No. | $R^1$ | $R^2$ | $R^3$ | $R^4$ | $R^5$ |
|---|---|---|---|---|---|
| 3733. | Cl | Cl | Cl | Me | $OCHF_2$ |
| 3734. | Cl | Cl | Br | Me | $OCHF_2$ |
| 3735. | Cl | Cl | Br | Me | $CF_3$ |
| 3736. | Cl | Me | $CF_3$ | tBu | Cl |
| 3737. | Cl | Me | $CF_3$ | $CHF_2$ | Cl |
| 3738. | Cl | Me | Cl | $CHF_2$ | $CF_3$ |
| 3739. | Cl | Me | $CF_3$ | Me | OMe |
| 3740. | Cl | Me | $CF_3$ | Me | CN |
| 3741. | Cl | Me | $CHF_2$ | Me | Cl |
| 3742. | Cl | Me | Me | Me | Me |
| 3743. | Cl | Me | Me | Me | Cl |
| 3744. | Cl | Me | $CF_3$ | Me | Cl |
| 3745. | Cl | Me | Cl | Me | $CF_3$ |
| 3746. | Cl | Me | $CF_3$ | Me | F |
| 3747. | Cl | Me | OMe | Me | $CF_3$ |
| 3748. | Cl | Me | $CF_3$ | Me | $OCHF_2$ |
| 3749. | Cl | Me | $OCHF_2$ | Me | $CF_3$ |
| 3750. | Cl | Me | $CF_3$ | Me | $OCH_2CHF_2$ |
| 3751. | Cl | Me | $CF_3$ | Me | $OCH_2CF_3$ |
| 3752. | Cl | Me | $CF_3$ | Me | $SO_2Me$ |
| 3753. | Cl | Me | $CF_3$ | Me | SEt |
| 3754. | Cl | Me | $CF_3$ | Et | Cl |
| 3755. | Cl | Me | $CF_3$ | iPr | Cl |
| 3756. | Cl | Me | $CF_3$ | tBu | Cl |
| 3757. | Cl | Me | Cl | tBu | $CF_3$ |
| 3758. | Cl | Me | $CF_3$ | cPen | Cl |
| 3759. | Cl | Me | $CF_3$ | $CHF_2$ | OMe |
| 3760. | Cl | Me | $CF_3$ | $CH_2CF_3$ | Cl |
| 3761. | Cl | Me | $CF_3$ | Ph | $OCHF_2$ |
| 3762. | Cl | Me | $CF_3$ | Ph | Cl |
| 3763. | Cl | Me | Me | Me | $OCH_2CF_3$ |
| 3764. | Cl | Me | $CF_3$ | Me | (oxetanyl) |
| 3765. | Cl | Me | $CF_3$ | Me | H |
| 3766. | Cl | Me | $CF_3$ | Me | $OCH_2CH_2OMe$ |
| 3767. | Cl | Me | $CF_3$ | Me | SMe |
| 3768. | Cl | Me | $CF_3$ | Me | $OCH_2CH_2CH_2F$ |
| 3769. | Cl | Me | $CF_3$ | Me | $OCH(CH_2F)_2$ |
| 3770. | Cl | Me | $CF_3$ | Me | $OCH_2CF_2CHF_2$ |
| 3771. | Cl | Me | $CF_3$ | Me | $OCH_2CF=CH_2$ |
| 3772. | Cl | Me | $CF_3$ | Me | $OCH(Me)CF_3$ |
| 3773. | Cl | Me | $CF_3$ | Me | $OCH(Me)CH_2F$ |
| 3774. | Cl | Me | $OCH_2CF_3$ | Me | $CF_3$ |
| 3775. | Cl | Me | $OCH_2CF_3$ | Me | $CHF_2$ |
| 3776. | Cl | Me | $CHF_2$ | Me | $CHF_2$ |
| 3777. | Cl | Me | $CF_3$ | Me | $CHF_2$ |
| 3778. | Cl | Me | Cl | Me | $OCHF_2$ |
| 3779. | Cl | Me | Br | Me | $OCHF_2$ |
| 3780. | Cl | Me | Br | Me | $CF_3$ |

The NMR data were measured at 400 MHz and in $CDCl_3$ as solvent. The chemical shift δ is stated in ppm (reference TMS).

Retention times ($R_t$, in minutes) and enantiomer ratios (ee) of chiral compounds were determined by analytical chiral HPLC [Chiralpak® IC column (250×4.6 mm, particle size 10 μm), temperature 25° C., flow rate 1 ml/min, n-heptane/2-propanol 80:20 v/v].

Data for Table 2:
Compound No. 2449: $R_t$=6.254 min.
Compound No. 2531: $R_t$=6.585 min.
Compound No. 2341: $R_t$=29.201 min [Chiralpak® IC column (250×4.6 mm, particle size 10 μm), temperature 25° C., flow rate 0.6 ml/min, n-heptane/2-propanol 90:10 v/v].
Compound No. 2288: $R_t$=6.912 min.

Data for Table 3:
Compound No. 3205: $R_t$=7.873 min.
Compound No. 3287: $R_t$=8.217 min.
Compound No. 3097: $R_t$=32.132 min [Chiralpak® IC column (250×4.6 mm, particle size 10 μm), temperature 25° C., flow rate 0.6 ml/min, n-heptane/2-propanol 90:10 v/v].
Compound No. 3044: $R_t$=13.384 min.

B. Formulation Examples a) A dust is obtained by mixing 10 parts by weight of a compound of the formula (I) and/or a salt thereof and 90 parts by weight of talc as inert substance and comminuting the mixture in a hammer mill.

b) A wettable powder which is readily dispersible in water is obtained by mixing 25 parts by weight of a compound of the formula (I) and/or a salt thereof, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A readily water-dispersible dispersion concentrate is obtained by mixing 20 parts by weight of a compound of the formula (I) and/or a salt thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I) and/or a salt thereof, 75 parts by weight of cyclohexanone as solvent and 10 parts by weight of oxethylated nonylphenol as emulsifier.

e) Water-dispersible granules are obtained by mixing
75 parts by weight of a compound of the formula (I) and/or a salt thereof,
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill, and granulating the powder in a fluidized bed by spraying on water as granulating liquid.

f) Water-dispersible granules are also obtained by homogenizing and precomminuting, in a colloid mill,
25 parts by weight of a compound of the formula (I) and/or a salt thereof,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture in a bead mill and atomizing and drying the resulting suspension in a spray tower by means of a single-substance nozzle.

C. Biological Examples

The compounds of the formula (I) according to the invention (and/or their salts), hereinbelow also referred to together as "compounds according to the invention", have excellent herbicidal efficacy against a broad spectrum of economically important monocotyledonous and dicotyledonous annual harmful plants. The active compounds act efficiently even on perennial harmful plants which produce shoots from rhizomes, root stocks and other perennial organs and which are difficult to control.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-sowing (if appropriate also by incorporation into the soil), pre-emergence or post-emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum*, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant's metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and plant-growth-regulatory properties, the active compounds can also be employed for controlling harmful plants in crops of genetically modified plants or plants modified by conventional mutagenesis. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition.

With regard to transgenic crops, it is preferred to use the compounds according to the invention in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetable varieties.

It is preferred to employ the compounds according to the invention as herbicides in crops of useful plants which are resistant, or have been made resistant by recombinant means, to the phytotoxic effects of the herbicides.

1. Pre-Emergence Herbicidal Effect and Crop Plant Compatibility

Seeds of monocotyledonous or dicotyledonous weed plants or crop plants are placed in sandy loam in wood-fiber pots and covered with soil. The compounds according to the invention, formulated in the form of wettable powders (WP), are then applied as aqueous suspension at a water application rate of 600 l/ha (converted) with the addition of 0.2% of wetting agent to the surface of the covering soil.

After the treatment, the pots are placed in a greenhouse and kept under good growth conditions for the test plants. After about 3 weeks, the effect of the preparations is scored visually in comparison with untreated controls (herbicidal effect in percent (%): 100% activity=the plants have died, 0% activity=like control plants).

As shown by the results, the compounds according to the invention have good herbicidal pre-emergence activity against a broad spectrum of weed grasses and broad-leaved weeds. The compounds Nos. 35, 50, 51, 230, 542, 788, 789, 1034, 2285, 2449, 2531 and other compounds from Tables 1-3, for example, have very good herbicidal activity against harmful plants such as, for example, *Avena fatua, Stellaria media, Echinochloa crus galli, Lolium multiflorum, Setaria viridis, Amaranthus retroflexus, Veronica persica, Matricaria inodora, Fallopia convolvulus* and *Alopecurus myosuroides* when applied by the pre-emergence method at an application rate of 0.32 kg and less of active substance per hectare.

In addition, compounds according to the invention applied by the pre-emergence method also spare dicotyledonous crops such as oilseed rape even at high active compound application rates. Some substances also spare gramineous crops such as corn. Some of the compounds according to the invention have high selectivity and are therefore suitable for controlling unwanted vegetation in agricultural crops by the pre-emergence method.

2. Post-Emergence Herbicidal Effect and Crop Plant Compatibility

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The compounds according to the invention, formulated in the form of wettable powders (WP), are then sprayed as aqueous suspension at a water application rate of 600 l/ha (converted) with the addition of 0.2% of wetting agent onto the green parts of the plants. After the test plants have been kept in the greenhouse under optimum growth conditions for about 3 weeks, the activity of the preparations is rated visually in comparison to untreated controls (herbicidal activity in percent (%): 100% activity=the plants have died, 0% activity=like control plants).

As shown by the results, the compounds according to the invention have good herbicidal post-emergence activity against a plurality of weed grasses and broad-leaved weeds. The compounds Nos. 35, 50, 51, 542, 230, 2285 and other compounds from Tables 1-3, for example, have very good herbicidal activity against harmful plants such as, for example, *Echinochloa crus galli, Lolium multiflorum*, and *Setaria viridis* when applied by the post-emergence method at an application rate of 0.32 kg and less of active substance per hectare.

In addition, compounds according to the invention applied by the pre-emergence method also spare dicotyledonous crops such as oilseed rape even at high active compound application rates. Some substances also spare gramineous crops such as corn. Some of the compounds according to the invention have high selectivity and are therefore suitable for controlling unwanted vegetation in agricultural crops by the post-emergence method.

The invention claimed is:

1. A compound of the formula (I) or an agrochemically acceptable salt thereof

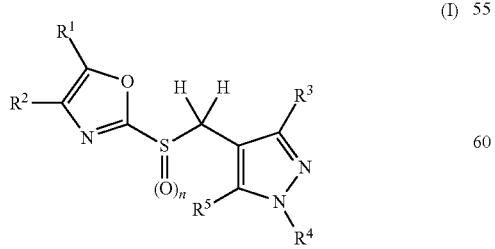

(I)

in which the radicals and indices have the following meaning:
is 0, 1, 2;

the substituents $R^1$ and $R^2$ are each independently of one another selected from the group consisting of
hydrogen, halogen, nitro, cyano, formyl, —C(O)OH, hydroxyl, and amino;
$(C_1-C_6)$-alkyl, $(C_1-C_6)$-alkylcarbonyl, $(C_1-C_6)$-alkylcarbonyl-$(C_1-C_4)$-alkyl and $(C_1-C_6)$-alkylcarbonyloxy;
$(C_1-C_6)$-alkoxy, $(C_1-C_6)$-alkoxy-carbonyl, $(C_1-C_6)$-alkoxycarbonyl-$(C_1-C_6)$-alkyl, $(C_1-C_6)$-alkoxy-$(C_1-C_6)$-alkyl, $(C_1-C_6)$-alkoxy-$(C_1-C_6)$-alkoxy and $(C_1-C_6)$-alkoxycarbonyl-$(C_1-C_6)$-alkoxy;
$(C_2-C_6)$-alkenyl, $(C_2-C_6)$-alkenyloxy, $(C_2-C_6)$-alkynyl and $(C_2-C_6)$-alkynyloxy;
$(C_1-C_6)$-alkylthio, $(C_1-C_6)$-alkylsulfinyl, $(C_1-C_6)$-alkylsulfonyl, $(C_1-C_6)$-alkylsulfonyloxy, $(C_1-C_6)$-alkylsulfonyl-$(C_1-C_6)$-alkyl, $(C_1-C_6)$-alkylsulfinyl-$(C_1-C_6)$-alkyl, $(C_1-C_6)$-alkylthio-$(C_1-C_6)$-alkyl and $(C_1-C_6)$-alkylthio-$(C_1-C_6)$-alkoxy;
mono-$((C_1-C_6)$-alkyl)amino, di-$((C_1-C_6)$-alkyl)amino, N—$((C_1-C_6)$-alkanoyl)amino, aminocarbonyl-$(C_1-C_6)$-alkyl, mono-$((C_1-C_6)$-alkyl)aminocarbonyl, di -$((C_1-C_6)$-alkyl)aminocarbonyl, mono-$((C_1-C_6)$-alkyl)aminosulfonyl and di-$((C_1-C_6)$-alkyl)aminosulfonyl;
$(C_3-C_8)$-cycloalkyl, $(C_3-C_8)$-cycloalkoxy, $(C_3-C_8)$-cycloalkyl-$(C_1-C_6)$-alkyl, $(C_3-C_8)$-cycloalkyl-$(C_1-C_6)$-alkoxy, $(C_3-C_8)$-cycloalkylcarbonyl and $(C_3-C_8)$-cycloalkoxycarbonyl;
$(C_3-C_8)$-cycloalkenyl, $(C_3-C_8)$-cycloalkenyloxy, $(C_3-C_8)$-cycloalkylthio, $(C_3-C_8)$-cycloalkylsulfinyl, $(C_3-C_8)$-cycloalkylsulfonyl and $(C_3-C_8)$-cycloalkylsulfonyloxy;
cyano-$(C_1-C_6)$-alkoxy and cyano-$(C_1-C_6)$-alkyl;
—CONH—SO$_2$—$(C_1-C_6)$-alkyl, —NHCHO, —NHCO—$(C_1-C_6)$-alkyl, —NHCO$_2$—$(C_1-C_6)$-alkyl, —NHCONH—$(C_1-C_6)$-alkyl, —NHSO$_2$—$(C_1-C_6)$-alkyl, —OCONH—$(C_1-C_6)$-alkyl, $(C_1-C_6)$-alkylaminosulfonyl-$(C_1-C_2)$-alkyl, di-$(C_1-C_6)$-alkylaminosulfonyl-$(C_1-C_2)$-alkyl,
—C(O)NHR$^9$, —C(O)NR$^9$R$^{10}$,
where R$^9$ and R$^{10}$ are each independently of one another selected from the group consisting of hydrogen, $(C_1-C_6)$-alkyl, $(C_3-C_6)$-cycloalkyl, $(C_1-C_6)$-haloalkyl, or
where R$^9$ and R$^{10}$ together form a $(C_1-C_6)$-alkylene group which may contain an oxygen or a sulfur atom or one or two amino or $(C_1-C_6)$-alkylamino groups,
the substituents R$^3$ to R$^5$ are each independently of one another selected from the group consisting of
hydrogen, halogen, hydroxyl, cyano, nitro, amino, C(O)OH and formyl;
$(C_1-C_6)$-alkyl, $(C_1-C_6)$-haloalkyl, $(C_1-C_6)$-alkylcarbonyl, $(C_1-C_6)$-haloalkylcarbonyl, $(C_1-C_6)$-alkylcarbonyloxy, $(C_1-C_6)$-haloalkylcarbonyloxy, $(C_1-C_6)$-alkylcarbonyl-$(C_1-C_4)$-alkyl, $(C_1-C_6)$-haloalkylcarbonyl-$(C_1-C_4)$-alkyl, $(C_1-C_6)$-alkylcarbonyl-$(C_1-C_4)$-haloalkyl and $(C_1-C_6)$-haloalkylcarbonyl-$(C_1-C_4)$-haloalkyl;
$(C_1-C_6)$-alkoxy, $(C_1-C_6)$-haloalkoxy, $(C_1-C_6)$-alkoxycarbonyl, $(C_1-C_6)$-haloalkoxycarbonyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl and $(C_1-C_6)$-haloalkoxycarbonyl-$(C_1-C_6)$-haloalkyl;
$(C_2-C_6)$-alkenyl, $(C_2-C_6)$-haloalkenyl, $(C_2-C_6)$-alkenylcarbonyl, $(C_2-C_6)$-haloalkenylcarbonyl, $(C_2-C_6)$-alkenyloxy, $(C_2-C_6)$-haloalkenyloxy, $(C_2-C_6)$-alkenyloxycarbonyl and $(C_2-C_6)$-haloalkenyloxycarbonyl;

$(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl and $(C_2-C_6)$-haloalkynyloxycarbonyl;

$(C_1-C_6)$-alkylthiocarbonyl, $(C_1-C_6)$-haloalkylthiocarbonyl, $(C_1-C_6)$-alkylthiocarbonyloxy and $(C_1-C_6)$-halo-al-kyl-thio-carbonyloxy;

$(C_1-C_6)$-alkylthio-$(C_1-C_6)$-alkoxy, $(C_1-C_6)$-alkylthio-$(C_1-C_6)$-alkylcarbonyl and $(C_1-C_6)$-alkylthio-$(C_1-C_6)$-alkylcarbonyloxy;

$(C_6-C_{14})$-aryl, $(C_6-C_{14})$-aryloxy, $(C_6-C_{14})$-arylcarbonyl, $(C_6-C_{14})$-aryloxycarbonyl, $(C_6-C_{14})$-aryl-$(C_1-C_6)$-alkyl, $(C_6-C_{14})$-aryl-$(C_1-C_6)$-alkoxy, $(C_6-C_{14})$-aryloxy-$(C_1-C_6)$-alkyl, $(C_6-C_{14})$-aryl-$(C_1-C_6)$-alkylcarbonyl, $(C_6-C_{14})$-aryl-$(C_1-C_6)$-alkylcarbonyloxy, $(C_6-C_{14})$-aryl-$(C_1-C_6)$-alkoxycarbonyl, $(C_6-C_{14})$-aryl-$(C_1-C_6)$-alkoxycarbonyloxy, $(C_1-C_6)$-alkylsulfonyl, $(C_1-C_6)$-alkylthio, $(C_1-C_6)$-alkylsulfinyl, $(C_1-C_6)$-haloalkylsulfonyl, $(C_1-C_6)$-haloalkylthio, $(C_1-C_6)$-halo-alkylsulfinyl, $(C_1-C_6)$-alkylsulfonyl-$(C_1-C_6)$-alkyl, $(C_1-C_6)$-alkyl-thio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, $(C_1-C_6)$-haloalkylsulfinyl-$(C_1-C_6)$-haloalkyl, $(C_1-C_6)$-alkylsulfonyloxy, $(C_1-C_6)$-haloalkylsulfonyloxy, $(C_6-C_{14})$-arylthio, $(C_6-C_{14})$-arylsulfinyl, mono-$((C_1-C_6)$-alkyl)amino, mono-$((C_1-C_6)$-haloalkyl)amino, di-$((C_1-C_6)$-alkyl)amino, di-$((C_1-C_6)$-haloalkyl)amino, $((C_1-C_6)$-alkyl-$(C_1-C_6)$-haloalkyl) amino, N—$((C_1-C_6)$-atkanoyl)arnino, N—$((C_1-C_6)$-haloalkanoyl)amino, aminocarbonyl-$(C_1-C_6)$-alkyl, mono-$(C_1-C_6)$-alkylaminocarbonyl-$(C_1-C_6)$-alkyl, di-$(C_1-C_6)$-alkylaminocarbonyl-$(C_1-C_6)$-alkyl and mono-$((C_1-C_6)$-alkyl)aminocarbonyl;

$(C_1-C_6)$-alkoxy -$(C_1-C_6)$-alkyl, $(C_1-C_6)$-alkoxy-$(C_1-C_6)$-alkoxy, $(C_1-C_6)$-alkoxycarbonyl-$(C_1-C_6)$-alkoxy, $(C_3-C_8)$-cycloalkyl, $(C_3-C_8)$-cycloalkoxy, $(C_3-C_8)$-cycloalkyl-$(C_1-C_6)$-alkyl, $(C_3-C_8)$-cycloalkyl-$(C_1-C_6)$-haloalkyl, $(C_3-C_8)$-cycloalkyl-$(C_1-C_6)$-alkoxy, $(C_3-C_8)$-cycloalkyl-$(C_1-C_6)$-haloalkoxy, $(C_3-C_8)$-cycloalkylcarbonyl, $(C_3-C_8)$-cycloalkoxycarbonyl, $(C_3-C_8)$-cycloalkyl-$(C_1-C_6)$-alkylcarbonyl, $(C_3-C_8)$-cycloalkyl-$(C_1-C_6)$-haloalkylcarbonyl, $(C_3-C_8)$-cycloalkyl-$(C_1-C_6)$-alkoxycarbonyl, $(C_3-C_8)$-cycloalkyl-$(C_1-C_6)$-haloalkoxycarbonyl, $(C_3-C_8)$-cycloalkylcarbonyloxy, $(C_3-C_8)$-cycloalkoxycarbonyloxy, $(C_3-C_8)$-cycloalkyl-$(C_1-C_6)$-alkylcarbonyloxy, $(C_3-C_8)$-cycloalkyl-$(C_1-C_6)$-haloalkylcarbonyloxy, $(C_3-C_8)$-cycloalkyl-$(C_1-C_6)$-alkoxycarbonyloxy and $(C_3-C_8)$-cycloalkyl-$(C_1-C_6)$-haloalkoxycarbonyloxy;

$(C_3-C_8)$-cycloalkenyl, $(C_3-C_8)$-cycloalkenyloxy, $(C_3-C_8)$-cycloalkenyl-$(C_1-C_6)$-alkoxy, $(C_3-C_8)$-cycloalkenyl-$(C_1-C_6)$-haloalkyl, $(C_3-C_8)$-cycloalkenyl-$(C_1-C_6)$-alkoxy, $(C_3-C_8)$-cycloalkenyl-$(C_1-C_6)$-haloalkoxy, $(C_3-C_8)$-cycloalkenylcarbonyl, $(C_3-C_8)$-cyclo-al-kenyloxycarbonyl, $(C_3-C_8)$-cycloalkenyl-$(C_1-C_6)$-alkylcarbonyl, $(C_3-C_8)$-cycloalkenyl-$(C_1-C_6)$-haloalkylcarbonyl, $(C_3-C_8)$-cycloalkenyl-$(C_1-C_6)$-alkoxycarbonyl, $(C_3-C_8)$-cycloalkenyl-$(C_1-C_6)$-haloalkoxycarbonyl, $(C_3-C_8)$-cycloalkenylcarbonyloxy, $(C_3-C_8)$-cycloalkenyloxycarbonyloxy, $(C_3-C_8)$-cycloalkenyl-$(C_1-C_6)$-alkylcarbonyloxy, $(C_3-C_8)$-cycloalkenyl-$(C_1-C_6)$-haloalkylcarbonyloxy, $(C_3-C_8)$-cycloalkenyl-$(C_1-C_6)$-alkoxycarbonyloxy and $(C_3-C_8)$-cycloalkenyl-$(C_1-C_6)$-haloalkoxycarbonyloxy;

$(C_3-C_8)$-cycloalkylthio, $(C_3-C_8)$-alkenylthio, $(C_3-C_8)$-cyclo-alkenylthio and $(C_3-C_6)$-alkynylthio;

hydroxy-$(C_1-C_6)$-alkyl, hydroxy-$(C_1-C_6)$-alkoxy, cyano-$(C_1-C_6)$-alkoxy and cyano-$(C_1-C_6)$-alkyl;

3-oxetanyloxy-,

—C(O)NR$^9$R$^{10}$, where R$^9$ and R$^{10}$ are each independently of one another selected from the group consisting of hydrogen, $(C_1-C_6)$-alkyl, $(C_3-C_6)$-cycloalkyl, $(C_1-C_6)$-haloalkyl, or where R$^9$ and R$^{10}$ together form a $(C_1-C_6)$-alkylene group which may contain an oxygen or a sulfur atom or one or two amino or $(C_1-C_6)$-alkylamino groups, where the radicals R$^3$ to R$^5$ mentioned above may be mono- or polysubstituted independently of one another, and/or mutually adjacent radicals R$^4$ and R$^5$ may be cyclically attached to one another and/or form a $(C_1-C_6)$-alkylene group which may contain one or more oxygen and/or sulfur atoms, where the $(C_1-C_6)$-alkylene group may be mono- or polysubstituted by halogen and the respective halogen substituents may be identical or different.

2. A compound as claimed in claim 1, wherein R$^1$ is selected from the group consisting of H, halogen, nitro, cyano, carboxyl, $(C_1-C_6)$-alkyl, $(C_3-C_6)$-cycloalkyl, $(C_3-C_6)$-cycloalkoxy, $(C_1-C_6)$-alkoxy, $(C_1-C_6)$-alkylearbonyl, $(C_3-C_6)$-cycloalkylcarbonyl, $(C_1-C_6)$-alkoxycarbonyl, $(C_3-C_6)$-cycloalkoxycarbonyl, mono-$((C_1-C_4)$-alkyl)aminocarbonyl, di-$((C_1-C_4)$-alkyl)aminocarbonyl, mono-$((C_1-C_4)$-alkyl)aminosulfonyl, di-$((C_1-C_4)$-alkyl)aminosulfonyl, $(C_1-C_4)$-alkylthio, $(C_3-C_6)$-cycloalkylthio, $(C_1-C_4)$-alkylsulfinyl, $(C_3-C_6)$-cycloalkylsulfinyl, $(C_1-C_4)$- alkylsulfonyl, $(C_3-C_6)$-cycloalkylsulfonyl, $(C_1-C_4)$-alkylsulfonyloxy, $(C_3-C_6)$-cycloalkylsulfonyloxy, $(C_2-C_3)$-alkenyl, $(C_2-C_3)$-alkynyl, $(C_2-C_3)$-alkenyloxy, $(C_2-C_3)$-alkynyloxy, —NHCO—$(C_1-C_3)$-alkyl, —NHCO$_2$—$(C_1-C_3)$-alkyl, —NHCONH—$(C_1-C_3)$-alkyl, —NHSO$_2$—$(C_1-C_3)$-alkyl, —OCONH—$(C_1-C_3)$-alkyl, —CONHR$^9$, —CONR$^9$R$^{10}$, where R$^9$ and R$^{10}$ independently ndependently of one another selected from the group consisting of hydrogen, $(C_1-C_6)$-alkyl, $(C_3-C_6)$-cycloalkyl and $(C_1-C_6)$-haloalkyl, where the radical R$^1$ mentioned above may be mono- or polysubstituted independently of one another by radicals selected from the group consisting of halogen and $(C_1-C_6)$-alkyl.

3. A compound as claimed in claim 1, wherein R$^2$ is selected from the group consisting of H, halogen, nitro, cyano, carboxyl, $(C_1-C_6)$-alkyl, $(C_3-C_6)$-cycloalkyl, $(C_3-C_6)$-cycloalkoxy, $(C_1-C_6)$-alkoxy, $(C_1-C_6)$-alkylcarbonyl, $(C_3-C_6)$-cycloalkylcarbonyl, $(C_1-C_6)$-alkoxycarbonyl, $(C_3-C_6)$-cycloalkoxycarbonyl, mono-$((C_1-C_4)$-alkyl)aminocarbonyl, di-$((C_1-C_4)$-alkyeaminocarbonyl, mono-$((C_1-C_4)$-alkyl)aminosulfonyl, di-$((C_1-C_4)$-alkyeaminosulfonyl, $(C_1-C_4)$-alkylthio, $(C_3-C_6)$-cycloalkylthio, $(C_1-C_4)$-alkylsulfinyl, $(C_3-C_6)$-cycloalkylsulfinyl, $(C_1-C_4)$-alkylsulfonyl, $(C_3-C_6)$-cycloalkyl-sul-fo-nyl, $(C_1-C_4)$-alkylsulfonyloxy, $(C_3-C_6)$- cycloalkylsulfonyloxy, $(C_2-C_3)$-alkenyl, $(C_2-C_3)$-alkynyl, $(C_2-C_3)$-alkenyloxy, $(C_2-C_3)$-alkynyloxy, —NHCO—$(C_1-C_3)$-alkyl, —NHCO$_2$—$(C_1-C_3)$-alkyl, —NHCONH—$(C_1-C_3)$-alkyl, —NHSO$_2$—$(C_1-C_3)$-alkyl, —OCONH—$(C_1-C_3)$-alkyl, —CONHR$^9$, —CONR$^9$R$^{10}$, where R$^9$ and R$^{10}$ independently ndependently of one another selected from the group consisting of hydrogen, $(C_1-C_6)$-alkyl, $(C_3-C_6)$-cycloalkyl and $(C_1-C_6)$-haloalkyl, where the radical R$^1$ mentioned above may be mono- or polysubstituted independently of one another by radicals selected from the group consisting of halogen and $(C_1-C_6)$-alkyl.

4. A compound as claimed in claim 1, wherein R$^3$ is selected from the group consisting of hydrogen, halogen, hydroxyl, cyano, nitro, amino, $(C_1-C_4)$-alkyl, $(C_3-C_6)$-cycloalkyl, $(C_1-C_4)$-haloalkyl, $(C_1-C_4)$-alkoxy, $(C_1-C_4)$-alkoxy-$(C_1-C_2)$-alkyl, $(C_3-C_6)$-cycloalkoxy, $(C_1-C_4)$-haloalkoxy, $(C_1-C_4)$-haloalkylthio, $(C_1-C_4)$-alkylthio-$(C_1-C_2)$-alkyl, $(C_1-C_4)$-alkylsulfinyl, $(C_1-C_4)$-alkylsulfinyl-$(C_1-C_2)$-alkyl, $(C_1-C_4)$-alkylsulfonyl, $(C_1-C_4)$-alkylsulfonyl-$(C_1-C_2)$-alkyl, di-$(C_1-C_4)$-alkylamino, $(C_2-C_4)$-alkenyl, $(C_2-C_4)$-alkynyl, $(C_3-C_4)$-alkenyloxy, $(C_3-C_4)$-alkynyloxy, $(C_3-C_6)$-cycloalkyl-$(C_1-C_2)$-alkoxy, hydroxyl-$(C_1-C_2)$-alkyl, hydroxyl-$(C_1-C_2)$-alkoxy, cyano-$(C_1-C_2)$-alkoxy, cyano-$(C_1-C_2)$-alkyl, phenyl, phenyl-$(C_1-C_2)$-alkyl, phenyl-$(C_1-C_2)$-alkoxy, phenoxy, $(C_1-C_4)$-alkylcarbonyloxy, $(C_3-C_6)$-cycloalkyl-$(C_1-C_2)$-alkyl, $(C_1-C_4)$-alkylcarbonyl-$(C_1-C_2)$-alkyl, $(C_1-C_4)$-alkoxycarbonyl-$(C_1-C_2)$-alkyl, aminocarbonyl-$(C_1-C_2)$-alkyl and 3-oxetanyloxy, —C(O)NR$^9$R$^{10}$, where R$^9$ and R$^{10}$ are independently of one another selected from the group consisting of hydrogen, $(C_1-C_6)$-alkyl, $(C_3-C_6)$-cycloalkyl, $(C_1-C_6)$-haloalkyl, or where R$^9$ and R$^{10}$ together form a $(C^1-C^6)$-alkylene group which may contain an oxygen or sulfur atom or one or two amino or $(C_1-C_6)$-alkylamino groups.

5. A compound as claimed in claim 1, wherein R$^4$ is selected from the group consisting of hydrogen, $(C_1-C_4)$-alkyl, $(C_1-C_4)$-haloalkyl, phenyl, phenyl-$(C_1-C_2)$-alkyl, $(C_3-C_6)$-cycloalkyl, $(C_3-C_6)$-cycloalkyl-$(C_1-C_2)$-alkyl, where the cycloalkyl radical is optionally substituted by $(C_1-C_4)$-alkyl, $(C_2-C_4)$-alkenyl, $(C_2-C_4)$-alkynyl, $(C_1-C_4)$-alkoxy-$(C_1-C_2)$-alkyl, $(C_1-C_4)$-alkylthio-$(C_1-C_2)$-alkyl, $(C_1-C_4)$-alkylsulfinyl-$(C_1-C_2)$-alkyl, cyano-$(C_1-C_2)$-alkyl, $(C_1-C_4)$-alkylsulfonyl-$(C_1-C_2)$-alkyl, $(C_1-C_4)$-alkoxycarbonyl-$(C_1-C_2)$-alkyl, aminocarbonyl-$(C_1-C_2)$-alkyl, mono-$(C_1-C_4)$-alkylaminocarbonyl-$C_1-C_2)$-alkyl, di-$(C_1-C_4)$-alkylaminocarbonyl-$(C_1-C_2)$-alkyl, hydroxyl-$(C_1-C_4)$-alkyl, $(C_1-C_4)$-alkylcarbonyl-$(C_1-C_4)$-alkyl, $(C_1-C_4)$-alkylsulfonyl;

phenylsulfonyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio;

$(C_1-C_4)$-alkylcarbonyl;

phenylcarbonyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; and $(C_1-C_4)$-alkoxycarbonyl.

6. A compound as claimed in claim 1, wherein R$^5$ is selected from the group consisting of hydrogen, hydroxyl, halogen, cyano, nitro, amino, $(C_1-C_4)$-alkyl, $(C_1-C_4)$-haloalkyl, $(C_3-C_6)$-cycloalkyl, $(C_1-C_4)$-alkoxy, $(C_1-C_4)$-alkoxy-$(C_1-C_4)$-alkoxy, $(C_1-C_4)$-alkoxy-$(C_1-C_2)$-alkyl, $(C_3-C_6)$-cycloalkoxy, $(C_1-C_4)$-haloalkoxy, $(C_1-C_4)$-alkylthio, $(C_1-C_4)$-alkylthio-$(C_1-C_2)$-alkyl, $(C_1-C_4)$-alkylsulfinyl, $(C_1-C_4)$-alkylsulfinyl-$(C_1-C_2)$-alkyl, $(C_1-C_4)$-alkylsulfonyl, $(C_1-C_4)$-alkylsulfonyl-$(C_1-C_2)$-alkyl, di-$(C_1-C_4)$-alkylamino, $(C_2-C_4)$-alkenyl, $(C_2-C_4)$-haloalkenyl, cyano-$(C_1-C_4)$-alkyl, $(C_2-C_4)$-alkynyl, $(C_3-C_4)$-alkenyloxy, $(C_3-C_4)$-alkynyloxy, $(C_3-C_6)$-cycloalkyl-$(C_1-C_2)$-alkoxt, hydroxyl-$(C_1-C_2)$-alkyl, hydroxyl-$(C_1-C_2)$-alkoxy, cyano-$(C_1-C_2)$-alkoxy, cyano-$(C_1-C_2)$-alkyl;

phenyl which is optionally substituted by one or more identical of different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio;

phenyl-$(C_1-C_2)$-alkyl which is optionally substituted by one or more identical of different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio;

phenoxy which is optionally substituted by one or more identical of different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio;

$(C_1-C_4)$-alkylcarbonyloxy, $(C_3-C_6)$-cycloalkyl-$(C_1-C_2)$-alkyl, $(C_1-C_4)$-alkylcarbonyloxy-$(C_1-C_2)$-alkyl, $(C_1-C_4)$-alkylcarbonyl-$(C_1-C_2)$-alkyl, aminocarbonyl-$(C_1-C_2)$-alkyl and 3-oxetanyloxy-, —C(O)NR$^9$R$^{10}$, where R$^9$ and R$^{10}$ are independently of one another are selected from the group consisting of hydrogen, $(C_1-C_6)$-alkyl, $(C_3-C_6)$-cycloalkyl, $(C_1-C_6)$-haloalkyl, or where R$^9$ and R$^{10}$ together form a $(C_1-C_6)$-alkylene group which may contain an oxygen or sulfur atom or one or two amino or $(C_1-C_6)$-alkylamino groups.

7. A compound as claimed in claim 1, wherein n is 1.

8. A compound as claimed in claim 7, wherein the compound of the formula (I) where n=1 is present in the (R) or (S) configuration in a stereochemical purity of more than 50% to 100%.

9. A process for preparing a compound of the formula (III) or a compound of the formula (IV), wherein R$^1$, R$^2$, R$^3$, R$^4$, R$^5$ have the meanings given in claim 1

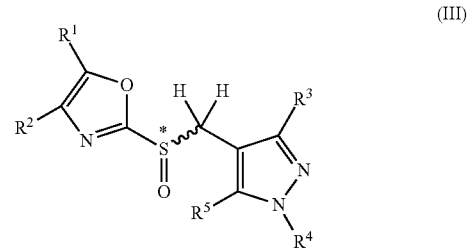

(III)

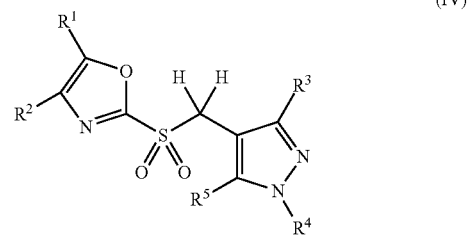

(IV)

by oxidation of a thioether of the formula (II) by means of an oxidizing agent,

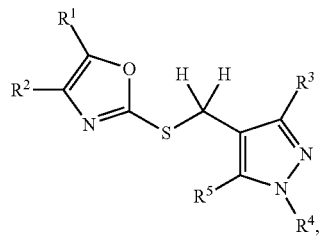
(II)

wherein $R^1, R^2, R^3, R^4, R^5$ have the meanings given in claim 1, wherein one equivalent of the oxidizing agent gives the sulfoxides of the formula (III) and two equivalents of an oxidizing agent gives the sulfones of formula (IV).

10. A process for preparing a thioether of the formula (II)

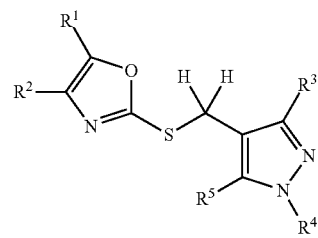
(II)

in which $R^1, R^2, R^3, R^4, R^5$ have the meanings given in claim 1, according to one of the processes below:

(a) reaction of 2-mercaptooxazole or an oxazole-2(3H)-thione or a salt thereof

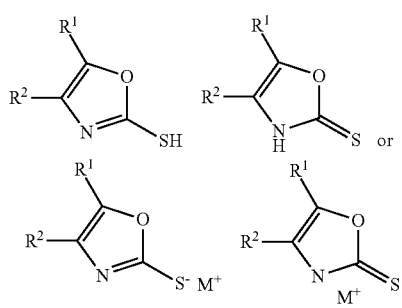
(V)

M = alkali metal, alkaline earth metal in which $R^1, R^2$ have the meanings given in claim 1, with a (1H-pyrazol-4-ylmethyl) derivative of the formula (VI)

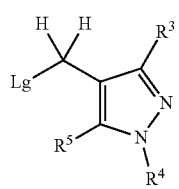
(VI)

in which $R^3, R^4, R^5$ have the meanings given claim 1 and Lg is a leaving group, in the presence of an alkali metal or alkaline earth metal base or an organic base in a solvent;

(b) reaction of an oxazole derivative of the formula (VII),

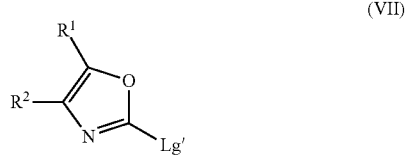
(VII)

in which $R^1, R^2$ have the meanings given in claim 1 and Lg' is a leaving group with a [(1H-pyrazol-4-ylmethyl)] imidothiocarbamate salt of the formula (VIII)

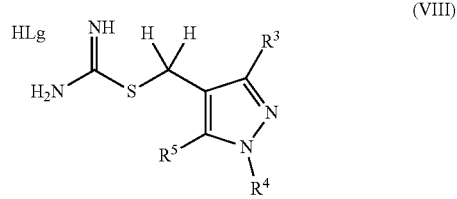
(VIII)

in which $R^3, R^4, R^5$ have the meaning given in claim 1, Lg is a leaving group, in a one-pot process in the presence of an aqueous alkali metal or alkaline earth metal base or an alkali metal or alkaline earth metal carbonate base and a solvent;

(c) reaction of an oxazole derivative of the formula (VII),

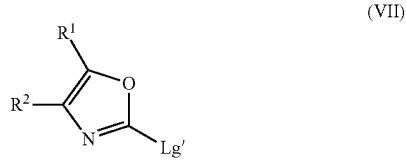
(VII)

in which $R^1, R^2$ have the meanings given in claim 1 and Lg' is a leaving group with a (1H-pyrazol-4-ylmethyl) mercaptan of the formula (IX)

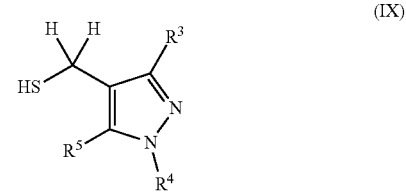
(IX)

in which $R^3, R^4, R^5$ have the meanings given in claim 1 in the presence of an alkali metal or alkaline earth metal base;

(d) reaction of an oxazole derivative of the formula (X),

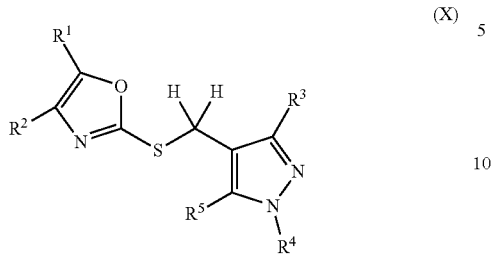

in which $R^2$, $R^3$, $R^4$, $R^5$ have the meanings given in claim 1 and $R^1$ is a halogen or $NO_2$ according to the formula scheme below:

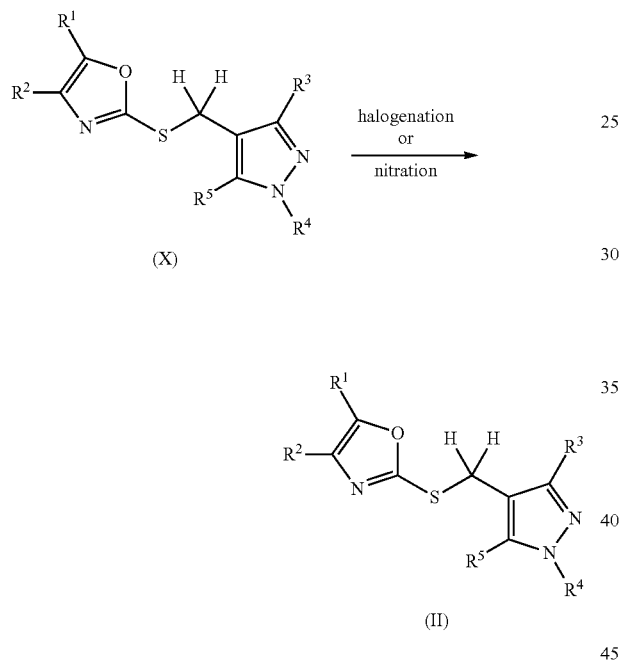

(e) reaction of a (1H-pyrazol-4-ylmethyl) disulfide derivative of the formula (XV) with 2-amino-oxazoles of the formula (XIV) and a diazotizing agent as shown in the scheme below,

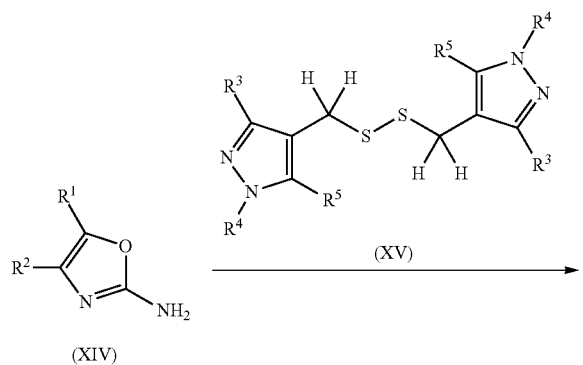

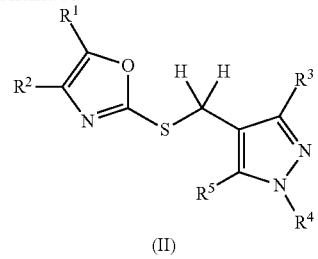

and in which $R^1$, $R^2$, $R^3$, $R^4$, $R^5$ have the meanings given in claim 1.

11. The process as claimed in claim 9 wherein the compound of the formula (II) obtained by the process as claimed in claim 10 is used as starting material in the process as claimed in claim 9.

12. A composition comprising at least one compound of the formula (I) according to claim 1.

13. The composition as claimed in claim 12 wherein the composition comprises at least one further active compound selected from the group consisting of at least one further herbicide and at least one safener.

14. A method of regulating plant growth which comprises administering an effective amount of the compound of formula (I) according to claim 1.

15. The method of claim 14 wherein the regulation of plant growth occurs within a specific crop plant.

16. The compound of claim 2, wherein
$R^2$ is selected from the group consisting of H, halogen, nitro, cyano, carboxyl, $(C_1-C_6)$-alkyl, $(C_3-C_6)$-cycloalkyl, $(C_3-C_6)$-cycloalkoxy, $(C_1-C_6)$-alkoxy, $(C_1-C_6)$-alkylcarbonyl, $(C_3-C_6)$-cycloalkylcarbonyl, $(C_1-C_6)$-alkoxycarbonyl, $(C_3-C_6)$-cycloalkoxycarbonyl, mono-$((C_1-C_4)$-alkyl)aminocarbonyl, di-$((C_1-C_4)$-alkyl)aminocarbonyl, mono-$((C_1-C_4)$-alkyl)aminosulfonyl, di- $((C_1-C_4)$-alkyeaminosulfonyl, $(C_1-C_4)$-alkylthio, $(C_3-C_6)$-cycloalkylthio, $(C_1-C_4)$-alkylsulfinyl, $(C_3-C_6)$-cycloalkylsulfinyl, $(C_1-C_4)$-alkylsulfonyl, $(C_3-C_6)$-cyclo-alkyl-sul-fo-nyl, $(C_1-C_4)$-alkylsulfonyloxy, $(C_3-C_6)$-cycloalkylsulfonyloxy, $(C_2-C_3)$-alkenyl, $(C_2-C_3)$-alkynyl, $(C_2-C_3)$-alkenyloxy, $(C_2-C_3)$-alkynyloxy, —NHCO—$(C_1-C_3)$-alkyl, —NHCO$_2$—$(C_1-C_3)$-alkyl, —NHCONH—$(C_1-C_3)$-alkyl, —NHSO$_2$—$(C_1-C_3)$-alkyl, —OCONH—$(C_1-C_3)$-alkyl, —CONHR$^9$, —CONR$^9$R$^{10}$,
where $R^9$ and $R^{10}$ are independently of one another selected from the group consisting of hydrogen, $(C_1-C_6)$-alkyl, $(C_3-C_6)$-cycloalkyl and $(C_1-C_6)$-haloalkyl, where the radical $R^1$ mentioned above may be mono- or polysubstituted independently of one another by radicals selected from the group consisting of halogen and $(C_1-C_6)$-alkyl;
$R^3$ is selected from the group consisting of hydrogen, halogen, hydroxyl, cyano, nitro, amino, $(C_1-C_4)$-alkyl, $(C_3-C_6)$-cycloalkyl, $(C_1-C_4)$-haloalkyl, $(C_1-C_4)$-alkoxy, $(C_1-C_4)$-alkoxy-$(C_1-C_2)$-alkyl, $(C_3-C_6)$-cycloalkoxy, $(C_1-C_4)$-haloalkoxy, $(C_1-C_4)$-haloalkylthio, $(C_1-C_4)$-alkylthio-$(C_1-C_2)$-alkyl, $(C_1-C_4)$-alkylsulfinyl, $(C_1-C_4)$-alkylsulfinyl-$(C_1-C_2)$-alkyl, $(C_1-C_4)$-alkylsulfonyl, $(C_1-C_4)$-alkylsulfonyl-$(C_1-C_2)$-alkyl, di-$(C_1-C_4)$-alkylamino, $(C_2-C_4)$-alkenyl, $(C_2-C_4)$-alkynyl, $(C_3-C_4)$-alkenyloxy, $(C_3-C_4)$-alkynyloxy, $(C_3-C_6)$-cycloalkyl-$(C_1-C_2)$-alkoxy, hydroxyl-$(C_1-C_2)$-alkyl, hydroxyl-$(C_1-C_2)$-alkoxy, cyano-$(C_1-C_2)$-alkoxy, cyano-$(C_1-C_2)$- alkyl, phenyl, phenyl-$(C_1-C_2)$-alkyl, phenyl-$(C_1-C_2)$-alkoxy, phenoxy, $(C_1-C_4)$-alkylcarbonyloxy, $(C_3-C_6)$-cycloalkyl-$(C_1-C_2)$-alkyl, $(C_1-C_4)$-alkylcarbonyl-$(C_1-C_2)$-alkyl, $(C_1-C_4)$-alkoxycarbonyl-$(C_1-C_2)$-alkyl, aminocarbonyl-$(C_1-C_2)$-alkyl and 3-oxetanyloxy, —C(O)NR$^9$R$^{10}$, where R$^9$ and R$^{10}$ are independently of one another selected from the group consisting of hydrogen, $(C_1-C_6)$-alkyl, $(C_3-C_6)$-cycloalkyl, $(C_1-C_6)$-haloalkyl, or where R$^9$ and R$^{10}$ together form a $(C^1-C^6)$-alkylene group which may contain an oxygen or sulfur atom or one or two amino or $(C_1-C_6)$-alkylamino groups;

R$^4$ is selected from the group consisting of hydrogen, $(C_1-C_4)$-alkyl, $(C_1-C_4)$-haloalkyl, phenyl, phenyl-$(C_1-C_2)$-alkyl, $(C_3-C_6)$-cycloalkyl, $(C_3-C_6)$-cycloalkyl-$(C_1-C_2)$-alkyl, where the cycloalkyl radical is optionally substituted by $(C_1-C_4)$-alkyl, $(C_2-C_4)$-alkenyl, $(C_2-C_4)$-alkynyl, $(C_1-C_4)$-alkoxy-$(C_1-C_2)$-alkyl, $(C_1-C_4)$-alkylthio-$(C_1-C_2)$-alkyl, $(C_1-C_4)$-alkylsulfinyl-$(C_1-C_2)$-alkyl, cyano-$(C_1-C_2)$-alkyl, $(C_1-C_4)$-alkylsulfonyl-$(C_1-C_2)$-alkyl, $(C_1-C_4)$-alkoxycarbonyl-$(C_1-C_2)$-alkyl, aminocarbonyl-$(C_1-C_2)$-alkyl, mono-$(C_1-C_4)$-alkylaminocarbonyl-$(C_1-C_2)$-alkyl, di-$(C_1-C_4)$-alkylaminocarbonyl-$(C_1-C_2)$-alkyl, hydroxyl-$(C_1-C_4)$-alkyl, $(C_1-C_4)$-alkylcarbonyl-$(C_1-C_4)$-alkyl, $(C_1-C_4)$-alkylsulfonyl;

phenylsulfonyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio;

$(C_1-C_4)$-alkylcarbonyl;

phenylcarbonyl which is optionally substituted by one or more identical or different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio; and $(C_1-C_4)$-alkoxycarbonyl;

R$^5$ is selected from the group consisting of hydrogen, hydroxyl, halogen, cyano, nitro, amino, $(C_1-C_4)$-alkyl, $(C_1-C_4)$-haloalkyl, $(C_3-C_6)$-cycloalkyl, $(C_1-C_4)$-alkoxy, $(C_1-C_4)$-alkoxy-$(C_1-C_4)$-alkoxy, $(C_1-C_4)$-alkoxy-$(C_1-C_2)$-alkyl, $(C_3-C_6)$-cycloalkoxy, $(C_1-C_4)$-haloalkoxy, $(C_1-C_4)$-alkylthio, $(C_1-C_4)$-alkylthio-$(C_1-C_2)$-alkyl, $(C_1-C_4)$-alkylsulfinyl, $(C_1-C_4)$-alkylsulfinyl-$(C_1-C_2)$-alkyl, $(C_1-C_4)$-alkylsulfonyl, $(C_1-C_4)$-alkylsulfonyl-$(C_1-C_2)$-alkyl, di-$(C_1-C_4)$-alkylamino, $(C_2-C_4)$-alkenyl, $(C_2-C_4)$-haloalkenyl, cyano-$(C_1-C_4)$-alkyl, $(C_2-C_4)$-alkynyl, $(C_3-C_4)$-alkenyloxy, $(C_3-C_4)$-alkynyloxy, $(C_3-C_6)$-cycloalkyl-$(C_1-C_2)$-alkoxt, hydroxyl-$(C_1-C_2)$-alkyl, hydroxyl-$(C_1-C_2)$-alkoxy, cyano-$(C_1-C_2)$-alkoxy, cyano-$(C_1-C_2)$-alkyl;

phenyl which is optionally substituted by one or more identical of different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio;

phenyl-$(C_1-C_2)$-alkyl which is optionally substituted by one or more identical of different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio;

phenoxy which is optionally substituted by one or more identical of different radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and $(C_1-C_6)$-alkylthio;

$(C_1-C_4)$-alkylcarbonyloxy, $(C_3-C_6)$-cycloalkyl-$(C_1-C_2)$-alkyl, $(C_1-C_4)$-alkylcarbonyloxy-$(C_1-C_2)$-alkyl, $(C_1-C_4)$-alkylcarbonyl-$(C_1-C_2)$-alkyl, aminocarbonyl-$(C_1-C_2)$-alkyl and 3-oxetanyloxy-, —C(O)NR$^9$R$^{10}$, where R$^9$ and R$^{10}$ are independently of one another are selected from the group consisting of hydrogen, $(C_1-C_6)$-alkyl, $(C_3-C_6)$-cycloalkyl, $(C_1-C_6)$-haloalkyl, or where R$^9$ and R$^{10}$ together form a $(C_1-C_6)$-alkylene group which may contain an oxygen or sulfur atom or one or two amino or $(C_1-C_6)$-alkylamino groups.

\* \* \* \* \*